US012577561B2

(12) United States Patent
Aznarez

(10) Patent No.: US 12,577,561 B2
(45) Date of Patent: \*Mar. 17, 2026

(54) ANTISENSE OLIGOMERS FOR TREATMENT OF CONDITIONS AND DISEASES

(71) Applicant: Stoke Therapeutics, Inc., Bedford, MA (US)

(72) Inventor: Isabel Aznarez, Jamaica Plain, MA (US)

(73) Assignee: STOKE THERAPEUTICS, INC., Bedford, MA (US)

( * ) Notice: Subject to any disclaimer, the term of this patent is extended or adjusted under 35 U.S.C. 154(b) by 935 days.

This patent is subject to a terminal disclaimer.

(21) Appl. No.: 17/412,664

(22) Filed: Aug. 26, 2021

(65) Prior Publication Data

US 2022/0162605 A1 May 26, 2022

Related U.S. Application Data

(63) Continuation of application No. PCT/US2020/020175, filed on Feb. 27, 2020.

(60) Provisional application No. 62/811,511, filed on Feb. 27, 2019.

(51) Int. Cl.
| | |
|---|---|
| *C07H 21/04* | (2006.01) |
| *C12N 15/113* | (2010.01) |

(52) U.S. Cl.
CPC ........ *C12N 15/113* (2013.01); *C12N 2310/11* (2013.01); *C12N 2310/315* (2013.01); *C12N 2310/321* (2013.01); *C12N 2320/11* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 4,476,116 | A | 10/1984 | Anik |
| 4,522,811 | A | 6/1985 | Eppstein et al. |
| 4,866,042 | A | 9/1989 | Neuwelt |
| 5,142,047 | A | 8/1992 | Summerton et al. |
| 5,151,510 | A | 9/1992 | Stec et al. |
| 5,185,444 | A | 2/1993 | Summerton et al. |
| 5,656,612 | A | 8/1997 | Monia |
| 5,665,593 | A | 9/1997 | Kole et al. |
| 5,914,396 | A | 6/1999 | Cook et al. |
| 5,916,808 | A | 6/1999 | Kole et al. |
| 5,976,879 | A | 11/1999 | Kole et al. |
| 6,083,482 | A | 7/2000 | Wang |
| 6,166,197 | A | 12/2000 | Cook et al. |
| 6,210,892 | B1 | 4/2001 | Bennett et al. |
| 6,294,520 | B1 | 9/2001 | Naito |
| 6,383,752 | B1 | 5/2002 | Agrawal et al. |
| 6,391,452 | B1 | 5/2002 | Antonsen et al. |
| 6,436,657 | B1 | 8/2002 | Famodu et al. |
| 6,451,991 | B1 | 9/2002 | Martin et al. |
| 6,485,960 | B1 | 11/2002 | Harris et al. |
| 6,531,591 | B1 | 3/2003 | Fensholdt |
| 6,573,073 | B2 | 6/2003 | Harris |
| 6,605,611 | B2 | 8/2003 | Simmonds et al. |
| 6,632,427 | B1 | 10/2003 | Finiels et al. |
| 6,639,059 | B1 | 10/2003 | Kochkine et al. |
| 6,670,461 | B1 | 12/2003 | Wengel et al. |
| 6,677,445 | B1 | 1/2004 | Innis et al. |
| 6,734,291 | B2 | 5/2004 | Kochkine et al. |
| 6,756,523 | B1 | 6/2004 | Kahn et al. |
| 6,770,748 | B2 | 8/2004 | Imanishi et al. |
| 6,794,499 | B2 | 9/2004 | Wengel et al. |
| 6,846,921 | B2 | 1/2005 | Innis et al. |
| 6,936,589 | B2 | 8/2005 | Naito |
| 6,963,589 | B1 | 11/2005 | Sugata et al. |
| 6,998,484 | B2 | 2/2006 | Koch et al. |
| 7,015,315 | B1 | 3/2006 | Cook et al. |
| 7,034,133 | B2 | 4/2006 | Wengel et al. |
| 7,053,199 | B2 | 5/2006 | Imanishi et al. |
| 7,053,207 | B2 | 5/2006 | Wengel |
| 7,060,809 | B2 | 6/2006 | Wengel et al. |
| 7,071,324 | B2 | 7/2006 | Preparata et al. |
| 7,084,125 | B2 | 8/2006 | Wengel |

(Continued)

FOREIGN PATENT DOCUMENTS

| | | | |
|---|---|---|---|
| AU | 2018322319 | B2 | 8/2021 |
| AU | 2016334804 | B2 | 3/2022 |

(Continued)

OTHER PUBLICATIONS

Arzimanoglou, A. et al., "A Review of the New Antiepileptic Drugs for Focal-Onset Seizures in Pediatrics: Role of Extrapolation," Pediatr. Drugs, 2018, vol. 20, No. 3, pp. 249-264.
Berecki, G. et al., "SCN1A Gain of Function in Early Infantile Encephalopathy", Ann Neurol., 2019, vol. 85, pp. 514-525.
Cestele, S. et al., "Nonfunctional NaV1.1 familial hemiplegic migraine mutant transformed into gain of function by partial rescue of folding defects", Proc. Natl. Acad. Sci., 2013, vol. 110, No. 43, pp. 17546-51.
Cheah, C. S. et al., "Correlations in timing of sodium channel expression, epilepsy, and sudden death in Dravet syndrome", Channels, 2013, vol. 7, No. 6, pp. 468-472.
Cheah, C. S. et al., "Specific deletion of NaV1.1 sodium channels in inhibitory interneurons causes seizures and premature death in a mouse model of Dravet syndrome", PNAS, 2012, vol. 109, No. 36, pp. 14646-14651.

(Continued)

*Primary Examiner* — Celine X Qian
(74) *Attorney, Agent, or Firm* — Wilson Sonsini Goodrich & Rosati

(57) ABSTRACT

Alternative splicing events in SCN1A gene can lead to non-productive mRNA transcripts which in turn can lead to aberrant protein expression, and therapeutic agents which can target the alternative splicing events in SCN1A gene can modulate the expression level of functional proteins in Dravet Syndrome patients and/or inhibit aberrant protein expression. Such therapeutic agents can be used to treat a condition caused by SCN1A, SCN8A or SCN5A protein deficiency.

17 Claims, 8 Drawing Sheets

Specification includes a Sequence Listing.

(56)            References Cited

U.S. PATENT DOCUMENTS

| | | | |
|---|---|---|---|
| 7,101,993 B1 | 9/2006 | Cook et al. |
| 7,169,594 B2 | 1/2007 | Guan |
| 7,214,783 B2 | 5/2007 | Jeon et al. |
| 7,217,805 B2 | 5/2007 | Imanishi et al. |
| 7,314,923 B2 | 1/2008 | Kaneko et al. |
| 7,335,765 B2 | 2/2008 | Kaneko et al. |
| 7,368,549 B2 | 5/2008 | Dempcy et al. |
| 7,399,845 B2 | 7/2008 | Seth et al. |
| 7,432,249 B2 | 10/2008 | Crooke |
| 7,432,250 B2 | 10/2008 | Crooke |
| 7,547,684 B2 | 6/2009 | Seth et al. |
| 7,553,644 B2 | 6/2009 | Germino et al. |
| 7,569,575 B2 | 8/2009 | Soerensen et al. |
| 7,569,686 B1 | 8/2009 | Bhat et al. |
| 7,572,582 B2 | 8/2009 | Wengel et al. |
| 7,595,304 B2 | 9/2009 | Zhao et al. |
| 7,615,619 B2 | 11/2009 | Imanishi et al. |
| 7,662,946 B2 | 2/2010 | Ginsburg et al. |
| 7,662,948 B2 | 2/2010 | Kurreck et al. |
| 7,666,854 B2 | 2/2010 | Seth et al. |
| 7,687,617 B2 | 3/2010 | Thrue et al. |
| 7,696,345 B2 | 4/2010 | Allerson et al. |
| 7,741,457 B2 | 6/2010 | Seth et al. |
| 7,750,131 B2 | 7/2010 | Seth et al. |
| 7,816,333 B2 | 10/2010 | Kaneko et al. |
| 7,846,686 B2 | 12/2010 | Kramer |
| 7,951,934 B2 | 5/2011 | Freier |
| 7,994,145 B2 | 8/2011 | Imanishi et al. |
| 8,022,193 B2 | 9/2011 | Seth et al. |
| 8,030,467 B2 | 10/2011 | Seth et al. |
| 8,048,998 B2 | 11/2011 | Rasmussen et al. |
| 8,067,569 B2 | 11/2011 | Iversen et al. |
| 8,084,458 B2 | 12/2011 | Soerensen et al. |
| 8,088,746 B2 | 1/2012 | Seth et al. |
| 8,090,542 B2 | 1/2012 | Khvorova et al. |
| 8,110,674 B2 | 2/2012 | Manoharan et al. |
| 8,124,745 B2 | 2/2012 | Allerson et al. |
| 8,129,515 B2 | 3/2012 | Esau et al. |
| 8,168,605 B2 | 5/2012 | Zhao et al. |
| 8,258,109 B2 | 9/2012 | Bennett et al. |
| 8,268,980 B2 | 9/2012 | Seth et al. |
| 8,278,036 B2 | 10/2012 | Kariko et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,293,684 B2 | 10/2012 | Mouritzen et al. |
| 8,361,979 B2 | 1/2013 | Aartsma-Rus et al. |
| 8,383,792 B2 | 2/2013 | Okamoto et al. |
| 8,394,947 B2 | 3/2013 | Bhat et al. |
| 8,415,465 B2 | 4/2013 | Freier |
| 8,436,163 B2 | 5/2013 | Iversen et al. |
| 8,450,467 B2 | 5/2013 | Manoharan et al. |
| 8,461,124 B2 | 6/2013 | Chattopadhyaya |
| 8,492,390 B2 | 7/2013 | Detlef et al. |
| 8,501,703 B2 | 8/2013 | Bennett et al. |
| 8,501,805 B2 | 8/2013 | Seth et al. |
| 8,518,908 B2 | 8/2013 | Hrdlicka et al. |
| 8,530,640 B2 | 9/2013 | Seth et al. |
| 8,541,562 B2 | 9/2013 | Obika et al. |
| 8,546,556 B2 | 10/2013 | Seth et al. |
| 8,592,156 B2 | 11/2013 | Liu et al. |
| 8,637,478 B2 | 1/2014 | Bennett |
| RE44,779 E | 2/2014 | Imanishi et al. |
| 8,653,252 B2 | 2/2014 | Elmen et al. |
| 8,673,560 B2 | 3/2014 | Leamon et al. |
| 8,680,254 B2 | 3/2014 | Lutz et al. |
| 8,691,783 B2 | 4/2014 | Thum et al. |
| 8,703,728 B2 | 4/2014 | Swayze et al. |
| 8,710,021 B2 | 4/2014 | Anro et al. |
| 8,735,366 B2 | 5/2014 | Bauer et al. |
| 8,748,089 B2 | 6/2014 | Kariko et al. |
| 8,779,118 B2 | 7/2014 | Allerson et al. |
| 8,796,437 B2 | 8/2014 | Swayze et al. |
| 8,809,516 B2 | 8/2014 | Manoharan et al. |
| 8,846,386 B2 | 9/2014 | Ambati et al. |
| 8,846,637 B2 | 9/2014 | Seth et al. |
| 8,846,639 B2 | 9/2014 | Swayze et al. |
| 8,846,885 B2 | 9/2014 | Hirai et al. |
| 8,895,722 B2 | 11/2014 | Iversen et al. |
| 8,957,040 B2 | 2/2015 | Bennett et al. |
| 8,957,200 B2 | 2/2015 | Seth et al. |
| 8,957,201 B2 | 2/2015 | Kaneko et al. |
| 9,005,906 B2 | 4/2015 | Swayze et al. |
| 9,006,194 B2 | 4/2015 | Katsikis et al. |
| 9,006,415 B2 | 4/2015 | Ren et al. |
| 9,012,139 B2 | 4/2015 | Collard et al. |
| 9,029,335 B2 | 5/2015 | Prakash et al. |
| 9,045,518 B2 | 6/2015 | Christensen et al. |
| 9,045,754 B2 | 6/2015 | Bhanot et al. |
| 9,057,066 B2 | 6/2015 | Hung et al. |
| 9,109,001 B2 | 8/2015 | Parsy et al. |
| 9,127,272 B2 | 9/2015 | Esau et al. |
| 9,127,276 B2 | 9/2015 | Prakash et al. |
| 9,156,873 B2 | 10/2015 | Prakash et al. |
| 9,157,081 B2 | 10/2015 | Bennett et al. |
| 9,181,549 B2 | 11/2015 | Prakash et al. |
| 9,187,515 B2 | 11/2015 | Mayes et al. |
| 9,192,621 B2 | 11/2015 | Mayes et al. |
| 9,193,752 B2 | 11/2015 | Migawa et al. |
| 9,193,969 B2 | 11/2015 | Montefeltro et al. |
| 9,211,300 B2 | 12/2015 | Mayes et al. |
| 9,217,147 B2 | 12/2015 | Singh et al. |
| 9,221,864 B2 | 12/2015 | Seth et al. |
| 9,243,245 B2 | 1/2016 | De Kimpe et al. |
| 9,290,534 B2 | 3/2016 | Seth et al. |
| 9,296,778 B2 | 3/2016 | Parsy et al. |
| 9,309,275 B2 | 4/2016 | Stewart et al. |
| 9,315,535 B2 | 4/2016 | Mitsuoka et al. |
| 9,334,495 B2 | 5/2016 | Khvorova et al. |
| 9,339,541 B2 | 5/2016 | Dousson et al. |
| 9,347,068 B2 | 5/2016 | Dhugga et al. |
| 9,359,445 B2 | 6/2016 | Finkbeiner et al. |
| 9,359,603 B2 | 6/2016 | Lutz et al. |
| 9,359,609 B2 | 6/2016 | Duffield et al. |
| 9,410,155 B2 | 8/2016 | Collard et al. |
| 9,428,534 B2 | 8/2016 | Christensen et al. |
| 9,447,166 B2 | 9/2016 | Ambati et al. |
| 9,453,261 B2 | 9/2016 | Lee et al. |
| 9,464,292 B2 | 10/2016 | Okumura et al. |
| 9,499,818 B2 | 11/2016 | Van |
| 9,518,259 B2 | 12/2016 | Rigo et al. |
| 9,534,222 B2 | 1/2017 | Ambati et al. |
| 9,550,988 B2 | 1/2017 | Swayze |
| 9,714,422 B2 | 7/2017 | Vorechovsky et al. |
| 9,745,577 B2 | 8/2017 | Vorechovsky et al. |
| 9,771,579 B2 | 9/2017 | Collard et al. |
| 9,914,922 B2 | 3/2018 | Freier et al. |
| 9,976,143 B2 | 5/2018 | Krainer et al. |
| 10,119,168 B2 | 11/2018 | Vaidya et al. |
| 10,196,639 B2 | 2/2019 | Vorechovsky et al. |
| 10,517,853 B2 | 12/2019 | Welch et al. |
| 10,583,128 B2 | 3/2020 | Collard et al. |
| 10,683,503 B2 | 6/2020 | Aznarez et al. |
| 10,696,969 B2 | 6/2020 | Krainer et al. |
| 10,913,947 B2 | 2/2021 | Aznarez et al. |
| 10,941,405 B2 | 3/2021 | Vorechovsky et al. |
| 11,390,869 B2 | 7/2022 | Vorechovsky et al. |
| 11,702,660 B2 | 7/2023 | Vorechovsky et al. |
| 11,873,490 B2 | 1/2024 | Aznarez et al. |
| 11,891,605 B2 | 2/2024 | Vorechovsky et al. |
| 2003/0087861 A1 | 5/2003 | Iversen |
| 2003/0148974 A1 | 8/2003 | Monia et al. |
| 2004/0063129 A1 | 4/2004 | Gaarde et al. |
| 2004/0219515 A1 | 11/2004 | Bentwich |
| 2005/0221354 A1 | 10/2005 | Mounts |
| 2005/0233327 A1 | 10/2005 | Welch et al. |
| 2006/0062790 A1 | 3/2006 | Reinhard et al. |
| 2006/0134670 A1 | 6/2006 | Piu |
| 2006/0166922 A1 | 7/2006 | Eichler et al. |
| 2007/0009899 A1 | 1/2007 | Mounts |
| 2007/0087376 A1 | 4/2007 | Potashkin |
| 2007/0249538 A1 | 10/2007 | Sazani et al. |
| 2008/0269123 A1 | 10/2008 | Li et al. |
| 2009/0186846 A1 | 7/2009 | Chabot et al. |

(56)        References Cited

U.S. PATENT DOCUMENTS

| | | |
|---|---|---|
| 2009/0186946 A1 | 7/2009 | Taketomi et al. |
| 2009/0264353 A1 | 10/2009 | Orum et al. |
| 2009/0270332 A1 | 10/2009 | Bare et al. |
| 2010/0088778 A1 | 4/2010 | Mulley et al. |
| 2010/0150839 A1 | 6/2010 | Kelleher |
| 2010/0166784 A1 | 7/2010 | Murphy et al. |
| 2011/0124591 A1 | 5/2011 | Bennett |
| 2011/0229891 A1 | 9/2011 | Michaud et al. |
| 2012/0190728 A1 | 7/2012 | Bennett et al. |
| 2012/0252877 A1 | 10/2012 | Lo |
| 2013/0072671 A1 | 3/2013 | Van Deutekom |
| 2013/0096183 A1 | 4/2013 | Collard et al. |
| 2013/0109850 A1 | 5/2013 | Prakash et al. |
| 2013/0136732 A1 | 5/2013 | Wagner et al. |
| 2013/0184223 A1 | 7/2013 | Land et al. |
| 2013/0253036 A1 | 9/2013 | Collard et al. |
| 2013/0266560 A1 | 10/2013 | Demopulos et al. |
| 2013/0289092 A1 | 10/2013 | Rigo et al. |
| 2014/0011761 A1 | 1/2014 | Hotamisligil et al. |
| 2014/0128449 A1 | 5/2014 | Liu et al. |
| 2014/0186839 A1 | 7/2014 | Margulies et al. |
| 2014/0194610 A1 | 7/2014 | Verdine et al. |
| 2014/0235605 A1 | 8/2014 | Shiffman et al. |
| 2014/0309181 A1 | 10/2014 | Collard et al. |
| 2014/0336238 A1 | 11/2014 | Collin et al. |
| 2014/0343127 A1 | 11/2014 | Kammler |
| 2014/0349290 A1 | 11/2014 | Watnick et al. |
| 2014/0378526 A1 | 12/2014 | Rossi et al. |
| 2014/0378527 A1 | 12/2014 | Van |
| 2014/0378533 A1 | 12/2014 | Freier |
| 2015/0004217 A1 | 1/2015 | Guild et al. |
| 2015/0018540 A1 | 1/2015 | Prakash et al. |
| 2015/0184153 A1 | 7/2015 | Freier et al. |
| 2015/0211006 A1 | 7/2015 | Butler et al. |
| 2015/0211010 A1 | 7/2015 | Kerem et al. |
| 2015/0232845 A1 | 8/2015 | Ozsolak |
| 2015/0232858 A1 | 8/2015 | Ozsolak |
| 2015/0238516 A1 | 8/2015 | Dowdy et al. |
| 2015/0267192 A1 | 9/2015 | Heartlein et al. |
| 2015/0291957 A1 | 10/2015 | Smith |
| 2015/0329918 A1 | 11/2015 | Kang et al. |
| 2015/0337310 A1 | 11/2015 | Walker et al. |
| 2015/0361497 A1 | 12/2015 | Rose |
| 2016/0017322 A1 | 1/2016 | Vorechovsky et al. |
| 2016/0024500 A1 | 1/2016 | Popplewell et al. |
| 2016/0046935 A1 | 2/2016 | Bentwich et al. |
| 2016/0122767 A1 | 5/2016 | Gouya et al. |
| 2016/0201063 A1 | 7/2016 | Ozsolak |
| 2016/0201064 A1 | 7/2016 | Ozsolak |
| 2016/0208264 A1 | 7/2016 | Wilton et al. |
| 2016/0215291 A1 | 7/2016 | Garcia et al. |
| 2016/0244762 A1 | 8/2016 | Vorechovsky et al. |
| 2016/0244767 A1 | 8/2016 | Hastings |
| 2016/0298121 A1 | 10/2016 | Krainer et al. |
| 2017/0044540 A1 | 2/2017 | Sætrom et al. |
| 2017/0159049 A9 | 6/2017 | Krainer et al. |
| 2017/0240904 A1 | 8/2017 | Tallent et al. |
| 2018/0002694 A1 | 1/2018 | Vorechovsky et al. |
| 2018/0296501 A1 | 10/2018 | During |
| 2018/0346907 A1 | 12/2018 | Crooke et al. |
| 2018/0362987 A1 | 12/2018 | Krainer et al. |
| 2018/0369275 A1 | 12/2018 | Arnarez et al. |
| 2019/0024118 A1 | 1/2019 | Tagliatela et al. |
| 2019/0024119 A1 | 1/2019 | Tagliatela et al. |
| 2019/0024120 A1 | 1/2019 | Tagliatela et al. |
| 2019/0024121 A1 | 1/2019 | Tagliatela et al. |
| 2019/0070213 A1 | 3/2019 | Aznarez et al. |
| 2019/0192691 A1 | 6/2019 | Barrett et al. |
| 2019/0218255 A1 | 7/2019 | Chung et al. |
| 2019/0225939 A1 | 7/2019 | Chambers et al. |
| 2019/0264211 A1 | 8/2019 | Vorechovsky et al. |
| 2020/0085838 A1 | 3/2020 | Martinez Botella et al. |
| 2020/0101174 A1 | 4/2020 | Coller et al. |
| 2021/0108208 A1 | 4/2021 | Krainer et al. |
| 2021/0155936 A1 | 5/2021 | Vorechovsky |
| 2021/0261963 A1 | 8/2021 | Uno et al. |
| 2021/0309996 A1 | 10/2021 | Aznarez et al. |
| 2021/0317462 A1 | 10/2021 | Petrou |
| 2022/0162605 A1 | 5/2022 | Aznarez et al. |
| 2023/0116704 A1 | 4/2023 | Aznarez et al. |
| 2023/0183693 A1 | 6/2023 | Vorechovsky et al. |
| 2023/0416756 A1 | 12/2023 | Vorechovsky et al. |
| 2024/0150760 A1 | 5/2024 | Aznarez et al. |
| 2024/0309377 A1 | 9/2024 | Vorechovsky et al. |
| 2025/0066781 A1 | 2/2025 | Ticho et al. |

FOREIGN PATENT DOCUMENTS

| | | |
|---|---|---|
| AU | 2022204606 A1 | 7/2022 |
| CN | 102171342 A | 8/2011 |
| CN | 103667438 A | 3/2014 |
| CN | 109312343 A | 2/2019 |
| CN | 111278991 A | 6/2020 |
| EP | 0549615 A1 | 7/1993 |
| EP | 1201678 B1 | 9/2004 |
| EP | 1409497 B1 | 1/2005 |
| EP | 1579015 A2 | 9/2005 |
| EP | 1007714 B1 | 12/2005 |
| EP | 1334109 B1 | 5/2006 |
| EP | 1178999 B1 | 3/2007 |
| EP | 1203827 B1 | 5/2007 |
| EP | 1501848 B1 | 8/2007 |
| EP | 1569661 B1 | 9/2009 |
| EP | 1161439 B1 | 4/2010 |
| EP | 1984381 B1 | 9/2010 |
| EP | 1013661 B1 | 1/2012 |
| EP | 2092065 B1 | 1/2012 |
| EP | 2099461 B1 | 3/2012 |
| EP | 2170917 B1 | 6/2012 |
| EP | 2066684 B1 | 7/2012 |
| EP | 2284269 A3 | 8/2012 |
| EP | 2356129 B1 | 4/2013 |
| EP | 2376516 B1 | 4/2013 |
| EP | 2114981 B1 | 5/2013 |
| EP | 2149605 B1 | 7/2013 |
| EP | 2285819 B1 | 10/2013 |
| EP | 2161038 B1 | 12/2013 |
| EP | 1562971 B1 | 2/2014 |
| EP | 2295441 B1 | 5/2014 |
| EP | 2314594 B1 | 7/2014 |
| EP | 2410053 B1 | 10/2014 |
| EP | 2176280 B2 | 6/2015 |
| EP | 2361921 B1 | 6/2015 |
| EP | 2462153 B1 | 7/2015 |
| EP | 1015469 B2 | 11/2015 |
| EP | 2173760 B2 | 11/2015 |
| EP | 1937312 B1 | 6/2016 |
| EP | 2141233 B1 | 10/2016 |
| EP | 2410054 B1 | 1/2017 |
| EP | 3329909 A1 | 6/2018 |
| EP | 3359685 A1 | 8/2018 |
| EP | 2753317 B1 | 2/2020 |
| EP | 3673080 A1 | 7/2020 |
| EP | 3155124 B1 | 11/2021 |
| EP | 4015648 A1 | 6/2022 |
| EP | 4069256 A1 | 10/2022 |
| GB | 1517937 A | 7/1978 |
| GB | 2546719 A | 8/2017 |
| JP | 2007534772 A | 11/2007 |
| JP | 6923517 B2 | 8/2021 |
| JP | 2021180669 A | 11/2021 |
| WO | WO-9402501 A1 | 2/1994 |
| WO | WO-9426887 A1 | 11/1994 |
| WO | WO-9747772 A2 | 12/1997 |
| WO | WO-0010608 A1 | 3/2000 |
| WO | WO-0107660 A1 | 2/2001 |
| WO | WO-2005049651 A2 | 6/2005 |
| WO | WO-2006107846 A2 | 10/2006 |
| WO | WO-2007002390 A2 | 1/2007 |
| WO | WO-2007048628 A2 | 5/2007 |
| WO | WO-2007048629 A2 | 5/2007 |
| WO | WO-2007056113 A2 | 5/2007 |
| WO | WO-2007002390 A3 | 11/2007 |
| WO | WO-2009084472 A1 | 7/2009 |

(56) References Cited

FOREIGN PATENT DOCUMENTS

| WO | WO-2009099942 A2 | 8/2009 | |
|---|---|---|---|
| WO | WO-2010148249 A1 | 12/2010 | |
| WO | WO-2011057350 A1 | 5/2011 | |
| WO | WO-2011163499 A2 | 12/2011 | |
| WO | WO-2012168435 A1 | 12/2012 | |
| WO | WO-2012178146 A1 | 12/2012 | |
| WO | WO-2013036105 A1 | 3/2013 | |
| WO | WO-2013081755 A1 | 6/2013 | |
| WO | WO-2013106770 A1 | 7/2013 | |
| WO | WO-2013119916 A2 | 8/2013 | |
| WO | WO-2013119916 A3 | 10/2013 | |
| WO | WO-2014012081 A2 | 1/2014 | |
| WO | WO-201428459 A1 | 2/2014 | |
| WO | WO-2014028459 A1 | 2/2014 | |
| WO | WO-2014031575 A1 | 2/2014 | |
| WO | WO-2014049536 A2 | 4/2014 | |
| WO | WO-2014121287 A2 | 8/2014 | |
| WO | WO-2014172698 A1 | 10/2014 | |
| WO | WO-2014201413 A1 | 12/2014 | |
| WO | WO-2014209841 A2 | 12/2014 | |
| WO | WO-2015024876 A2 | 2/2015 | |
| WO | WO-2015035091 A1 | 3/2015 | |
| WO | WO-2015024876 A3 | 7/2015 | |
| WO | WO-2014209841 A3 | 10/2015 | |
| WO | WO-2015190922 A1 | 12/2015 | |
| WO | WO-2015193651 A1 | 12/2015 | |
| WO | WO-2015198054 A1 | 12/2015 | |
| WO | WO-2016027168 A2 | 2/2016 | |
| WO | WO-2015193651 A4 | 3/2016 | |
| WO | WO-2016027168 A3 | 4/2016 | |
| WO | WO-2016054615 A2 | 4/2016 | |
| WO | WO-2016061509 A1 | 4/2016 | |
| WO | WO-2016054615 A3 | 5/2016 | |
| WO | WO-2016077837 A1 | 5/2016 | |
| WO | WO-2016087842 A1 | 6/2016 | |
| WO | WO-2016118697 A1 | 7/2016 | |
| WO | WO-2016128343 A1 | 8/2016 | |
| WO | WO-2016138534 A2 | 9/2016 | |
| WO | WO-2016161429 A1 | 10/2016 | |
| WO | WO-2016196386 A1 | 12/2016 | |
| WO | WO-2017053982 A1 | 3/2017 | |
| WO | WO-2017060731 A1 | 4/2017 | |
| WO | WO-2017106210 A1 | 6/2017 | |
| WO | WO-2017106211 A1 | 6/2017 | |
| WO | WO-2017106283 A1 | 6/2017 | |
| WO | WO-2017106292 A1 | 6/2017 | |
| WO | WO-2017106364 | 6/2017 | |
| WO | WO-2017106364 A2 | 6/2017 | |
| WO | WO-2017106370 A1 | 6/2017 | |
| WO | WO-2017106375 A1 | 6/2017 | |
| WO | WO-2017106377 A1 | 6/2017 | |
| WO | WO-2017106382 A1 | 6/2017 | |
| WO | WO-2017106364 A3 | 7/2017 | |
| WO | WO-2018007980 A1 | 1/2018 | |
| WO | WO-2018187363 A1 | 10/2018 | |
| WO | WO-2018191482 A2 | 10/2018 | |
| WO | WO-2018206924 A1 | 11/2018 | |
| WO | WO-2019040923 A1 * | 2/2019 | ......... A61K 31/7088 |
| WO | WO-2019084050 A1 | 5/2019 | |
| WO | WO-2019109051 A1 | 6/2019 | |
| WO | WO-2019191341 A1 | 10/2019 | |
| WO | WO-2019199867 A1 | 10/2019 | |
| WO | WO-2019224864 A1 | 11/2019 | |
| WO | WO-2019227096 A1 | 11/2019 | |
| WO | WO-2019236750 A2 | 12/2019 | |
| WO | WO-2019243430 A1 | 12/2019 | |
| WO | WO-2020041348 A1 | 2/2020 | |
| WO | WO-2020176776 A1 | 9/2020 | |
| WO | WO-2021113541 A1 | 6/2021 | |
| WO | WO-2023028575 A2 | 3/2023 | |
| WO | WO-2024026122 A2 | 2/2024 | |
| WO | WO-2024173582 A2 | 8/2024 | |
| WO | WO-2025024568 A1 | 1/2025 | |
| WO | WO-2025199503 A1 | 9/2025 | |

OTHER PUBLICATIONS

De-Lange et al., "Influence of contraindicated medication use on cognitive outcome in Dravet syndrome and age at first afebrile seizure as a clinical predictor in SCN1A-related seizure phenotypes", Epilepsia 59:1154-65 (2018).

Depienne, C. et al., "Spectrum of SCN1A gene mutations associated with Dravet syndrome: analysis of 333 patients", J. Med Genet., 2009, vol. 46, pp. 183-191.

Dhifallah, S. et al., "Gain of Function for the SCN1A/hNav1.1-L1670W Mutation Responsible for Familial Hemiplegic Migraine", Front Mol. Neurosci., 2018, vol. 11, No. 232, pp. 1-14.

Djemie, T. et al., "Pitfalls in genetic testing: the story of missed SCN1A mutations", Mol Genet Genomic Med., 2016, vol. 4, No. 4, pp. 457-464.

Fan, C. et al., "Early-onset familial hemiplegic migraine due to a novel SCN1A mutation," Cephalalgia, 2016, vol. 36, No. 13, pp. 1238-1247.

Gataullina, S. et al., "From genotype to phenotype in Dravet disease", Seizure, 2017, vol. 44, pp. 58-64.

Genton, P. et al., "Dravet syndrome: the long-term outcome", Epilepsia, 2011, vol. 52, Suppl 2, pp. 44-49.

Gomez, et al. Telomerase downregulation induced by the G-quadruplex ligand 12459 in A549 cells is mediated by hTERT RNA alternative splicing. Nucleic Acids Res. Jan. 16, 2004;32(1):371-9. Print 2004.

Hsiao, J. et al., "Upregulation of Haploinsufficient Gene Expression in the Brain by Targeting a Long Non-coding RNA Improves Seizure Phenotype in a Model of Dravet", EBioMedicine, 2016, vol. 9, pp. 257-277.

Khorkova et al., Oligonucleotide therapies for disorders of the nervous system. Nat Biotechnol. Mar. 2017;35(3):249-263. doi: 10.1038/nbt.3784. Epub Feb. 27, 2017. PMID: 28244991; PMCID: PMC6043900.

Lagae, L. et al., "Quality of life and comorbidities associated with Dravet syndrome severity: a multinational cohort survey", Dev. Med. Child Neurol., 2018, vol. 60, No. 1, pp. 63-72.

Liu, Y. et al., "Dravet syndrome patient-derived neurons suggest a novel epilepsy mechanism", Ann Neurol., 2013, vol. 74, No. 1, pp. 128-139.

Meng, H. et al., "The SCN1A Mutation Database: Updating Information and Analysis of the Relationships among Genotype, Functional Alteration, and Phenotype", Hum Mutation, 2015, vol. 36, No. 6, pp. 573-580.

Ragona, F. et al., "Cognitive development in Dravet syndrome: A retrospective, multicenter study of 26 patients", Epilepsia, 2011, vol. 52, No. 2, pp. 386-392.

Palhais, Bruno et al.: Splice-shifting oligonucleotide (SSO) mediated blocking of an exonic splicing enhancer (ESE) created by the prevalent c.903+469TC MTRR mutation corrects splicing and restores enzyme activity in patient cells. Nucleic Acids Research 43(9):4627. 4639 (2015). https://doi.org/10.1093/nar/gkv275.

Aartsma-Rus, et al. Antisense-mediated exon skipping: a versatile tool with therapeutic and research applications.RNA. Oct. 2007;13(10):1609-24. Epub Aug. 7, 2007.

Aceti, et al. "Syngap1 haploinsufficiency damages a postnatal critical period of pyramidal cell structural maturation linked to cortical circuit assembly", (2015) Biol Psychiatry, 77(9): 805-815.

Aizer AA, et al. Lack of reduction in racial disparities in cancer-specific mortality over a 20-year period. Cancer. 2014;120:1532-9.

Altschul SF et al.Basic local alignment search tool. J. Mol. Biol., vol. 215, No. 3, pp. 403-410, (Oct. 5, 1990).

Aly, et al. Extreme genetic risk for type 1A diabetes. Proc Natl Acad Sci U S A. Sep. 19, 2006;103(38):14074-9. Epub Sep. 11, 2006.

Amarnath, S. et al. The PDL1-PD1 Axis Converts Human TH1 Cells into Regulatory T Cells. Science Translational Medicine, vol. 3, No. 111, pp. 1-13. (Nov. 30, 2011).

Anders S. et al. Detecting differential usage of exons from RNA-seq data. Genome Res. 2012;22(10):2008-17. Epub Jun. 23, 2012.doi: gr.133744.111 [pii] 10.1101/gr.133744.111. PubMed PMID: 22722343.

Au, K.S. et al. Molecular Genetic Basis of Tuberous Sclerosis Complex: From Bench to Bedside.Journal of Child Neurology. vol. 19, No. 9 (Sep. 2004).

(56)     References Cited

OTHER PUBLICATIONS

Audentes Therapeutics Announces Expansion of AAV Technology Platform and Pipeline with New Development Programs for Duchenne Muscular Dystrophy and Myotonic Dystrophy. PRNewswire Apr. 8, 2019 (7 pgs).

Aznarez, et al. TANGO-Targeted augmentation of nuclear gene output—for the treatment of genetic diseases [abstract]. In: 2018 Annual Meeting Abstract of the American Society of Gene and Cell Therapy; May 16-19, 2018; Chicago, IL; 2018. Abstract No. 304.

Bakkenist CJ, Kastan MB. DNA damage activates ATM through intermolecular autophosphorylation and dimer dissociation. Nature. 2003;421(6922):499-506. doi: 10.1038/nature01368. PubMed PMID: 12556884.

Balagurumoorthy, et al. Hairpin and parallel quartet structures for telomeric sequences. Nucleic Acids Res. Aug. 11, 1992;20(15):4061-7.

Balkwill, et al. Repression of translation of human estrogen receptor alpha by G-quadruplex formation. Biochemistry. Dec. 8, 2009;48(48):11487-95. doi: 10.1021/bi901420k.

Barratt, et al. Remapping the insulin gene/IDDM2 locus in type 1 diabetes. Diabetes. Jul. 2004;53(7):1884-9.

Bassi et al. A novel mutation in the ATP1A2 gene causes alternating hemiplegia of childhood. J. Med. Genet. 41:621-628 (2004).

Battistini et al. A new CACNA1A gene mutation in acetazolamide-responsive familial hemiplegic migraine and ataxia. Neurology, vol. 53, No. 1, pp. 38-43 (Jul. 13, 1999).

Baughan, et al. Delivery of bifunctional RNAs that target an intronic repressor and increase SMN levels in an animal model of spinal muscular atrophy. Hum Mol Genet. May 1, 2009;18(9):1600-11. doi: 10.1093/hmg/ddp076. Epub Feb. 19, 2009.

Bauman et al. Therapeutic potential of splice-switching oligonucleotides. Oligonucleotides 19.1 (2009): 1-13.

Beaudoin, et al. 5'-UTR G-quadruplex structures acting as translational repressors. Nucleic Acids Res. Nov. 2010;38(20):7022-36. doi: 10.1093/nar/gkq557. Epub Jun. 22, 2010.

Beli P, et al., Proteomic investigations reveal a role for RNA processing factor THRAP3 in the DNA damage response. Mol Cell. 2012;46(2):212-25. doi: 10.1016/j.molcel.2012.01.026. PubMed PMID: 22424773; PubMed Central PMCID: PMC3565437.

Berge, SM et al. Pharmaceutical Salts Journal of Pharmaceutical Sciences, vol. 66, No. 1, pp. 1-19 (1977).

Berger, W. et al. The molecular basis of human retinal and vitreoretinal diseases. Progress in Retinal and Eye Research . vol. 29, pp. 335-375 (2010).

Bethke L, et al. Comprehensive analysis of the role of DNA repair gene polymorphisms on risk of glioma. Hum Mol Genet. 2008;17(6):800-5. Epub Dec. 1, 2007.doi: ddm351 [pii] 10.1093/hmg/ddm351. PubMed PMID: 18048407.

Bicknell, et al. Introns in UTRs: why we should stop ignoring them. Bioessays. Dec. 2012;34(12):1025-34. doi: 10.1002/bies.201200073. Epub Oct. 26, 2012.

Blencowe, Benjamin. Reflections for the 20th anniversary issue of RNA journal.RNA Journal, vol. 21, No. 4, pp. 573-575 (2015).

Blencowe BJ. Splicing regulation: the cell cycle connection. Curr Biol. 2003;13(4):R149-51. PubMed PMID: 12593819.

Bonnen, P.E., et al. Haplotypes at ATM identify coding-sequence variation and indicate a region of extensive linkage disequilibrium. Am J Hum Genet. 2000;67(6):1437-51. Epub Nov. 15, 2000.doi: S0002-9297(07)63213-3 [pii] 10.1086/316908. PubMed PMID: 11078475.

Boothby, T. et al. Removal of Retained Introns Regulates Translation in the Rapidly Developing Gametophyte of Marsilea vestita. Developmental Cell vol. 24, pp. 517-529, (Mar. 11, 2013).

Booy, et al. The RNA helicase RHAU (DHX36) unwinds a G4-quadruplex in human telomerase RNA and promotes the formation of the P1 helix template boundary. Nucleic Acids Res. May 2012;40(9):4110-24. doi: 10.1093/nar/gkr1306. Epub Jan. 11, 2012.

Boutz, et al., Detained intron are a novel, widespread class of post-transcriptionally spliced introns, Genes & Development 29: 63-80.

Boutz, et al. Detained introns are a novel, widespread class of post-transcriptionally spliced introns. Genes Dev. Jan. 1, 2015;29(1):63-80. doi: 10.1101/gad.247361.114.

Braunschweig et al., "Widespread intron retention in mammal functionally tunes transcriptomes", Chold Spring Harbor Laboratory Press, 2014 p. 1-14.

Braunschweig, et al. Widespread intron retention in mammals functionally tunes transcriptomes. Widespread intron retention in mammals functionally tunes transcriptomes. Genome Res. Nov. 2014;24(11):1774-86. doi: 10.1101/gr.177790.114. Epub Sep. 25, 2014.

Braunschweig, Intron Retention, Supplemental Figure Legends.

Bravo-Gil, et al., Improving the management of Inherited Retinal Dystrophies by targeted sequencing of a population-specific gene panel, Scientific Reports, 6:23910, 10 pages.

Brooks, A.N., et al. A pan-cancer analysis of transcriptome changes associated with somatic mutations in U2AF1 reveals commonly altered splicing events. PLoS One. 2014; 9(1):e87361. Epub Feb. 6, 2014.doi: 10.1371/journal.pone.0087361 PONE-D-13-26905 [pii]. PubMed PMID: 24498085.

Buchman, et al. Comparison of intron-dependent and intron-independent gene expression. Mol Cell Biol. Oct. 1988;8(10):4395-405.

Buckley, P.T. et al. Cytoplasmic intron retention, function, splicing, and the sentinel RNA hypothesis. WIREs RNA, vol. 5, pp. 223-2330 (Mar./Apr. 2014).

Bugaut, et al. 5'-UTR RNA G-quadruplexes: translation regulation and targeting. Nucleic Acids Res. Jun. 2012;40(11):4727-41. doi: 10.1093/nar/gks068. Epub Feb. 20, 2012.

Bugaut, et al. An RNA hairpin to G-quadruplex conformational transition. J Am Chem Soc. Dec. 12, 2012;134(49):19953-6. doi: 10.1021/ja308665g. Epub Nov. 29, 2012.

Buratti, et al. DBASS3 and DBASS5: databases of aberrant 3'- and 5'-splice sites. Nucleic Acids Res. Jan. 2011;39(Database issue):D86-91. doi: 10.1093/nar/gkq887. Epub Oct. 6, 2010.

Buratti, et al. RNA folding affects the recruitment of SR proteins by mouse and human polypurinic enhancer elements in the fibronectin EDA exon. Mol Cell Biol. Feb. 2004;24(3):1387-400.

Burnette et al. Subdivision of large introns in Drosophila by recursive splicing at non-exonic elements. Genetics (2005).

Burns, CG, et al. Connections between pre-mRNA processing and regulation of the eukaryotic cell cycle. Front Horm Res. 1999; 25:59-82.

Buschmann et al. Chitosans for delivery of nucleic acids. Advanced drug delivery reviews 65.9 (2013): 1234-1270.

Busslinger, et al. Bβ Thalassemia: Aberrant splicing results from a single point mutation in an intron. Cell 27.2 (1981): 289-298.

Callis, et al. Introns increase gene expression in cultured maize cells. Genes Dev. Dec. 1987;1(10):1183-200.

Carvill, et al., "Aberrant Inclusion of a Poison Exon Causes Dravet Syndrome and Related SCN1A-Associated Genetic Epilepsies", (2018) The American Journal of Human Genetics, vol. 103, No. 6, pp. 1022-1029.

Catterall, et al. Nav1.1 channels and epilepsy. J Physiol. Jun. 1, 2010;588(Pt 11):1849-59.

Cavaloc, et al. The splicing factors 9G8 and SRp20 transactivate splicing through different and specific enhancers. RNA. Mar. 1999;5(3):468-83.

Cazzola, et al. Translational pathophysiology: a novel molecular mechanism of human disease. Blood. Jun. 1, 2000;95(11):3280-8.

Chambers, A.L., et al. The INO80 chromatin remodeling complex prevents polyploidy and maintains normal chromatin structure at centromeres. Genes Dev. 2012; 26(23):2590-603. Epub Dec. 5, 2012.doi: 26/23/2590 [pii] 10.1101/gad.199976.112. PubMed PMID: 23207916.

Chen, M.S., et al. Chk1 kinase negatively regulates mitotic function of Cdc25A phosphatase through 14-3-3 binding. Mol Cell Biol. 2003; 23(21):7488-97. PubMed PMID: 14559997; PubMed Central PMCID: PMC207598.

Chen, T., et al. A functional single nucleotide polymorphism in promoter of ATM is associated with longevity. Mech Ageing Dev. 2010; 131:636-40.

(56)  References Cited

OTHER PUBLICATIONS

Choi, HH, et al. CHK2 kinase promotes pre-mRNA splicing via phosphorylating CDK11p110. Oncogene. 2014; 33:108-15.

Colla, S., et al. Telomere dysfunction drives aberrant hematopoietic differentiation and myelodysplastic syndrome. Cancer Cell. 2015; 27(5):644-57. doi: 10.1016/j.ccell.2015.04.007. PubMed PMID: 25965571.

Collie, et al. The application of DNA and RNA G-quadruplexes to therapeutic medicines. Chem Soc Rev. Dec. 2011;40(12):5867-92. doi: 10.1039/c1cs15067g. Epub Jul. 25, 2011.

Collin, et al., "Antisense Oligonucleotide (AON)-based Therapy for Leber Congenital Amaurosis caused by a Frequent Mutation in CEP290", (2012) Molecular Therapy-Nucleic Acids, pp. 1-7.

Consortium. TGP. An integrated map of genetic variation from 1,092 human genomes. Nature (London). 2012; 491:56-65.

Co-pending U.S. Appl. No. 15/619,984, inventors Vorechovsky; Igor et al., filed Jun. 12, 2016.

Co-pending U.S. Appl. No. 16/213,535, inventors Vorechovsky; Igor et al., filed Dec. 7, 2018.

Corallini et al. Transcriptional and Posttranscriptional Regulation of the CTNS Gene. Pediatric Research 70(2):130-135 (Aug. 2011).

Corey, S.J., et al. A non-classical translocation involving 17q12 (retinoic acid receptor alpha) in acute promyelocytic leukemia (APML) with atypical features. Leukemia. 1994; 8(8):1350-3. PubMed PMID: 8057672.

Corvelo, A., et al. Genome-wide association between branch point properties and alternative splicing. PLoS Comput Biol. 2010; 6(11):e1001016. Epub Dec. 3, 2010.doi: 10.1371/journal.pcbi. 1001016. PubMed PMID: 21124863.

Coulombe-Huntington J., et al. Fine-Scale Variation and Genetic Determinants of Alternative Splicing across Individuals. PLoS Genet. 2009; 5(12):e1000766. Epub Dec. 17, 2009.doi: 10.1371/journal.pgen.1000766. PubMed PMID: 20011102.

Coutinho, G., et al. Functional significance of a deep intronic mutation in the ATM gene and evidence for an alternative exon 28a. Hum Mutat. 2005; 25(2):118-24. Epub Jan. 12, 2005.doi: 10.1002/humu.20170. PubMed PMID: 15643608.

Creacy, et al. G4 resolvase 1 binds both DNA and RNA tetramolecular quadruplex with high affinity and is the major source of tetramolecular quadruplex G4-DNA and G4-RNA resolving activity in HeLa cell lysates. J Biol Chem. Dec. 12, 2008;283(50):34626-34. doi: 10.1074/jbc.M806277200. Epub Oct. 7, 2008.

Creson, et al. "Re-expression of SynGAP Protein in Adulthood Improves Translatable Measures of Brain Function and Behavior in a Model of Neurodevelopmental Disorders" (2018) Departments of Neuroscience and Molecular medicine, The Scripps Research Institute.

Culler, et al. Functional selection and systematic analysis of intronic splicing elements identify active sequence motifs and associated splicing factors. Nucleic Acids Res. Aug. 2010;38(15):5152-65. doi: 10.1093/nar/gkq248. Epub Apr. 12, 2010.

Database Geneseq [Online], Nov. 13, 2008 (Nov. 13, 2008), Dual label detection probe, QF probe 1, 5. 3.11, XP055572852, retrieved from EBI Accession No. GSN:ARK21623.

Davies, et al. A genome-wide search for human type 1 diabetes susceptibility genes. Nature. Sep. 8, 1994;371(6493):130-6.

Decorsiere, et al. Essential role for the interaction between hnRNP H/F and a G quadruplex in maintaining p53 pre-mRNA 3'-end processing and function during DNA damage. Genes Dev. Feb. 1, 2011;25(3):220-5. doi: 10.1101/gad.607011.

Dedic, T. et al. Alagille Syndrome Mimicking Biliary Atresia in Early Infancy, PLOS OONE, 10(11):e0143939: pp. 1-7 (Nov. 20, 2015).

Deere, J. et al. AntisensePhosphorodiamidate Morpholino OligomerLengthand TargetPositionEffects on Gene-SpecificInhibitionin *Escherichia coli*. Antimicrobial Agents Andchemotherapy, vol. 49, No. 1, p. 249-255(Jan. 2005.

Derecka, et al. Occurrence of a quadruplex motif in a unique insert within exon C of the bovine estrogen receptor alpha gene (ESR1). Biochemistry. Sep. 7, 2010;49(35):7625-33. doi: 10.1021/bi100804f.

Dias, N. et al. Antisense oligonucleotides: basic concepts and mechanisms Mol. Cancer Ther. vol. 1, pp. 347-355, (Mar. 2002).

Didiot, et al. The G-quartet containing FMRP binding site in FMR1 mRNA is a potent exonic splicing enhancer. Nucleic Acids Res. Sep. 2008;36(15):4902-12. doi: 10.1093/nar/gkn472. Epub Jul. 24, 2008.

Ding, H. et al. DeliveringPD-1 inhibitory signal concomitant with blocking ICOS co-stimulation suppresses lupus-like syndrome in autoimmune BXSB mice.Clinical Immunology, vol. 118, pp. 258-267, (2006).

Divina, P. et al. Ab initio prediction of cryptic splice-site activation and exon skipping. Eur J Hum Genet. 2009; 17:759-65.

Dominski, et al. Restoration of correct splicing in thalassemic pre-mRNA by antisense oligonucleotides. Proc Natl Acad Sci U S A. Sep. 15, 1993;90(18):8673-7.

Dredge, et al. NeuN/Rbfox3 Nuclear and Cytoplasmic Isoforms Differentially Regulate Alternative Splicing and Nonsense-Mediated Decay of Rbfox2. PLoS One. 2011; 6(6): e21585.

Du, et al. Correction of prototypic ATM splicing mutations and aberrant ATM function with antisense morpholino oligonucleotides. Proc Natl Acad Sci U S A. Apr. 3, 2007;104(14):6007-12. Epub Mar. 26, 2007.

Du, et al. "Correction of prototypic ATM splicing utations and aberrant ATM function with antisense morpholino oligonucleotides" (2007) PNAS, vol. 104, No. 14, pp. 6007-6012.

Du, et al., "Downregulation of neuronal sodium channel subunits Nav.1. and Nav1.6 in the sinoatrial node from vol. overloaded heart failure rat", Pflugers Arch—Eur J Physiol (2007) 454:451-459.

Ducros et al.Recurrence of the T666M calcium channel CACNA1A gene mutation in familial hemiplegic migraine with progressive cerebellar ataxia.Am J Hum Genet. vol. 64, No. 1, pp. 89-98 (Jan. 1999).

Duikers, et al. "Antisense Oligonucleotide-Based Splicing Correction in Individuals with Leber Congenital Amaurosis due to Compound Heterozygosity for the c.2991+1655AG Mutation in CEP290" (2018) International Journal of Molecular Sciences, 19, 753, pp. 1-12.

Dulla, et al., "Splice-Modulating Oligonucleotide QR-110 Restores CEP290 mRNA and Function in Human c.2991+1655AG LCA10 Models" (2018) Molecular Therapy: Nucleic Acids, vol. pp. 730-740.

Duryagina R, et al. Overexpression of Jagged-1 and its intracellular domain in human mesenchymal stromal cells differentially affect the interaction with hematopoietic stem and progenitor cells.Stem Cells Dev. vol. 22, No. 20, pp. 2736-2750 (2013).

Dutertre, M., et al. et al. DNA damage: RNA-binding proteins protect from near and far. Trends Biochem Sci. 2014; 39(3):141-9. Epub Feb. 19, 2014.doi: S0968-0004(14)00015-2 [pii] 10.1016/j.tibs.2014.01.003. PubMed PMID: 24534650.

Eddy, et al. G4 motifs correlate with promoter-proximal transcriptional pausing in human genes. Nucleic Acids Res. Jul. 2011;39(12):4975-83. doi: 10.1093/nar/gkr079. Epub Mar. 3, 2011.

El Bougrini, J., et al. PML positively regulates interferon gamma signaling. Biochimie. 2011; 93(3):389-98. doi: 10.1016/j.biochi. 2010.11.005. PubMed PMID: 21115099.

Emerick, et al. Multivariate analysis and visualization of splicing correlations in single-gene transcriptomes. BMC Bioinformatics. Jan. 18, 2007;8:16.

EP 15846242.4 Partial Supplementary Search Report and Search Opinion dated May 2, 2018.

EP 16876621.0 Extended European Search Report and Search Opinion dated Mar. 7, 2019.

EP15729929.8 Office Action dated Dec. 22, 2017.

EP15729929.8 Office Action dated Oct. 30, 2018.

EP15846242.4 Extended European Search Report dated Aug. 21, 2018.

EP16781187.6 Office Action dated May 20, 2019.

EP16876499.1 Extended Search Report dated Jun. 14, 2019.

EP168766061.1 Extended Search Report dated May 24, 2019.

(56)                   References Cited

OTHER PUBLICATIONS

Escayg et al., Sodium channel SCN1A and epilepsy: mutations and mechanisms, Epilepsia, Sep. 2010, vol. 51, No. 9, pp. 1-16.

Fairbrother, W.G., et al. Predictive identification of exonic splicing enhancers in human genes. Science. 2002; 297(5583):1007-13. PubMed PMID: 12114529.

Fededa, et al. A polar mechanism coordinates different regions of alternative splicing within a single gene. Mol Cell. Aug. 5, 2005;19(3):393-404.

Ferreira, P.G., et al. Transcriptome characterization by RNA sequencing identifies a major molecular and clinical subdivision in chronic lymphocytic leukemia. Genome Res. 2014; 24:212-26.

Fletcher, et al., " Antisense suppression of donor splice site mutations in the dystrophin gene transcript", Molecular Genetics & Genomic Medicine (2013) 1: 162-173.

Fletcher, Sue et al. Antisense suppression of donor splice site mutations in the dystrophin gene transcript. Molecular Genetics & Genomic Medicine, vol. 1, No. 3, pp. 162-173, Jun. 13, 2013.

Fred, et al. The human insulin mRNA is partly translated via a cap- and eIF4A-independent mechanism. Biochem Biophys Res Commun. Sep. 9, 2011;412(4):693-8. doi: 10.1016/j.bbrc.2011.08.030. Epub Aug. 16, 2011.

Friedman, et al., "Correction of Aberrant Splicing of the Cystic Fibrosis Transmembrane conductance Regulator (CFTR) Gene by Antisense Oligonucleotides" (1999) The Journal of Biological Chemistry, vol. 274, No. 51, pp. 36193-36199.

Friedman, KJ et al. Correction of aberrant splicing of the cystic fibrosis transmembrane conductance regulator (CFTR) gene by antisense oligonucleotides. J Biol Chem. Dec. 17, 1999;274(51):36193-36199.

Friend, KL et al. Detection of a novel missense mutation and second recurrent mutation in the CACNA1A gene in individuals with EA-2 and FHM. Hum Genet. vol. 105(3):261-5 (Sep. 1999).

Furukawa & Kish 2008, GeneReviews Pagon Ra et al. eds. Univ. of WA Seattle, NCBI Bookshelf ID NBK1437.

Galante, et al. Detection and evaluation of intron retention events in the human transcriptome. RNA. May 2004;10(5):757-65.

Garanto, et al., "In vitro and in vivo rescue of aberrant splicing in CEP290-associted LCA by antisense oligonucleotide delivery" (2016) Human Molecular Genetics, vol. 25, No. 12, pp. 2552-2563.

Garner, et al. Selectivity of small molecule ligands for parallel and anti-parallel DNA G-quadruplex structures. Org Biomol Chem. Oct. 21, 2009;7(20):4194-200. doi: 10.1039/b910505k. Epub Aug. 14, 2009.

Geary et al. Absolute Bioavailability of 29-O-(2-Methoxyethyl)-Modified Antisense Oligonucleotides following Intraduodenal Instillation in Rats. J Pharmacal Exp Ther. vol. 296, No. 3, pp. 898-904 (Mar. 2001).

Geary, et al., "Pharmacokinetics, biodistribution and cell uptake of antisense oligonucleotides", (2015) Advance Drug Delivery Reviews.

Geary, RS, et al., Pharmacokinetic properties of 2'-O-(2-methoxyethyl)-modified oligonucleotide analogs in ratsJ Pharmacal Exp Ther. vol. 296, No. 3, pp. 890-897 (Mar. 2001).

Gerard, et al., "AON-mediated Exon Skipping Restores ciliation in Fibroblasts Harboring the Common Leber Congenital Amaurosis CEP290 Mutation" (2012) Molecular Therapy-Nucleic Acids, pp. 1-9.

Gianchecchi et al. Recent insights into the role of the PD-1/PD-L1 pathway in immunological tolerance and autoimmunity. Autoimmunity Reviews 12:1091-1100 (2013).

Gibson, G. Hints of hidden heritability in GWAS. Nat Genet. 2010; 42(7):558-60. Epub Jun. 29, 2010.doi: ng0710-558 [pii] 10.1038/ng0710-558. PubMed PMID: 20581876.

Gohring, J. et al. Imaging of Endogenous MessengerRNA Splice Variants in Living Cells Reveals Nuclear Retention of Transcripts Inaccessible to Nonsense-Mediated Decay in Arabidopsis.The Plant Cell.vol. 26, pp. 754-764.(Feb. 2014).

Gomes et al. Translating chitosan to clinical delivery of nucleic acid-based drugs. MRS bulletin 39.1 (2014): 60-70.

Goncharova et al. Tuberin regulates p70 S6 kinase activation and ribosomal protein S6 phosphorylation. A role for the TSC2 tumor suppressor gene in pulmonary lymphangioleiomyomatosis (LAM). J. Biol. Chem. (Aug. 23, 2002) 277(34);30958-67. EPub Jun. 3, 2002.

Gonzalez-Santos, et al., Mutation in the splicing factor Hprp3p linked to retinitis pigmentosa impairs interactions within the U4/U6 snRNP pigmentosa impairs interactions within the U4/U6 snRNP complex, PubMed Central Canada , Author Manuscript, 29 pages.

Goto, et al., "Targeted skipping of a Single Exon Harboring a Premature termination Codon Mutation: Implications and Potential for Gene Correction Therapy for Selective Dystrophic Epiderolysis Bullosa Patients" (2006) Journal of Investigative Dermatology, vol. 126, pp. 2614-262.

Goyenvalie, et al. Therapeutic approaches to muscular dystrophy. Hum Mol Genet. Apr. 15, 2011;20(R1):R69-78. doi: 10.1093/hmg/ddr105. Epub Mar. 24, 2011.

Gozani, O., et al. A potential role for U2AF-SAP 155 interactions in recruiting U2 snRNP to the branch site. Mol Cell Biol. 1998; 18(8):4752-60. PubMed PMID: 9671485.

Graveley, B.R. The haplo-spliceo-transcriptome: common variations in alternative splicing in the human population. Trends Genet. 2008; 24(1):5-7. Epub Dec. 7, 2007.doi: S0168-9525(07)00349-6 [pii] 10.1016/j.tig.2007.10.004. PubMed PMID: 18054116.

Gutell, R.R., et al. A story: unpaired adenosine bases in ribosomal RNAs. J Mol Biol. 2000; 304(3):335-54. Epub Nov. 25, 2000.doi: 10.1006/jmbi.2000.4172 S0022-2836(00)94172-X [pii]. PubMed PMID: 11090278.

Guth, S., et al. Dual function for U2AF(35) in AG-dependent pre-mRNA splicing. Mol Cell Biol. 2001;21(22):7673-81. PubMed PMID: 11604503.

Guy et al. A mouse Mecp2-null mutation causes neurological symptoms that mimic Rett syndrome. Nat Genet 27:322-326 (2001).

Hai, et al. A G-tract element in apoptotic agents-induced alternative splicing. Nucleic Acids Res. Jun. 2008;36(10):3320-31. doi: 10.1093/nar/gkn207. Epub Apr. 24, 2008.

Hamdan, F. et al. Mutations in SYNGAP1 in Autosomal Nonsyndromic Mental Retardation.The New England Journal of Medicine.N.Engl. Med. vol. 360, No. 6, pp. 599, (Feb. 5, 2009).

Hamdan, F. F. et al. De Novo SYNGAP1 Mutations in Nonsyndromic Intellectual Disability and Autism, Biol. Psychiatry, 69:898-901 (2011).

Hammond, et al"Genetic therapies for RNA mis-splicing diseases" (2011) Cell Press 10 pages.

Han, et al., "Antisense oligonucleotides increase Scn1a expression and reduce seizures and SUDEP incidence in a mouse model of Dravet syndrome" (2020) Science Translational Medicine, 12, pp. 1-14.

Han, et al., "TANGO-Targeted Augmentation of Nuclear Gene Output for the Treatment of Genetic Diseases" Poster.

Han, et al. TANGO-Targeted augmentation of nuclear gene output for the treatment of genetic diseases. Poster session presented at the American Society of Gene and Cell Therapy, Chicago, IL. (2018, May).

Hargous, et al. Molecular basis of RNA recognition and TAP binding by the SR proteins SRp20 and 9G8. EMBO J. Nov. 1, 2006;25(21):5126-37. Epub Oct. 12, 2006.

Harkin, et al. The spectrum of SCN1A-related infantile epileptic encephalopathies. Brain. Mar. 2007;130(Pt 3):843-52.

Hastings, M.L., et al. Control of pre-mRNA splicing by the general splicing factors PUF60 and U2AF. PLoS ONE. 2007;2:e538. PubMed PMID: 17579712.

Havens, et al., "Targeting RNA Splicing fo rDisease Therapy" (2013) Wiley Interdiscip Rev RNA , 4(3): 247-266.

He, Y.H., et al. Association of the insulin-like growth factor binding protein 3 (IGFBP-3) polymorphism with longevity in Chinese nonagenarians and centenarians. Aging (Milano). 2014;6:944-56.

Hegele, et al. Dynamic protein-protein interaction wiring of the human spliceosome. Mol Cell. Feb. 24, 2012;45(4):567-80. doi: 10.1016/j.molcel.2011.12.034.

(56)    References Cited

OTHER PUBLICATIONS

Hernan, I. et al. Cellular Expression and siRNA-Mediated Interference of Rhodopsin cis-Acting Splicing Mutants Associated with Autosomal Dominant Retinitis Pigmentosa, Invest Ophthalmol. Vis. Sci. (2011) 52:3723-3729.

Heyn, P. et al. Introns and gene expression: Cellular constraints, transcriptional regulation, and evolutionary consequences. Bioessays vol. 37, pp. 148-154 (2014).

Hiller et al. Pre-mRNA secondary structures influence exon recognition. PLoS genetics 3.11 (2007): e204.

Hirata et al.Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand.J. Immunology vol. 174 pp. 1888-1897 (2005).

Hishida, A. et al. Polymorphisms in PPAR Genes (PPARD, PPARG, and PPARGC1A) and the Risk of Chronic Kidney Disease in Japanese: Cross-Sectional Data from the J-MICC Study. PPAR 2013; 980471 pp. 1-8.

Hishida, et al., Polymorphisms in PPAR Genes (PPARD, PPARG, and PPARGC1A) and the Risk of Chronic Kidney Disease in Japanese: Cross-Sectional Data from the J-MICC Study, PPAR Research, vol. 2013, Article ID 980471, 8 pages.

*Homo sapiens* pre-mRNA processing factor 3 (PRPF3), mRNA, NCBI Reference Sequence: NM_004698.2 Accessed Apr. 6, 2017.

Hua et al. Antisense masking of an hnRNP A1/A2 intronic splicing silencer corrects SMN2 splicing in transgenic mice. Am. J. Hum. Genet. 82:834-848 (Mar. 27, 2008).

Hua, et al. Antisense correction of SMN2 splicing in the CNS rescues necrosis in a type III SMA mouse model. Genes Dev. Aug. 1, 2010;24(15):1634-44. doi: 10.1101/gad.1941310. Epub Jul. 12, 2010.

Hua, Y., et al. Enhancement of SMN2 exon 7 inclusion by antisense oligonucleotides targeting the exon. PLoS Biol. 2007;5(4):e73. Epub Mar. 16, 2007.doi: 06-PLBI-RA-1492R3 [pii] 10.1371/journal.pbio.0050073. PubMed PMID: 17355180.

Hug, et al., "Mechanism and regulation of the nonsense-mediated decay pathway", Nucleic Acids Research, 2016, vol. 44, No. 4 1483-1495.

Hunt, et al. Negligible impact of rare autoimmune-locus coding-region variants on missing heritability. Nature. Jun. 13, 2013;498(7453):232-5. doi: 10.1038/nature12170. Epub May 22, 2013.

Huynh, K.D., et al. BCoR, a novel corepressor involved in BCL-6 repression. Genes Dev. 2000;14(14):1810-23. PubMed PMID: 10898795; PubMed Central Pmcid: PMC316791.

International Application No. PCT/GB2015/051756 International Preliminary Report on Patentability, Dec. 26, 2016.

International Application No. PCT/GB2015/051756 International Search Report and Written Opinion Mailed Nov. 30, 2015.

International Application No. PCT/GB2016/053136 International Search Report and Written Opinion Mailed Mar. 6, 2017.

International Application No. PCT/GB2016/053136 Partial International Search Report Mailed Jan. 19, 2017.

International Application No. PCT/US16/66576 International Search Report and Written Opinion Mailed May 4, 2017.

International Application No. PCT/US16/66691 International Search Report and Written Opinion Mailed May 10, 2017.

International Application No. PCT/US16/66708 International Search Report and Written Opinion Mailed May 8, 2017.

International Application No. PCT/US16/66721 International Search Report and Written Opinion mailed May 1, 2017.

International Application No. PCT/US2015/053896 International Preliminary Report on Patentability Mailed Apr. 4, 2017.

International Application No. PCT/US2015/53896 International Search Report and Written Opinion dated Mar. 3, 2016.

International Application No. PCT/US2016/066414 International Search Report and Written Opinion Mailed Apr. 19, 2017.

International Application No. PCT/US2016/066417 International Search Report and Written Opinion Mailed Apr. 19, 2017.

International Application No. PCT/US2016/066564 International Search Report and Written Opinion Mailed May 4, 2017.

International Application No. PCT/US2016/066705 International Search Report and Written Opinion Mailed Apr. 24, 2017.

International Application No. PCT/US2018/048031 International Search Report and Written Opinion Mailed Jan. 22, 2019.

International search report and written opinion dated Jun. 5, 2017 for PCT Application No. PCT/US2016/066684.

International search report and written opinion dated Jun. 26, 2020 for PCT Application No. PCT/US20/20175.

International Search Report and Written Opinion for corresponding PCT application PCT/GB2016/053136 issued Jan. 19, 2017.

International Search Report and Written Opinion dated Mar. 28, 2019 for PCT/US2018/057165.

Itoh et al. Methyl CpG-binding Protein Isoform MeCP2_e2 Is Dispensable for Rett Syndrome Phenotypes but Essential for Embryo Viability and Placenta Development. J Biol Chem 287:13859-13867 (2012).

Iwamoto, et al. Transcription-dependent nucleolar cap localization and possible nuclear function of DExH RNA helicase RHAU. Exp Cell Res. Apr. 1, 2008;314(6):1378-91. doi: 10.1016/j.yexcr.2008.01.006. Epub Jan. 16, 2008.

Jacob, et al., "Intron retention as a component of regulated gene expression programs", (2017) Hum Genet 136: 1043-1057.

Jacob et al. Intron retention as a component of regulated gene expression programs. Hum Genet 136:1043-1057 (2017).

Jarver, P. et al., A Chemical View of Oligonucleotides for Exon Skipping and Related Drug Applications, Nucleic Acid Therapeutics vol. 24, No. (1), pp. 37-47, (2014).

Jearawiriyapaisarn et al. Sustained Dystrophin Expression Induced by Peptide-conjugated Morpholino Oligomers in the Muscles of mdx Mice. Mol Ther. 16(9): 1624-1629 (2008).

Jurka et al. Identification of new medium reiteration frequency repeats in the genomes of Primates, Rodentia and Lagomorpha. Genetica98.3 (1996): 235-247.

Jurkiewicz, D. et al. Spectrum of JAG1 gene mutations in Polish patients with Alagille syndrome J. Appl. Genetics vol. 55, pp. 329-336, (2014).

Kach et al. A novel antisense oligonucleotide approach to treat eye diseases by increasing target gene expression. No. 3423-A0194 ARVO Poster Apr. 19, 2019 (1 pg.).

Kaminker, P.G., et al. A novel form of the telomere-associated protein TIN2 localizes to the nuclear matrix. Cell Cycle. 2009;8(6):931-9. PubMed PMID: 19229133; PubMed Central PMCID: PMC2751576.

Kang et al. Up-regulation of luciferase gene expression with antisense oligonucleotides: implications and applications in functional assay development. Biochemistry 37.18 (1998): 6235-6239.

Kaplan et al. Medium reiteration frequency repetitive sequences in the human genome. Nucleic acids research 19.17 (1991): 4731-4738.

Katsani, K.R. et al. Functional Genomics Evidence Unearths New Moonlighting Roles of Outer Ring Coat Nucleoporins Scientific Reports vol. 4, No. 4655 (Apr. 11, 2014).

Kawamata, N., et al. Genetic differences between Asian and Caucasian chronic lymphocytic leukemia. Int J Oncol. 2013;43(2):561-5. doi: 10.3892/ijo.2013.1966. PubMed PMID: 23708256; PubMed Central PMCID: PMC3775563.

Ke, et al. Quantitative evaluation of all hexamers as exonic splicing elements. Genome Res. Aug. 2011;21(8):1360-74. doi: 10.1101/gr.119628.110. Epub Jun. 9, 2011.

Keir, M.E. et al. PD-1 and Its Ligands in Tolerance and Immunity. Annu. Rev. Immunol. vol. 26, pp. 677-704 (2008).

Kervestin et al. NMD: a multifaceted response to premature translational termination. Nature reviews Molecular cell biology13.11 (2012): 700.

Kikin, et al. QGRS Mapper: a web-based server for predicting G-quadruplexes in nucleotide sequences. Nucleic Acids Res. Jul. 1, 2006;34(Web Server issue):W676-82.

Kim, E., et al. SRSF2 Mutations Contribute to Myelodysplasia by Mutant-Specific Effects on Exon Recognition. Cancer Cell. 2015;27(5):617-30. doi: 10.1016/j.ccell.2015.04.006. PubMed PMID: 25965569; PubMed Central PMCID: PMC4429920.

(56) References Cited

OTHER PUBLICATIONS

Kim, et al. "Reduced Sodium Channel nav1.1 Levels in BACE1-NULL Mice", JBC (2010) 1-21.

Kim et al. The role of synaptic GTPase-activating protein in neuronal development and synaptic plasticity. J. Neurosci. 23(4):1119-1124 (Feb. 15, 2003).

Kim, J. et al. The splicing factor U2AF65 stabilizes TRF1 protein by inhibiting its ubiquitin-dependent proteolysis. Biochem Biophys Res Commun. 2014;443(3):1124-30. doi: 10.1016/j.bbrc.2013.12.118. PubMed PMID: 24389012.

Kim P., et al. ChimerDB 2.0—a knowledgebase for fusion genes updated. Nucleic Acids Res. 2009;38(Database issue):D81-5. Epub Nov. 13, 2009.doi: gkp982 [pii] 10.1093/nar/gkp982. PubMed PMID: 19906715.

Knudsen et al. Increased skewing of X chromosome inactivation in Rett syndrome patients and their mothers. Eur J Hum Genet 14:1189-1194(2006).

Kole, et al. RNA therapeutics: beyond RNA interference and antisense oligonucleotides. Nat Rev Drug Discov. Jan. 20, 2012;11(2):125-40. doi: 10.1038/nrd3625.

Kralovicova, et al., " Optimal antisense target reducing INS intron 1 retention is adjacent to a parallel G quadruplex" (2014) Nucleic Acids Research, v. 42, n. 12, p. 8161-8173.

Kralovicova, et al. Allele-specific recognition of the 3' splice site of INS intron 1. Hum Genet. Oct. 2010;128(4):383-400. doi: 10.1007/s00439-010-0860-1. Epub Jul. 14, 2010.

Kralovicova, et al. Compensatory signals associated with the activation of human GC 5' splice sites. Nucleic Acids Res. Sep. 1, 2011;39(16):7077-91. doi: 10.1093/nar/gkr306. Epub May 23, 2011.

Kralovicova, et al., "Exon-Centric Regulation of ATM expression is population-dependent and amenable to antisense modification by pseudoexon targeting", Scientific Reports (2016) p. 1-13.

Kralovicova et al. Exon-centric regulation of ATM expression is population-dependent and amenable to antisense modification by pseudoexon targeting, Scientific Reports, 6:18741, doi:10.1038/srep18741, Jan. 6, 2016, 13 pages.

Kralovicova, et al., "Global control of aberrant splice-site activation by auxiliary splicing sequences: evidence for a gradient in exon and intron definition", (2007) Nucleic Acids Research, v. 35, n. 19, p. 6399-6413.

Kralovicova, et al. Global control of aberrant splice-site activation by auxiliary splicing sequences: evidence for a gradient in exon and intron definition. Nucleic Acids Res. Oct. 2007; 35(19): 6399-6413.

Kralovicova, et al. Identification of U2AF(35)-dependent exons by RNA-Seq reveals a link between 3' splice-site organization and activity of U2AF-related proteins. Nucleic Acids Res. Apr. 20, 2015;43(7):3747-63. doi: 10.1093/nar/gkv194. Epub Mar. 16, 2015.

Kralovicova, et al. Optimal antisense target reducing INS intron 1 retention is adjacent to a parallel G quadruplex. Nucleic Acids Res. Jul. 2014;42(12):8161-73. doi: 10.1093/nar/gku507. Epub Jun. 17, 2014.

Kralovicova, et al. Phenotypic consequences of branch point substitutions. Hum Mutat. Aug. 2006;27(8):803-13.

Kralovicova, et al. Position-dependent repression and promotion of DQB1 intron 3 splicing by GGGG motifs. J Immunol. Feb. 15, 2006;176(4):2381-8.

Kralovicova, et al. Variants in the human insulin gene that affect pre-mRNA splicing: is—23Hphl a functional single nucleotide polymorphism at IDDM2? Diabetes. Jan. 2006;55(1):260-4.

Kralovicova, et al. Antisense Oligonucleotides Modulating Activation of a Nonsense-Mediated RNA Decay Switch Exon in the ATM Gene. Nucleic Acid Ther. Dec. 1, 2016; 26(6): 392-400.

Kralovicova, J. et al. Branch sites haplotypes that control alternative splicing. Hum Mol Genet. 2004;13:3189-202.

Kralovicova, J. et al. The role of short RNA loops in recognition of a single-hairpin exon derived from a mammalian-wide interspersed repeat. RNA Biol. 2015;12(1):54-69. doi: 10.1080/15476286.2015.1017207. PubMed PMID: 25826413.

Kriaucionis et al. The major form of MeCP2 has a novel N-terminus generated by alternative splicing. Nucleic Acids Res 32:1818-1823 (2004).

Krishnaraj et al. RettBASE: Rett syndrome database update. Hum Mutat 38:922-931 (2017).

Laceerra, et al., "Restoration of hemoglobin A synthesis in erythroid cells from peripheral blood of thalassemic patients" (2000) PNAS, vol. 97, No. 17, pp. 9591-9596.

Lander, et al. Initial sequencing and analysis of the human genome. Nature, 409 (Feb. 15, 2001): 860-921.

LaPlanche et al. Phosphorothioate-modified oligodeoxyribonucleotides. III. NMR and UV spectroscoptc studies of thRp-Rp, Sp-Sp, anRp-Sduplexes, [d(GGSAATTCC)]2, derived from diastereomeriO-ethyl phosphorothioates Nucleic Acids Res. vol. 14, No. 22, pp. 9081-9093 (Nov. 25, 1986).

Le Gal, et al., "A case of SUDEP in a patient with Dravet syndrome with SCNIA mutation" (2010) Epilepsia, 5199): 1915-1918.

Le Hir, et al. How introns influence and enhance eukaryotic gene expression. Trends Biochem Sci. Apr. 2003;28(4):215-20.

Lee, E.S. et al. The Consensus 5' Splice Site Motif Inhibits mRNA Nuclear Export.PLoS One vol. 10, No. 3, p. e0122743 (Mar. 31, 2015).

Lee, J., et al. Metastasis of neuroendocrine tumors are characterized by increased cell proliferation and reduced expression of the ATM gene. PLoS ONE. 2012;7:e34456.

LeFave, et al., "Splicing factor hnRNPH drives an oncogenic splicing switch in gliomas",(2011) The EMBO Journal, vol. 30, No. 19, pp. 4084-4097.

LeHir, H. et al. 5'-End RET Splicing: Absence of Variants in Normal Tissues and Intron Retention in Pheochromocytomas, Oncology 63:84-91 (2002).

Lei et al. Exonization of Alu Ya5 in the human ACE gene requires mutations in both 3' and 5' splice sites and is facilitated by a conserved splicing enhancer. Nucleic acids research 33.12 (2005): 3897-3906.

Lei, et al. Identification of splicing silencers and enhancers in sense Alus: a role for pseudoacceptors in splice site repression. Mol Cell Biol. Aug. 2005;25(16):6912-20.

Lemaire, M., et al. CDC25B phosphorylation by p38 and MK-2. Cell Cycle. 2006;5(15):1649-53. PubMed PMID: 16861915.

Levin, et al., "Treating Disease at the RNA Level with Oligonucle-otides" (2019) The New England Journal of Medicine 380:57-70.

Lev-Maor et al. Intronic Alus influence alternative splicing. PLoS genetics 4.9 (2008): e1000204.

Lev-Maor et al. The birth of an alternatively spliced exon: 3'splice-site selection in Alu exons. Science 300.5623 (2003): 1288-1291.

Levy et al.TranspoGene and micro TranspoGene: transposed elements influence on the transcriptome of seven vertebrates and invertebrates. Nucleic acids research 36.suppl_1 (2007): D47-D52.

Li et al. JAG1 Mutation Spectrum and Origin in Chinese Children with Clinical Features of Alagille Syndrome. PLoS One 10(6):e0130355 (2015).

Li et al. PD-L1-Driven Tolerance Protects Neurogenin3-Induced Islet Neogenesis to Reverse Established Type 1 Diabetes in NOD Mice.Diabetes vol. 64, pp. 529-540 (Feb. 2015; epub Oct. 20, 2014).

Liang et al. Short intronic repeat sequences facilitate circular RNA production. Genes & development (2014): gad-251926.

Liang, et al., "Translation efficiency of mRNAs is increased by antisnse oligonucleotides targeting upstream open reading frames" (2016) Nature Biotechnology, V. 34, N. 8, p. 875-882.

Liang, Xue-Hai et al., T ranslation efficiency of mRNAs is increased by antisense oligonucleotides targeting upstream open reading frames, Nature Biotechnology, 34(8):875-882 (Aug. 2016).

Lianoglou, S., et al. Ubiquitously transcribed genes use alternative polyadenylation to achieve tissue-specific expression. Genes Dev. 2013;27(21):2380-96. Epub Oct. 23, 2013.doi: gad.229328.113 [pii] 10.1101/gad.229328.113. PubMed PMID: 24145798.

Lim et al. A computational analysis of sequence features involved in recognition of short introns. Proceedings of the National Academy of Sciences98.20 (2001): 11193-11198.

Lim, et al., "Antisense oligonucleotide modulation of non-productive alternative splicing upregulates gene expression" (2020) Nature Communication.

(56)         References Cited

OTHER PUBLICATIONS

Litchfield, D.W., et al. Pin1: Intimate involvement with the regulatory protein kinase networks in the global phosphorylation landscape. Biochem Biophys Acta. 2015. doi: 10.1016/j.bbagen.2015.02.018. PubMed PMID: 25766872.

Liu et al. Alternative splicing and retinal degeneration. Clinical Genetics 84(2):142-149 (2013).

Llorian et al. Position-dependent alternative splicing activity revealed by global profiling of alternative splicing events regulated by PTB. Nature structural & molecular biology 17.9 (2010): 1114.

Lo, et al., "ATM polymorphisms and risk of lung cancer among never smokers", (2010) Lund Cancer 69, p. 148-154.

Lo, YL et al. ATM Polymorphisms and risk of lung cancer among never smokers, Lung Cancer 69(2):148-154 (2010).

Long et al. Correction of diverse muscular dystrophy mutations in human engineered heart muscle by single-site genome editing. Sci Adv 4:eaap9004 (2018).

Lorenz, et al. 2D meets 4G: G-Quadruplexes in RNA Secondary Structure Prediction. IEEE/ACM Trans Comput Biol Bioinform. Jul.-Aug. 2013;10(4):832-44. doi: 10.1109/TCBB.2013.7.

Lu, F. Conditional JAG1 MutationShows the Developing Heart Is More Sensitive Than Developing Liver to JAG1 Dosage.Am. J. Hum. Genet. vol. 72, pp. 1065-1070 (2003).

Ludecke et al.Recessively inherited L-DOPA-responsive parkinsonism in infancy caused by a point mutation (L205P) in the tyrosine hydroxylase gene Hum. Mol. Genet. vol. 5, pp. 1023-1028, (1996).

Luo et al. Palmitic Acid Suppresses Apolipoprotein M Gene Expression via the Pathway of PPARb/d in HepG2 Cells. Biochemical and Biophysical Research Communications, 445(1):203-207 (Feb. 2014).

Magi-Galuzzi, C. et al. TMPRSS2-ERG gene fusion prevalence and class are significantly difference in prostate cancer of Caucasian, African-American and Japanese patients. The Prostate. 2011;71:489-97.

Makishima, et al. Mutations in the spliceosome machinery, a novel and ubiquitous pathway in leukemogenesis. Blood. Apr. 5, 2012;119(14):3203-10. doi: 10.1182/blood-2011-12-399774. Epub Feb. 9, 2012.

"Maljevic, et al., "Models for discovery of targeted therapy in genetic epileptic encephalopathies", Journal of Neurochemistry (2017) vol. 143, No. 1, pp. 30-48".

Maniatis et al. An extensive network of coupling among gene expression machines. Nature 416.6880 (2002): 499.

Mansouri, S. et al. Epstein-Barr Virus EBNA1 Protein Regulates Viral Latency through Effects on let-7 MicroRNA and Dicer. Journal of Virology, vol. 88, No. 19, pp. 11166-11177, (Oct. 2014).

Mantegazza et al., Identification of a Nav1.1 sodium channel (SCN1A) loss-of-function mutation associated with familial simple febrile seizures, PNAS, Dec. 13, 2005, vol. 102, No. 50, p. 18177-18182.

Marcel, et al. G-quadruplex structures in TP53 intron 3: role in alternative splicing and in production of p53 mRNA isoforms. Carcinogenesis. Mar. 2011;32(3):271-8. doi: 10.1093/carcin/bgq253. Epub Nov. 26, 2010.

Marquez, Y. et al. Unmasking alternative splicing inside protein-coding exons defines exitrons and their role inproteome plasticity. Genome vol. 25, pp. 995-1007 (2015).

Martinez-Losa, et al."Nav1.1-Overexpressing Interneuron Transplants Restore Brain Tyhthms and Cognition in a Mouse Model of Alzheimer's Disease", Neuron. Apr. 4, 2018; 98(1): 75-89.

Matsuoka, S., et al. Ataxia telangiectasia-mutated phosphorylates Chk2 in vivo and in vitro. Proc Natl Acad Sci USA. 2000;97:10389-94.

Matsuoka, S., et al. ATM and ATR substrate analysis reveals extensive protein networks responsive to DNA damage. Science. 2007;316(5828):1160-6. Epub May 26, 2007.doi: 316/5828/1160 [pii] 10.1126/science.1140321. PubMed PMID: 17525332.

Mayeda, et al. Surveying cis-acting sequences of pre-mRNA by adding antisense 2'-O-methyl oligoribonucleotides to a splicing reaction. J Biochem. Sep. 1990;108(3):399-405.

Mckie et al. Mutations in the pre-mRNA splicing factor gene PRPC8 in autosomal dominant retinitis pigmentosa (RP13). Human Molecular Genetics 10(15):1555-1562 (2001).

Melhuish, et al. The Tgif2 gene contains a retained intron within the coding sequence, BMC Molecular Biology 7(2);1-10 (2006).

Melhushi, et al., "The Tgif2 gene contains a retained intron within the coding sequence", (2006) BMC Molecular Biology 7: 1-10.

Melko, et al. Functional characterization of the AFF (AF4/FMR2) family of RNA-binding proteins: insights into the molecular pathology of FRAXE intellectual disability. Hum Mol Genet. May 15, 2011;20(10):1873-85. doi: 10.1093/hmg/ddr069. Epub Feb. 17, 2011.

Mendell, J.T., ap Rhys CM, Dietz HC. Separable roles for rent1/hUpf1 in altered splicing and decay of nonsense transcripts. Science. 2002;298(5592):419-22. Epub Sep. 14, 2002.doi: 10.1126/science.1074428 1074428 [pii]. PubMed PMID: 12228722.

Menzi, et al., "Towards Improved Oligonucleotide Therapeutics Through Faster Target Binding Kinetics", (2017) ChemPubSoc Europe, 23, p. 14221-14230.

Merendino, L., et al. Inhibition of msl-2 splicing by Sex-lethal reveals interaction between U2AF35 and the 3' splice site AG. Nature. 1999;402(6763):838-41. PubMed PMID: 10617208.

Michael, et al. Mfold web server for nucleic acid folding and hybridization prediction. Nucleic Acids Research. 31 (2003): 3406-3415.

Miller at al. 1993-2015 GeneReviews Eds. Pagon RA et al. Seattle (WA); University of WA, Seattle Bookshelf ID NBK1318.

Millevoi, et al. G-quadruplexes in RNA biology. Wiley Interdiscip Rev RNA. Jul.-Aug. 2012;3(4):495-507. doi: 10.1002/wrna.1113. Epub Apr. 4, 2012.

Min et al. Optimization of a novel series of ataxia-telangiectasia mutated kinase inhibitors as potential radiosensitizing agents. Journal of medicinal chemistry 59.2 (2016): 559-577.

Mirey, G., et al. CDC25B phosphorylated by pEg3 localizes to the centrosome and the spindle poles at mitosis. Cell Cycle. 2005;4(6):806-11. PubMed PMID: 15908796.

Mitelman, F., et al. The impact of translocations and gene fusions on cancer causation. Nat Rev Cancer. 2007;7(4):233-45. Epub Mar. 16, 2007.

"Smith, et al., "Nonsense-mediated RNA decay-a switch and dial for regulating gene expression" Bioessays (2015); 37(6): 612-623".

Mnatzakanian et al. A previously unidentified MECP2 open reading frame defines a new protein isoform relevant to Rett syndrome. Nat Genet 36:339-341 (2004).

Mochizuki, T. et al. PKD2, a gene for polycystic kidney disease that encodes an integral membrane protein.Science vol. 272, pp. 1339-1342 (1996).

Montecucco, A., et al. Pre-mRNA processing factors meet the DNA damage response. Front Genet. 2013;4:102. doi: 10.3389/fgene.2013.00102. PubMed PMID: 23761808; PubMed Central PMCID: PMC3674313.

Moreno et al. Delivery of splice switching oligonucleotides by amphiphilic chitosan-based nanoparticles. Molecular pharmaceutics13.2 (2016): 344-356.

Morris, et al. An RNA G-quadruplex is essential for cap-independent translation initiation in human VEGF IRES. J Am Chem Soc. Dec. 22, 2010;132(50):17831-9. doi: 10.1021/ja106287x. Epub Nov. 24, 2010.

Morrison, A.J., et al. Mec1/Tel1 phosphorylation of the INO80 chromatin remodeling complex influences DNA damage checkpoint responses. Cell. 2007;130(3):499-511. doi: 10.1016/j.cell.2007.06.010. PubMed PMID: 17693258.

Moskowitz, et al., Mutation in Scheie syndrome (MPS IS): a G-->A transition creates new splice site in intron 5 of one IDUA allele, Hum. Mutat. 2(2):141-144 (1993).

Mulley et al. A new molecular mechanism for severe myoclonic epilepsy of infancy: Exonic deletions in SCN1A.Neurol. vol. 67, pp. 1094-1095 (2006).

Mulley et al. SCN1A mutations and epilepsy.Hum. Muta. vol. 25, pp. 535-542 (2005).

Murray, S.F. et al. Allele-Specific Inhibition of Rhodopsin with an Antisense Oligonucleotide Slows Photoreceptor Cell Degeneration, Invest Ophthalmol. Vis. Sci. 56:6362-6375 (Oct. 2015).

(56)          References Cited

OTHER PUBLICATIONS

Neidle, S. and Balasubramanian, S. (2006) Quadruplex Nucleic Acids. RSC Biomolecular Sciences, Cambridge, UK.

Nemeroff et al. Identification of cis-acting intron and exon regions in influenza virus NS1 mRNA that inhibit splicing and cause the formation of aberrantly sedimenting presplicing complexes. Molecular and cellular biology 12.3 (1992): 962-970.

Nguyen, L.A., et al. Physical and functional link of the leukemia-associated factors AML1 and PML. Blood. 2005;105(1):292-300. doi: 10.1182/blood-2004-03-1185. PubMed PMID: 15331439.

Nishi, M. et al. Insulin gene mutations and diabetes. Journal of Diabetes Investigation vol. 2 Issue 2 (Apr. 2011).

Nishida, A. et al. Tissue- and Case-specific retention of intron 40 in mature dystrophin mRNA, Journal of Human Genetic 60;327-333 (2015).

Nishida, et al., "Tissue-and case-specific retention of intron 40 in mature dystrophin mRNA", Journal of Human Genetics (2015) 60, 327-333.

Nisole, S., et al. Differential Roles of PML Isoforms. Front Oncol. 2013;3:125. doi: 10.3389/fonc.2013.00125. PubMed PMID: 23734343; PubMed Central PMCID: PMC3660695.

Nomakuchi et al. Antisense-oligonucleotide-directed inhibition of nonsense-mediated mRNA decay. Nat. Biotechnol. 34(2):164-166 (Feb. 2016).

"Notice of Allowability issued in corresponding U.S. Appl. No. 16/561,960 issued Apr. 22, 2020".

"Notice of Allowance issued in correponding U.S. Appl. No. 16/561,960 issued Apr. 22, 2020".

Nozu et al. Alport syndrome caused by a COL4A5 deletion and exonization of an adjacent AluY. Molecular genetics & genomic medicine 2.5 (2014): 451-453.

Nussinov. Conserved quartets near 5' intron junctions in primate nuclear pre-mRNA. J Theor Biol. Jul. 8, 1988;133(1):73-84.

Oda, T. et al. Identification and cloning of the human homolog (JAG) of the rat Jagged1 gene from the Alagille syndrome critical region at 20p12.Genomics vol. 43, No. 3, pp. 376-379 (1997).

Okazaki, T. et al. PD-1 and PD-1 ligands: from discovery to clinical application. International Immunology(The Japanese Society for Immunology), vol. 19, No. 7, pp. 813-824, (2007).

Oustric, V. et al. Antisense oligonucleotide-based therapy in human erythropoietic protoporphyria. Am J Hum Genet. 2014;94(4):611-7. doi: 10.1016/j.ajhg.2014.02.010. PubMed PMID: 24680888; PubMed Central PMCID: PMC3980518.

Pacheco, et al. Diversity of vertebrate splicing factor U2AF35: identification of alternatively spliced U2AF1 mRNAs. J Biol Chem. Jun. 25, 2004;279(26):27039-49. Epub Apr. 19, 2004.

Pacheco, et al. RNA interference knockdown of hU2AF35 impairs cell cycle progression and modulates alternative splicing of Cdc25 transcripts. Mol Biol Cell. Oct. 2006;17(10):4187-99. Epub Jul. 19, 2006.

Page-McCaw, P.S., et al. PUF60: a novel U2AF65-related splicing activity. RNA. 1999;5(12):1548-60. PubMed PMID: 10606266.

Palazzo et al. Non-coding RNA: what is functional and what is junk?. Frontiers in genetics 6 (2015): 2.

Pandit et al. Genome-wide analysis reveals SR protein cooperation and competition in regulated splicing. Molecular cell 50.2 (2013): 223-235.

Papaemmanuil, et al. Clinical and biological implications of driver mutations in myelodysplastic syndromes. Blood. Nov. 21, 2013;122(22):3616-27; quiz 3699. doi: 10.1182/blood-2013-08-518886. Epub Sep. 12, 2013.

Parihar, et al., "The SCN1A gene variants and epileptic encephalophathies", Journal of Human Genetics (2013) 58, 573-580.

Passamonti, C. et al. A novel inherited SCN1A mutation associated with different neuropsychological phenotypes: Is there a common core deficit? Epilepsy & Behavior 43:89-92 (2015).

Pastor, et al. Interaction of hnRNPA1/A2 and DAZAP1 with an Alu-derived intronic splicing enhancer regulates ATM aberrant splicing. PLoS One. 2011;6(8):e23349. doi: 10.1371/journal.pone.0023349. Epub Aug. 8, 2011.

Pastor, F., et al. Induction of tumour immunity by targeted inhibition of nonsense-mediated mRNA decay. Nature. 2010;465(7295):227-30. doi: 10.1038/nature08999. PubMed PMID: 20463739; PubMed Central PMCID: PMC3107067.

Paz, A., et al. SPIKE: a database of highly curated human signaling pathways. Nucleic Acids Res. 2011;39(Database issue):D793-9. doi: 10.1093/nar/gkq1167. PubMed PMID: 21097778; PubMed Central PMCID: PMC3014840.

Pear, Warren S. New roles for Notch in tuberous sclerosis, Journal of Clinical Investigation, 120(1):84-87 (Jan. 4, 2010).

Pecarelli et al. Regulation of natural mRNAs by the nonsense-mediated mRNA decay pathway. Eukaryotic cell(2014): EC-00090.

Pellagatti, A., et al. Deregulated gene expression pathways in myelodysplastic syndrome hematopoietic stem cells. Leukemia. 2010;24(4):756-64. doi: 10.1038/leu.2010.31. PubMed PMID: 20220779.

Peng, et al. Functional importance of different patterns of correlation between adjacent cassette exons in human and mouse. BMC Genomics. Apr. 26, 2008;9:191. doi: 10.1186/1471-2164-9-191.

Penton, A.L.Notch signaling in humandevelopment and disease. Seminars in Cell & Developmental Biology. vol. 23, pp. 450-457 (2012).

Perdiguero, E., et al. Regulation of Cdc25C activity during the meiotic G2/M transition. Cell Cycle. 2004;3(6):733-7. PubMed PMID: 15136768.

Piaceri, I., et al. Ataxia-telangiectasia mutated (ATM) genetic variant in Italian centenarians. Neurophysiology. 2013;34:573-5.

Pilia et al. Jagged-1 mutation analysis in Italian Alagille syndrome patients. Hum Mut 14(5):394-400 (1999).

Pomentel et al. A dynamic intron retention program enriched in RNA processing genes regulates gene expression during terminal erythropoiesis. Nucleic acids research 44.2 (2015): 838-851.

Precursor mRNA-PROCESSING Factor 3, S. cerevisiae, Homolog of; PRPF3m, 3 pages.

Przychodzen, B., et al. Patterns of missplicing due to somatic U2AF1 mutations in myeloid neoplasms. Blood. 2013; 122:999-1006. Epub Jun. 19, 2013.doi: blood-2013-01-480970 [pii] 10.1182/blood-2013-01-480970. PubMed PMID: 23775717.

Pugliese, et al. The insulin gene is transcribed in the human thymus and transcription levels correlated with allelic variation at the INS VNTR-IDDM2 susceptibility locus for type 1 diabetes. Nat Genet. Mar. 1997;15(3):293-7.

Raghavan, et al., "The spliceosomal U1 snRNP component Mud1 is autoregulated by promoting premature cleavage and polyadenylation of its own transcript", The Nineteenth Annual Meeting of the RNA Society.

Rainey et al. Transient inhibition of ATM kinase is sufficient to enhance cellular sensitivity to ionizing radiation. Cancer research68. 18 (2008): 7466-7474.

Ramocki et al. The MECP2 duplication syndrome. Am J Med Genet A 152A:1079-1088 (2010).

Rangasamy et al. Reduced neuronal size and mTOR pathway activity in the Mecp2 A140V Rett syndrome mouse model. F1000research 5:2269 (2016).

"Rashmi, et al., "The SCN1A gene variants and epileptic encephalopathies", Journal of Human Genetics, (2013), vol. 58, No. 9, pp. 573-580".

Ray, D. et al. A compendium of RNA-binding motifs for decoding gene regulation. Nature. vol. 499, No. 7457, pp. 172-177 (Jul. 11, 2013).

Reineke, E.L., et al. Degradation of the tumor suppressor PML by Pin1 contributes to the cancer phenotype of breast cancer MDA-MB-231 cells. Mol Cell Biol. 2008;28(3):997-1006. doi: 10.1128/MCB.01848-07. PubMed PMID: 18039859; PubMed Central PMCID: PMC2223389.

Rendu, J. et al. Hum Gene Ther. Exon skipping as a therapeutic strategy applied to an RYR1 mutation with pseudo-exon inclusion causing a severe core myopathy. Jul. 2013;24(7):702-13. doi: 10.1089/hum.2013.052.

(56)          References Cited

OTHER PUBLICATIONS

Reynolds, DM et al.Aberrant Splicing in the PKD2 Gene as a Cause of Polycystic Kidney Disease.Am. Soc. Nephrol. vol. 10, pp. 2342-2351 (1999).

Reynolds, et al., "Aberrant Splicing in the PKD2 Gene as a Cause of Polycystic Kidney Disease", J. Am. Soc. Nephrol. (1999) 10: 2342-2435.

Ritprajak et al. Keratinocyte-Associated B7-H1 Directly Regulates Cutaneous Effector CD8+ T Cell Responses.J Immunology vol. 184, pp. 4918-4925 (2010).

RNA 2-14 The Nineteenth Annual Meeting of the RNA Society. Quebec City, Canada. (Jun. 3-8, 2014).

Roberts, Jennifer et al. Efficient and Persistent Splice Switching by Systemically Delivered LNA Oligonucleotides in Mice. Molecular Therapy, Nature Publishing, vol. 14, No. 4, pp. 471-475, Oct. 1, 2006.

Romero, P.R., et al. Alternative splicing in concert with protein intrinsic disorder enables increased functional diversity in multicellular organisms. Proc Natl Acad Sci USA. 2006;103(22):8390-5. Epub May 24, 2006.doi: 0507916103 [pii] 10.1073/pnas. 0507916103. PubMed PMID: 16717195.

Rosenbloom et al. The UCSC Genome Browser database: 2015 Update. Nucleic Acids Research 43, Database Issue doi:101093/nar/gku1177.

Ruchlemer, R., et al. Geography, ethnicity and "roots" in chronic lymphocytic leukemia. Leuk Lymphoma. 2013;54(6):1142-50. doi: 10.3109/10428194.2012.740670. PubMed PMID: 23121522.

Rudd, M.F., et al. Variants in the ATM-BRCA2-CHEK2 axis predispose to chronic lymphocytic leukemia. Blood. 2006; 108(2):638-44. Epub Apr. 1, 2006.doi: 2005-12-5022 [pii] 10.1182/blood-2005-12-5022. PubMed PMID: 16574953.

Ruskin, et al. A factor, U2AF, is required for U2 snRNP binding and splicing complex assembly. Cell. Jan. 29, 1988;52(2):207-19.

Sadleir, et al. Not all SCN1A epileptic encephalopathies are Dravet syndrome. Neurology. Sep. 5, 2017; 89(10): 1-8.

Sahashi et al. Pathological impact of SMN2 mis-splicing in adult SMA mice. EMBO Mol. Med. 5(10):1586-601 (Oct. 2013).

Sahashi et al. TSUNAMI: an antisense method to phenocopy splicing-associated diseases in animals. Genes Dev. 26(16):1874-1884 (Aug. 15, 2012).

Sakabe, et al. Sequence features responsible for intron retention in human. BMC Genomics. Feb. 26, 2007;8:59.

Samatanga, et al. The high kinetic stability of a G-quadruplex limits hnRNP F qRRM3 binding to G-tract RNA. Nucleic Acids Res. Feb. 1, 2013;41(4):2505-16. doi: 10.1093/nar/gks1289. Epub Dec. 28, 2012.

Sazani, et al., "Splice Switching Oligonucleotides as Potential Therapeutics", Antisense Drug Technology, Second Edition, p. 90-114.

Sazani, et al., "Therapeutic potential of antisense oligonucleotides as modulators of alternative splicing" (2003) The Journal of clinical Investigation, 112(4):481-486.

Schanen et al. A Severely Affected Male Born into a Rett Syndrome Kindred Supports X-Linked Inheritance and Allows Extension of the Exclusion Map. Am J Hum Genetics 63:267-269 (1998).

Scheffer, et al., "SCN1A-related pehnotypes: Epilepsy and beyond" Epilepsia (2019);60(s3):S17-S24.

Schwarze, et al. Redefinition of exon 7 in the COL1A1 gene of type I collagen by an intron 8 splice-donor-site mutation in a form of osteogenesis imperfecta: influence of intron splice order on outcome of splice-site mutation. Am J Hum Genet. Aug. 1999;65(2):336-44.

Scott, S.P., et al. Missense mutations but not allelic variants alter the function of ATM by dominant interference in patients with breast cancer. Proc Natl Acad Sci USA. 2002;99:925-30.

SG 11201702682P Search Report and Written Opinion dated Apr. 9, 2018.

Shao, C., et al. Mechanisms for U2AF to define 3' splice sites and regulate alternative splicing in the human genome. Nat Struct Mol Biol. 2014;doi: 10.1038/nsmb.2906.

Shcherbakova, I., et al. Alternative spliceosome assembly pathways revealed by single-molecule fluorescence microscopy. Cell Rep. 2013;5(1):151-65. Epub Oct. 1, 2013.doi: S2211-1247(13)00467-1 [pii] 10.1016/j.celrep.2013.08.026. PubMed PMID: 24075986.

Shen, M., et al. Characterization and cell cycle regulation of the related human telomeric proteins Pin2 and TRF1 suggest a role in mitosis. Proc Natl Acad Sci USA. 1997;94(25):13618-23. PubMed PMID: 9391075; PubMed Central PMCID: PMC28355.

Shiloh, Y., et al.The ATM protein kinase: regulating the cellular response to genotoxic stress, and more. Nat Rev Mol Cell Biol. 2013;14(4):197-210. doi: 10.1038/nrm3546. PubMed PMID: 23486281.

Shiria, C.L. et al. Mutant U2AF1 Expression Alters Hematopoiesis and Pre-mRNA Splicing In Vivo. Cancer Cell. 2015;27(5):631-43. doi: 10.1016/j.ccell.2015.04.008. PubMed PMID: 25965570; PubMed Central PMCID: PMC4430854.

Shirley, M.H., et al.Incidence of haematological malignancies by ethnic group in England, 2001-7. Br J Haematol. 2013;163(4):465-77. doi: 10.1111/bjh.12562. PubMed PMID: 24033296.

Sierakowska, et al., "Repair of thalassemic human B-globin mRNA in mammalian cells by antisense oligonucleotides", (1996) PNAS 93: 12840-4.

Sierakowska, H et al. Repair of thalassemic human beta-globin mRNA in mammalian cells by antisense oligonucleotides. Proc Natl Acad Sci U S A. Nov. 12, 1996;93(23):12840-4.

Singh, et al. An antisense microwalk reveals critical role of an intronic position linked to a unique long-distance interaction in pre-mRNA splicing. RNA. Jun. 2010;16(6):1167-81. doi: 10.1261/rna.2154310. Epub Apr. 22, 2010.

Sirand-Pugnet, et al. An intronic (A/U)GGG repeat enhances the splicing of an alternative intron of the chicken beta-tropomyosin pre-mRNA. Nucleic Acids Res. Sep. 11, 1995;23(17):3501-7.

Skjevik et al. The N-Terminal Sequence of Tyrosine Hydroxylase Is a Conformationally Versatile Motif That Binds 14-3-3 Proteins and Membranes.J. Mol. Bio. vol. 426, pp. 150-168 (2014).

Smith, C.W., et al. Scanning and competition between AGs are involved in 3' splice site selection in mammalian introns. Mol Cell Biol. 1993;13(8):4939-52. PubMed PMID: 8336728.

Smith, et al. Alternative pre-mRNA splicing: the logic of combinatorial control. Trends Biochem Sci. Aug. 2000;25(8):381-8.

Smith, P.J., et al. An increased specificity score matrix for the prediction of SF2/ASF-specific exonic splicing enhancers. Hum Mol Genet. 2006; 15(16):2490-508. PubMed PMID: 16825284.

Soo, R.A., et al. Ethnic differences in survival outcome in patients with advanced stage non-small cell lung cancer. J Thorac Oncol. 2011;6:1030-8.

Sorek et al. Minimal conditions for exonization of intronic sequences: 5' splice site formation in alu exons. Molecular cell 14.2 (2004): 221-231.

Soutar et al. Mechanisms of disease: genetic causes of familial hpercholesterolemia. Nat. Clin. Pract. Cardiovasc. Med. 4:214-255 (Apr. 1, 2007).

Spellman et al. Regulation of alternative splicing by PTB and associated factors. (2005): 457-460.

Spinner et al. Jagged1 mutations in alagille syndrome. Hum Mutat 17(1):18-33 (2001).

Stamm, S. Regulation of alternative splicing by reversible protein phosphorylation. J Biol Chem. 2008;283(3):1223-7. PubMed PMID: 18024427.

Stankovic, T., et al. Inactivation of ataxia telangiectasia mutated gene in B-cell chronic lymphocytic leukaemia. Lancet. 1999;353(9146):26-9. doi: 10.1016/S0140-6736(98)10117-4. PubMed PMID: 10023947.

Staropoli et al. Rescue of gene-expression changes in an induced mouse model of spinal muscular atrophy by an antisense oligonucleotide that promotes inclusion of SMN2 exon 7. Genomics 105:220-228 (2015).

Stead, et al. Global haplotype diversity in the human insulin gene region. Genome Res. Sep. 2003;13(9):2101-11.

Stec et al. Automated solid-phase synthesis, separation, and stereochemistry of phosphorothioate analogs of oligodeoxyribonucleotides J. Am. Chem. Soc., 1984, 106 (20), pp. 6077-6079 (1984).

(56) References Cited

OTHER PUBLICATIONS

Stein et al. FDA-Approved Oligonucleotide Therapies in 2017. Mol Ther 25:1069-1075 (2017).

Stein et al. Physicochemical properties of phosphorothioate oligodeoxynucleotides. Nucleic Acids Res. Apr. 25, 1988;16(8):3209-21.

Story, M.D. et al. ATM has a major role in the double-stand break repair pathway dysregulation in sporadic breast carcinomas and is an independent prognostic marker at both mRNA and protein levels, Breast Diseases: A Yearbook Quarterly, 26(4);297-299 (Mar. 17, 2015).

Strausfeld, U., et al. Activation of p34cdc2 protein kinase by microinjection of human cdc25C into mammalian cells. Requirement for prior phosphorylation of cdc25C by p34cdc2 on sites phosphorylated at mitosis. J Biol Chem. 1994;269(8):5989-6000. PubMed PMID: 8119945.

Suarez, F. et al. Incidence, presentation, and prognosis of malignancies in ataxia-telangiectasia: a report from the French national registry of primary immune deficiencies. J Clin Oncol. 2015;33(2):202-8. doi: 10.1200/JCO.2014.56.5101. PubMed PMID: 25488969.

Summerton, James. Morpholino Antisense Oligos: Applications in Biopharmaceutical ResearchMorpholinos constitute a radical redesign of DNA, providing decisive advantages over the moreconventional oligo types used for modulating gene expression. Innovations in Pharmaceutical Technology Issue No. 17 (2005).

Sun, H., et al. Multiple splicing defects in an intronic false exon. Mol Cell Biol. 2000;20(17):6414-25. PubMed PMID: 10938119.

Supplementary European Search Report dated Apr. 18, 2019 for EP16876615.2.

Svasti, et al. RNA repair restores hemoglobin expression in IVS2-654 thalassemic mice. Proc Natl Acad Sci U S A. Jan. 27, 2009; 106(4): 1205-1210.

Swaans, RJM et al. Four novel mutations in the Tyrosine Hydroxylase gene in patients with infantile parkinsonism Annals of Human Genetic, vol. 64, No. 1, pp. 25-31, (Jan. 2000).

Tabrez, S. et al. A Synopsis of the Role of Tyrosine Hydroxylase in Parkinson's Disease.CNS & Neurological Disorders—Drug Targets vol. 11, No. 4 (2012).

Takahashi et al. Skewed X chromosome inactivation failed to explain the normal phenotype of a carrier female with MECP2 mutation resulting in Rett syndrome. Clin Genet 73:257-261 (2008).

Tavanez, J.P., et al. hnRNP A1 proofreads 3' splice site recognition by U2AF. Mol Cell. 2012;45(3):314-29. Epub Feb. 14, 2012. doi: S1097-2765(12)00032-9 [pii] 10.1016/j.molcel.2011.11.033. PubMed PMID: 22325350.

Taylor, A.M., et al. Ataxia telangiectasia: more variation at clinical and cellular levels. Clin Genet. 2015;87(3):199-208. doi: 10.1111/cge.12453. PubMed PMID: 25040471.

Taylor, A.M., et al. Leukemia and lymphoma in ataxia telangiectasia. Blood. 1996;87(2):423-38. PubMed PMID: 8555463.

Thisted, et al. Optimized RNA targets of two closely related triple KH domain proteins, heterogeneous nuclear ribonucleoprotein K and alphaCP-2KL, suggest Distinct modes of RNA recognition. J Biol Chem. May 18, 2001;276(20):17484-96. Epub Feb. 2, 2001.

Tilgner et al. Deep Sequencing of subcellular RNA factions shows splicing to be predominantly co-transcriptional in the human genome but inefficient for lncRNAs.Genome Research vol. 22, No. 9, pp. 1616-1625 (2012).

Tillotson et al. Radically truncated MeCP2 rescues Rett syndrome-like neurological defects. Nature 550:398 (2017).

Torres, V.E. et al. Autosomal dominant polycystic kidney disease: the last 3 years. Kidney International vol. 76, pp. 149-168 (May 20, 2009).

Trabattoni, M. et al.Costimulatory Pathways in Multiple Disease Sclerosis: Distinctive Expression of PD-1 and PD-L1 in Patients with Different Patterns of Disease.J. Immunol. vol. 183, pp. 4984-4993 (2009).

Trapnell, C. et al. Differential gene and transcript expression analysis of RNA-seq experiments with Top Hat and Cufflinks. Nat Protoc.

2012;7(3):562-78. Epub Mar. 3, 2012.doi: nprot.2012.016 [pii] 10.1038/nprot.2012.016. PubMed PMID: 22383036.

Turnpenny, P.D. et al. Alagille syndrome: pathogenesis, diagnosis and management.European Journal of Human Genetics vol. 20, pp. 251-257 (2012.

Uhlmann, E. et al. Antisense oligonucleotides: a new therapeutic principle. Chemical Reviews vol. 90, No. 4, pp. 543-584 (Jun. 1990).

"Supplemental European Search Report issued in corresponding EP application No. 18848036 issued Apr. 15, 2021".

U.S. Appl. No. 14/741,071 Non-Final Office Action mailed Dec. 1, 2016.

U.S. Appl. No. 14/741,071 Notice of Allowability Mailed May 12, 2017.

U.S. Appl. No. 14/874,420 Non-Final Office Action Mailed Mar. 21, 2017.

U.S. Appl. No. 15/148,303 Notice of Allowance Mailed Jun. 7, 2017.

U.S. Appl. No. 16/561,960 Pre-Interview First Office Action Mailed Dec. 19, 2019.

U.S. Appl. No. 14/874,420 Notice of Allowance dated Jan. 11, 2018.

U.S. Appl. No. 14/874,420 Office Action dated Oct. 24, 2017 .

U.S. Appl. No. 15/619,984 Office Action dated Dec. 17, 2018.

U.S. Appl. No. 15/949,902 Office Action dated Mar. 1, 2019.

U.S. Appl. No. 15/288,415 Office Action dated Jun. 26, 2018.

Vacher, et al., "ATM has a major role in the double-strand break repair pathway dysregulation in sporadic breast carcinomas and is an independent prognostic marker at both mRNA and protein levels", (2015), Br J Cancer 112: 1059-1066.

Vafiadis, et al. Insulin expression in human thymus is modulated by INS VNTR alleles at the IDDM2 locus. Nat Genet. Mar. 1997;15(3):289-92.

Van Nostrand et al. Robust transcriptome-wide discovery of RNA-binding protein binding sites with enhanced CLIP (eCLIP). Nature methods 13.6 (2016): 508.

Van Wart, et al., "Imparied Firing an dCell-Specific compensation in Neurons Lacking Navv1.6 sodium Channels" The Journal of Neuroscience, (2006), 26(27):7172-7180.

Verhaart, I.E.C. AON-Mediated Exon Skipping for Duchenne Muscular Dystrophy. Chapter 3. pp. 1-26 (Aug. 1, 2012).

Verret et al., Inhibitory Interneuron Deficit Links Altered Network Activity and Cognitive Dysfunction in Alzheimer Model, Cell, 149(3): 708-721 (2012).

Vickers, et al., "Fully modified 2' MOE oligonucleotides redirect polyadenylation", Isis Pharmaceuticals, Department of Molecular and Structural Biology, Nucleic Acids Research, 2001, vol. 29, No. 6 p. 1293-1299.

Vieira, N. et al. Jagged 1Rescues the Duchenne Muscular Dystrophy Phenotype. Cell vol. 163, pp. 1204-1213 (Nov. 19, 2015).

Voelker, et al. A comprehensive computational characterization of conserved mammalian intronic sequences reveals conserved motifs associated with constitutive and alternative splicing. Genome Res. Jul. 2007;17(7):1023-33. Epub May 24, 2007.

Vorechovsky Correspondence Pediatric Research 2010.

Vorechovsky, I. Letter to the Editor: MER91B-assisted cryptic exon activation in Gitelman syndrome. Pediatric research 67.4 (2010): 444-445.

Vorechovsky, "Modulating Splicing-Mediated gene expression using antisense technology", Southhampton.sc.uk/business.

Vorechovsky Transposable elements in disease-associated cryptic exons. Human genetics 127.2 (2010): 135-154.

Wahl, et al. The spliceosome: design principles of a dynamic RNP machine. Cell. Feb. 20, 2009;136(4):701-18. doi: 10.1016/j.cell. 2009.02.009.

Wan et al.Synthesis, biophysical properties and biological activity of second generation antisense oligonucleotides containing chiral phosphorothioate linkages.Nucleic Acids Research, vol. 42, No. 22, pp. 13456-13468 (2014).

Wang, et al. A complex network of factors with overlapping affinities represses splicing through intronic elements. Nat Struct Mol Biol. Jan. 2013;20(1):36-45. doi: 10.1038/nsmb.2459. Epub Dec. 16, 2012.

(56)　　　　　　References Cited

OTHER PUBLICATIONS

Wang et al. Alternative isoform regulation in human tissue transcriptomes. Nature. 2008;456(Nov.):470-476.

Wang et al. Human Adenovirus Type 36 Enhances Glucose Uptake in Diabetic and Nondiabetic Human Skeletal Muscle Cells Independent of Insulin Signaling.Diabetes vol. 57, pp. 1861-1869 (2008).

Wang, et al. Intronic splicing enhancers, cognate splicing factors and context-dependent regulation rules. Nat Struct Mol Biol. Oct. 2012;19(10):1044-52. doi: 10.1038/nsmb.2377. Epub Sep. 16, 2012.

Wang, et al. Regulation of insulin preRNA splicing by glucose. Proc Natl Acad Sci U S A. Apr. 29, 1997;94(9):4360-5.

Wang, Z. et al. Systematic identification and analysis of exonic splicing silencers. Cell. 2004;119(6):831-45. PubMed PMID: 15607979.

Warf, M.B., et al. Role of RNA structure in regulating pre-mRNA splicing. Trends Biochem Sci. 2010;35(3):169-78. Epub Dec. 5, 2009.doi: S0968-0004(09)00196-0 [pii].

Weiss, et al., "Sodium channels SCN1A, SCN2A, SCN3A in familial autism", (2003) 8, p. 186-194.

Wieland, et al. RNA quadruplex-based modulation of gene expression. Chem Biol. Jul. 2007;14(7):757-63.

Wilton, et al. Splice modification to restore functional dystrophin synthesis in Duchenne muscular dystrophy. Current pharmaceutical design 16.8 (2010): 988-1001.

Wong et al. Orchestrated intron retention regulates normal granulocyte differentiation. Cell 154.3 (2013): 583-595.

Wu et al. AT-AC Pre-mRNA Splicing Mechanisms and Conservation of Minor Introns in Voltage-Gated Ion Channel Genes. Molecular and Cellular Biology 19(5): 3225-3236 (May 1999).

Wu, J.Y., et al. Specific interactions between proteins implicated in splice site selection and regulated alternative splicing. Cell. 1993;75(6):1061-70. Epub Dec. 17, 1993.doi: 0092-8674(93)90316-I [pii]. PubMed PMID: 8261509.

Wu, S. et al. Functional recognition of the 3' splice site AG by the splicing factor U2AF35.Nature. 1999;402(6763):832-5. PubMed PMID: 10617206.

Wu, Y. et al. MRE11-RAD50-NBS1 and ATM function as co-mediators of TRF1 in telomere length control. Nat Struct Mol Biol. 2007;14(9):832-40. doi: 10.1038/nsmb1286. PubMed PMID: 17694070.

Xia, Y. et al. Frequencies of SF3B1, NOTCH1, MYD88, BIRC3 and IGHV mutations and TP53 disruptions in Chinese with chronic lymphocytic leukemia: disparities with Europeans. Oncotarget. 2015;6(7):5426-34. PubMed PMID: 25605254.

Xing, et al. The multiassembly problem: reconstructing multiple transcript isoforms from EST fragment mixtures. Genome Res. Mar. 2004;14(3):426-41. Epub Feb. 12, 2004.

Yamamoto et al. Mib-Jag1-Notch signalling regulates patterning and structural roles of the notochord by controlling cell-fate decisions. Development 137(15):2527-2537 (2010).

Yamamoto, Y., et al. BCOR as a novel fusion partner of retinoic acid receptor alpha in a t(X;17)(p11;q12) variant of acute promyelocytic leukemia. Blood. 2010;116(20):4274-83. doi: 10.1182/blood-2010-01-264432. PubMed PMID: 20807888.

Yan, et al. Systematic discovery of regulated and conserved alternative exons in the mammalian brain reveals NMD modulating chromatin regulators. Proc Natl Acad Sci U S A. Mar. 17, 2015; 112(11): 3445-3450.

Yang et al. Biophysical analysis and small-angle X-ray scattering-derived structures of MeCP2-nucleosome complexes. Nucleic Acids Res 39:4122-4135 (2011).

Yang, S. et al. PML-dependent apoptosis after DNA damage is regulated by the checkpoint kinase hCds1/Chk2. Nat Cell Biol. 2002;4(11):865-70. doi: 10.1038/ncb869. PubMed PMID: 12402044.

Yang, S., et al. Promyelocytic leukemia activates Chk2 by mediating Chk2 autophosphorylation. J Biol Chem. 2006;281(36):26645-54. doi: 10.1074/jbc.M604391200. PubMed PMID: 16835227.

Yang, Y. et al.Oligomerization of the polycystin-2 C-terminal tail and effects on its Ca2+binding properties.J. Bio. Chem. vol. 290, No. 16, pp. 10544-10554 (2015).

Yeo, et al. Discovery and analysis of evolutionarily conserved intronic splicing regulatory elements. PLoS Genet. May 25, 2007;3(5):e85. Epub Apr. 13, 2007.

Yoshida, et al. Frequent pathway mutations of splicing machinery in myelodysplasia. Nature. Sep. 11, 2011;478(7367):64-9. doi: 10.1038/nature10496.

Yoshida, K., et al. Splicing factor mutations and cancer. Wiley Interdiscip Rev RNA. 2014;5(4):445-59. doi: 10.1002/wrna.1222. PubMed PMID: 24523246.

Young et al. 915—a GABA-Selective AAV Vector-Based Approach to Up-Regulate Endogenous Scn1a Expression reverses key Phenotypes in a Mouse Model of Dravet Syndrome. 22nd Annual Meeting American Society of Gene & Cell Therapy. Washington, D.C. Apr. 29-May 2, 2019 (Abstract).

Yu, E.Y., et al. Regulation of telomere structure and functions by subunits of the INO80 chromatin remodeling complex. Mol Cell Biol. 2007;27(16):5639-49. doi: 10.1128/MCB.00418-07. PubMed PMID: 17562861; PubMed Central PMCID: PMC1952117.

Yuan et al. Brain localization and neurotoxicity evaluation of polysorbate 80-modified chitosan nanoparticles in rats. PloS one 10.8 (2015): e0134722.

Yuan X., et al. Nuclear protein profiling of Jurkat cells during heat stress-induced apoptosis by 2-DE and MS/MS. Electrophoresis. 2007;28(12):2018-26. doi: 10.1002/elps.200600821. PubMed PMID: 17523140.

Zammarchi, et al. "Antitumorigenic potential of STAT3 alternative splicing modulation", (2011) PNAS, vol. 108, No. 43, pp. 17779-17784.

Zamore, P.D., et al. Identification, purification, and biochemical characterization of U2 small nuclear ribonucleoprotein auxiliary factor. Proc Natl Acad Sci USA. 1989;86(23):9243-7. PubMed PMID: 2531895.

Zarnack K., et al. Direct competition between hnRNP C and U2AF65 protects the transcriptome from the exonization of Alu elements. Cell. 2013;152(3):453-66. Epub Feb. 5, 2013.doi: S0092-8674(12)01545-0 [pii] 10.1016/j.cell.2012.12.023. PubMed PMID: 23374342.

Zhang C., et al. RNA landscape of evolution for optimal exon and intron discrimination. Proc Natl Acad Sci USA. 2008;105(15):5797-802. Epub Apr. 9, 2008.doi: 0801692105 [pii] 10.1073/pnas. 0801692105. PubMed PMID: 18391195.

Zhang, et al. Insulin as an autoantigen in NOD/human diabetes. Curr Opin Immunol. Feb. 2008;20(1):111-8. doi: 10.1016/j.coi.2007. 11.005.

Zhang, et al. The kinetics and folding pathways of intramolecular G-quadruplex nucleic acids. J Am Chem Soc. Nov. 21, 2012;134(46):19297-308. doi: 10.1021/ja309851t. Epub Nov. 12, 2012.

Zhang, J. et al. PowerBLAST: A New Network BLAST Application for Interactive or Automated Sequence Analysis and Annotation Genome Res., vol. 7, pp. 649-656, (1997).

Zhang, X.H., et al. Computational definition of sequence motifs governing constitutive exon splicing. Genes Dev. 2004;18:1241-50. PubMed PMID: 15145827.

Zimrin et al. An Antisense Oligonucleotide to the Notch Ligand Jagged Enhances Firbroblast Growth Factor-induced Angiogenesis in Vitro. J. Biol. Chem. 271(51):32499-502 (Dec. 20, 1996).

Zon et al. Phosphorothioate oligonucleotides: chemistry, purification, analysis, scale-up and future directions. Anti Cancer Drug Design vol. 6, No. 6, pp. 539-568 (1991).

Zon G. and Stec, W.J. (1991) In Eckstein,F. (ed.), Oligonucleotides and Analogues: A Practical Approach. Oxford University Press, Oxford, UK, pp. 87-108.

Zorio, D.A., et al. Both subunits of U2AF recognize the 3' splice site in Caenorhabditis elegans. Nature. 1999;402(6763):835-8. PubMed PMID: 10617207.

Zuker, M. Mfold web server for nucleic acid folding and hybridization prediction. Nucleic Acids Res. 31, 3406-3415 (2003).

Abramova, Tatyana V. et al. Novel Oligonucleotide Analogues Based on Morpholino Nucleoside Subunits Antisense Technologies: New Chemical Possibilities. Indian Journal of Chemistry 48B:1721-1726 (2009).

(56) References Cited

OTHER PUBLICATIONS

Boisguerin, P. et al. Delivery of therapeutic oligonucleotides with cell penetrating peptides. Advanced Drug Delivery Reviews 87:56-27 (2015).

Co-pending U.S. Appl. No. 18/672,649, filed May 23, 2024.

Gong, Q. et al. Inhibition of nonsense-mediated mRNA decay by antisense morpholino oligonucleotides restores functional expression of hERG nonsense and frameshift mutations in long-QT syndrome. J Mol Cell Cardiol. 50(1):223-9 (2011).

Harris, et al. Single-molecule DNA sequencing of a viral genome. Science 320(5872):106-9 (2008).

Koizumi, Makoto. ENA Oligonucleotides as Therapeutics. Current Opinion in Molecular Therapeutics 8(2):144-149 (2006).

Kuzmiak, HA. et al. Applying nonsense-mediated mRNA decay research to the clinic: progress and challenges. Trends Mol Med. 12(7):306-16 (2006).

Lochmann, D. et al. Drug delivery of oligonucleotides by peptides. European Journal of Pharmaceutics and Biopharmaceutics 58: 237-251 (2004).

Margulies et al.: Genome sequencing in microfabricated high-density picolitre reactors. Nature. 437(7057):376-380 (2005).

Martin, L et al. Identification and characterization of small molecules that inhibit nonsense-mediated RNA decay and suppress nonsense p53 mutations. Cancer Res. 74(11):3104-13 (2014).

Michaels, W. et al. Antisense oligonucleotide-mediated correction of CFTR splicing improves chloride secretion in cystic fibrosis patient-derived bronchial epithelial cells. Nucleic Acids Research 48(13): 7454-7467 (2020).

Obika, et al. Synthesis of 2'-O,4'-C-methyleneuridine and -cytidine. Novel bicyclic nucleosides having a fixed C3, -endo sugar puckering. Tetrahedron Letters 38 (50): 8735 (1997).

PCT/US2020/063157 International Search Report and Written Opinion dated Mar. 10, 2021.

PCT/US2023/029040 International Search Report and Written Opinion dated Feb. 16, 2024.

PCT/US2024/015838 International Search Report and Written Opinion dated Sep. 3, 2024.

Popp, MW et al. Attenuation of nonsense-mediated mRNA decay facilitates the response to chemotherapeutics. Nat Commun. 6(6632): 1-32 (2015).

Scheffer, Ingrid E. Diagnosis and Long-term Course of Dravet Syndrome. European Journal of Paediatric Neurology 16(Suppl 1):S5-S8 (2012).

Singh et al. Encyclopedia of Pharmaceutical Technology 2nd Ed. pp. 751-753 (2002).

Stoke Therapeutics Presents Data from the Phase 1/2a MONARCH Study of STK-001 in Children and Adolescents with Dravet Syndrome at the American Epilepsy Society (AES) 2021 Annual Meeting. Stoke Therapeutics. American Epilepsy Society (AES) 2021 Annual Meeting: 1-3 (2021).

Wagnon, J. TANGO With SCN1A: Can This Molecular Dance Defeat Dravet Syndrome? Epilpesy Currents 21(1):60-61 (2021).

Wang, W. et al. The developmental changes of Na(v) 1.1 and Na(v)1.2 expression in the human hippocampus and temporal lobe, Brain Res 1389:61-70 (2011).

Wu, Y. et al. Incidence of Dravet Syndrome in a US Population. Pediatrics 136(5): e1310-e1315 (2015).

EP16781187.6 European Second Office Action dated Feb. 24, 2023.

EP20763143.3 Extended European Search Report dated Nov. 13, 2023.

European Patent Application No. 21209655.6 Search Report dated May 23, 2022.

European Supplementary Search Report dated Sep. 20, 2023 issued in European Patent Application No. 20897381.

Han et al.: Antisense-Mediated Increase of SCN1A Expression Using TANGO Technology for the Treatment of Dravet Syndrome. Molecular Therapy 22nd Annual Meeting of the American Society of Gene and Cell Therapy (ASGCT) 27(4):304-305 (2019).

Minn; Alexandra H. et al.: Insulinomas and expression of an insulin splice variant. Lancet 363(9406):363-367 (2004). doi: 10.1016/S0140-6736(04)15438-X. Abstract.

Ogiwara et al.: Nav1.1 Localizes to Axons of Parvalbumin-Positive Inhibitory Interneurons: A Circuit Basis for Epileptic Seizures in Mice Carrying an Scn1a Gene Mutation. The Journal of Neuroscience 27(22):5903-5914 (May 30, 2007).

Takeshima Y et al.: Modulation of in vitro splicing of the upstream intron by modifying an intra-exon sequence which is deleted from the dystrophin gene in dystrophin Kobe. The Journal of Clinical Investigation 95(2):515-20 (1995). doi: 10.1172/JCI117693.

Tsuchiya, Teizo et al.: Evidence for the Essential Role of Myosin Subfragment-2 in the ATP-Dependent Actin-Myosin Sliding in Muscle Contraction. The Japanese Journal of Physiology 48(5):383-387 (1998). https://doi.org/10.2170/jjphysiol.48.383.

Kosei, T. et al. Physiological Function Analysis by Antisense Oligonucleotides. Molecular Biology for Physiologists, 60: 383-400 (1998).

Lebedeva, I.V. et al., Chapter 6:Phosphorothioate Oligodeoxynucleotides as Inhibitors Of Gene Expression: Antisense and Non-Antisense Effects, Applications of Antisense Therapies to Restenosis, p. 101 (1999).

Madocsai, C. et al., Correction of SMN2 Pre-mRNA Splicing by Antisense U7 Small Nuclear RNAs. Molecular Therapy 12(6): 1013-1022 (2005).

PCT/US2024/039369 International Search Report and Written Opinion dated Dec. 26, 2024.

Phillips, M., Antisense Inhibition and Adeno-Associated Viral Vector Delivery for Reducing Hypertension. Hypertension 29(1): 177-187 (1997).

U.S. Appl. No. 16/696,635 Final Office Action mailed Sep. 17, 2021.

U.S. Appl. No. 16/696,635 Non-Final Office Action mailed Feb. 23, 2021.

Zhang Y. et al., Pharmacological characterization of an antisense knockdown zebrafish model of Dravet syndrome: inhibition of epileptic seizures by the serotonin agonist fenfluramine. PLoS One, 10(5): 1-19, Article e0125898: I2015).

Co-pending U.S. Appl. No. 19/293,632, inventors Paul; Hatala et al., filed Aug. 7, 2025.

Ge, Y. et al. The functional consequences of intron retention: alternative splicing coupled to NMD as a regulator of gene expression. BioEssays 36(3): 236-243 (2013).

U.S. Appl. No. 17/832,182 Office Action dated Aug. 11, 2025.

* cited by examiner

Mouse – Neuro 2A

SCN1A NMD exon in RenCells
Cyto RNA

| | Coordinates | |
|---|---|---|
| Region 1 | chr2:166007834-166008296 | 90 ASOs |
| Region 2 | chr2:166007384-166007846 | 90 ASOs |
| Region 3 | chr2:166006677-166007139 | 90 ASOs |
| Region 4 | chr2:166006227-166006689 | 90 ASOs |
| NMD-exon | chr2:166007230-166007293 | |

1

ANTISENSE OLIGOMERS FOR TREATMENT OF CONDITIONS AND DISEASES

CROSS-REFERENCE

This application is a continuation of international patent application no. PCT/US2020/020175, filed Feb. 27, 2020, which claims the benefit of U.S. Provisional Application No. 62/811,511, filed on Feb. 27, 2019, each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Aug. 6, 2025, is named 47991-724_301_SL.txt and is 222,375 bytes in size. The sequence listing submitted electronically contains no new matter.

BACKGROUND

Nervous system disorders are often associated with channelopathy, characterized by the disturbed function of ion channels that mediate neuronal excitability, neuronal interactions, and brain functions at large. Mutations in the SCN1A gene, which is part of the SCN1A-SCN2A-SCN3A gene cluster that encodes alpha-pore forming subunits of the neuronal voltage gated sodium channel, are associated with development of disease number of diseases and conditions, such as Dravet Syndrome (DS) (Miller, et al., 1993-2015, GeneReviews, Eds. Pagon R A, et al. Seattle (Wash.): University of Washington, Seattle, Bookshelf ID: NBK1318, and Mulley, et al., 2005, Hum. Mutat. 25: 535-542).

SUMMARY

Disclosed herein, in certain embodiments, is a method of modulating expression of SCN1A protein in a cell having an mRNA that contains a non-sense mediated RNA decay-inducing exon (NMD exon mRNA) and encodes SCN1A protein, the method comprising contacting a therapeutic agent to the cell, whereby the therapeutic agent modulates splicing of the NMD exon from the NMD exon mRNA encoding SCN1A protein, thereby modulating the level of processed mRNA encoding SCN1A protein, and modulating expression of SCN1A protein in the cell, wherein the therapeutic agent binds to a targeted portion of the NMD exon mRNA encoding SCN1A, and wherein the targeted portion is: from about 1000 nucleotides upstream from the 5' end of an NMD-inducing exon (NIE) to about 100 nucleotides upstream from the 5' end of the NIE; or from about 100 nucleotides downstream of the 3' end of the NIE to about 1000 nucleotides downstream of the 3' end of the NIE. In some embodiments, the therapeutic agent interferes with binding of a factor involved in splicing of the NMD exon from a region of the targeted portion. In some embodiments, the targeted portion is at most about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NIE. In some embodiments, the targeted portion is at least about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NIE. In some embodiments, the targeted portion is at most about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NIE. In some embodiments, the targeted portion is at least about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NIE. In some embodiments, the therapeutic agent is an antisense oligomer (ASO). In some embodiments, the ASO comprises a sequence that is at least about 80%, 85%, 90%, 95%, 97%, or 100% identity to any one of SEQ ID NOs: 12-731. In some embodiments, the therapeutic agent promotes exclusion of the NMD exon from the processed mRNA encoding SCN1A protein. In some embodiments, exclusion of the NMD exon from the processed mRNA encoding SCN1A protein in the cell contacted with the therapeutic agent is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to exclusion of the NMD exon from the processed mRNA encoding SCN1A protein in a control cell. In some embodiments, the therapeutic agent increases level of the processed mRNA encoding SCN1A protein in the cell. In some embodiments, an amount of the processed mRNA encoding SCN1A protein in the cell contacted with the therapeutic agent is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to an total amount of the processed mRNA encoding SCN1A protein in a control cell.

Disclosed herein, in certain embodiments, is a method of treating a disease or condition in a subject in need thereof by modulating expression of SCN1A protein in a cell of the subject, comprising: contacting the cell of the subject with a therapeutic agent that modulates splicing of a non-sense mediated mRNA decay-inducing exon (NMD exon) from an mRNA in the cell that contains the NMD exon and encodes SCN1A, thereby modulating the level of processed mRNA encoding the SCN1A protein, and modulating expression of SCN1A protein in the cell of the subject; wherein the therapeutic agent binds to a targeted portion of the NMD exon mRNA encoding SCN1A, and wherein the targeted portion is: from about 1000 nucleotides upstream from the 5' end of an NMD-inducing exon (NIE) to about 100 nucleotides upstream from the 5' end of the NIE; or from about 100 nucleotides downstream of the 3' end of the NIE to about 1000 nucleotides downstream of the 3' end of the NIE. In some embodiments, the therapeutic agent interferes with binding of a factor involved in splicing of the NMD exon from a region of the targeted portion. In some embodiments, the targeted portion is at most about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NIE. In some embodiments, the targeted portion is at least about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NIE. In some embodiments, the targeted portion is at most about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NIE. In some embodiments, the targeted portion is at least about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NIE. In some embodiments, the therapeutic agent is an antisense oligomer (ASO). In some embodiments, the ASO comprises a sequence that is at least about 80%, 85%, 90%, 95%, 97%, or 100% identity to any one of SEQ ID NOs: 12-731. In some embodiments, the therapeutic agent promotes exclusion of the NMD exon from the processed mRNA encoding SCN1A protein. In some embodiments, exclusion of the NMD exon from the processed mRNA encoding SCN1A protein in the cell contacted with the therapeutic agent is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to exclusion of the NMD exon from the processed mRNA encoding SCN1A protein in a control cell. In some embodiments, the therapeutic agent increases level of the processed mRNA encoding SCN1A protein in the cell. In some embodiments, an amount of the processed mRNA encoding SCN1A protein in the cell contacted with the therapeutic agent is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to an total amount of the processed mRNA encoding SCN1A protein in a control cell. In some embodiments, the disease or condition is induced by a loss-of-function mutation in $Na_v1.1$. In some embodiments, the disease or condition is associated with haploinsufficiency of the SCN1A gene, and wherein the subject has a first allele encoding a functional SCN1A, and a second allele from which SCN1A is not produced or produced at a reduced level, or a second allele encoding a nonfunctional SCN1A or a partially functional SCN1A. In some embodiments, the disease or condition is encephalopathy. In some embodiments, the encephalopathy is epileptic encephalopathy. In some embodiments, the disease or condition is Dravet Syndrome (DS); severe myoclonic epilepsy of infancy (SMEI)-borderland (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; sudden unexpected death in epilepsy (SUDEP); sick sinus syndrome 1; autism; or malignant migrating partial seizures of infancy. In some embodiments, GEFS+ is epilepsy, generalized, with febrile seizures plus, type 2. In some embodiments, the Febrile seizure is Febrile seizures, familial, 3A. In some embodiments, SMEB is SMEB without generalized spike wave (SMEB-SW), SMEB without myoclonic seizures (SMEB-M), SMEB lacking more than one feature of SMEI (SMEB-O), or intractable childhood epilepsy with generalized tonic-clonic seizures (ICEGTC).

Disclosed herein, in certain embodiments, is a method of modulating expression of SCN1A protein in a cell having an mRNA that contains a non-sense mediated RNA decay-inducing exon (NMD exon mRNA) and encodes SCN1A protein, the method comprising contacting a therapeutic agent to the cell, whereby the therapeutic agent modulates splicing of the NMD exon from the NMD exon mRNA encoding SCN1A protein, thereby modulating the level of processed mRNA encoding SCN1A protein, and modulating expression of SCN1A protein in the cell, wherein the therapeutic agent binds to a targeted portion of the NMD exon mRNA encoding SCN1A, and wherein the targeted portion is from about 1000 nucleotides upstream from the 5' end of an NMD-inducing exon (NIE) to about 1000 nucleotides downstream of the 3' end of the NIE.

Disclosed herein, in certain embodiments, is a method of treating a disease or condition in a subject in need thereof by modulating expression of SCN1A protein in a cell of the subject, comprising: contacting the cell of the subject with a therapeutic agent that modulates splicing of a non-sense mediated mRNA decay-inducing exon (NMD exon) from an mRNA in the cell that contains the NMD exon and encodes SCN1A, thereby modulating the level of processed mRNA encoding the SCN1A protein, and modulating expression of SCN1A protein in the cell of the subject; wherein the therapeutic agent binds to a targeted portion of the NMD exon mRNA encoding SCN1A, and wherein the targeted portion is from about 1000 nucleotides upstream from the 5' end of an NMD-inducing exon (NIE) to about 1000 nucleotides downstream of the 3' end of the NIE.

Disclosed herein, in certain embodiments, is an antisense oligomer (ASO) comprising a sequence that is at least about 80%, 85%, 90%, 95%, 97%, or 100% identity to any one of SEQ ID NOs: 12-731.

Disclosed herein, in certain embodiments, is an antisense oligomer (ASO) consisting of a sequence selected from SEQ ID NOs: 12-731.

Disclosed herein, in certain embodiments, is a method of treating a disease or condition in a subject in need thereof by modulating expression of SCN1A protein in a cell of the subject, comprising: contacting the cell of the subject with an ASO comprising a sequence that is at least about 80/a, 85%, 90%, 95%, 97%, or 100% identity to any one of SEQ ID NOs: 12-731; or an ASO consisting of a sequence selected from SEQ ID NOs: 12-731.

Disclosed herein, in certain embodiments, is a kit comprising an ASO comprising a sequence that is at least about 80%, 85%, 90%, 95%, 97%, or 100% identity to any one of SEQ ID NOs: 12-731; or an ASO consisting of a sequence selected from SEQ ID NOs: 12-731.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 depicts a schematic representation of a target mRNA that contains a non-sense mediated RNA decay-inducing exon (NMD exon mRNA) and therapeutic agent-mediated exclusion of the nonsense-mediated mRNA decay-inducing exon to increase expression of the full-length target protein or functional RNA.

that is degraded in the cytoplasm, thus leading to no target protein production.

FIG. 2 discloses SEQ ID NO: 732.

DETAILED DESCRIPTION OF THE INVENTION

Splicing and Nonsense-Mediated mRNA Decay

Figure 1A:
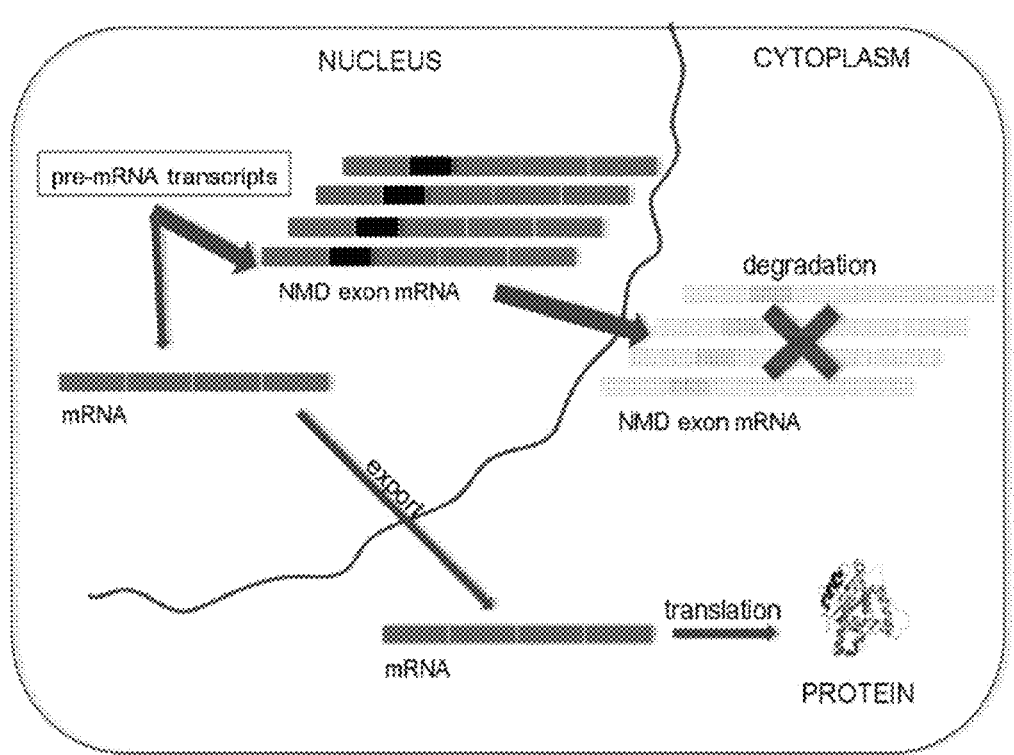
FIG. 1A shows a cell divided into nuclear and cytoplasmic compartments. In the nucleus, a pre-mRNA transcript of a target gene undergoes splicing to generate mRNA, and this mRNA is exported to the cytoplasm and translated into target protein. For this target gene, some fraction of the mRNA contains a nonsense-mediated mRNA decay-inducing exon (NMD exon mRNA)
Figure 1B:
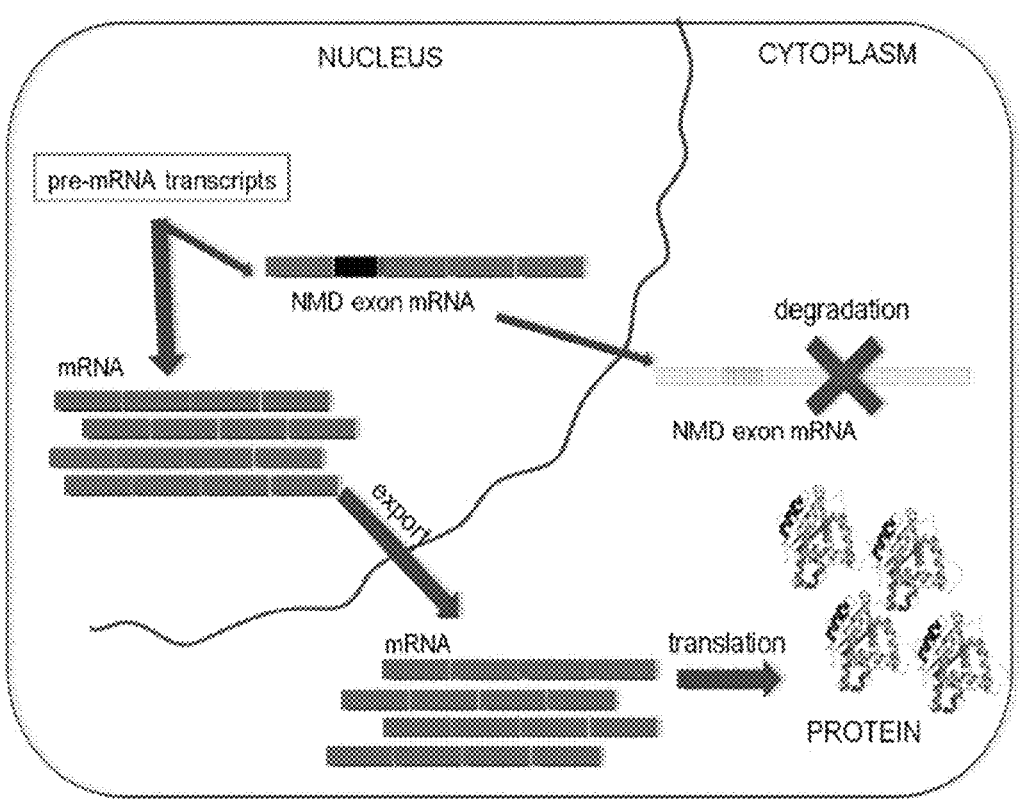
FIG. 1B shows an example of the same cell divided into nuclear and cytoplasmic compartments. Treatment with a therapeutic agent, such as an antisense oligomer (ASO), promotes the exclusion of the nonsense-mediated mRNA decay-inducing exon and results in an increase in mRNA, which is in turn translated into higher levels of target protein.
Figure 1C:
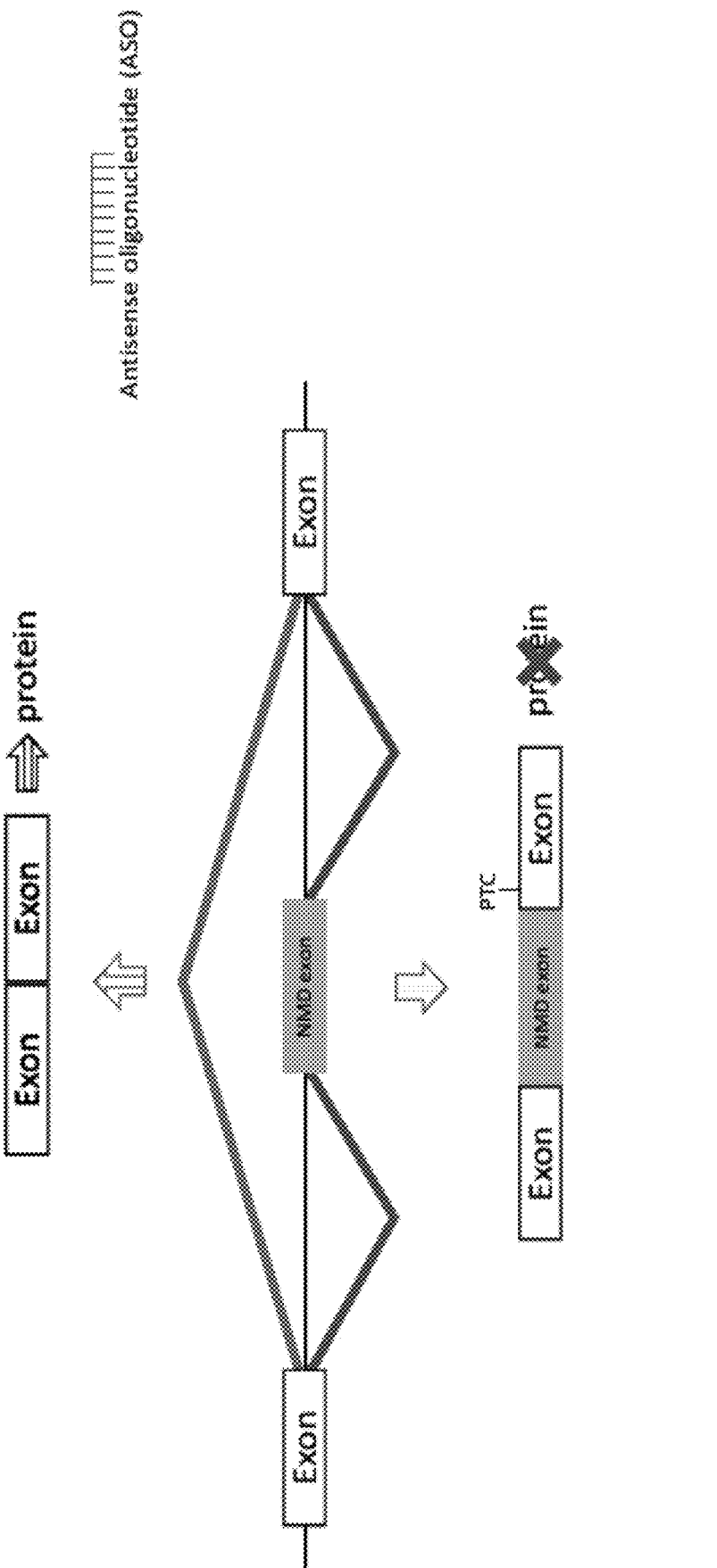
FIG. 1C is a schematic representation of therapeutic ASO-mediated exclusion of a nonsense-mediated mRNA decay-inducing exon, which decreases non-productive mRNA and increases productive mRNA and increases expression of the full-length target protein from the productive mRNA.

Intervening sequences or introns are removed by a large and highly dynamic RNA-protein complex termed the spliceosome, which orchestrates complex interactions between primary transcripts, small nuclear RNAs (snRNAs) and a large number of proteins. Spliceosomes assemble ad hoc on each intron in an ordered manner, starting with recognition of the 5' splice site (5'ss) by U1 snRNA or the 3'splice site (3'ss) by the U2 pathway, which involves binding of the U2 auxiliary factor (U2AF) to the 3'ss region to facilitate U2 binding to the branch point sequence (BPS). U2AF is a stable heterodimer composed of a U2AF2-encoded 65-kD subunit (U2AF65), which binds the polypyrimidine tract (PPT), and a U2AF1-encoded 35-kD subunit (U2AF35), which interacts with highly conserved AG dinucleotides at 3'ss and stabilizes U2AF65 binding. In addition to the BPS/PPT unit and 3'ss/5'ss, accurate splicing requires auxiliary sequences or structures that activate or repress splice site recognition, known as intronic or exonic splicing enhancers or silencers. These elements allow genuine splice sites to be recognized among a vast excess of cryptic or pseudo-sites in the genome of higher eukaryotes, which have the same sequences but outnumber authentic sites by an order of magnitude. Although they often have a regulatory function, the exact mechanisms of their activation or repression are poorly understood.

The decision of whether to splice or not to splice can be typically modeled as a stochastic rather than deterministic process, such that even the most defined splicing signals can sometimes splice incorrectly. However, under normal conditions, pre-mRNA splicing proceeds at surprisingly high fidelity. This is attributed in part to the activity of adjacent cis-acting auxiliary exonic and intronic splicing regulatory elements (ESRs or ISRs). Typically, these functional elements are classified as either exonic or intronic splicing enhancers (ESEs or ISEs) or silencers (ESSs or ISSs) based on their ability to stimulate or inhibit splicing, respectively. Although there is now evidence that some auxiliary cis-acting elements may act by influencing the kinetics of spliceosome assembly, such as the arrangement of the complex between U1 snRNP and the 5'ss, it seems very likely that many elements function in concert with trans-acting RNA-binding proteins (RBPs). For example, the serine- and arginine-rich family of RBPs (SR proteins) is a conserved family of proteins that have a key role in defining exons. SR proteins promote exon recognition by recruiting components of the pre-spliceosome to adjacent splice sites or by antagonizing the effects of ESSs in the vicinity. The repressive effects of ESSs can be mediated by members of the heterogeneous nuclear ribonucleoprotein (hnRNP) family and can alter recruitment of core splicing factors to adjacent splice sites. In addition to their roles in splicing regulation, silencer elements are suggested to have a role in repression of pseudo-exons, sets of decoy intronic splice sites with the typical spacing of an exon but without a functional open reading frame. ESEs and ESSs, in cooperation with their cognate trans-acting RBPs, represent important components in a set of splicing controls that specify how, where and when mRNAs are assembled from their precursors.

The sequences marking the exon-intron boundaries are degenerate signals of varying strengths that can occur at high frequency within human genes. In multi-exon genes, different pairs of splice sites can be linked together in many different combinations, creating a diverse array of transcripts from a single gene. This is commonly referred to as alternative pre-mRNA splicing. Although most mRNA isoforms produced by alternative splicing can be exported from the nucleus and translated into functional polypeptides, different mRNA isoforms from a single gene can vary greatly in their translation efficiency. Those mRNA isoforms with premature termination codons (PTCs) at least 50 bp upstream of an exon junction complex are likely to be targeted for degradation by the nonsense-mediated mRNA decay (NMD) pathway. Mutations in traditional (BPS/PPT/3'ss/5'ss) and auxiliary splicing motifs can cause aberrant splicing, such as exon skipping or cryptic (or pseudo-) exon inclusion or splice-site activation, and contribute significantly to human morbidity and mortality. Both aberrant and alternative splicing patterns can be influenced by natural DNA variants in exons and introns.

Given that exon-intron boundaries can occur at any of the three positions of a codon, it is clear that only a subset of alternative splicing events can maintain the canonical open reading frame. For example, only exons that are evenly divisible by 3 can be skipped or included in the mRNA without any alteration of reading frame. Splicing events that do not have compatible phases will induce a frame-shift. Unless reversed by downstream events, frame-shifts can certainly lead to one or more PTCs, probably resulting in subsequent degradation by NMD. NMD is a translation-coupled mechanism that eliminates mRNAs containing PTCs. NMD can function as a surveillance pathway that exists in all eukaryotes. NMD can reduce errors in gene expression by eliminating mRNA transcripts that contain premature stop codons. Translation of these aberrant mRNAs could, in some cases, lead to deleterious gain-of-function or dominant-negative activity of the resulting proteins. NMD targets not only transcripts with PTCs but also a broad array of mRNA isoforms expressed from many endogenous genes, suggesting that NMD is a master regulator that drives both fine and coarse adjustments in steady-state RNA levels in the cell.

A NMD-inducing exon (NIE) is an exon or a pseudo-exon that is a region within an intron and can activate the NMD pathway if included in a mature RNA transcript. In the constitutive splicing events, the intron containing an NIE is usually spliced out, but the intron or a portion thereof (e.g. NIE) can be retained during alternative or aberrant splicing events. Mature mRNA transcripts containing such an NIE can be non-productive due to frame shift which induce NMD pathway. Inclusion of a NIE in mature RNA transcripts can downregulate gene expression. mRNA transcripts containing an NIE can be referred as "NIE containing mRNA" or "NMD exon mRNA" in the current disclosure.

Cryptic (or pseudo-splice sites) have the same splicing recognition sequences as genuine splice sites but are not used in the splicing reactions. They outnumber genuine splice sites in the human genome by an order of a magnitude and are normally repressed by thus far poorly understood molecular mechanisms. Cryptic 5' splice sites have the consensus NNN/GUNNNN or NNN/GCNNNN where N is any nucleotide and/is the exon-intron boundary. Cryptic 3' splice sites have the consensus NAG/N. Their activation is positively influenced by surrounding nucleotides that make them more similar to the optimal consensus of authentic splice sites, namely MAG/GURAGU and YAG/G, respectively, where M is C or A, R is G or A, and Y is C or U.

Splice sites and their regulatory sequences can be readily identified by a skilled person using suitable algorithms publicly available, listed for example in Kralovicova, J. and Vorechovsky, I. (2007) Global control of aberrant splice site activation by auxiliary splicing sequences: evidence for a gradient in exon and intron definition. *Nucleic Acids Res.,* 35, 6399-6413, (http://www.ncbi.nlm.nih.gov/pmc/articles/PMC2095810/pdf/gkm680.pdf)

The cryptic splice sites or splicing regulatory sequences may compete for RNA-binding proteins such as U2AF with a splice site of the NIE. In one embodiment, an agent may bind to the cryptic splice site or splicing regulatory sequences to prevent the binding of RNA-binding proteins and thereby favoring utilization of the NIE splice sites.

In one embodiment, the cryptic splice site may not comprise the 5' or 3' splice site of the NIE. The cryptic splice site may be at least 10 nucleotides upstream of the NIE 5' splice site. The cryptic splice site may be at least 20 nucleotides upstream of the NIE 5' splice site. The cryptic splice site may be at least 50 nucleotides upstream of the NIE 5' splice site. The cryptic splice site may be at least 100 nucleotides upstream of the NIE 5' splice site. The cryptic splice site may be at least 200 nucleotides upstream of the NIE 5' splice site.

The cryptic splice site may be at least 10 nucleotides downstream of the NIE 3' splice site. The cryptic splice site may be at least 20 nucleotides downstream of the NIE 3' splice site. The cryptic splice site may be at least 50 nucleotides downstream of the NIE 3' splice site. The cryptic splice site may be at least 100 nucleotides downstream of the NIE 3' splice site. The cryptic splice site may be at least 200 nucleotides downstream of the NIE 3' splice site.

Target Transcripts

In some embodiments, the methods of the present disclosure exploit the presence of NIE in the pre-mRNA transcribed from the SCN1A gene. Splicing of the identified SCN1A NIE pre-mRNA species to produce functional mature SCN1A mRNA can be induced using a therapeutic agent such as an ASO that stimulates exon skipping of an NIE. Induction of exon skipping can result in inhibition of an NMD pathway. The resulting mature SCN1A mRNA can be translated normally without activating NMD pathway, thereby increasing the amount of SCN1A protein in the patient's cells and alleviating symptoms of a condition associated with SCN1A deficiency, such as Dravet Syndrome (DS); Epilepsy, generalized, with febrile seizures plus, type 2; Febrile seizures, familial, 3A; Autism; Epileptic encephalopathy, early infantile, 13; Sick sinus syndrome 1; Alzheimer's disease; or SUDEP.

In various embodiments, the present disclosure provides a therapeutic agent which can target SCN1A mRNA transcripts to modulate, e.g., enhance or inhibit, splicing or protein expression level. The therapeutic agent can be a small molecule, polynucleotide, or polypeptide. In some embodiments, the therapeutic agent is an ASO. Various regions or sequences on the SCN1A pre-mRNA can be targeted by a therapeutic agent, such as an ASO. In some embodiments, the ASO targets a SCN1A pre-mRNA transcript containing an NIE. In some embodiments, the ASO targets a sequence within an NIE of a SCN1A pre-mRNA transcript. In some embodiments, the ASO targets a sequence upstream (or 5') from the 5' end of an NIE (3'ss) of a SCN1A pre-mRNA transcript. In some embodiments, the ASO targets a sequence downstream (or 3') from the 3' end of an NIE (5'ss) of a SCN1A pre-mRNA transcript. In some embodiments, the ASO targets a sequence that is within an intron flanking on the 5' end of the NIE of a SCN1A pre-mRNA transcript. In some embodiments, the ASO targets a sequence that is within an intron flanking the 3' end of the NIE of a SCN1A pre-mRNA transcript. In some embodiments, the ASO targets a sequence comprising an NIE-intron boundary of a SCN1A pre-mRNA transcript. An NIE-intron boundary can refer to the junction of an intron sequence and an NIE region. The intron sequence can flank the 5' end of the NIE, or the 3' end of the NIE. In some embodiments, the ASO targets a sequence within an exon of a SCN1A pre-mRNA transcript. In some embodiments, the ASO targets a sequence within an intron of a SCN1A pre-mRNA transcript. In some embodiments, the ASO targets a sequence comprising both a portion of an intron and a portion of an exon.

In some embodiments, a therapeutic agent described herein modulates binding of a factor involved in splicing of the NMD exon mRNA.

In some embodiments, a therapeutic agent described herein interferes with binding of a factor involved in splicing of the NMD exon mRNA.

In some embodiments, a therapeutic agent described herein prevents binding of a factor involved in splicing of the NMD exon mRNA.

In some embodiments, a therapeutic agent targets a targeted portion located in an intronic region between two canonical exonic regions of the NMD exon mRNA encoding SCN1A, and wherein the intronic region contains the NMD exon.

In some embodiments, a therapeutic agent targets a targeted portion at least partially overlaps with the NMD exon.

In some embodiments, a therapeutic agent targets a targeted portion that is at least partially overlaps with an intron upstream of the NMD exon.

In some embodiments, a therapeutic agent targets a targeted portion within the NMD exon.

In some embodiments, a therapeutic agent targets a targeted portion comprising at least about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon. In some embodiments, a therapeutic agent targets a targeted portion comprising at most about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon. In some embodiments, a therapeutic agent targets a targeted portion comprising about 5, 6, 7, 8, 9, 10, 11, 12, 13, 14, 15, 16, 17, 18, 19, 20, 21, 22, 23, 24, 25, 26, 27, 28, 29, 30, or more consecutive nucleotides of the NMD exon.

In some embodiments, a therapeutic agent targets a targeted portion proximal to the NMD exon.

In some embodiments, the ASO targets a sequence from about 1 to about 5000 nucleotides downstream from the 5' end of the intron comprising the NIE. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, about 1950 to about 2000 nucleotides, about 2000 to about 3000 nucleotides, about 3000 to about 4000 nucleotides, or about 4000 to about 5000 nucleotides, downstream from the 5' end of the intron comprising the NIE. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, or about 950 to about 1000 nucleotides downstream from the 5' end of the intron comprising the NIE.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleotides, at least about 1500 nucleotides, at least about 1600 nucleotides, at least about 1800 nucleotides, at least about 2000 nucleotides, at least about 3000 nucleotides, at least about 4000 nucleotides, or at least about 5000 nucleotides downstream from the 5' end of the intron comprising the NIE.

In some embodiments, the ASO targets a sequence from about 1 to about 2000 nucleotides upstream (or 5') from the 5' end of the NIE. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, or about 1950 to about 2000 nucleotides upstream (or 5') from the 5' end of the NIE. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, or about 950 to about 1000 nucleotides upstream (or 5') from the 5' end of the NIE.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleotides, at least about 1500 nucleotides, at least about 1600 nucleotides, at least about 1800 nucleotides, or at least about 2000 nucleotides upstream (or 5') from the 5' end of the NIE.

In some embodiments, the ASO targets a sequence from about 1 to about 500 nucleotides downstream from the 5' end of the NIE. In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, or at least about 500 nucleotides downstream from the 5' end of the NIE region.

In some embodiments, the ASO targets a sequence from about 1 to about 500 nucleotides upstream from the 3' end of the NIE. In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, or at least about 500 nucleotides upstream from the 3' end of the NIE region.

In some embodiments, the ASO targets a sequence from about 1 to about 2000 nucleotides downstream (or 3') from the 3' end of the NIE. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, or about 1950 to about 2000 nucleotides downstream (or 3') from the 3' end of the NIE. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, or about 950 to about 1000 nucleotides downstream (or 3') from the 3' end of the NIE.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleotides, at least about 1500 nucleotides, at least about 1600 nucleotides, at least about 1800 nucleotides, or at least about 2000 nucleotides downstream (or 3') from the 3' end of the NIE.

In some embodiments, the ASO targets a sequence from about 1 to about 5000 nucleotides upstream from the 3' end of the intron comprising the NIE. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, about 1950 to about 2000 nucleotides, about 2000 to about 3000 nucleotides, about 3000 to about 4000 nucleotides, or about 4000 to about 5000 nucleotides, upstream from the 3' end of the intron comprising the NIE. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, or about 950 to about 1000 nucleotides upstream from the 3' end of the intron comprising the NIE.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleotides, at least about 1500 nucleotides, at least about 1600 nucleotides, at least about 1800 nucleotides, at least about 2000 nucleotides, at least about 3000 nucleotides, at least about 4000 nucleotides, or at least about 5000 nucleotides upstream from the 3' end of the intron comprising the NIE.

In some embodiments, the ASO targets a sequence from about 4 to about 300 nucleotides upstream (or 5') from the 5' end of the NIE. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, or about 1450 to about 1500 nucleotides upstream (or 5') from the 5' end of the NIE region. In some embodiments, the ASO may target a sequence more than 300 nucleotides upstream from the 5' end of the NIE. In some embodiments, the ASO targets a sequence from about 4 to about 300 nucleotides downstream (or 3') from the 3' end of the NIE. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, or about 1450 to about 1500 nucleotides downstream from the 3' end of the NIE. In some embodiments, the ASO targets a sequence more than 300 nucleotides downstream from the 3' end of the NIE.

In some embodiments, the ASO targets a sequence from about 4 to about 300 nucleotides upstream (or 5') from the 5' end of the NIE. In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, or at least about 1000 nucleotides upstream (or 5') from the 5' end of the NIE region. In some embodiments, the ASO targets a sequence about 4 to about 300 nucleotides downstream (or 3') from the 3' end of the NIE. In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, or at least about 1000 nucleotides downstream from the 3' end of the NIE. In some embodiments, the ASO targets a sequence more than 300 nucleotides downstream from the 3' end of the NIE.

In some embodiments, the ASO targets a sequence from about 4 to about 300 nucleotides upstream (or 5') from the 5' end of the NIE. In some embodiments, the ASO targets a sequence at most about 10 nucleotides, at most about 20 nucleotides, at most about 50 nucleotides, at most about 80 nucleotides, at most about 85 nucleotides, at most about 90 nucleotides, at most about 95 nucleotides, at most about 96 nucleotides, at most about 97 nucleotides, at most about 98 nucleotides, at most about 99 nucleotides, at most about 100 nucleotides, at most about 101 nucleotides, at most about 102 nucleotides, at most about 103 nucleotides, at most about 104 nucleotides, at most about 105 nucleotides, at most about 110 nucleotides, at most about 120 nucleotides, at most about 150 nucleotides, at most about 200 nucleotides, at most about 300 nucleotides, at most about 400 nucleotides, at most about 500 nucleotides, at most about 600 nucleotides, at most about 700 nucleotides, at most about 800 nucleotides, at most about 900 nucleotides, at most about 1000 nucleotides, at most about 1100 nucleotides, at most about 1200 nucleotides, at most about 1300 nucleotides, at most about 1400 nucleotides, or at most about 1500 nucleotides upstream (or 5') from the 5' end of the NIE region. In some embodiments, the ASO targets a sequence about 4 to about 300 nucleotides downstream (or 3') from the 3' end of the NIE. In some embodiments, the ASO targets a sequence at most about 10 nucleotides, at most about 20 nucleotides, at most about 50 nucleotides, at most about 80 nucleotides, at most about 85 nucleotides, at most about 90 nucleotides, at most about 95 nucleotides, at most about 96 nucleotides, at most about 97 nucleotides, at most about 98 nucleotides, at most about 99 nucleotides, at most about 100 nucleotides, at most about 101 nucleotides, at most about 102 nucleotides, at most about 103 nucleotides, at most about 104 nucleotides, at most about 105 nucleotides, at most about 110 nucleotides, at most about 120 nucleotides, at most about 150 nucleotides, at most about 200 nucleotides, at most about 300 nucleotides, at most about 400 nucleotides, at most about 500 nucleotides, at most about 600 nucleotides, at most about 700 nucleotides, at most about 800 nucleotides, at most about 900 nucleotides, or at most about 1000 nucleotides, at most about 1100 nucleotides, at most about 1200 nucleotides, at most about 1300 nucleotides, at most about 1400 nucleotides, or at most about 1500 nucleotides downstream from the 3' end of the NIE. In some embodiments, the ASO targets a sequence more than 300 nucleotides downstream from the 3' end of the NIE.

In some embodiments, the NIE (exon 23) as described herein is located between GRCh38/hg38:chr2:166007230 and chr2:166007293. In some embodiments, the 5' end of the NIE is located at GRCh38/hg38:chr2:166007230. In some embodiments, the 3' end of the NIE is located at GRCh38/hg38:chr2:166007293.

In some embodiments, the ASO targets a sequence from about 1 to about 2000 nucleotides upstream (or 5') from genomic site GRCh38/hg38:chr2:166007230. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, or about 1950 to about 2000 nucleotides upstream (or 5') from genomic site GRCh38/hg38:chr2:166007230. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, or about 950 to about 1000 nucleotides upstream (or 5') from genomic site GRCh38/hg38:chr2: 166007230.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleotides, at least about 1500 nucleotides, at least about 1600 nucleotides, at least about 1800 nucleotides, or at least about 2000 nucleotides upstream (or 5') from genomic site GRCh38/hg38:chr2:166007230.

In some embodiments, the ASO targets a sequence from about 1 to about 500 nucleotides downstream from genomic site GRCh38/hg38:chr2:166007230. In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, or at least about 500 nucleotides downstream from genomic site GRCh38/hg38:chr2: 166007230.

In some embodiments, the ASO targets a sequence from about 1 to about 500 nucleotides upstream from genomic site GRCh38/hg38:chr2:166007293. In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, or at least about 500 nucleotides upstream from genomic site GRCh38/hg38:chr2: 166007293.

In some embodiments, the ASO targets a sequence from about 1 to about 2000 nucleotides downstream (or 3') from genomic site GRCh38/hg38:chr2:166007293. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, or about 1950 to about 2000 nucleotides downstream (or 3') from genomic site GRCh38/hg38:chr2:166007293. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, or about 950 to about 1000 nucleotides downstream (or 3') from genomic site GRCh38/hg38:chr2: 166007293.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleotides, at least about 1500 nucleotides, at least about 1600 nucleotides, at least about 1800 nucleotides, or at least about 2000 nucleotides downstream (or 3') from genomic site GRCh38/hg38:chr2:166007293.

In some embodiments, the intron comprising the NIE is located between GRCh38/hg38:chr2:166002754 and chr2: 166009718. In some embodiments, the 5' end of the intron comprising the NIE is located at GRCh38/hg38:chr2: 166002754. In some embodiments, the 3' end of the intron comprising the NIE is located at GRCh38/hg38:chr2: 166009718.

In some embodiments, the ASO targets a sequence from about 1 to about 5000 nucleotides downstream from genomic site GRCh38/hg38:chr2:166002754. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, about 1950 to about 2000 nucleotides, about 2000 to about 3000 nucleotides, about 3000 to about 4000 nucleotides, or about 4000 to about 5000 nucleotides, downstream from genomic site GRCh38/hg38:chr2:166002754. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleo- tides, about 650 to about 700 nucleotides, about 750 to about 800 nucleotides, about 850 to about 900 nucleotides, or about 950 to about 1000 nucleotides downstream from genomic site GRCh38/hg38:chr2:166002754.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleo- tides, at least about 1500 nucleotides, at least about 1600 nucleotides, at least about 1800 nucleotides, at least about 2000 nucleotides, at least about 3000 nucleotides, at least about 4000 nucleotides, or at least about 5000 nucleotides downstream from genomic site GRCh38/hg38:chr2: 166002754.

In some embodiments, the ASO targets a sequence from about 1 to about 5000 nucleotides upstream from genomic site GRCh38/hg38:chr2:166007229. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleo- tides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, about 1950 to about 2000 nucleotides, about 2000 to about 3000 nucleotides, about 3000 to about 4000 nucleotides, or about 4000 to about 5000 nucleotides, upstream from genomic site GRCh38/hg38: chr2:166007229. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleo- tides, about 550 to about 600 nucleotides, about 650 to about 700 nucleotides, about 750 to about 800 nucleotides, about 850 to about 900 nucleotides, or about 950 to about 1000 nucleotides upstream from genomic site GRCh38/hg38: chr2:166007229.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleo- tides, at least about 1500 nucleotides, at least about 1600 nucleotides, at least about 1800 nucleotides, at least about 2000 nucleotides, at least about 3000 nucleotides, at least about 4000 nucleotides, or at least about 5000 nucleotides upstream from genomic site GRCh38/hg38:chr2: 166007229.

In some embodiments, the ASO targets a sequence from about 1 to about 5000 nucleotides downstream from genomic site GRCh38/hg38:chr2:166007294. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleo- tides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, about 1950 to about 2000 nucleotides, about 2000 to about 3000 nucleotides, about 3000 to about 4000 nucleotides, or about 4000 to about 5000 nucleotides, downstream from genomic site GRCh38/hg38:chr2:166007294. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, or about 950 to about 1000 nucleotides downstream from genomic site GRCh38/hg38:chr2:166007294.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleotides, at least about 1500 nucleotides, at least about 1600 nucleotides, at least about 1800 nucleotides, at least about 2000 nucleotides, at least about 3000 nucleotides, at least about 4000 nucleotides, or at least about 5000 nucleotides downstream from genomic site GRCh38/hg38:chr2:166007294.

In some embodiments, the ASO targets a sequence from about 1 to about 5000 nucleotides upstream from genomic site GRCh38/hg38:chr2:166009718. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, about 1450 to about 1500 nucleotides, about 1550 to about 1600 nucleotides, about 1650 to about 1700 nucleotides, about 1750 to about 1800 nucleotides, about 1850 to about 1900 nucleotides, about 1950 to about 2000 nucleotides, about 2000 to about 3000 nucleotides, about 3000 to about 4000 nucleotides, or about 4000 to about 5000 nucleotides, upstream from genomic site GRCh38/hg38: chr2:166009718. In some embodiments, the ASO targets a sequence from about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, or about 950 to about 1000 nucleotides upstream from genomic site GRCh38/hg38: chr2:166009718.

In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, at least about 1000 nucleotides, at least about 1200 nucleotides, at least about 1400 nucleotides, at least about 1500 nucleotides, at least about 1600 nucleotides, at least about 1800 nucleotides, at least about 2000 nucleotides, at least about 3000 nucleotides, at least about 4000 nucleotides, or at least about 5000 nucleotides upstream from genomic site GRCh38/hg38:chr2: 166009718.

Figure 2:
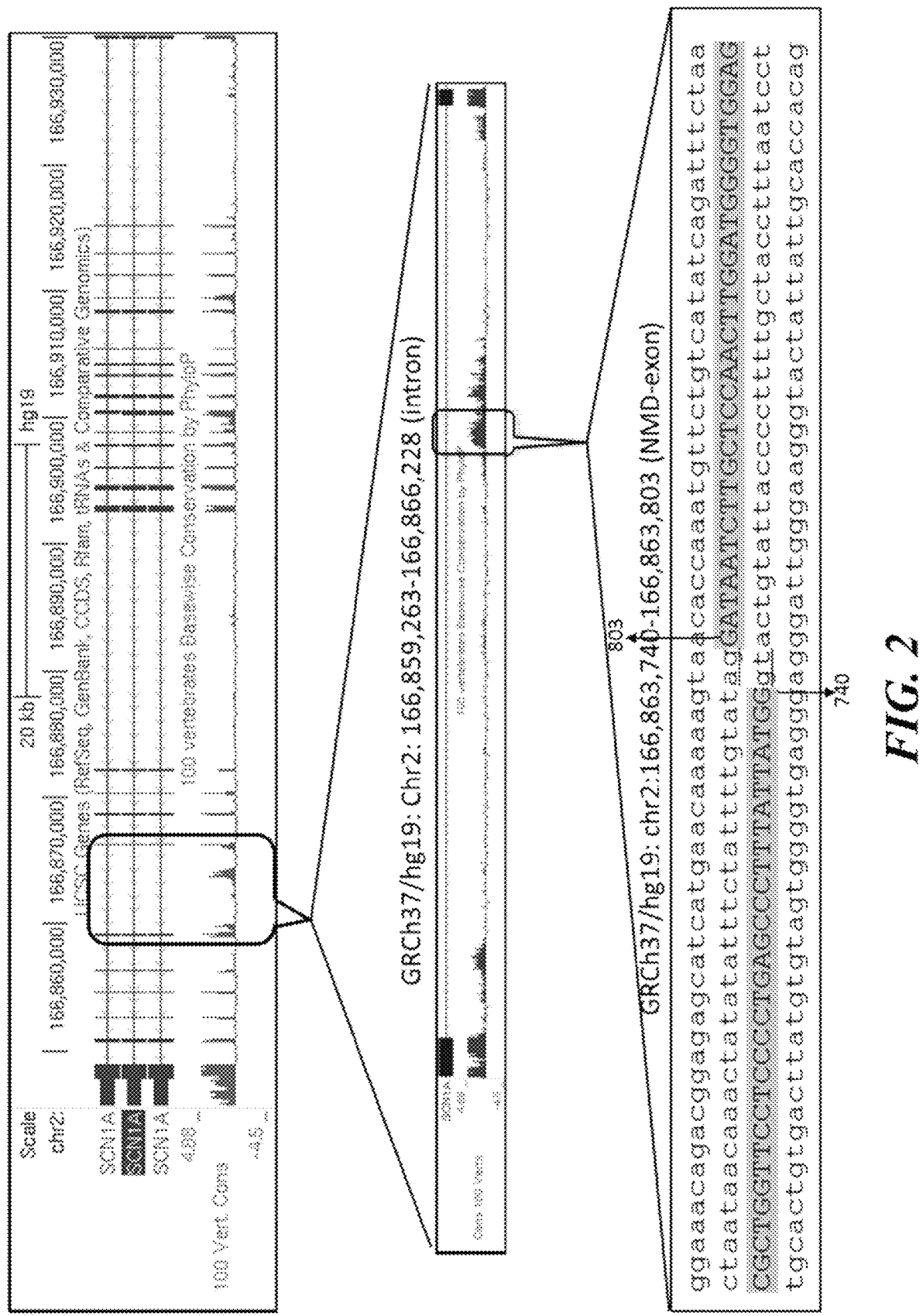
FIG. 2 depicts identification of an exemplary nonsense-mediated Mrna decay (NMD)-inducing exon in the SCN1A gene. The identification of the NMD-inducing exon in the SCN1A gene using comparative genomics is shown, visualized in the UCSC genome browser. The upper panel shows a graphic representation of the SCN1A gene to scale. The conservation level across 100 vertebrate species is shown as peaks. The highest peaks correspond to exons (black boxes), while no peaks are observed for the majority of the introns (lines with arrow heads). Peaks of conservation were identified in intron 20 (NM_006920), shown in the middle panel. Inspection of the conserved sequences identified an exon-like sequence of 64 bp (bottom panel, sequence highlighted in grey) flanked by 3' and 5' splice sites (underlined sequence), which we refer to as exon 20x. Inclusion of this exon leads to a frameshift and the introduction of a premature termination codon in exon 21 rendering the transcript a target of NMD.

In some embodiments, the NIE as described herein is located between GRCh37/hg19: chr2:166,863,740 and GRCh37/hg19: chr2:166,863,803, as depicted in FIG. 2. In some embodiments, the 5' end of the NIE is located at GRCh37/hg19: chr2:166,863,803. In some embodiments, the 3' end of the NIE is located at GRCh37/hg19: chr2:166, 863,740.

In some embodiments, In some embodiments, the ASO targets a sequence from about 4 to about 300 nucleotides upstream (or 5') from genomic site GRCh37/hg19: chr2: 166,863,803. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, or about 1450 to about 1500 nucleotides upstream (or 5') from genomic site GRCh37/hg19: chr2:166,863,803. In some embodiments, the ASO may target a sequence more than 300 nucleotides upstream from genomic site GRCh37/hg19: chr2:166,863, 803. In some embodiments, the ASO targets a sequence from about 4 to about 300 nucleotides downstream (or 3') from GRCh37/hg19: chr2:166,863,740. In some embodiments, the ASO targets a sequence about 1 to about 20 nucleotides, about 20 to about 50 nucleotides, about 50 to about 100 nucleotides, about 100 to about 150 nucleotides, about 150 to about 200 nucleotides, about 200 to about 250 nucleotides, about 250 to about 300 nucleotides, about 350 to about 400 nucleotides, about 450 to about 500 nucleotides, about 550 to about 600 nucleotides, about 650 to about 700 nucleotides, about 750 to about 800 nucleotides, about 850 to about 900 nucleotides, about 950 to about 1000 nucleotides, about 1050 to about 1100 nucleotides, about 1150 to about 1200 nucleotides, about 1250 to about 1300 nucleotides, about 1350 to about 1400 nucleotides, or about 1450 to about 1500 nucleotides downstream from GRCh37/hg19: chr2:166,863,740. In some embodiments, the ASO targets a sequence more than 300 nucleotides downstream from GRCh37/hg19: chr2:166,863,740.

In some embodiments, the ASO targets a sequence from about 4 to about 300 nucleotides upstream (or 5') from genomic site GRCh37/hg19: chr2:166,863,803. In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, or at least about 1000 nucleotides upstream (or 5') from genomic site GRCh37/hg19: chr2:166,863,803. In some embodiments, the ASO targets a sequence from about 4 to about 300 nucleotides downstream (or 3') from GRCh37/hg19: chr2:166,863,740. In some embodiments, the ASO targets a sequence at least about 1 nucleotide, at least about 10 nucleotides, at least about 20 nucleotides, at least about 50 nucleotides, at least about 80 nucleotides, at least about 85 nucleotides, at least about 90 nucleotides, at least about 95 nucleotides, at least about 96 nucleotides, at least about 97 nucleotides, at least about 98 nucleotides, at least about 99 nucleotides, at least about 100 nucleotides, at least about 101 nucleotides, at least about 102 nucleotides, at least about 103 nucleotides, at least about 104 nucleotides, at least about 105 nucleotides, at least about 110 nucleotides, at least about 120 nucleotides, at least about 150 nucleotides, at least about 200 nucleotides, at least about 300 nucleotides, at least about 400 nucleotides, at least about 500 nucleotides, at least about 600 nucleotides, at least about 700 nucleotides, at least about 800 nucleotides, at least about 900 nucleotides, or at least about 1000 nucleotides downstream from GRCh37/hg19: chr2:166,863,740. In some embodiments, the ASO targets a sequence more than 300 nucleotides downstream from GRCh37/hg19: chr2:166,863,740.

In some embodiments, the ASO targets a sequence from about 4 to about 300 nucleotides upstream (or 5') from genomic site GRCh37/hg19: chr2:166,863,803. In some embodiments, the ASO targets a sequence at most about 10 nucleotides, at most about 20 nucleotides, at most about 50 nucleotides, at most about 80 nucleotides, at most about 85 nucleotides, at most about 90 nucleotides, at most about 95 nucleotides, at most about 96 nucleotides, at most about 97 nucleotides, at most about 98 nucleotides, at most about 99 nucleotides, at most about 100 nucleotides, at most about 101 nucleotides, at most about 102 nucleotides, at most about 103 nucleotides, at most about 104 nucleotides, at most about 105 nucleotides, at most about 110 nucleotides, at most about 120 nucleotides, at most about 150 nucleotides, at most about 200 nucleotides, at most about 300 nucleotides, at most about 400 nucleotides, at most about 500 nucleotides, at most about 600 nucleotides, at most about 700 nucleotides, at most about 800 nucleotides, at most about 900 nucleotides, at most about 1000 nucleotides, at most about 1100 nucleotides, at most about 1200 nucleotides, at most about 1300 nucleotides, at most about 1400 nucleotides, or at most about 1500 nucleotides upstream (or 5') from genomic site GRCh37/hg19: chr2:166,863,803. In some embodiments, the ASO targets a sequence from about 4 to about 300 nucleotides downstream (or 3') from GRCh37/hg19: chr2:166,863,740. In some embodiments, the ASO targets a sequence at most about 10 nucleotides, at most about 20 nucleotides, at most about 50 nucleotides, at most about 80 nucleotides, at most about 85 nucleotides, at most about 90 nucleotides, at most about 95 nucleotides, at most about 96 nucleotides, at most about 97 nucleotides, at most about 98 nucleotides, at most about 99 nucleotides, at most about 100 nucleotides, at most about 101 nucleotides, at most about 102 nucleotides, at most about 103 nucleotides, at most about 104 nucleotides, at most about 105 nucleotides, at most about 110 nucleotides, at most about 120 nucleotides, at most about 150 nucleotides, at most about 200 nucleotides, at most about 300 nucleotides, at most about 400 nucleotides, at most about 500 nucleotides, at most about 600 nucleotides, at most about 700 nucleotides, at most about 800 nucleotides, at most about 900 nucleotides, or at most about 1000 nucleotides, at most about 1100 nucleotides, at most about 1200 nucleotides, at most about 1300 nucleotides, at most about 1400 nucleotides, or at most about 1500 nucleotides downstream from GRCh37/hg19: chr2:166,863,740. In some embodiments, the ASO targets a sequence more than 300 nucleotides downstream from GRCh37/hg19: chr2:166,863,740.

As described herein in the Examples, the SCN1A gene (SEQ ID NO. 1) was analyzed for NIE and inclusion of a portion of intron 20 (see SEQ ID NO. 6 which encodes the Intron 20 pre-mRNA) (this portion is referred as Exon 23 or Exon 20x throughout the present disclosure) was observed. In some embodiments, the ASOs disclosed herein target a NIE containing pre-mRNA (SEQ ID NO. 2) transcribed from a SCN1A genomic sequence. In some embodiments, the ASO targets a NIE containing pre-mRNA transcript from a SCN1A genomic sequence comprising a portion of intron 20. In some embodiments, the ASO targets a NIE containing pre-mRNA transcript from a SCN1A genomic sequence comprising exon 23 (or exon 20x) (SEQ ID NO. 4). In some embodiments, the ASO targets a NIE containing pre-mRNA transcript of SEQ ID NO. 2 or 9. In some embodiments, the ASO targets a NIE containing pre-mRNA transcript of SEQ ID NO. 2 or 9 comprising an NIE. In some embodiments, the ASO targets a NIE containing pre-mRNA transcript of SEQ ID NO. 2 comprising exon 23 (or exon 20x) (SEQ ID NO. 7). In some embodiments, the ASOs disclosed herein target a SCN1A pre-mRNA sequence (SEQ ID NO. 2 or 9). In some embodiments, the ASO targets a SCN1A pre-mRNA sequence comprising an NIE (SEQ ID NO. 7 or 11). In some embodiments, the ASO targets a SCN1A pre-mRNA sequence according to any one of SEQ ID NOs: 6, 7, 10, or 11. In some embodiments, the ASO has a sequence according to any one of SEQ ID NOs: 12-731. In some embodiments, the ASO has a sequence according to any one of SEQ ID NOs: 12-371. In some embodiments, the ASO has a sequence according to any one of SEQ ID NOs: 372-731.

In some embodiments, the SCN1A NIE containing pre-mRNA transcript is encoded by a genetic sequence with at least about 80%, 85%, 90%, 95%, 96%, 97%, 98%, 99% or 100% sequence identity to SEQ ID NO.: 1 or 8. In some embodiments, the SCN1A NIE pre-mRNA transcript comprises a sequence with at least about 80%, 85%, 90%, 95%, 96%, 97%, 98%, 99% or 100% sequence identity to any one of SEQ ID NOs.: 2-7 and 9-11.

In some embodiments, the SCN1A NIE containing pre-mRNA transcript (or NMD exon mRNA) comprises a sequence with at least about 80%, 85%, 90%, 95%, 97%, or 100% sequence identity to any one of SEQ ID NOs: 2, 6, 7, 9, 10, and 12. In some embodiments, SCN1A NIE containing pre-mRNA transcript (or NMD exon mRNA) is encoded by a sequence with at least about 80%, 85%, 90%, 95%, 97%, or 100% sequence identity to SEQ ID NOs: 1 and 8. In some embodiments, the targeted portion of the NMD exon mRNA comprises a sequence with at least 80%, 85%, 90%, 95%, 97%, or 100% sequence identity to a region comprising at least 8 contiguous nucleic acids of SEQ ID NOs: 2, 6, 7, 9, 10, and 12.

In some embodiments, the ASO targets a sequence upstream from the 5' end of an NIE. For example, ASOs targeting a sequence upstream from the 5' end of an NIE (e.g. exon 23 (or exon 20x) in human SCN1A, or exon 21x in mouse SCN1A) can comprise a sequence with at least 80%, 85%, 90%, 95%, 97%, or 100% sequence identity to any one of SEQ ID NOs: 12-191 or 372-551. For another example, ASOs targeting a sequence upstream from the 5' end of an NIE (e.g. exon 23 (or exon 20x) in human SCN1A, or exon 21x in mouse SCN1A) can comprise a sequence with at least 80%, 85%, 90%, 95%, 97%, or 100% sequence identity to any one of SEQ ID NOs: 12-191. For an additional example, ASOs targeting a sequence upstream from the 5' end of an NIE (e.g. exon 23 (or exon 20x) in human SCN1A, or exon 21x in mouse SCN1A) can comprise a sequence with at least 80%, 85%, 90%, 95%, 97%, or 100% sequence identity to any one of SEQ ID NOs: 372-551.

In some embodiments, the ASO targets exon 23 (or exon 20x) in a SCN1A NIE containing pre-mRNA comprising exon 23. In some embodiments, the ASO targets an exon 23 sequence downstream (or 3') from the 5' end of the exon 23 of a SCN1A pre-mRNA. In some embodiments, the ASO targets an exon 23 sequence upstream (or 5') from the 3' end of the exon 20x of a SCN1A pre-mRNA.

In some embodiments, the ASO targets a sequence downstream from the 3' end of an NIE. For example, ASOs targeting a sequence downstream from the 3' end of an NIE (e.g. exon 23 (or exon 20x) in human SCN1A, or exon 21x in mouse SCN1A) can comprise a sequence with at least 80%, 85%, 90%, 95%, 97%, or 100% sequence identity to any one of SEQ ID NOs: 192-371 or 552-731. For another example, ASOs targeting a sequence downstream from the 3' end of an NIE (e.g. exon 23 (or exon 20x) in human SCN1A, or exon 21x in mouse SCN1A) can comprise a sequence with at least 80%, 85%, 90%, 95%, 97%, or 100% sequence identity to any one of SEQ ID NOs: 192-371. For an additional example, ASOs targeting a sequence downstream from the 3' end of an NIE (e.g. exon 23 (or exon 20x) in human SCN1A, or exon 21x in mouse SCN1A) can comprise a sequence with at least 80%, 85%, 90%, 95%, 97%, or 100% sequence identity to any one of SEQ ID NOs: 552-731.

In some embodiments, the targeted portion of the SCN1A NIE containing pre-mRNA is in intron 1, 2, 3, 4, 5, 6, 7, 8, 9, 10, 11, 12, 13, 14, 15, 16, 17, 18, 19, 20, 21, 22, 23, 24, or 25 (intron numbering corresponding to the mRNA sequence at NM_006920). In some embodiments, hybridization of an ASO to the targeted portion of the NIE pre-mRNA results in exon skipping of at least one of NIE within intron 1, 2, 3, 4, 5, 6, 7, 8, 9, 10, 11, 12, 13, 14, 15, 16, 17, 18, 19, 20, 21, 22, 23, 24, or 25, and subsequently increases SCN1A protein production. In some embodiments, hybridization of an ASO to the targeted portion of the NIE pre-mRNA inhibits or blocks exon skipping of at least one of NIE within intron 1, 2, 3, 4, 5, 6, 7, 8, 9, 10, 11, 12, 13, 14, 15, 16, 17, 18, 19, 20, 21, 22, 23, 24, or 25, and subsequently decreases SCN1A protein production. In some embodiments, the targeted portion of the SCN1A NIE containing pre-mRNA is in intron 20. One of skill in the art can determine the corresponding intron number in any isoform based on an intron sequence provided herein or using the number provided in reference to the mRNA sequence at NM_006920, NM_001202435, NM_001165964, or NM_001165963. One of skill in the art also can determine the sequences of flanking exons in any SCN1A isoform for targeting using the methods of the invention, based on an intron sequence provided herein or using the intron number provided in reference to the mRNA sequence at NM_006920, NM_001202435, NM_001165964, or NM_001165963.

In some embodiments, the methods and compositions of the present disclosure are used to modulate, e.g., increase or decrease, the expression of SCN1A by inducing or inhibiting exon skipping of a pseudo-exon of an SCN1A NIE containing pre-mRNA. In some embodiments, the pseudo-exon is a sequence within any of introns 1-25. In some embodiments, the pseudo-exon is a sequence within any of introns 2, 4, 6, 13, 14, 15, 16, 17, 18, 20, 21, 22, 23, 24, and 25. In some embodiments, the pseudo-exon is a sequence within any of introns 15, 18, and 19. In some embodiments, the pseudo-exon can be any SCN1A intron or a portion thereof. In some embodiments, the pseudo-exon is within intron 20. The SCN1A intron numbering used herein corresponds to the mRNA sequence at NM_006920. It is understood that the intron numbering may change in reference to a different SCN1A isoform sequence.

SCN1A Protein

The SCN1A gene can encode SCN1A (sodium channel, voltage-gated, type I, alpha subunit) protein, which can also be referred to as alpha-subunit of voltage-gated sodium channel $Na_v1.1$. Also described above, SCN1A mutations in DS are spread across the entire protein. More than 100 novel mutations have been identified throughout the gene with the more debilitating arising de novo. These comprise of truncations (47%), missense (43%), deletions (3%), and splice site mutations (7%). The percentage of subjects carrying SCN1A mutations varies between 33 and 100%. The majority of mutations are novel changes (88%).

In some embodiments, the methods described herein are used to modulate, e.g., increase or decrease, the production of a functional SCN1A protein. As used herein, the term "functional" refers to the amount of activity or function of a SCN1A protein that is necessary to eliminate any one or more symptoms of a treated condition, e.g., Dravet syndrome; Epilepsy, generalized, with febrile seizures plus, type 2; Febrile seizures, familial, 3A; Autism; Epileptic encephalopathy, early infantile, 13; Sick sinus syndrome 1; Alzheimer's disease; or SUDEP. In some embodiments, the methods are used to increase the production of a partially functional SCN1A protein. As used herein, the term "partially functional" refers to any amount of activity or function of the SCN1A protein that is less than the amount of activity or function that is necessary to eliminate or prevent any one or more symptoms of a disease or condition. In some embodiments, a partially functional protein or RNA will have at least 10%, at least 20%, at least 30%, at least 40%, at least 50%, at least 60%, at least 70%, at least 75%, at least 80%, at least 85%, at least 90%, or at least 95% less activity relative to the fully functional protein or RNA.

In some embodiments, the method is a method of increasing the expression of the SCN1A protein by cells of a subject having a NIE containing pre-mRNA encoding the SCN1A protein, wherein the subject has Dravet syndrome caused by a deficient amount of activity of SCN1A protein, and wherein the deficient amount of the SCN1A protein is caused by haploinsufficiency of the SCN1A protein. In such an embodiment, the subject has a first allele encoding a functional SCN1A protein, and a second allele from which the SCN1A protein is not produced. In another such embodiment, the subject has a first allele encoding a functional SCN1A protein, and a second allele encoding a nonfunctional SCN1A protein. In another such embodiment, the subject has a first allele encoding a functional SCN1A protein, and a second allele encoding a partially functional SCN1A protein. In any of these embodiments, the antisense oligomer binds to a targeted portion of the NIE containing pre-mRNA transcribed from the second allele, thereby inducing exon skipping of the pseudo-exon from the pre-mRNA, and causing an increase in the level of mature mRNA encoding functional SCN1A protein, and an increase in the expression of the SCN1A protein in the cells of the subject.

In related embodiments, the method is a method of using an ASO to increase the expression of a protein or functional RNA. In some embodiments, an ASO is used to increase the expression of SCN1A protein in cells of a subject having a NIE containing pre-mRNA encoding SCN1A protein, wherein the subject has a deficiency, e.g., Dravet Syndrome (DS) (also known as SMEI); severe myoclonic epilepsy of infancy (SMEI)-borderland (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; sudden unexpected death in epilepsy (SUDEP); sick sinus syndrome 1; early infantile SCN1A encephalopathy; early infantile epileptic encephalopathy (EIEE); or autism, in the amount or function of a SCN1A protein. In some embodiments, an ASO is used to increase the expression of SCN1A protein in cells of a subject, wherein the subject has a deficiency, e.g., Epileptic encephalopathy, early infantile, 13; in the amount or function of a SCN8A protein. In some embodiments, an ASO is used to increase the expression of SCN1A protein in cells of a subject, wherein the subject has a deficiency, e.g., Sick sinus syndrome 1; in the amount or function of a SCN5A protein.

In some embodiments, the NIE containing pre-mRNA transcript that encodes the protein that is causative of the disease or condition is targeted by the ASOs described herein. In some embodiments, a NIE containing pre-mRNA transcript that encodes a protein that is not causative of the disease is targeted by the ASOs. For example, a disease that is the result of a mutation or deficiency of a first protein in a particular pathway may be ameliorated by targeting a NIE containing pre-mRNA that encodes a second protein, thereby increasing production of the second protein. In some embodiments, the function of the second protein is able to compensate for the mutation or deficiency of the first protein (which is causative of the disease or condition).

In some embodiments, the subject has:
(a) a first mutant allele from which
 (i) the SCN1A protein is produced at a reduced level compared to production from a wild-type allele,
 (ii) the SCN1A protein is produced in a form having reduced function compared to an equivalent wild-type protein, or
 (iii) the SCN1A protein or functional RNA is not produced; and
(b) a second mutant allele from which
 (i) the SCN1A protein is produced at a reduced level compared to production from a wild-type allele,
 (ii) the SCN1A protein is produced in a form having reduced function compared to an equivalent wild-type protein, or
 (iii) the SCN1A protein is not produced, and wherein the NIE containing pre-mRNA is transcribed from the first allele and/or the second allele. In these embodiments, the ASO binds to a targeted portion of the NIE containing pre-mRNA transcribed from the first allele or the second allele, thereby inducing exon skipping of the pseudo-exon from the NIE containing pre-mRNA, and causing an increase in the level of mRNA encoding SCN1A protein and an increase in the expression of the target protein or functional RNA in the cells of the subject. In these embodiments, the target protein or functional RNA having an increase in expression level resulting from the exon skipping of the pseudo-exon from the NIE containing pre-mRNA is either in a form having reduced function compared to the equivalent wild-type protein (partially-functional), or having full function compared to the equivalent wild-type protein (fully-functional).

In some embodiments, the level of mRNA encoding SCN1A protein is increased 1.1 to 10-fold, when compared to the amount of mRNA encoding SCN1A protein that is produced in a control cell, e.g., one that is not treated with the antisense oligomer or one that is treated with an antisense oligomer that does not bind to the targeted portion of the SCN1A NIE containing pre-mRNA.

In some embodiments, a subject treated using the methods of the present disclosure expresses a partially functional SCN1A protein from one allele, wherein the partially functional SCN1A protein is caused by a frameshift mutation, a nonsense mutation, a missense mutation, or a partial gene deletion. In some embodiments, a subject treated using the methods of the invention expresses a nonfunctional SCN1A protein from one allele, wherein the nonfunctional SCN1A protein is caused by a frameshift mutation, a nonsense mutation, a missense mutation, a partial gene deletion, in one allele. In some embodiments, a subject treated using the methods of the invention has a SCN1A whole gene deletion, in one allele.

In some embodiments, the method is a method of decreasing the expression of the SCN1A protein by cells of a subject having a NIE containing pre-mRNA encoding the SCN1A protein, and wherein the subject has a gain-of-function mutation in $Na_v1.1$. In such an embodiment, the subject has an allele from which the SCN1A protein is produced in an elevated amount or an allele encoding a mutant SCN1A that induces increased activity of $Na_v1.1$ in the cell. In some embodiments, the increased activity of $Na_v1.1$ is characterized by a prolonged or near persistent sodium current mediated by the mutant $Na_v1.1$ channel, a slowing of fast inactivation, a positive shift in steady-state inactivation, higher channel availability during repetitive stimulation, increased non-inactivated depolarization-induced persistent sodium currents, delayed entry into inactivation, accelerated recovery from fast inactivation, and/or rescue of folding defects by incubation at lower temperature or co-expression of interacting proteins. In any of these embodiments, the antisense oligomer binds to a targeted portion of the NIE containing pre-mRNA transcribed from the second allele, thereby inhibiting or blocking exon skipping of the pseudo-exon from the pre-mRNA, and causing a decrease in the level of mature mRNA encoding functional SCN1A protein, and a decrease in the expression of the SCN1A protein in the cells of the subject.

In related embodiments, the method is a method of using an ASO to decrease the expression of a protein or functional RNA. In some embodiments, an ASO is used to decrease the expression of SCN1A protein in cells of a subject having a NIE containing pre-mRNA encoding SCN1A protein. In some embodiments, the subject has a gain-of-function mutation in $Na_v1.1$, e.g., migraine. In some embodiments, an ASO is used to decrease the expression of SCN1A protein in cells of a subject, the subject has a gain-of-function mutation in $Na_v1.1$, e.g., migraine, familial hemiplegic, 3.

In some embodiments, the level of mRNA encoding SCN1A protein is decreased 1.1 to 10-fold, when compared to the amount of mRNA encoding SCN1A protein that is produced in a control cell, e.g., one that is not treated with the antisense oligomer or one that is treated with an anti-sense oligomer that does not bind to the targeted portion of the SCN1A NIE containing pre-mRNA.

In some embodiments, a subject treated using the methods of the present disclosure expresses a mutant SCN1A protein from one allele, wherein the mutant SCN1A protein is caused by a frameshift mutation, a nonsense mutation, a missense mutation, or a partial gene deletion, and wherein the mutant SCN1A protein causes an elevated activity level of $Na_v1.1$. In some embodiments, a subject treated using the methods of the present disclosure expresses an elevated amount of SCN1A protein from one allele due to a frame-shift mutation, a nonsense mutation, a missense mutation, or a partial gene deletion.

In embodiments of the present invention, a subject can have a mutation in SCN1A. Mutations in SCN1A can be spread throughout said gene. SCN1A protein can consist of four domains. Said SCN1A domains can have transmem-brane segments. Mutations in said SCN1A protein may arise throughout said protein. Said SCN1A protein may consist of at least two isoforms. Mutations in SCN1A may comprise of R931C, R946C, M934I, R1648C, or R1648H. In some cases, mutations may be observed in a C-terminus of a SCN1A protein. Mutations in a SCN1A protein may also be found in loops between segments 5 and 6 of the first three domains of said SCN1A protein. In some cases, mutations may be observed in an N-terminus of a SCN1A protein. Exemplary mutations within SCN1A include, but are not limited to, R222X, R712X, I227S, R1892X, W952X, R1245X, R1407X, W1434R, c.4338+1G>A, S1516X, L1670fsX1678, or K1846fsX1856. Mutations that can be targeted with the present invention may also encode a pore of an ion channel.

In some embodiments, the methods and compositions described herein can be used to treat DS. In other embodi-ments, the methods and compositions described herein can be used to treat severe myoclonic epilepsy of infancy (SMEI). In other embodiments, the methods and composi-tions described herein can be used to treat borderline Dravet syndrome; Epilepsy, generalized, with febrile seizures plus, type 2; Febrile seizures, familial, 3A; Migraine, familial hemiplegic, 3; Autism; Epileptic encephalopathy, early infantile, 13; Sick sinus syndrome 1; Alzheimer's disease or SUDEP. The methods and compositions described herein can also be used to treat borderline SMEI. Additionally, the methods and compositions described herein can be used to treat generalized epilepsy with febrile seizures plus (GEFS+). GEFS+ may be associated with mutations in epilepsy-associated ion channel subunits such as SCN1B or GABRG2. The methods and compositions described herein can also be used to treat sodium channelopathies. Sodium channelopathies may be associated with mutations in SCN1A. Sodium channelopathies may also be associated with subunits of SCN1A, such as the beta subunit, SCN1B. In some cases, additional diseases associated with SCN1A mutations may also be treated with the present disclosure. Related SCN1A diseases associated with SCN1A mutations include, but are not limited to, atypical myotonia congenita, hyperkalemic periodic paralysis, and paramyotonia con-genita.

In some embodiments, a subject having any SCN1A mutation known in the art and described in the literature referenced above (e.g., by Hamdan, et al., 2009, Mulley, et al., 2005) can be treated using the methods and compositions described herein. In some embodiments, the mutation is within any SCN1A intron or exon.

Exon Inclusion

As used herein, a "NIE containing pre-mRNA" is a pre-mRNA transcript that contains at least one pseudo-exon. Alternative or aberrant splicing can result in inclusion of the at least one pseudo-exon in the mature mRNA transcripts. The terms "mature mRNA," and "fully-spliced mRNA," are used interchangeably herein to describe a fully processed mRNA. Inclusion of the at least one pseudo-exon can be non-productive mRNA and lead to NMD of the mature mRNA. NIE containing mature mRNA may sometimes lead to aberrant protein expression.

In some embodiments, the included pseudo-exon is the most abundant pseudo-exon in a population of NIE contain-ing pre-mRNAs transcribed from the gene encoding the target protein in a cell. In some embodiments, the included pseudo-exon is the most abundant pseudo-exon in a popu-lation of NIE containing pre-mRNAs transcribed from the gene encoding the target protein in a cell, wherein the population of NIE containing pre-mRNAs comprises two or more included pseudo-exons. In some embodiments, an antisense oligomer targeted to the most abundant pseudo-exon in the population of NIE containing pre-mRNAs encoding the target protein induces exon skipping of one or two or more pseudo-exons in the population, including the pseudo-exon to which the antisense oligomer is targeted or binds. In embodiments, the targeted region is in a pseudo-exon that is the most abundant pseudo-exon in a NIE containing pre-mRNA encoding the SCN1A protein.

The degree of exon inclusion can be expressed as percent exon inclusion, e.g., the percentage of transcripts in which a given pseudo-exon is included. In brief, percent exon inclu-sion can be calculated as the percentage of the amount of RNA transcripts with the exon inclusion, over the sum of the average of the amount of RNA transcripts with exon inclu-sion plus the average of the amount of RNA transcripts with exon exclusion.

In some embodiments, an included pseudo-exon is an exon that is identified as an included pseudo-exon based on a determination of at least about 5%, at least about 10%, at least about 15%, at least about 20%, at least about 25%, at least about 30%, at least about 35%, at least about 40%, at least about 45%, or at least about 50%, inclusion. In embodi-ments, a included pseudo-exon is an exon that is identified as a included pseudo-exon based on a determination of about 5% to about 100%, about 5% to about 95%, about 5% to about 90%, about 5% to about 85%, about 5% to about 80%, about 5% to about 75%, about 5% to about 70%, about 5% to about 65%, about 5% to about 60%, about 5% to about 55%, about 5% to about 50%, about 5% to about 45%, about 5% to about 40%, about 5% to about 35%, about 5% to about 30%, about 5% to about 25%, about 5% to about 20%, about 5% to about 15%, about 10% to about 100%, about 10% to about 95%, about 10% to about 90%, about 10% to about 85%, about 10% to about 80%, about 10% to about 75%, about 10% to about 70%, about 10% to about 65%, about 10% to about 60%, about 10% to about 55%, about 10% to about 50%, about 10% to about 45%, about 10% to about 40%, about 10% to about 35%, about 10% to about 30%, about 10% to about 25%, about 10% to about 20%, about 15% to about 100%, about 15% to about 95%, about 15% to about 90%, about 15% to about 85%, about 15% to about 80%, about 15% to about 75%, about 15% to about 70%, about 15% to about 65%, about 15% to about 60%, about 15% to about 55%, about 15% to about 50%, about 15% to about 45%, about 15% to about 40%, about 15% to about 35%, about 15% to about 30%, about 15% to about 25%, about 20% to about 100%, about 20% to about 95%, about 20% to about 90%, about 20% to about 85%, about 20% to about 80%, about 20% to about 75%, about 20% to about 70%, about 20% to about 65%, about 20% to about 60%, about 20% to about 55%, about 20% to about 50%, about 20% to about 45%, about 20% to about 40%, about 20% to about 35%, about 20% to about 30%, about 25% to about 100%, about 25% to about 95%, about 25% to about 90%, about 25% to about 85%, about 25% to about 80%, about 25% to about 75%, about 25% to about 70%, about 25% to about 65%, about 25% to about 60%, about 25% to about 55%, about 25% to about 50%, about 25% to about 45%, about 25% to about 40%, or about 25% to about 35%, inclusion. ENCODE data (described by, e.g., Tilgner, et al., 2012, "Deep sequencing of subcellular RNA fractions shows splicing to be predominantly co-transcriptional in the human genome but inefficient for lncRNAs," Genome Research 22(9):1616-25) can be used to aid in identifying exon inclusion.

In some embodiments, contacting cells with an ASO that is complementary to a targeted portion of a SCN1A pre-mRNA transcript results in an increase in the amount of SCN1A protein produced by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of SCN1A protein produced by the cell to which the antisense oligomer is contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the amount of target protein produced by a control compound. A control compound can be, for example, an oligonucleotide that is not complementary to a targeted portion of the pre-mRNA.

In some embodiments, contacting cells with an ASO that is complementary to a targeted portion of a SCN1A pre-mRNA transcript results in a decrease in the amount of SCN1A protein produced by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of SCN1A protein produced by the cell to which the antisense oligomer is contacted is decreased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the amount of target protein produced by a control compound. A control compound can be, for example, an oligonucleotide that is not complementary to a targeted portion of the pre-mRNA.

In some embodiments, contacting cells with an ASO that is complementary to a targeted portion of a SCN1A pre-mRNA transcript results in an increase in the amount of mRNA encoding SCN1A, including the mature mRNA encoding the target protein. In some embodiments, the amount of mRNA encoding SCN1A protein, or the mature mRNA encoding the SCN1A protein, is increased by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of the mRNA encoding SCN1A protein, or the mature mRNA encoding SCN1A protein produced in the cell to which the antisense oligomer is contacted is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the amount of mature RNA produced in an untreated cell, e.g., an untreated cell or a cell treated with a control compound. A control compound can be, for example, an oligonucleotide that is not complementary to a targeted portion of the SCN1A NIE containing pre-mRNA.

In some embodiments, contacting cells with an ASO that is complementary to a targeted portion of a SCN1A pre-mRNA transcript results in a decrease in the amount of mRNA encoding SCN1A, including the mature mRNA encoding the target protein. In some embodiments, the amount of mRNA encoding SCN1A protein, or the mature mRNA encoding the SCN1A protein, is decreased by at least 10, 20, 30, 40, 50, 60, 80, 100, 150, 200, 250, 300, 350, 400, 450, 500, or 1000%, compared to the amount of the protein produced by a cell in the absence of the ASO/absence of treatment. In some embodiments, the total amount of the mRNA encoding SCN1A protein, or the mature mRNA encoding SCN1A protein produced in the cell to which the antisense oligomer is contacted is decreased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the amount of mature RNA produced in an untreated cell, e.g., an untreated cell or a cell treated with a control compound. A control compound can be, for example, an oligonucleotide that is not complementary to a targeted portion of the SCN1A NIE containing pre-mRNA.

The NIE can be in any length. In some embodiments, the NIE comprises a full sequence of an intron, in which case, it can be referred to as intron retention. In some embodiments, the NIE can be a portion of the intron. In some embodiments, the NIE can be a 5' end portion of an intron including a 5'ss sequence. In some embodiments, the NIE can be a 3' end portion of an intron including a 3'ss sequence. In some embodiments, the NIE can be a portion within an intron without inclusion of a 5'ss sequence. In some embodiments, the NIE can be a portion within an intron without inclusion of a 3'ss sequence. In some embodiments, the NIE can be a portion within an intron without inclusion of either a 5'ss or a 3'ss sequence. In some embodiments, the NIE can be from 5 nucleotides to 10 nucleotides in length, from 10 nucleotides to 15 nucleotides in length, from 15 nucleotides to 20 nucleotides in length, from 20 nucleotides to 25 nucleotides in length, from 25 nucleotides to 30 nucleotides in length, from 30 nucleotides to 35 nucleotides in length, from 35 nucleotides to 40 nucleotides in length, from 40 nucleotides to 45 nucleotides in length, from 45 nucleotides to 50 nucleotides in length, from 50 nucleotides to 55 nucleotides in length, from 55 nucleotides to 60 nucleotides in length, from 60 nucleotides to 65 nucleotides in length, from 65 nucleotides to 70 nucleotides in length, from 70 nucleotides to 75 nucleotides in length, from 75 nucleotides to 80 nucleotides in length, from 80 nucleotides to 85 nucleotides in length, from 85 nucleotides to 90 nucleotides in length, from 90 nucleotides to 95 nucleotides in length, or from 95 nucleotides to 100 nucleotides in length. In some embodiments, the NIE can be at least 10 nucleotides, at least 20 nucleotides, at least 30 nucleotides, at least 40 nucleotides, at least 50 nucleotides, at least 60 nucleoids, at least 70 nucleotides, at least 80 nucleotides in length, at least 90 nucleotides, or at least 100 nucleotides in length. In some embodiments, the NIE can be from 100 to 200 nucleotides in length, from 200 to 300 nucleotides in length, from 300 to 400 nucleotides in length, from 400 to 500 nucleotides in length, from 500 to 600 nucleotides in length, from 600 to 700 nucleotides in length, from 700 to 800 nucleotides in length, from 800 to 900 nucleotides in length, from 900 to 1,000 nucleotides in length. In some embodiments, the NIE may be longer than 1,000 nucleotides in length.

Inclusion of a pseudo-exon can lead to a frameshift and the introduction of a premature termination codon (PIC) in the mature mRNA transcript rendering the transcript a target of NMD. Mature mRNA transcript containing NIE can be non-productive mRNA transcript which does not lead to protein expression. The PIC can be present in any position downstream of an NIE. In some embodiments, the PIC can be present in any exon downstream of an NIE. In some embodiments, the PIC can be present within the NIE. For example, inclusion of exon 20x in an mRNA transcript encoded by the SCN1A gene can induce a PIC in the mRNA transcript, e.g., a PIC in exon 21 of the mRNA transcript.

Therapeutic Agents

In various embodiments of the present disclosure, compositions and methods comprising a therapeutic agent are provided to modulate protein expression level of SCN1A. In some embodiments, provided herein are compositions and methods to modulate alternative splicing of SCNA1 pre-mRNA. In some embodiments, provided herein are compositions and methods to induce exon skipping in the splicing of SCN1A pre-mRNA, e.g., to induce skipping of a pseudo-exon during splicing of SCN1A pre-mRNA. In other embodiments, therapeutic agents may be used to induce the inclusion of an exon in order to decrease the protein expression level.

In some embodiment, a therapeutic agent disclosed herein is a small molecule, a polypeptide, or a polynucleic acid polymer. In some instances, the therapeutic agent is a small molecule. In some instances, the therapeutic agent is a polypeptide. In some instances, the therapeutic agent is a polynucleic acid polymer. In some cases, the therapeutic agent is a repressor agent. In additional cases, the therapeutic agent is an enhancer agent.

A therapeutic agent disclosed herein can be a NIE repressor agent. A therapeutic agent may comprise a polynucleic acid polymer.

According to one aspect of the present disclosure, provided herein is a method of treatment or prevention of a condition associated with a functional-SCN1A protein deficiency, comprising administering a NIE repressor agent to a subject to increase levels of functional SCN1A protein, wherein the agent binds to a region of the pre-mRNA transcript to decrease inclusion of the NIE in the mature transcript. For example, provided herein is a method of treatment or prevention of a condition associated with a functional-SCN1A protein deficiency, comprising administering a NIE repressor agent to a subject to increase levels of functional SCN1A protein, wherein the agent binds to a region of an intron containing an NIE (e.g., intron 20 in human SCN1A gene) of the pre-mRNA transcript or to a NIE-activating regulatory sequence in the same intron.

Where reference is made to reducing NIE inclusion in the mature mRNA, the reduction may be complete, e.g., 100%, or may be partial. The reduction may be clinically significant. The reduction/correction may be relative to the level of NIE inclusion in the subject without treatment, or relative to the amount of NIE inclusion in a population of similar subjects. The reduction/correction may be at least 10% less NIE inclusion relative to the average subject, or the subject prior to treatment. The reduction may be at least 20% less NIE inclusion relative to an average subject, or the subject prior to treatment. The reduction may be at least 40% less NIE inclusion relative to an average subject, or the subject prior to treatment. The reduction may be at least 50% less NIE inclusion relative to an average subject, or the subject prior to treatment. The reduction may be at least 60% less NIE inclusion relative to an average subject, or the subject prior to treatment. The reduction may be at least 80% less NIE inclusion relative to an average subject, or the subject prior to treatment. The reduction may be at least 90% less NIE inclusion relative to an average subject, or the subject prior to treatment.

Where reference is made to increasing active-SCN1A protein levels, the increase may be clinically significant. The increase may be relative to the level of active-SCN1A protein in the subject without treatment, or relative to the amount of active-SCN1A protein in a population of similar subjects. The increase may be at least 10% more active-SCN1A protein relative to the average subject, or the subject prior to treatment. The increase may be at least 20% more active-SCN1A protein relative to the average subject, or the subject prior to treatment. The increase may be at least 40% more active-SCN1A protein relative to the average subject, or the subject prior to treatment. The increase may be at least 50% more active-SCN1A protein relative to the average subject, or the subject prior to treatment. The increase may be at least 80% more active-SCN1A protein relative to the average subject, or the subject prior to treatment. The increase may be at least 100% more active-SCN1A protein relative to the average subject, or the subject prior to treatment. The increase may be at least 200% more active-SCN1A protein relative to the average subject, or the subject prior to treatment. The increase may be at least 500% more active-SCN1A protein relative to the average subject, or the subject prior to treatment.

In embodiments wherein the NIE repressor agent comprises a polynucleic acid polymer, the polynucleic acid polymer may be about 50 nucleotides in length. The polynucleic acid polymer may be about 45 nucleotides in length. The polynucleic acid polymer may be about 40 nucleotides in length. The polynucleic acid polymer may be about 35 nucleotides in length. The polynucleic acid polymer may be about 30 nucleotides in length. The polynucleic acid polymer may be about 24 nucleotides in length. The polynucleic acid polymer may be about 25 nucleotides in length. The polynucleic acid polymer may be about 20 nucleotides in length. The polynucleic acid polymer may be about 19 nucleotides in length. The polynucleic acid polymer may be about 18 nucleotides in length. The polynucleic acid polymer may be about 17 nucleotides in length. The polynucleic acid polymer may be about 16 nucleotides in length. The polynucleic acid polymer may be about 15 nucleotides in length. The polynucleic acid polymer may be about 14 nucleotides in length. The polynucleic acid polymer may be about 13 nucleotides in length. The polynucleic acid polymer may be about 12 nucleotides in length. The polynucleic acid polymer may be about 11 nucleotides in length. The polynucleic acid polymer may be about 10 nucleotides in length. The polynucleic acid polymer may be between about 10 and about 50 nucleotides in length. The polynucleic acid polymer may be between about 10 and about 45 nucleotides in length. The polynucleic acid polymer may be between about 10 and about 40 nucleotides in length. The polynucleic acid polymer may be between about 10 and about 35 nucleotides in length. The polynucleic acid polymer may be between about 10 and about 30 nucleotides in length. The polynucleic acid polymer may be between about 10 and about 25 nucleotides in length. The polynucleic acid polymer may be between about 10 and about 20 nucleotides in length. The polynucleic acid polymer may be between about 15 and about 25 nucleotides in length. The polynucleic acid polymer may be between about 15 and about 30 nucleotides in length. The polynucleic acid polymer may be between about 12 and about 30 nucleotides in length.

The sequence of the polynucleic acid polymer may be at least 50%, 55%, 60%, 65%, 70%, 75%, 80%, 85%, 90%, 91%, 92%, 93%, 94%, 95%, 96%, 97%, 98%, 99%, or 99.5% complementary to a target sequence of an mRNA transcript, e.g., a partially processed mRNA transcript. The sequence of the polynucleic acid polymer may be 100% complementary to a target sequence of a pre-mRNA transcript.

The sequence of the polynucleic acid polymer may have 4 or fewer mismatches to a target sequence of the pre-mRNA transcript. The sequence of the polynucleic acid polymer may have 3 or fewer mismatches to a target sequence of the pre-mRNA transcript. The sequence of the polynucleic acid polymer may have 2 or fewer mismatches to a target sequence of the pre-mRNA transcript. The sequence of the polynucleic acid polymer may have 1 or fewer mismatches to a target sequence of the pre-mRNA transcript. The sequence of the polynucleic acid polymer may have no mismatches to a target sequence of the pre-mRNA transcript.

The polynucleic acid polymer may specifically hybridize to a target sequence of the pre-mRNA transcript. For example, the polynucleic acid polymer may have 91%, 92%, 93%, 94%, 95%, 96%, 97%, 98%, 99%, 99.5% or 100% sequence complementarity to a target sequence of the pre-mRNA transcript. The hybridization may be under high stringent hybridization conditions.

The polynucleic acid polymer may have a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from the group consisting of SEQ ID NOs: 12-731. The polynucleic acid polymer may have a sequence with 100% sequence identity to a sequence selected from the group consisting of SEQ ID NOs: 12-731. In some instances, the polynucleic acid polymer may have a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from the group consisting of SEQ ID NOs: 12-371. In some cases, the polynucleic acid polymer may have a sequence with 100% sequence identity to a sequence selected from the group consisting of SEQ ID NOs: 12-371. In some instances, the polynucleic acid polymer may have a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from the group consisting of SEQ ID NOs: 372-731. In some cases, the polynucleic acid polymer may have a sequence with 100% sequence identity to a sequence selected from the group consisting of SEQ ID NOs: 372-731.

Where reference is made to a polynucleic acid polymer sequence, the skilled person will understand that one or more substitutions may be tolerated, optionally two substitutions may be tolerated in the sequence, such that it maintains the ability to hybridize to the target sequence; or where the substitution is in a target sequence, the ability to be recognized as the target sequence. References to sequence identity may be determined by BLAST sequence alignment using standard/default parameters. For example, the sequence may have 99% identity and still function according to the present disclosure. In other embodiments, the sequence may have 98% identity and still function according to the present disclosure. In another embodiment, the sequence may have 95% identity and still function according to the present disclosure. In another embodiment, the sequence may have 90% identity and still function according to the present disclosure.

Antisense Oligomers

Provided herein is a composition comprising an antisense oligomer that induces exon skipping by binding to a targeted portion of a SCN1A NIE containing pre-mRNA. As used herein, the terms "ASO" and "antisense oligomer" are used interchangeably and refer to an oligomer such as a polynucleotide, comprising nucleobases that hybridizes to a target nucleic acid (e.g., a SCN1A NIE containing pre-mRNA) sequence by Watson-Crick base pairing or wobble base pairing (G-U). The ASO may have exact sequence complementary to the target sequence or near complementarity (e.g., sufficient complementarity to bind the target sequence and enhancing splicing at a splice site). ASOs are designed so that they bind (hybridize) to a target nucleic acid (e.g., a targeted portion of a pre-mRNA transcript) and remain hybridized under physiological conditions. Typically, if they hybridize to a site other than the intended (targeted) nucleic acid sequence, they hybridize to a limited number of sequences that are not a target nucleic acid (to a few sites other than a target nucleic acid). Design of an ASO can take into consideration the occurrence of the nucleic acid sequence of the targeted portion of the pre-mRNA transcript or a sufficiently similar nucleic acid sequence in other locations in the genome or cellular pre-mRNA or transcriptome, such that the likelihood the ASO will bind other sites and cause "off-target" effects is limited. Any antisense oligomers known in the art, for example in PCT Application No. PCT/US2014/054151, published as WO 2015/035091, titled "Reducing Nonsense-Mediated mRNA Decay," incorporated by reference herein, can be used to practice the methods described herein.

In some embodiments, ASOs "specifically hybridize" to or are "specific" to a target nucleic acid or a targeted portion of a NIE containing pre-mRNA. Typically such hybridization occurs with a $T_m$ substantially greater than 37° C., preferably at least 50° C., and typically between 60° C. to approximately 90° C. Such hybridization preferably corresponds to stringent hybridization conditions. At a given ionic strength and pH, the $T_m$ is the temperature at which 50% of a target sequence hybridizes to a complementary oligonucleotide.

Oligomers, such as oligonucleotides, are "complementary" to one another when hybridization occurs in an anti-parallel configuration between two single-stranded polynucleotides. A double-stranded polynucleotide can be "complementary" to another polynucleotide, if hybridization can occur between one of the strands of the first polynucleotide and the second. Complementarity (the degree to which one polynucleotide is complementary with another) is quantifiable in terms of the proportion (e.g., the percentage) of bases in opposing strands that are expected to form hydrogen bonds with each other, according to generally accepted base-pairing rules. The sequence of an antisense oligomer (ASO) need not be 100% complementary to that of its target nucleic acid to hybridize. In certain embodiments, ASOs can comprise at least 70%, at least 75%, at least 80%, at least 85%, at least 90%, at least 95%, at least 96%, at least 97%, at least 98%, or at least 99% sequence complementarity to a target region within the target nucleic acid sequence to which they are targeted. For example, an ASO in which 18 of 20 nucleobases of the oligomeric compound are complementary to a target region, and would therefore specifically hybridize, would represent 90 percent complementarity. In this example, the remaining non-complementary nucleobases may be clustered together or interspersed with complementary nucleobases and need not be contiguous to each other or to complementary nucleobases. Percent complementarity of an ASO with a region of a target nucleic acid can be determined routinely using BLAST programs (basic local alignment search tools) and PowerBLAST programs known in the art (Altschul, et al., J. Mol. Biol., 1990, 215, 403-410; Zhang and Madden, Genome Res., 1997, 7, 649-656).

An ASO need not hybridize to all nucleobases in a target sequence and the nucleobases to which it does hybridize may be contiguous or noncontiguous. ASOs may hybridize over one or more segments of a pre-mRNA transcript, such that intervening or adjacent segments are not involved in the hybridization event (e.g., a loop structure or hairpin structure may be formed). In certain embodiments, an ASO hybridizes to noncontiguous nucleobases in a target pre-mRNA transcript. For example, an ASO can hybridize to nucleobases in a pre-mRNA transcript that are separated by one or more nucleobase(s) to which the ASO does not hybridize.

The ASOs described herein comprise nucleobases that are complementary to nucleobases present in a targeted portion of a NIE containing pre-mRNA. The term ASO embodies oligonucleotides and any other oligomeric molecule that comprises nucleobases capable of hybridizing to a complementary nucleobase on a target mRNA but does not comprise a sugar moiety, such as a peptide nucleic acid (PNA). The ASOs may comprise naturally-occurring nucleotides, nucleotide analogs, modified nucleotides, or any combination of two or three of the preceding. The term "naturally occurring nucleotides" includes deoxyribonucleotides and ribonucleotides. The term "modified nucleotides" includes nucleotides with modified or substituted sugar groups and/or having a modified backbone. In some embodiments, all of the nucleotides of the ASO are modified nucleotides. Chemical modifications of ASOs or components of ASOs that are compatible with the methods and compositions described herein will be evident to one of skill in the art and can be found, for example, in U.S. Pat. No. 8,258,109 B2, U.S. Pat. No. 5,656,612, U.S. Patent Publication No. 2012/0190728, and Dias and Stein, Mol. Cancer Ther. 2002, 347-355, herein incorporated by reference in their entirety.

One or more nucleobases of an ASO may be any naturally occurring, unmodified nucleobase such as adenine, guanine, cytosine, thymine and uracil, or any synthetic or modified nucleobase that is sufficiently similar to an unmodified nucleobase such that it is capable of hydrogen bonding with a nucleobase present on a target pre-mRNA. Examples of modified nucleobases include, without limitation, hypoxanthine, xanthine, 7-methylguanine, 5, 6-dihydrouracil, 5-methylcytosine, and 5-hydroxymethoylcytosine.

The ASOs described herein also comprise a backbone structure that connects the components of an oligomer. The term "backbone structure" and "oligomer linkages" may be used interchangeably and refer to the connection between monomers of the ASO. In naturally occurring oligonucleotides, the backbone comprises a 3'-5' phosphodiester linkage connecting sugar moieties of the oligomer. The backbone structure or oligomer linkages of the ASOs described herein may include (but are not limited to) phosphorothioate, phosphorodithioate, phosphoroselenoate, phosphorodiselenoate, phosphoroanilothioate, phosphoranilidate, phosphoramidate, and the like. See, e.g., LaPlanche, et al., Nucleic Acids Res. 14:9081 (1986); Stec, et al., J. Am. Chem. Soc. 106:6077 (1984), Stein, et al., Nucleic Acids Res. 16:3209 (1988), Zon, et al., Anti-Cancer Drug Design 6:539 (1991); Zon, et al., Oligonucleotides and Analogues: A Practical Approach, pp. 87-108 (F. Eckstein, Ed., Oxford University Press, Oxford England (1991)); Stec, et al., U.S. Pat. No. 5,151,510; Uhlmann and Peyman, Chemical Reviews 90:543 (1990). In some embodiments, the backbone structure of the ASO does not contain phosphorous but rather contains peptide bonds, for example in a peptide nucleic acid (PNA), or linking groups including carbamate, amides, and linear and cyclic hydrocarbon groups. In some embodiments, the backbone modification is a phosphothioate linkage. In some embodiments, the backbone modification is a phosphoramidate linkage.

In embodiments, the stereochemistry at each of the phosphorus internucleotide linkages of the ASO backbone is random. In embodiments, the stereochemistry at each of the phosphorus internucleotide linkages of the ASO backbone is controlled and is not random. For example, U.S. Pat. App. Pub. No. 2014/0194610, "Methods for the Synthesis of Functionalized Nucleic Acids," incorporated herein by reference, describes methods for independently selecting the handedness of chirality at each phosphorous atom in a nucleic acid oligomer. In embodiments, an ASO used in the methods of the invention, including, but not limited to, any of the ASOs set forth herein in Tables 5 and 6, comprises an ASO having phosphorus internucleotide linkages that are not random. In embodiments, a composition used in the methods of the invention comprises a pure diastereomeric ASO. In embodiments, a composition used in the methods of the invention comprises an ASO that has diastereomeric purity of at least about 90%, at least about 91%, at least about 92%, at least about 93%, at least about 94%, at least about 95%, at least about 96%, at least about 97%, at least about 98%, at least about 99%, about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, or about 99% to about 100%.

In embodiments, the ASO has a nonrandom mixture of Rp and Sp configurations at its phosphorus internucleotide linkages. For example, it has been suggested that a mix of Rp and Sp is required in antisense oligonucleotides to achieve a balance between good activity and nuclease stability (Wan, et al., 2014, "Synthesis, biophysical properties and biological activity of second generation antisense oligonucleotides containing chiral phosphorothioate linkages," Nucleic Acids Research 42(22): 13456-13468, incorporated herein by reference). In embodiments, an ASO used in the methods of the invention, including, but not limited to, any of the ASOs set forth herein in SEQ ID NOs: 12-731, comprises about 5-100% Rp, at least about 5% Rp, at least about 10% Rp, at least about 15% Rp, at least about 20% Rp, at least about 25% Rp, at least about 30% Rp, at least about 35% Rp, at least about 40% Rp, at least about 45% Rp, at least about 50% Rp, at least about 55% Rp, at least about 60% Rp, at least about 65% Rp, at least about 70% Rp, at least about 75% Rp, at least about 80% Rp, at least about 85% Rp, at least about 90% Rp, or at least about 95% Rp, with the remainder Sp, or about 100% Rp. In embodiments, an ASO used in the methods of the invention, including, but not limited to, any of the ASOs set forth herein in SEQ ID NOs: 12-731, comprises about 10% to about 100% Rp, about 15% to about 100% Rp, about 20% to about 100% Rp, about 25% to about 100% Rp, about 30% to about 100% Rp, about 35% to about 100% Rp, about 40% to about 100% Rp, about 45% to about 100% Rp, about 50% to about 100% Rp, about 55% to about 100% Rp, about 60% to about 100% Rp, about 65% to about 100% Rp, about 70% to about 100% Rp, about 75% to about 100% Rp, about 80% to about 100% Rp, about 85% to about 100% Rp, about 90% to about 100% Rp, or about 95% to about 100% Rp, about 20% to about 80% Rp, about 25% to about 75% Rp, about 30% to about 70% Rp, about 40% to about 60% Rp, or about 45% to about 55% Rp, with the remainder Sp.

In embodiments, an ASO used in the methods of the invention, including, but not limited to, any of the ASOs set forth herein in SEQ ID NOs: 12-731, comprises about 5-100% Sp, at least about 5% Sp, at least about 10% Sp, at least about 15% Sp, at least about 20% Sp, at least about 25% Sp, at least about 30% Sp, at least about 35% Sp, at least about 40% Sp, at least about 45% Sp, at least about 50% Sp, at least about 55% Sp, at least about 60% Sp, at least about 65% Sp, at least about 70% Sp, at least about 75% Sp, at least about 80% Sp, at least about 85% Sp, at least about 90% Sp, or at least about 95% Sp, with the remainder Rp, or about 100% Sp. In embodiments, an ASO used in the methods of the invention, including, but not limited to, any of the ASOs set forth herein in SEQ ID NOs: 12-731, comprises about 10% to about 100% Sp, about 15% to about 100% Sp, about 20% to about 100% Sp, about 25% to about 100% Sp, about 30% to about 100% Sp, about 35% to about 100% Sp, about 40% to about 100% Sp, about 45% to about 100% Sp, about 50% to about 100% Sp, about 55% to about 100% Sp, about 60% to about 100% Sp, about 65% to about 100% Sp, about 70% to about 100% Sp, about 75% to about 100% Sp, about 80% to about 100% Sp, about 85% to about 100% Sp, about 90% to about 100% Sp, or about 95% to about 100% Sp, about 20% to about 80% Sp, about 25% to about 75% Sp, about 30% to about 70% Sp, about 40% to about 60% Sp, or about 45% to about 55% Sp, with the remainder Rp.

Any of the ASOs described herein may contain a sugar moiety that comprises ribose or deoxyribose, as present in naturally occurring nucleotides, or a modified sugar moiety or sugar analog, including a morpholine ring. Non-limiting examples of modified sugar moieties include 2' substitutions such as 2'-O-methyl (2'-O-Me), 2'-O-methoxyethyl (2'MOE), 2'-O-aminoethyl, 2'F; N3'->P5' phosphoramidate, 2'dimethylaminooxyethoxy, 2'dimethylaminoethoxyethoxy, 2'-guanidinium, 2'-O-guanidinium ethyl, carbamate modified sugars, and bicyclic modified sugars. In some embodiments, the sugar moiety modification is selected from 2'-O-Me, 2'F, and 2'MOE. In some embodiments, the sugar moiety modification is an extra bridge bond, such as in a locked nucleic acid (LNA). In some embodiments the sugar analog contains a morpholine ring, such as phosphorodiamidate morpholino (PMO). In some embodiments, the sugar moiety comprises a ribofuranosyl or 2'deoxyribofuranosyl modification. In some embodiments, the sugar moiety comprises 2'4'-constrained 2'O-methyoxyethyl (cMOE) modifications. In some embodiments, the sugar moiety comprises cEt 2', 4' constrained 2'-O ethyl BNA modifications. In some embodiments, the sugar moiety comprises tricycloDNA (tcDNA) modifications. In some embodiments, the sugar moiety comprises ethylene nucleic acid (ENA) modifications. In some embodiments, the sugar moiety comprises MCE modifications. Modifications are known in the art and described in the literature, e.g., by Jarver, et al., 2014, "A Chemical View of Oligonucleotides for Exon Skipping and Related Drug Applications," Nucleic Acid Therapeutics 24(1): 37-47, incorporated by reference for this purpose herein.

In some embodiments, each monomer of the ASO is modified in the same way, for example each linkage of the backbone of the ASO comprises a phosphorothioate linkage or each ribose sugar moiety comprises a 2'O-methyl modification. Such modifications that are present on each of the monomer components of an ASO are referred to as "uniform modifications." In some examples, a combination of different modifications may be desired, for example, an ASO may comprise a combination of phosphorodiamidate linkages and sugar moieties comprising morpholine rings (morpholinos). Combinations of different modifications to an ASO are referred to as "mixed modifications" or "mixed chemistries."

In some embodiments, the ASO comprises one or more backbone modifications. In some embodiments, the ASO comprises one or more sugar moiety modification. In some embodiments, the ASO comprises one or more backbone modifications and one or more sugar moiety modifications. In some embodiments, the ASO comprises a 2'MOE modification and a phosphorothioate backbone. In some embodiments, the ASO comprises a phosphorodiamidate morpholino (PMO). In some embodiments, the ASO comprises a peptide nucleic acid (PNA). Any of the ASOs or any component of an ASO (e.g., a nucleobase, sugar moiety, backbone) described herein may be modified in order to achieve desired properties or activities of the ASO or reduce undesired properties or activities of the ASO. For example, an ASO or one or more components of any ASO may be modified to enhance binding affinity to a target sequence on a pre-mRNA transcript; reduce binding to any non-target sequence; reduce degradation by cellular nucleases (i.e., RNase H); improve uptake of the ASO into a cell and/or into the nucleus of a cell; alter the pharmacokinetics or pharmacodynamics of the ASO; and/or modulate the half-life of the ASO.

In some embodiments, the ASOs are comprised of 2'-O-(2-methoxyethyl) (MOE) phosphorothioate-modified nucleotides. ASOs comprised of such nucleotides are especially well-suited to the methods disclosed herein; oligomers having such modifications have been shown to have significantly enhanced resistance to nuclease degradation and increased bioavailability, making them suitable, for example, for oral delivery in some embodiments described herein. See e.g., Geary, et al., J Pharmacol Exp Ther. 2001; 296(3):890-7; Geary, et al., J Pharmacol Exp Ther. 2001; 296(3):898-904.

Methods of synthesizing ASOs will be known to one of skill in the art. Alternatively or in addition, ASOs may be obtained from a commercial source.

Unless specified otherwise, the left-hand end of single-stranded nucleic acid (e.g., pre-mRNA transcript, oligonucleotide, ASO, etc.) sequences is the 5' end and the left-hand direction of single or double-stranded nucleic acid sequences is referred to as the 5' direction. Similarly, the right-hand end or direction of a nucleic acid sequence (single or double stranded) is the 3' end or direction. Generally, a region or sequence that is 5' to a reference point in a nucleic acid is referred to as "upstream," and a region or sequence that is 3' to a reference point in a nucleic acid is referred to as "downstream." Generally, the 5' direction or end of an mRNA is where the initiation or start codon is located, while the 3' end or direction is where the termination codon is located. In some aspects, nucleotides that are upstream of a reference point in a nucleic acid may be designated by a negative number, while nucleotides that are downstream of a reference point may be designated by a positive number. For example, a reference point (e.g., an exon-exon junction in mRNA) may be designated as the "zero" site, and a nucleotide that is directly adjacent and upstream of the reference point is designated "minus one," e.g., "−1," while a nucleotide that is directly adjacent and downstream of the reference point is designated "plus one," e.g., "+1."

In some embodiments, the ASOs are complementary to (and bind to) a targeted portion of a SCN1A NIE containing pre-mRNA that is downstream (in the 3' direction) of the 5' splice site (or 3' end of the NIE) of the included exon in a SCN1A NIE containing pre-mRNA (e.g., the direction designated by positive numbers relative to the 5' splice site). In some embodiments, the ASOs are complementary to a targeted portion of the SCN1A NIE containing pre-mRNA that is within the region about +1 to about +500 relative to the 5' splice site (or 3' end) of the included exon. In some embodiments, the ASOs may be complementary to a targeted portion of a SCN1A NIE containing pre-mRNA that is within the region between nucleotides +6 and +496 relative to the 5' splice site (or 3' end) of the included exon. In some aspects, the ASOs are complementary to a targeted portion that is within the region about +1 to about +500, about +1 to about +490, about +1 to about +480, about +1 to about +470, about +1 to about +460, about +1 to about +450, about +1 to about +440, about +1 to about +430, about +1 to about +420, about +1 to about +410, about +1 to about +400, about +1 to about +390, about +1 to about +380, about +1 to about +370, about +1 to about +360, about +1 to about +350, about +1 to about +340, about +1 to about +330, about +1 to about +320, about +1 to about +310, about +1 to about +300, about +1 to about +290, about +1 to about +280, about +1 to about +270, about +1 to about +260, about +1 to about +250, about +1 to about +240, about +1 to about +230, about +1 to about +220, about +1 to about +210, about +1 to about +200, about +1 to about +190, about +1 to about +180, about +1 to about +170, about +1 to about +160, about +1 to about +150, about +1 to about +140, about +1 to about +130, about +1 to about +120, about +1 to about +110, about +1 to about +100, about +1 to about +90, about +1 to about +80, about +1 to about +70, about +1 to about +60, about +1 to about +50, about +1 to about +40, about +1 to about +30, or about +1 to about +20 relative to 5' splice site (or 3' end) of the included exon. In some aspects, the ASOs are complementary to a targeted portion that is within the region from about +1 to about +100, from about +100 to about +200, from about +200 to about +300, from about +300 to about +400, or from about +400 to about +500 relative to 5' splice site (or 3' end) of the included exon.

In some embodiments, the ASOs are complementary to (and bind to) a targeted portion of a SCN1A NIE containing pre-mRNA that is upstream (in the 5' direction) of the 5' splice site (or 3' end) of the included exon in a SCN1A NIE containing pre-mRNA (e.g., the direction designated by negative numbers relative to the 5' splice site). In some embodiments, the ASOs are complementary to a targeted portion of the SCN1A NIE containing pre-mRNA that is within the region about −4 to about −270 relative to the 5' splice site (or 3' end) of the included exon. In some embodiments, the ASOs may be complementary to a targeted portion of a SCN1A NIE containing pre-mRNA that is within the region between nucleotides −1 and −264 relative to the 5' splice site (or 3' end) of the included exon. In some aspects, the ASOs are complementary to a targeted portion that is within the region about −1 to about −270, about −1 to about −260, about −1 to about −250, about −1 to about −240, about −1 to about −230, about −1 to about −220, about −1 to about −210, about −1 to about −200, about −1 to about −190, about −1 to about −180, about −1 to about −170, about −1 to about −160, about −1 to about −150, about −1 to about −140, about −1 to about −130, about −1 to about −120, about −1 to about −110, about −1 to about −100, about −1 to about −90, about −1 to about −80, about −1 to about −70, about −1 to about −60, about −1 to about −50, about −1 to about −40, about −1 to about −30, or about −1 to about −20 relative to 5' splice site (or 3' end) of the included exon. In some aspects, the ASOs are complementary to a targeted portion that is within the region from about −1 to about −50, from about −50 to about −100, from about −100 to about −150, from about −150 to about −200, or from about −200 to about −250 relative to 5' splice site (or 3' end) of the included exon.

In some embodiments, the ASOs are complementary to a targeted region of a SCN1A NIE containing pre-mRNA that is upstream (in the 5' direction) of the 3' splice site (or 5' end) of the included exon in a SCN1A NIE containing pre-mRNA (e.g., in the direction designated by negative numbers). In some embodiments, the ASOs are complementary to a targeted portion of the SCN1A NIE containing pre-mRNA that is within the region about −1 to about −500 relative to the 3' splice site (or 5' end) of the included exon. In some embodiments, the ASOs are complementary to a targeted portion of the SCN1A NIE containing pre-mRNA that is within the region −1 to −496 relative to the 3' splice site of the included exon. In some aspects, the ASOs are complementary to a targeted portion that is within the region about −1 to about −500, about −1 to about −490, about −1 to about −480, about −1 to about −470, about −1 to about −460, about −1 to about −450, about −1 to about −440, about −1 to about −430, about −1 to about −420, about −1 to about −410, about −1 to about −400, about −1 to about −390, about −1 to about −380, about −1 to about −370, about −1 to about −360, about −1 to about −350, about −1 to about −340, about −1 to about −330, about −1 to about −320, about −1 to about −310, about −1 to about −300, about −1 to about −290, about −1 to about −280, about −1 to about −270, about −1 to about −260, about −1 to about −250, about −1 to about −240, about −1 to about −230, about −1 to about −220, about −1 to about −210, about −1 to about −200, about −1 to about −190, about −1 to about −180, about −1 to about −170, about −1 to about −160, about −1 to about −150, about −1 to about −140, about −1 to about −130, about −1 to about −120, about −1 to about −110, about −1 to about −100, about −1 to about −90, about −1 to about −80, about −1 to about −70, about −1 to about −60, about −1 to about −50, about −1 to about −40, or about −1 to about −30 relative to 3' splice site of the included exon. In some aspects, the ASOs are complementary to a targeted portion that is within the region from about −1 to about −100, from about −100 to about −200, from about −200 to about −300, from about −300 to about −400, or from about −400 to about −500 relative to 3' splice site of the included exon.

In some embodiments, the ASOs are complementary to a targeted region of a SCN1A NIE containing pre-mRNA that is downstream (in the 3' direction) of the 3' splice site (5' end) of the included exon in a SCN1A NIE containing pre-mRNA (e.g., in the direction designated by positive numbers). In some embodiments, the ASOs are complementary to a targeted portion of the SCN1A NIE containing pre-mRNA that is within the region of about +1 to about +100 relative to the 3' splice site of the included exon. In some aspects, the ASOs are complementary to a targeted portion that is within the region about +1 to about +90, about +1 to about +80, about +1 to about +70, about +1 to about +60, about +1 to about +50, about +1 to about +40, about +1 to about +30, about +1 to about +20, or about +1 to about +10 relative to 3' splice site of the included exon.

In some embodiments, the targeted portion of the SCN1A NIE containing pre-mRNA is within the region +100 relative to the 5' splice site (3' end) of the included exon to −100 relative to the 3' splice site (5' end) of the included exon. In some embodiments, the targeted portion of the SCN1A NIE containing pre-mRNA is within the NIE. In some embodiments, the targeted portion of the SCN1A NIE containing pre-mRNA comprises a pseudo-exon and intron boundary.

The ASOs may be of any length suitable for specific binding and effective enhancement of splicing. In some embodiments, the ASOs consist of 8 to 50 nucleobases. For example, the ASO may be 8, 9, 10, 11, 12, 13, 14, 15, 16, 17, 18, 19, 20, 21, 22, 23, 24, 25, 26, 27, 28, 29, 30, 31, 32, 33, 34, 35, 40, 45, or 50 nucleobases in length. In some embodiments, the ASOs consist of more than 50 nucleobases. In some embodiments, the ASO is from 8 to 50 nucleobases, 8 to 40 nucleobases, 8 to 35 nucleobases, 8 to 30 nucleobases, 8 to 25 nucleobases, 8 to 20 nucleobases, 8 to 15 nucleobases, 9 to 50 nucleobases, 9 to 40 nucleobases, 9 to 35 nucleobases, 9 to 30 nucleobases, 9 to 25 nucleobases, 9 to 20 nucleobases, 9 to 15 nucleobases, 10 to 50 nucleobases, 10 to 40 nucleobases, 10 to 35 nucleobases, 10 to 30 nucleobases, 10 to 25 nucleobases, 10 to 20 nucleobases, 10 to 15 nucleobases, 11 to 50 nucleobases, 11 to 40 nucleobases, 11 to 35 nucleobases, 11 to 30 nucleobases, 11 to 25 nucleobases, 11 to 20 nucleobases, 11 to 15 nucleobases, 12 to 50 nucleobases, 12 to 40 nucleobases, 12 to 35 nucleobases, 12 to 30 nucleobases, 12 to 25 nucleobases, 12 to 20 nucleobases, 12 to 15 nucleobases, 13 to 50 nucleobases, 13 to 40 nucleobases, 13 to 35 nucleobases, 13 to 30 nucleobases, 13 to 25 nucleobases, 13 to 20 nucleobases, 14 to 50 nucleobases, 14 to 40 nucleobases, 14 to 35 nucleobases, 14 to 30 nucleobases, 14 to 25 nucleobases, 14 to 20 nucleobases, 15 to 50 nucleobases, 15 to 40 nucleobases, 15 to 35 nucleobases, 15 to 30 nucleobases, 15 to 25 nucleobases, 15 to 20 nucleobases, 20 to 50 nucleobases, 20 to 40 nucleobases, 20 to 35 nucleobases, 20 to 30 nucleobases, 20 to 25 nucleobases, 25 to 50 nucleobases, 25 to 40 nucleobases, 25 to 35 nucleobases, or 25 to 30 nucleobases in length. In some embodiments, the ASOs are 18 nucleotides in length. In some embodiments, the ASOs are 15 nucleotides in length. In some embodiments, the ASOs are 25 nucleotides in length.

In some embodiments, two or more ASOs with different chemistries but complementary to the same targeted portion of the NIE containing pre-mRNA are used. In some embodiments, two or more ASOs that are complementary to different targeted portions of the NIE containing pre-mRNA are used.

In embodiments, the antisense oligonucleotides of the invention are chemically linked to one or more moieties or conjugates, e.g., a targeting moiety or other conjugate that enhances the activity or cellular uptake of the oligonucleotide. Such moieties include, but are not limited to, a lipid moiety, e.g., as a cholesterol moiety, a cholesteryl moiety, an aliphatic chain, e.g., dodecandiol or undecyl residues, a polyamine or a polyethylene glycol chain, or adamantane acetic acid. Oligonucleotides comprising lipophilic moieties and preparation methods have been described in the published literature. In embodiments, the antisense oligonucleotide is conjugated with a moiety including, but not limited to, an abasic nucleotide, a polyether, a polyamine, a polyamide, a peptides, a carbohydrate, e.g., N-acetylgalactosamine (GalNAc), N—Ac-Glucosamine (GluNAc), or mannose (e.g., mannose-6-phosphate), a lipid, or a polyhydrocarbon compound. Conjugates can be linked to one or more of any nucleotides comprising the antisense oligonucleotide at any of several positions on the sugar, base or phosphate group, as understood in the art and described in the literature, e.g., using a linker. Linkers can include a bivalent or trivalent branched linker. In embodiments, the conjugate is attached to the 3' end of the antisense oligonucleotide. Methods of preparing oligonucleotide conjugates are described, e.g., in U.S. Pat. No. 8,450,467, "Carbohydrate conjugates as delivery agents for oligonucleotides," incorporated by reference herein.

In some embodiments, the nucleic acid to be targeted by an ASO is a SCN1A NIE containing pre-mRNA expressed in a cell, such as a eukaryotic cell. In some embodiments, the term "cell" may refer to a population of cells. In some embodiments, the cell is in a subject. In some embodiments, the cell is isolated from a subject. In some embodiments, the cell is ex vivo. In some embodiments, the cell is a condition or disease-relevant cell or a cell line. In some embodiments, the cell is in vitro (e.g., in cell culture).

Pharmaceutical Compositions

Pharmaceutical compositions or formulations comprising the agent, e.g., antisense oligonucleotide, of the described compositions and for use in any of the described methods can be prepared according to conventional techniques well known in the pharmaceutical industry and described in the published literature. In embodiments, a pharmaceutical composition or formulation for treating a subject comprises an effective amount of any antisense oligomer as described herein, or a pharmaceutically acceptable salt, solvate, hydrate or ester thereof. The pharmaceutical formulation comprising an antisense oligomer may further comprise a pharmaceutically acceptable excipient, diluent or carrier.

Pharmaceutically acceptable salts are suitable for use in contact with the tissues of humans and lower animals without undue toxicity, irritation, allergic response, etc., and are commensurate with a reasonable benefit/risk ratio. (See, e.g., S. M. Berge, et al., J. Pharmaceutical Sciences, 66: 1-19 (1977), incorporated herein by reference for this purpose. The salts can be prepared in situ during the final isolation and purification of the compounds, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other documented methodologies such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In embodiments, the compositions are formulated into any of many possible dosage forms such as, but not limited to, tablets, capsules, gel capsules, liquid syrups, soft gels, suppositories, and enemas. In embodiments, the compositions are formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers. In embodiments, a pharmaceutical formulation or composition of the present invention includes, but is not limited to, a solution, emulsion, microemulsion, foam or liposome-containing formulation (e.g., cationic or noncationic liposomes).

The pharmaceutical composition or formulation described herein may comprise one or more penetration enhancers, carriers, excipients or other active or inactive ingredients as appropriate and well known to those of skill in the art or described in the published literature. In embodiments, liposomes also include sterically stabilized liposomes, e.g., liposomes comprising one or more specialized lipids. These specialized lipids result in liposomes with enhanced circulation lifetimes. In embodiments, a sterically stabilized liposome comprises one or more glycolipids or is derivatized with one or more hydrophilic polymers, such as a polyethylene glycol (PEG) moiety. In embodiments, a surfactant is included in the pharmaceutical formulation or compositions. The use of surfactants in drug products, formulations and emulsions is well known in the art. In embodiments, the present invention employs a penetration enhancer to effect the efficient delivery of the antisense oligonucleotide, e.g., to aid diffusion across cell membranes and/or enhance the permeability of a lipophilic drug. In embodiments, the penetration enhancers are a surfactant, fatty acid, bile salt, chelating agent, or non-chelating nonsurfactant.

In embodiments, the pharmaceutical formulation comprises multiple antisense oligonucleotides. In embodiments, the antisense oligonucleotide is administered in combination with another drug or therapeutic agent.

Combination Therapies

In some embodiments, the ASOs disclosed in the present disclosure can be used in combination with one or more additional therapeutic agents. In some embodiments, the one or more additional therapeutic agents can comprise a small molecule. For example, the one or more additional therapeutic agents can comprise a small molecule described in WO2016128343A1, WO2017053982A1, WO2016196386A1, WO201428459A1, WO201524876A2, WO2013119916A2, and WO2014209841A2, which are incorporated by reference herein in their entirety. In some embodiments, the one or more additional therapeutic agents comprise an ASO that can be used to correct intron retention. In some embodiments, the one or more other agents are selected from the ASOs listed in Table 4.

Treatment of Subjects

Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In embodiments, the individual is a human. In embodiments, the individual is a fetus, an embryo, or a child. In other embodiments, the individual may be another eukaryotic organism, such as a plant. In some embodiments, the compositions provided herein are administered to a cell ex vivo.

In some embodiments, the compositions provided herein are administered to an individual as a method of treating a disease or disorder. In some embodiments, the individual has a genetic disease, such as any of the diseases described herein. In some embodiments, the individual is at risk of having a disease, such as any of the diseases described herein. In some embodiments, the individual is at increased risk of having a disease or disorder caused by insufficient amount of a protein or insufficient activity of a protein. If an individual is "at an increased risk" of having a disease or disorder caused insufficient amount of a protein or insufficient activity of a protein, the method involves preventative or prophylactic treatment. For example, an individual may be at an increased risk of having such a disease or disorder because of family history of the disease. Typically, individuals at an increased risk of having such a disease or disorder benefit from prophylactic treatment (e.g., by preventing or delaying the onset or progression of the disease or disorder).

In embodiments, a fetus is treated in utero, e.g., by administering the ASO composition to the fetus directly or indirectly (e.g., via the mother).

Suitable routes for administration of ASOs of the present invention may vary depending on cell type to which delivery of the ASOs is desired. Multiple tissues and organs are affected by Dravet syndrome; Epilepsy, generalized, with febrile seizures plus, type 2; Febrile seizures, familial, 3A; Migraine, familial hemiplegic, 3; Autism; Epileptic encephalopathy, early infantile, 13; Sick sinus syndrome 1; Alzheimer's disease or SUDEP, with the brain being the most significantly affected tissue. The ASOs of the present invention may be administered to patients parenterally, for example, by intrathecal injection, intracerebroventricular injection, intraperitoneal injection, intramuscular injection, subcutaneous injection, intravitreal injection, or intravenous injection.

In some embodiments, the disease or condition is induced by a mutation in $Na_v1.1$ (a protein encoded by the SCN1A gene). In some instances, the mutation is a loss-of-function mutation in $Na_v1.1$. In some cases, the loss-of-function mutation in $Na_v1.1$ comprises one or more mutations that decreases or impairs the function of $Na_v1.1$ (e.g., by 10%, 20%, 30%, 40%, 50%, 60%, 70%, 80%, 90%, 95%, or more) relative to the function of a wild-type $Na_v1.1$. In some cases, the loss-of-function mutation in $Na_v1.1$ comprises one or more mutations that result in a disease phenotype. Exemplary loss-of-function mutations include, but are not limited to, R859C, T875M, V1353L, I1656M, R1657C, A1685V, M1841T, and R1916G.

In other instances, the mutation is a gain-of-function mutation in $Na_v1.1$. In such cases, the gain-of-function mutation comprises one or more mutations that prolongs activation of $Na_v1.1$ (e.g., by 10%, 20%, 30%, 40%, 50%, 60%, 70%, 80%, 90%, 95%, or more) relative to the function of a wild-type $Na_v1.1$. In such cases, the gain-of-function mutation in $Na_v1.1$ comprises one or more mutations that result in a disease phenotype. Exemplary gain-of-function mutations include, but are not limited to, D188V, W1204R, R1648H, and D1866Y.

In some embodiments, the disease or condition is an encephalopathy. In some cases, the encephalopathy is induced by a loss-of-function mutation in $Na_v1.1$.

In some embodiments, the encephalopathy is epileptic encephalopathy. Exemplary epileptic encephalopathies include, but are not limited to, Dravet Syndrome (DS) (also known as severe myoclonic epilepsy of infancy or SMEI); severe myoclonic epilepsy of infancy (SMEI)-borderland (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; sudden unexpected death in epilepsy (SUDEP); early infantile SCN1A encephalopathy; early infantile epileptic encephalopathy (EIEE); or sick sinus syndrome 1. In some embodiments, the disease or condition is epileptic encephalopathy, optionally selected from Dravet Syndrome (DS) (also known as severe myoclonic epilepsy of infancy or SMEI); severe myoclonic epilepsy of infancy (SMEI)-borderland (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; sudden unexpected death in epilepsy (SUDEP); and sick sinus syndrome 1.

In some instances, GEFS+ is epilepsy, generalized, with febrile seizures plus, type 2.

In some instances, the Febrile seizure is Febrile seizures, familial, 3A.

In some instances, SMEB is SMEB without generalized spike wave (SMEB-SW), SMEB without myoclonic seizures (SMEB-M), SMEB lacking more than one feature of SMEI (SMEB-O), or intractable childhood epilepsy with generalized tonic-clonic seizures (ICEGTC).

In some embodiments, the diseases or conditions induced by a loss-of-function mutation in $Na_v1.1$ include, but are not limited to, Dravet Syndrome (DS) (also known as SMEI); severe myoclonic epilepsy of infancy (SMEI)-borderland (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; sudden unexpected death in epilepsy (SUDEP); sick sinus syndrome 1; early infantile SCN1A encephalopathy; early infantile epileptic encephalopathy (EIEE); autism; or malignant migrating partial seizures of infancy.

In some embodiments, the disease or condition is induced by a gain-of-function mutation in $Na_v1.1$. Exemplary diseases or conditions associated with a gain-of-function mutation in $Na_v1.1$ include, but are not limited to, migraine. In some instances, the disease or condition induced by a gain-of-function mutation in $Na_v1.1$ is migraine.

In some instances, the migraine is migraine, familial hemiplegic, 3.

In some embodiments, the disease or condition is a $Na_v1.1$ genetic epilepsy. The $Na_v1.1$ genetic epilepsy can include a loss-of-function mutation in $Na_v1.1$ or a gain-of-function mutation in $Na_v1.1$. In some cases, the $Na_v1.1$ genetic epilepsy includes one or more hereditary mutations. In other cases, the $Na_v1.1$ genetic epilepsy includes one or more de novo mutations. In some cases, the $Na_v1.1$ genetic epilepsy includes Dravet Syndrome (DS) (also known as severe myoclonic epilepsy of infancy or SMEI); severe myoclonic epilepsy of infancy (SMEI)-borderland (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; early infantile SCN1A encephalopathy; early infantile epileptic encephalopathy (EIEE); sudden unexpected death in epilepsy (SUDEP); or malignant migrating partial seizures of infancy. In some cases, the $Na_v1.1$ genetic epilepsy associated with a loss-of-function mutation in $Na_v1.1$ includes Dravet Syndrome (DS) (also known as severe myoclonic epilepsy of infancy or SMEI); severe myoclonic epilepsy of infancy (SMEI)-borderland (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; early infantile SCN1A encephalopathy; early infantile epileptic encephalopathy (EIEE); sudden unexpected death in epilepsy (SUDEP); malignant migrating partial seizures of infancy.

In some embodiments, the disease or condition is associated with a haploinsufficiency of the SCN1A gene. Exemplary diseases or conditions associated with a haploinsufficiency of the SCN1A gene include, but are not limited to, Dravet Syndrome (DS) (also known as SMEI); severe myoclonic epilepsy of infancy (SMEI)-borderland (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; sudden unexpected death in epilepsy (SUDEP); sick sinus syndrome 1; early infantile SCN1A encephalopathy; early infantile epileptic encephalopathy (EIEE); or malignant migrating partial seizures of infancy. In some cases, the disease or condition is Dravet Syndrome (DS) (also known as SMEI); severe myoclonic epilepsy of infancy (SMEI)-borderland (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; sudden unexpected death in epilepsy (SUDEP); sick sinus syndrome 1; early infantile SCN1A encephalopathy; early infantile epileptic encephalopathy (EIEE); or malignant migrating partial seizures of infancy.

In some cases, the disease or condition is Dravet Syndrome (DS).

Dravet syndrome (DS), otherwise known as severe myoclonic epilepsy of infancy (SMEI), is an epileptic encephalopathy presenting in the first year of life. Dravet syndrome is an increasingly recognized epileptic encephalopathy in which the clinical diagnosis is supported by the finding of sodium channel gene mutations in approximately 70-80% of patients. Mutations of ion channel genes play a major role in the pathogenesis of a range of epilepsy syndromes, resulting in some epilepsies being regarded as channelopathies. Voltage-gated sodium channels (VGSCs) play an essential role in neuronal excitability; therefore, it is not surprising that many mutations associated with DS have been identified in the gene encoding a VGSC subunit. The disease is described by, e.g., Mulley, et al., 2005, and the disease description at OMIM #607208 (Online Mendelian Inheritance in Man, Johns Hopkins University, 1966-2015), both incorporated by reference herein.

Between 70/a and 80% of patients carry sodium channel al subunit gene (SCN1A) abnormalities, and truncating mutations account for about 40%, and have a significant correlation with an earlier age of seizures onset. Sequencing mutations are found in about 70% of cases and comprise truncating (40%) and missense mutations (40%) with the remaining being splice-site changes. Most mutations are de novo, but familial mutations occur in 5-10% of cases and are usually missense in nature. The remaining SCN1A mutations comprise splice-site and missense mutations, most of which fall into the pore-forming region of the sodium channel. At present, over 500 mutations have been associated with DS and are randomly distributed along the gene (Mulley, et al., *Neurol.* 2006, 67, 1094-1095).

The SCN1A gene is located in the cluster of sodium channel genes on human chromosome 2q24 and encodes the α-pore forming subunits known as $Na_v1.1$ of the neuronal voltage gated sodium channel. The SCN1A gene spans approximately 100 kb of genomic DNA and comprises 26 exons. The SCN1A protein consists of four domains, each with six-transmembrane segments. Two splice variants have been identified that result in a long and short isoform that differ in the presence or absence of 11 amino acids in the cytoplasmic loop between domains 1 and 2, in exon 11 (Miller, et al., 1993-2015, and Mulley, et al., 2005, 25, 535-542, incorporated herein by reference).

Alternative splicing events in SCN1A gene can lead to non-productive mRNA transcripts which in turn can lead to aberrant protein expression, and therapeutic agents which can target the alternative splicing events in SCN1A gene can modulate the expression level of functional proteins in DS patients and/or inhibit aberrant protein expression. Such therapeutic agents can be used to treat a condition caused by SCN1A protein deficiency.

One of the alternative splicing events that can lead to non-productive mRNA transcripts is the inclusion of an extra exon in the mRNA transcript that can induce non-sense mediated mRNA decay. The present disclosure provides compositions and methods for modulating alternative splicing of SCN1A to increase the production of protein-coding mature mRNA, and thus, translated functional SCN1A protein. These compositions and methods include antisense oligomers (ASOs) that can cause exon skipping and promote constitutive splicing of SCN1A pre-mRNA. In various embodiments, functional SCN1A protein can be increased using the methods of the disclosure to treat a condition caused by SCN1A protein deficiency.

In some cases, the disease or condition is SMEB.

In some cases, the disease or condition is GEFS+.

In some cases, the disease or condition is a Febrile seizure (e.g., Febrile seizures, familial, 3A).

In some cases, the disease or condition is autism (also known as autism spectrum disorder or ASD).

In some cases, the disease or condition is migraine (e.g., migraine, familial hemiplegic, 3).

In some cases, the disease or condition is Alzheimer's disease.

In some embodiments, the disease or condition is SCN2A encephalopathy.

In some embodiments, the disease or condition is SCN8A encephalopathy.

In some embodiments, the disease or condition is SCN5A arrhythmia.

In embodiments, the antisense oligonucleotide is administered with one or more agents capable of promoting penetration of the subject antisense oligonucleotide across the blood-brain barrier by any method known in the art. For example, delivery of agents by administration of an adenovirus vector to motor neurons in muscle tissue is described in U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is described, e.g., in U.S. Pat. No. 6,756, 523, "Adenovirus vectors for the transfer of foreign genes into cells of the central nervous system particularly in brain," incorporated herein by reference.

In embodiments, the antisense oligonucleotides are linked or conjugated with agents that provide desirable pharmaceutical or pharmacodynamic properties. In embodiments, the antisense oligonucleotide is coupled to a substance, known in the art to promote penetration or transport across the blood-brain barrier, e.g., an antibody to the transferrin receptor. In embodiments, the antisense oligonucleotide is linked with a viral vector, e.g., to render the antisense compound more effective or increase transport across the blood-brain barrier. In embodiments, osmotic blood brain barrier disruption is assisted by infusion of sugars, e.g., meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids, e.g., glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 9,193,969, "Compositions and methods for selective delivery of oligonucleotide molecules to specific neuron types," U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," each incorporated herein by reference.

In embodiments, an ASO of the invention is coupled to a dopamine reuptake inhibitor (DRI), a selective serotonin reuptake inhibitor (SSRI), a noradrenaline reuptake inhibitor (NRI), a norepinephrine-dopamine reuptake inhibitor (NDRI), and a serotonin-norepinephrine-dopamine reuptake inhibitor (SNDRI), using methods described in, e.g., U.S. Pat. No. 9,193,969, incorporated herein by reference.

In embodiments, subjects treated using the methods and compositions are evaluated for improvement in condition using any methods known and described in the art.

Methods of Identifying Additional ASOs that Induce Exon Skipping

Also within the scope of the present disclosure are methods for identifying or determining ASOs that induce exon skipping of a SCN1A NIE containing pre-mRNA. For example, a method can comprise identifying or determining ASOs that induce pseudo-exon skipping of a SCN1A NIE containing pre-mRNA. ASOs that specifically hybridize to different nucleotides within the target region of the pre-mRNA may be screened to identify or determine ASOs that improve the rate and/or extent of splicing of the target intron. In some embodiments, the ASO may block or interfere with the binding site(s) of a splicing repressor(s)/silencer. Any method known in the art may be used to identify (determine) an ASO that when hybridized to the target region of the exon results in the desired effect (e.g., pseudo-exon skipping, protein or functional RNA production). These methods also can be used for identifying ASOs that induce exon skipping of the included exon by binding to a targeted region in an intron flanking the included exon, or in a non-included exon. An example of a method that may be used is provided below.

A round of screening, referred to as an ASO "walk" may be performed using ASOs that have been designed to hybridize to a target region of a pre-mRNA. For example, the ASOs used in the ASO walk can be tiled every 5 nucleotides from approximately 100 nucleotides upstream of the 3' splice site of the included exon (e.g., a portion of sequence of the exon located upstream of the target/included exon) to approximately 100 nucleotides downstream of the 3' splice site of the target/included exon and/or from approximately 100 nucleotides upstream of the 5' splice site of the included exon to approximately 100 nucleotides downstream of the 5' splice site of the target/included exon (e.g., a portion of sequence of the exon located downstream of the target/included exon). For example, a first ASO of 15 nucleotides in length may be designed to specifically hybridize to nucleotides+6 to +20 relative to the 3' splice site of the target/included exon. A second ASO may be designed to specifically hybridize to nucleotides+11 to +25 relative to the 3' splice site of the target/included exon. ASOs are designed as such spanning the target region of the pre-mRNA. In embodiments, the ASOs can be tiled more closely, e.g., every 1, 2, 3, or 4 nucleotides. Further, the ASOs can be tiled from 100 nucleotides downstream of the 5' splice site, to 100 nucleotides upstream of the 3' splice site. In some embodiments, the ASOs can be tiled from about 1,160 nucleotides upstream of the 3' splice site, to about 500 nucleotides downstream of the 5' splice site. In some embodiments, the ASOs can be tiled from about 500 nucleotides upstream of the 3' splice site, to about 1,920 nucleotides downstream of the 3' splice site.

One or more ASOs, or a control ASO (an ASO with a scrambled sequence, sequence that is not expected to hybridize to the target region) are delivered, for example by transfection, into a disease-relevant cell line that expresses the target pre-mRNA (e.g., a NIE containing pre-mRNA described herein). The exon skipping effects of each of the ASOs may be assessed by any method known in the art, for example by reverse transcriptase (RT)-PCR using primers that span the splice junction, as described in Example 4. A reduction or absence of a longer RT-PCR product produced using the primers spanning the region containing the included exon (e.g. including the flanking exons of the NIE) in ASO-treated cells as compared to in control ASO-treated cells indicates that splicing of the target NIE has been enhanced. In some embodiments, the exon skipping efficiency (or the splicing efficiency to splice the intron containing the NIE), the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

A second round of screening, referred to as an ASO "micro-walk" may be performed using ASOs that have been designed to hybridize to a target region of a pre-mRNA. The ASOs used in the ASO micro-walk are tiled every 1 nucleotide to further refine the nucleotide acid sequence of the pre-mRNA that when hybridized with an ASO results in exon skipping (or enhanced splicing of NIE).

Regions defined by ASOs that promote splicing of the target intron are explored in greater detail by means of an ASO "micro-walk", involving ASOs spaced in 1-nt steps, as well as longer ASOs, typically 18-25 nt.

As described for the ASO walk above, the ASO micro-walk is performed by delivering one or more ASOs, or a control ASO (an ASO with a scrambled sequence, sequence that is not expected to hybridize to the target region), for example by transfection, into a disease-relevant cell line that expresses the target pre-mRNA. The splicing-inducing effects of each of the ASOs may be assessed by any method known in the art, for example by reverse transcriptase (RT)-PCR using primers that span the NIE, as described herein (see, e.g., Example 4). A reduction or absence of a longer RT-PCR product produced using the primers spanning the NIE in ASO-treated cells as compared to in control ASO-treated cells indicates that exon skipping (or splicing of the target intron containing an NIE) has been enhanced. In some embodiments, the exon skipping efficiency (or the splicing efficiency to splice the intron containing the NIE), the ratio of spliced to unspliced pre-mRNA, the rate of splicing, or the extent of splicing may be improved using the ASOs described herein. The amount of protein or functional RNA that is encoded by the target pre-mRNA can also be assessed to determine whether each ASO achieved the desired effect (e.g., enhanced functional protein production). Any method known in the art for assessing and/or quantifying protein production, such as Western blotting, flow cytometry, immunofluorescence microscopy, and ELISA, can be used.

ASOs that when hybridized to a region of a pre-mRNA result in exon skipping (or enhanced splicing of the intron containing a NIE) and increased protein production may be tested in vivo using animal models, for example transgenic mouse models in which the full-length human gene has been knocked-in or in humanized mouse models of disease. Suitable routes for administration of ASOs may vary depending on the disease and/or the cell types to which delivery of the ASOs is desired. ASOs may be administered, for example, by intrathecal injection, intracerebroventricular injection, intraperitoneal injection, intramuscular injection, subcutaneous injection, intravitreal injection, or intravenous injection. Following administration, the cells, tissues, and/or organs of the model animals may be assessed to determine the effect of the ASO treatment by for example evaluating splicing (efficiency, rate, extent) and protein production by methods known in the art and described herein. The animal models may also be any phenotypic or behavioral indication of the disease or disease severity.

As described herein in various examples, exon 20x in human SCN1A gene is equivalent to exon 21x in mouse SCN1A gene.

Figure 3A:
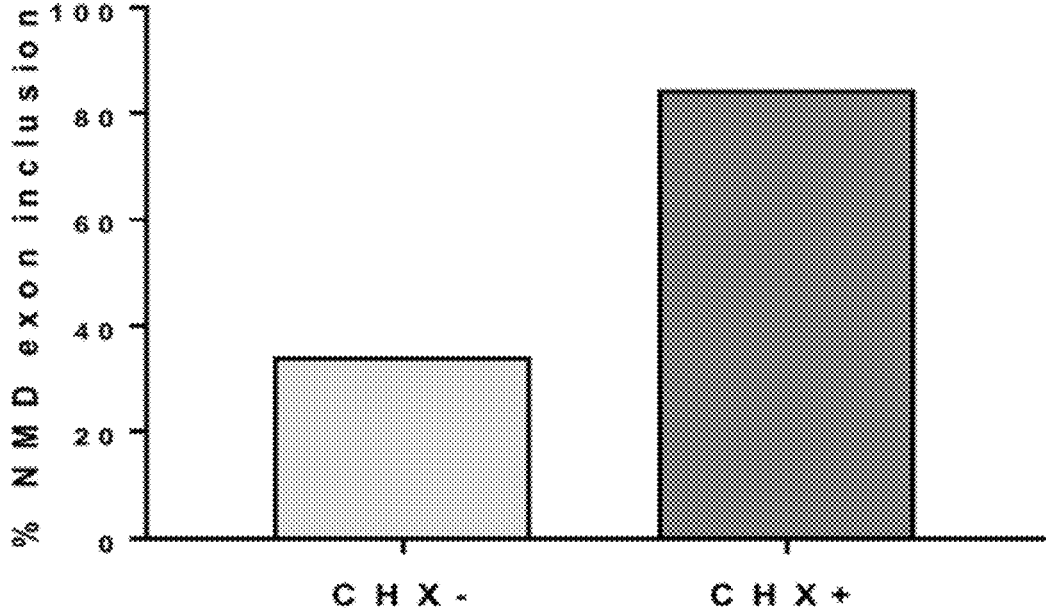
FIG. 3A depicts confirmation of NMD-inducing exon via cycloheximide treatment. RT-PCR analysis using cytoplasmic RNA from DMSO-treated (CHX−) or cycloheximide-treated (CHX+) Neuro 2A (mouse neural progenitor cells) and primers in exon 21 and a downstream exon confirmed the presence of a band corresponding to the NMD-inducing exon (21x). The identity of the product was confirmed by sequencing. Densitometry analysis of the bands was performed to calculate percent exon 21x inclusion of total SCN1A transcript. Treatment of Neuro 2A with cycloheximide (CHX+) to inhibit NMD led to a 2-fold increase of the product corresponding to the NMD-inducing exon 21x in the cytoplasmic fraction (cf. light grey bar, CHX−, to dark grey bar, CHX+).
Figure 3B:
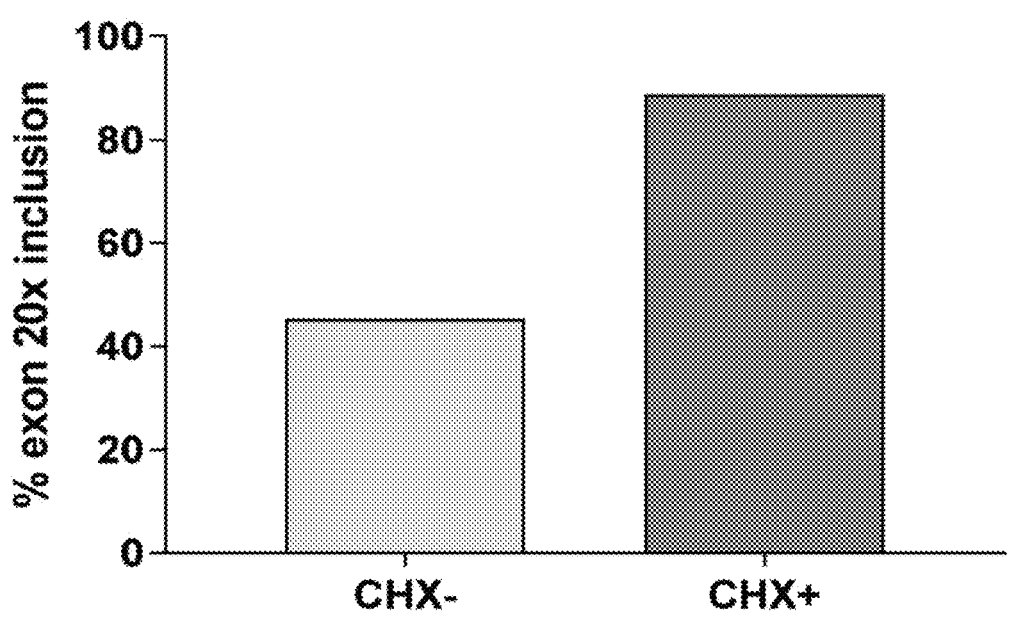
FIG. 3B depicts confirmation of NMD-inducing exon via cycloheximide treatment. RT-PCR analysis using cytoplasmic RNA from DMSO-treated (CHX−) or cycloheximide-treated (CHX+) RenCell VM (human neural progenitor cells) and primers in exon 20 and exon 23 confirmed the presence of a band corresponding to the NMD-inducing exon (20x). The identity of the product was confirmed by sequencing. Densitometry analysis of the bands was performed to calculate percent exon 20x inclusion of total SCN1A transcript. Treatment of RenCell VM with cycloheximide (CHX+) to inhibit NMD led to a 2-fold increase of the product corresponding to the NMD-inducing exon 20x in the cytoplasmic fraction (cf. light grey bar, CHX−, to dark grey bar, CHX+).
Figure 4:
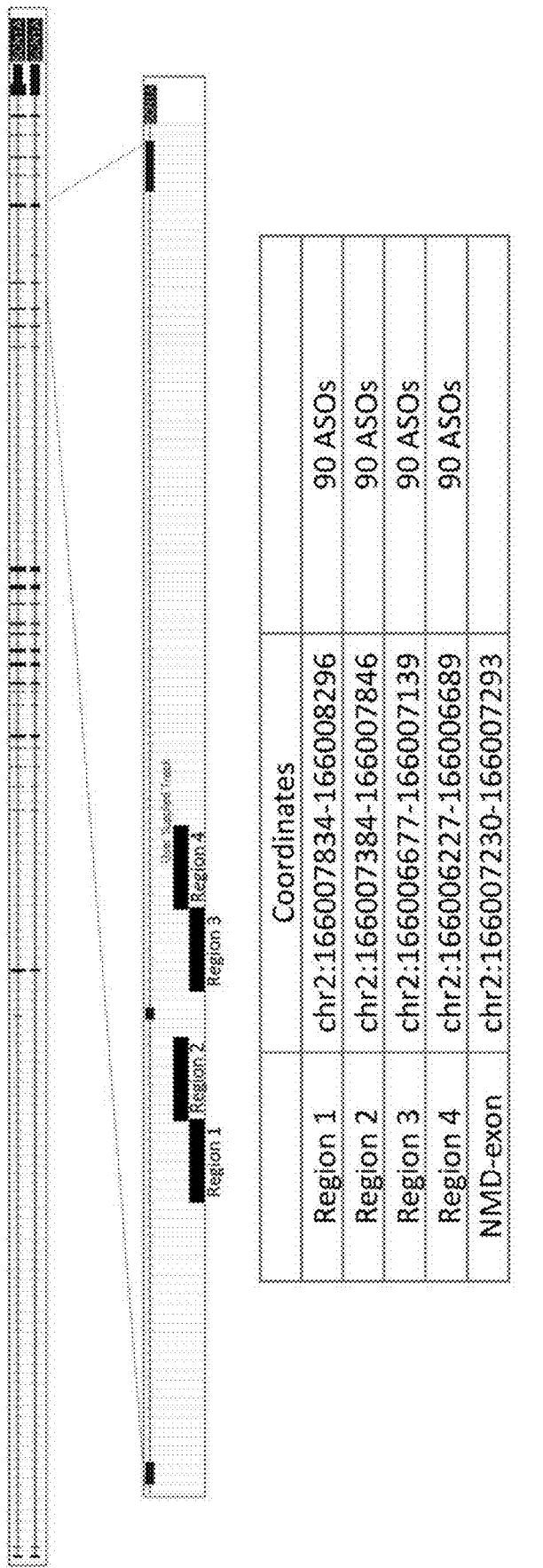
FIG. 4. depicts an exemplary graphic representation of an ASO walk performed for SCN1A exon 20x region targeting two indicated regions (region 1 and region 2) upstream of the 3' splice site of exon 20x and two indicated regions (region 3 and region 4) downstream of the 5' splice site of exon 20x. ASOs were designed to cover these regions by shifting 5 nucleotides at a time.

Also within the scope of the present disclosure is a method to identify or validate an NMD-inducing exon in the presence of an NMD inhibitor, for example, cycloheximide. An exemplary method is provided in FIG. 3 and Example 2.

SPECIFIC EMBODIMENTS

Embodiment 1. A method of modulating expression of SCN1A protein in a cell having an mRNA that contains a non-sense mediated RNA decay-inducing exon (NMD exon mRNA) and encodes SCN1A protein, the method comprising contacting a therapeutic agent to the cell, whereby the therapeutic agent modulates splicing of the NMD exon from the NMD exon mRNA encoding SCN1A protein, thereby modulating the level of processed mRNA encoding SCN1A protein, and modulating expression of SCN1A protein in the cell, wherein the therapeutic agent binds to a targeted portion of the NMD exon mRNA encoding SCN1A, and wherein the targeted portion is: from about 1000 nucleotides upstream from the 5' end of an NMD-inducing exon (NIE) to about 100 nucleotides upstream from the 5' end of the NIE; or from about 100 nucleotides downstream of the 3' end of the NIE to about 1000 nucleotides downstream of the 3' end of the NIE.

Embodiment 2. A method of treating a disease or condition in a subject in need thereof by modulating expression of SCN1A protein in a cell of the subject, comprising: contacting the cell of the subject with a therapeutic agent that modulates splicing of a non-sense mediated mRNA decay-inducing exon (NMD exon) from an mRNA in the cell that contains the NMD exon and encodes SCN1A, thereby modulating the level of processed mRNA encoding the SCN1A protein, and modulating expression of SCN1A protein in the cell of the subject; wherein the therapeutic agent binds to a targeted portion of the NMD exon mRNA encoding SCN1A, and wherein the targeted portion is: from about 1000 nucleotides upstream from the 5' end of an NMD-inducing exon (NIE) to about 100 nucleotides upstream from the 5' end of the NIE; or from about 100 nucleotides downstream of the 3' end of the NIE to about 1000 nucleotides downstream of the 3' end of the NIE.

Embodiment 3. The method of embodiment 1 or 2, wherein the therapeutic agent interferes with binding of a factor involved in splicing of the NMD exon from a region of the targeted portion.

Embodiment 4. The method of embodiment 1 or 2, wherein the targeted portion is at most about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides upstream of 5' end of the NIE.

Embodiment 5. The method of embodiment 1 or 2, wherein the targeted portion is at least about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides upstream of 5' end of the NIE.

Embodiment 6. The method of embodiment 1 or 2, wherein the targeted portion is at most about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides downstream of 3' end of the NIE.

Embodiment 7. The method of embodiment 1 or 2, wherein the targeted portion is at least about 800 nucleotides, about 700 nucleotides, about 600 nucleotides, about 500 nucleotides, about 400 nucleotides, about 300 nucleotides, about 200 nucleotides, about 100 nucleotides, about 80 nucleotides, about 70 nucleotides, about 60 nucleotides, about 50 nucleotides, about 40 nucleotides, about 30 nucleotides, about 20 nucleotides, about 10 nucleotides, about 5 nucleotides, about 4 nucleotides, about 2 nucleotides, about 1 nucleotides downstream of 3' end of the NIE.

Embodiment 8. The method of any one of the embodiments 1-7, wherein the therapeutic agent is an antisense oligomer (ASO).

Embodiment 9. The method of embodiment 8, wherein the ASO comprises a sequence that is at least about 80%, 85%, 90%, 95%, 97%, or 100% identity to any one of SEQ ID NOs: 12-731.

Embodiment 10. The method of any one of the embodiments 1-9, wherein the therapeutic agent promotes exclusion of the NMD exon from the processed mRNA encoding SCN1A protein.

Embodiment 11. The method of embodiment 10, wherein exclusion of the NMD exon from the processed mRNA encoding SCN1A protein in the cell contacted with the therapeutic agent is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to exclusion of the NMD exon from the processed mRNA encoding SCN1A protein in a control cell.

Embodiment 12. The method of embodiment 10, wherein the therapeutic agent increases level of the processed mRNA encoding SCN1A protein in the cell.

Embodiment 13. The method of embodiment 10, wherein an amount of the processed mRNA encoding SCN1A protein in the cell contacted with the therapeutic agent is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to an total amount of the processed mRNA encoding SCN1A protein in a control cell.

Embodiment 14. The method of embodiment 2, wherein the disease or condition is induced by a loss-of-function mutation in Na$_v$1.1.

Embodiment 15. The method of embodiment 14, wherein the disease or condition is associated with haploinsufficiency of the SCN1A gene, and wherein the subject has a first allele encoding a functional SCN1A, and a second allele from which SCN1A is not produced or produced at a reduced level, or a second allele encoding a nonfunctional SCN1A or a partially functional SCN1A.

Embodiment 16. The method of embodiment 14, wherein the disease or condition is encephalopathy.

Embodiment 17. The method of embodiment 16, wherein the encephalopathy is epileptic encephalopathy.

Embodiment 18. The method of embodiment 14, wherein the disease or condition is Dravet Syndrome (DS); severe myoclonic epilepsy of infancy (SMEI)-border-land (SMEB); Febrile seizure (FS); epilepsy, generalized, with febrile seizures plus (GEFS+); epileptic encephalopathy, early infantile, 13; cryptogenic generalized epilepsy; cryptogenic focal epilepsy; myoclonic-astatic epilepsy; Lennox-Gastaut syndrome; West syndrome; idiopathic spasms; early myoclonic encephalopathy; progressive myoclonic epilepsy; alternating hemiplegia of childhood; unclassified epileptic encephalopathy; sudden unexpected death in epilepsy (SUDEP); sick sinus syndrome 1; autism; or malignant migrating partial seizures of infancy.

Embodiment 19. The method of embodiment 18, wherein GEFS+ is epilepsy, generalized, with febrile seizures plus, type 2.

Embodiment 20. The method of embodiment 18, wherein the Febrile seizure is Febrile seizures, familial, 3A.

Embodiment 21. The method of embodiment 18, wherein SMEB is SMEB without generalized spike wave (SMEB-SW), SMEB without myoclonic seizures (SMEB-M), SMEB lacking more than one feature of SMEI (SMEB-O), or intractable childhood epilepsy with generalized tonic-clonic seizures (ICEGTC).

Embodiment 22. The method of embodiments 1 or 2, wherein the ASO consists of a sequence selected from SEQ ID NOs: 72 or 432.

Embodiment 23. The method of embodiments 1 or 2, wherein the ASO consists of a sequence selected from SEQ ID NOs: 73 or 433.

Embodiment 24. The method of embodiments 1 or 2, wherein the ASO consists of a sequence selected from SEQ ID NOs: 76 or 436.

Embodiment 25. The method of embodiments 1 or 2, wherein the ASO consists of a sequence selected from SEQ ID NOs: 181 or 541.

Embodiment 26. The method of embodiments 1 or 2, wherein the ASO consists of a sequence selected from SEQ ID NOs: 220 or 580.

Embodiment 27. A method of modulating expression of SCN1A protein in a cell having an mRNA that contains a non-sense mediated RNA decay-inducing exon (NMD exon mRNA) and encodes SCN1A protein, the method comprising contacting a therapeutic agent to the cell, whereby the therapeutic agent modulates splicing of the NMD exon from the NMD exon mRNA encoding SCN1A protein, thereby modulating the level of processed mRNA encoding SCN1A protein, and modulating expression of SCN1A protein in the cell, wherein the therapeutic agent binds to a targeted portion of the NMD exon mRNA encoding SCN1A, and wherein the targeted portion is from about 1000 nucleotides upstream from the 5' end of an NMD-inducing exon (NIE) to about 1000 nucleotides downstream of the 3' end of the NIE.

Embodiment 28. A method of treating a disease or condition in a subject in need thereof by modulating expression of SCN1A protein in a cell of the subject, comprising: contacting the cell of the subject with a therapeutic agent that modulates splicing of a non-sense mediated mRNA decay-inducing exon (NMD exon) from an mRNA in the cell that contains the NMD exon and encodes SCN1A, thereby modulating the level of processed mRNA encoding the SCN1A protein, and modulating expression of SCN1A protein in the cell of the subject; wherein the therapeutic agent binds to a targeted portion of the NMD exon mRNA encoding SCN1A, and wherein the targeted portion is from about 1000 nucleotides upstream from the 5' end of an NMD-inducing exon (NIE) to about 1000 nucleotides downstream of the 3' end of the NIE.

Embodiment 29. An antisense oligomer (ASO) comprising a sequence that is at least about 80%, 85%, 90%, 95%, 97%, or 100% identity to any one of SEQ ID NOs: 12-731.

Embodiment 30. An antisense oligomer (ASO) consisting of a sequence selected from SEQ ID NOs: 12-731.

Embodiment 31. A method of treating a disease or condition in a subject in need thereof by modulating expression of SCN1A protein in a cell of the subject, comprising: contacting the cell of the subject with an ASO of embodiment 29 or embodiment 30.

Embodiment 32. A kit comprising an ASO of embodiment 29 or embodiment 30.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The present invention will be more specifically illustrated by the following Examples. However, it should be understood that the present invention is not limited by these examples in any manner.

Example 1: Identification of NMD-Inducing Exon Inclusion Events in SCN1A Transcripts by RNAseq Using Next Generation Sequencing Whole transcriptome shotgun sequencing was carried out using next generation sequencing to reveal a snapshot of transcripts produced by the SCN1A gene to identify NIE inclusion events. For this purpose, polyA+RNA from nuclear and cytoplasmic fractions of HCN (human cortical neurons) was isolated and cDNA libraries constructed using Illumina's TruSeq Stranded mRNA library Prep Kit. The libraries were pair-end sequenced resulting in 100-nucleotide reads that were mapped to the human genome (February 2009, GRCh37/hg19 assembly). The sequencing results for SCN1A are shown in FIG. 2. Briefly, FIG. 2 shows the mapped reads visualized using the UCSC genome browser (operated by the UCSC Genome Informatics Group (Center for Biomolecular Science & Engineering, University of California, Santa Cruz, 1156 High Street, Santa Cruz, CA 95064) and described by, e.g., Rosenbloom, et al., 2015, "The UCSC Genome Browser database: 2015 update," Nucleic Acids Research 43, Database Issue, doi: 10.1093/nar/gku1177) and the coverage and number of reads can be inferred by the peak signals. The height of the peaks indicates the level of expression given by the density of the reads in a particular region. The upper panel shows a graphic representation of the SCN1A gene to scale. The conservation level across 100 vertebrate species is shown as peaks. The highest peaks correspond to exons (black boxes), while no peaks are observed for the majority of the introns (lines with arrow heads). Peaks of conservation were identified in intron 20 (NM_006920), shown in the middle panel. Inspection of the conserved sequences identified an exon-like sequence of 64 bp (bottom panel, sequence highlighted in grey) flanked by 3' and 5' splice sites (underlined sequence). Inclusion of this exon leads to a frameshift and the introduction of a premature termination codon in exon 21 rendering the transcript a target of NMD.

Exemplary SCN1A gene, pre-mRNA, exon, and intron sequences are summarized in Table 1. The sequence for each exon or intron is summarized in Table 2.

TABLE 1

List of target SCN1A gene and pre-mRNA sequences.

| Species | SEQ ID NO. | Sequence Type |
|---------|-----------|---------------|
| Human | SEQ ID NO. 1 | SCN1A gene (NC_000002.12) |
|  | SEQ ID NO. 2 | SCN1A pre-mRNA (encoding e.g., SCN1A mRNA NM_006920.5) |
|  | SEQ ID NO. 3 | Intron 22 gene (GRCh38/hg38 assembly) (coordinate: chr2 166002754 166007229) |
|  | SEQ ID NO. 4 | Exon 23 (Exon 20x) gene (GRCh38/hg38 assembly) (coordinate: chr2 166007230 166007293) |
|  | SEQ ID NO. 5 | Intron 23 gene (GRCh38/hg38 assembly) (coordinate: chr2 166007294 166009718) |
|  | SEQ ID NO. 6 | IVS 22 + IVS 23 pre-mRNA (pre-mRNA sequence of introns 22 and 23) |
|  | SEQ ID NO. 7 | Exon 23 (Exon 20x) pre-mRNA |
| Mouse | SEQ ID NO. 8 | SCN1A gene (NC_000068.7) |
|  | SEQ ID NO. 9 | SCN1A pre-mRNA (encoding e.g., SCN1A mRNA NM_001313997.1) |
|  | SEQ ID NO. 10 | Intron 21 pre-mRNA |
|  | SEQ ID NO. 11 | Exon 21x pre-mRNA |

TABLE 2

Sequences of target exon or intron to SCN1A pre-mRNA transcripts.

| SEQ ID NO. | Sequence Type | Sequence |
|------------|---------------|----------|
| 3 | Intron 22 gene | gtaagaaaatgaaagaacctgaagtattgtatatagccaaaattaaactaaattaaatttagaaaaagga aaatctatgcatgcaaaaggaatggcaaattcttgcaaaattgctactttattgttttatctgttgcatatttactt ctaggtgatatgcaagagaaataggcctctcttgaaatgatataatatcatttatctgctgtgcttatttaaatg actttatttcctaatccatcttgggagtttccttacaaatctatatacaaaaaaaagctgatgcattattaaagta ctatgtgtaatgatataatggtaatctaaagtaaattctatatcaggtacttattctagtgatgatatactgtact taacgagttttcctgaaaataatgtgaatcacacatgtgcctaagtatgagtgttaagaaaaaaatgaaagg agttgttaaaacttttgtctgtataatgccaaagtttgcattatttgaatatattcaagattagatggttagatatt aagtgttgactgaatttataaaactagtaatactaacttaaagattacatacaaatccacatcatttttataaca ataaagtaaaacacttataatgaacagaaaatataattttgactcattactataggtaatttatacattaaccttt aacttgcatcttattggtcagagtcacacaaaatgttattttatccttttcaaagatgcaataatcattttccatc atgcataacagattagaaattttgccattattgacttattttccatgcctttttttacggcatgaagcattagttta tagatatataatataaaaaaattagttctgctttttttttaaaaaaaaaatattatcaaaacaaaacactgaattgtgt |

TABLE 2-continued

Sequences of target exon or intron to SCN1A pre-mRNA transcripts.

| SEQ ID NO. | Sequence Type | Sequence |
|---|---|---|
| | | gattccaatagaaaaacactgctctttcacctcctaaggtgtagttacttttatggaaactaagctgtattgta gacttccatttgcactttgtagattgtaatagccttatgttctatctcaagtcttattataaatgtcactttgtaa gaacgtaggacttgtcttcgatttccctaacatatatgaaaactttgtcctcattatcgacaactcagaacaat ataatacaagtagtcctcttttatttctcacagagagcctcaaattttcaccaaaatgttaacagaaattatctc tggggtgtataagaattaagtctgttaccaattaaatgtcactttgltttgtttcagactggcagtttcagttctg gagaaaaaaaatgtcatttgtgtacattctacttgaaaacatgttgcctgaatcaaaataatatattttatatgg cttgtgaaatctgaacaatgctaaacatttgaaaatattataaacctttacatttgaccatttgaaagtttatta aattcattggtcaagtgctcagatatttccatacattacacttcatttctataaaaaagctgatcttatcggtata cttttaattttctcagaaataaccatatctataattattaatcaataatgccttttatattaaaagaggttagtttttg aaacttggagtttagacataaaatccttatataatgctgatagtgatataactaatagtttaaatggtcagattt atgaatatggctctattcctcataatgacaacatacacacagcactaaaatgactaatctcttcaatacgtgtt tggcattgtagagtcaaaataacgttataattgattctattttttatacttctagtgtgtaggatattttattttgtaaa aatataatcatgaatgatggtgaggttggatataagaatgatgattatgattgggaagtgagatttgaacat gctcagaaactctcatttaattctttgccctagcagcataaaatcacaatagctgcgtcaaagcgtaactca ggcactcattttatttttgttgttctgttattttttcaaagcatgtgctttatgcaacattactgaataaagcatgtt gtacagtgcttgataagaagttagaaagtaacaaataaattatcatcacgttgcactttgtgttttgcatgtttt atgcacatttctggctgacagcttttaaacatttattgtatttcaaatttccagtccaaattttttcaacttgtaaaa ttaaactgagtgaattgatgtcgtgaatatctagggtaaaataaaatttgtgtttaaatttgtatttttaatttcct aacctaggaaatcttaaataccttcttttttcaaaagaactcaagtcttaatggataggaaacagacggaga gcatcatgaacaaaaagtaacaccaaatgttctgtcatatcagatttctaactaataacaaactatatatttct attttgtatag |
| 4 | Exon 23 (Exon 20x) gene | GATAATCTTGCTCCAACTTGGATGGGGTGGAGCGCTGGTTCCT CCCCTGAGCCCTTTATTATGG |
| 5 | Intron 23 gene | gtactgtattacccctttgctacctttaatccttgcactgtgacttatgtgtagtggggtgagggagggattg ggaagggtactattattgcaccacagtagggaaaatacattatttacatcctaatcccctcttttcaattgtctt aaatttcatttgaaaaaaaaaaaacctttatgaatttaccctctgtggattttaacccaatggttgatatctttt attaagtttcattgaatatgatttagttatgtgtatatggagttatccatcttgggggagattactggattggtga gggcgggggaccctggtgtagaatgattatgtgaaaaaacaattaacttgttaagctcatgatactgtttg aggcatacagcccctgctgtttagtacattggtctgggtcctgaaaattaccagttagataccatcagttgat tattgatatgtatgagcagatactagggtgcaatatttcaggtttcataagactggtattgattgtgaccactc tcattItttattgtgtaagttcatatggggtatttttcaaaatgttaacaaggcaaaaatatattaagaaatagtt gaataagcacatgtgaattgtgttgtaaacaaaaagttagaataaaaaaatccacttatttgaattatgcaga atagaatacatacctagaaataaaacaaaaacgtcttatcatgagtattaagataaaatttaaggcataaact cacttcttagaataagtaactcccaactaactttctaggattttaaaacataacacagtgaaaacatacataa acataactctacattttatttattcttaaagtttaagtgtattatacaagaagaagagttttatattcgagagaca gaaaaagtcagaatttlllgtttggatcaccaatatatcatagcttacaaaaaaactgtcttaattaaaacccac aacataattttttttagattttttaagaaagattctattattcttctttatacttaaaaatggatgattcctactttgccc acttttattttttattcacatagattttctttatttctattagagaagcactagaattcatgaatagtgttgatttgaa gttcaaagtaattaattcagataaaaagacatttctgcatgtatgaaaatttctaatgtgaatttgcatatttaat tatcaatccttcatttagtgtagacttattttttaaaaatgcaggtaatgaaccagaaatagaattggttgtgcta gagtagagaaactttatttgatgattgltttgaaaaaaaagcttctgagaagaaacaacctctagtacagtat taattcattaagatagctccttctcagacatttcctttcatgtagcctgaaagttcaatttgaaatttgttcttcc aatttattcagactaattctgcctactttcttcccccataagaaccaatttactgcagctttattgagactgaaa aaagttaatacaccctccttattgctgaaccaaggaatggcttggaactcttgggaaaagacaatcttttcta tgatctttcattgtctaatttaatacatcat100110113100t0100gt100taataaactccccaatactgtgcc agatgltttctaagataaagtta111111111111111tt |

TABLE 2-continued

Sequences of target exon or intron to SCN1A pre-mRNA transcripts.

| SEQ ID NO. | Sequence Type | Sequence |
|---|---|---|
| | | aaaaaaaaaaaagtagataataattgaacacagaacttcatgtgatcacatcagatttgagaactatgtatg |
| | | gcatccctcttttttcttattttcctaagaaatgatttctattatgtttcatttgaaataagtttllltgaattaaactcag |
| | | taaatgaaacaactgacatgactggagcttgaaataaacgatgtgatgatctaatgaaatacataatgcaa |
| | | attgtcttgcttcttatgcaaaaattattagtcatagcaatgcatgaataattaaagacaattatattaggtattt |
| | | aataatalttttttatatttatcatctgaatttttaagttattttaaaaatatattggtcaaatcaactcaggtccaaat |
| | | gtttttagttttgttctttaatatattgccttttttaaaatgagttaaacttctgtataggcttttttaacttttctttattc |
| | | tgataacacaattctgacttcatctggcagcaagttcctctgattttccttttccttttaaccttttaatgcttctccct |
| | | cccttttttttaaaaacatttttgtttcatttcttggttatattgcctatagttgtttttcctaagtgtattgcttaagaa |
| | | aaaaaaatgaattttaagatttttttgaaccttgcttttacatatcctagaataaatagcattgatagaaaaaaa |
| | | gaatggaaagaccagagattactaggggaattttttttctttattaacagataagaattctgacttttctttttttc |
| | | catttgtgtattag |
| 6 | IVS 22 + IVS 23 pre-mRNA | guaagaaaaaugaaagaaccugaaguauuguauauagccaaaauuaaacuaaauuaaauuuag |
| | | aaaaaggaaaaucuaugcaugcaaaaggaauggcaaauucuugcaaaauugcuacuuuauugu |
| | | uuuaucuguugcauauuuacuucuaggugauaugcaagagaaauaggccucucuugaaauga |
| | | uauaauaucauuuaucugcugugcuuauuuaaaugacuuuauuuccuaauccaucuugggag |
| | | uuuccuuacaaaucuauauacaaaaaaaagcugaugcauuauuaaaguacuauguguaaugau |
| | | auaaugguaaucuaaaguaaauucuauaucagguacuuauucuuugugaugauauacuguac |
| | | uuaacgaguuuuccugaaaauaaugugaaucacacaugugccuaaguaugaguguuaagaaa |
| | | aaaugaaaggaguuguuaaaacuuuugucuguauaaugccaaaguuugcauuauuugaaua |
| | | uauucaagauuagaugguuagauauuaagguugacugaauuuauaaaacuaguaauacuaa |
| | | cuuaaagauuacauacaaauccacaucauuuuuauaacaauaaaguaaaacacuuuauaugaac |
| | | agaaaauauaauuuugcacucauuacuauagguaauuuauacauuaaccuuaacuugcaucuua |
| | | uuggucagagucacacaaaaugcauauauuauccuuuucaaagaugcaauaaucauuuuccau |
| | | caugcauaacagauuagaaauuuugccauuauugacuuauuuuccaugccuuuuuuuacggc |
| | | augaagcauuaguuuauagauauauaauauaaaaaauuaguucugcuuuuuuuuaaaaaaaa |
| | | auauuaucaaaacaaaacacugaauugugugauuccaauagaaaaacacugcucuuucaccuc |
| | | cuaaggguguaguuacuuuuauggaaacuaagcuguauuguuagacuuccauuugcacuuugua |
| | | gauuguuuauagccuuauguucucuucucaagucuuuauuaaaaugcacuuuuguaagaacg |
| | | uaggacuugucuucgauuucccuaacauauaugaaaacuuuguccucauuaucgacaacucag |
| | | aacaauauaauacaaguaguccucuuuuauuucucacagagagccucaaauuuucaccaaaau |
| | | guuaacagaaauuaucucugggguguauaagaauuaagucuguuuuccaauuaaaaugucacu |
| | | uuguuuuuguuucagacuggcaguuucaguucaguguguacauuc |
| | | uacuugaaaacauguugccugaaucaaaauaauauauuuuauauggcuugugaaaucugaac |
| | | aaugcuaaacauuugaaaauauuauaaaaccuuuuacauuugaccauuugaaaguuuauuaaau |
| | | ucauuggucaagugcucagauauuuccauacauuacacuucauuucuauaaaaaagcugaucu |
| | | uaucgguauacuuuuaauuuucucagaaauaaccauuacuauaauuauuuauucaauaauugccu |
| | | uuuauauuaaaagagguuaguuuuugaaacuuggaguuuuagacauaaaauccuuauaaaug |
| | | cugauagugauauaaucuaauaguguuaaauggucagauuuaugaauauaggcucuauuccucau |
| | | aaugacaacauacacacagcacuaaaaaugacuaaucucuucaauacguguuuggcauuguaga |
| | | gucaaaauaacguuauaauuguuauucuauuuuuauacuucuuucagugguuuggauuauuuuauuu |
| | | uguaaaaauauaaucaugaaugauggugaggguugaauauaagaaugaugauuaugauuuggga |
| | | aguagagauuugaacaugcucagaaacucucauuuaauucuuugcccuagcagcauaaaaaucac |
| | | aauagcugcgucaaagcguaacucaggcacucauuuuauuuuuuguuguucuguuauuuuuuc |
| | | aaagcaugugcuuuuaugcaacauuacugaauaaagcaugguguacagugcuugauaagaag |
| | | uuagaaaguaacaaauaaauuaucaucacguugcacuuuguguuuugcauguuuuaugcaca |
| | | uuucuggcugacagcuuuuaaacauuuauuguauuucaaauuuccaguccaaauuuuucaac |
| | | uuguaaaauuaaacugagugaauugaugucgugaauaucuaggguaaaauaaaaauuugugu |
| | | uaaauuuguauuuuuaaauuccuaaccuaggaaaucuaaaaaaccuucuuuuuucaaaaagaac |
| | | ucaagucuuaauggauaggggaaacagacggagagcaucaugaacaaaaaguaacaccaaaugu |
| | | ucugucauaucagauuucuaacuaauaacaaacuauauauuucuauuuuguauaggguacugu |
| | | auuacccuuuugcuaccuuuaauccuugcacugugacuuauguguaguggggugaggga |
| | | gaauugggaagggguacuauuauugcaccacaguagggaaaauacauuauuuacauccuaauc |
| | | cccucuuuucaauugucuuaaauuucauuugaaaaaaaaaaaccuuuaugaauuuuacccuc |
| | | ugugauuuuaaccccaauggguugauaucuuuauuaaaguuucauugaauaugauuuaguua |
| | | uguguauauggaguuauccaucuuuggggagauuacuggauuggugagggcgggggacccu |
| | | ggguguagaaugauuauguagaaaaaacaauuuaacuuguuaagcucaugauuacuguuugaggc |
| | | auacagcccuggcuguuuaguacauugucugggguccugaaaauuaccaguuagauaccauc |
| | | aguugcauuauugauaugugaugagcagauacuagggugcaauauuucaguuucauuaagacug |
| | | guauugauugugaccacucucauuuuuuauuguguaaguucauuaugggguuauuuuucaaaa |
| | | uguuaacaaggcaaaaauauauuaagaauauaguuaauaagcacaugugaauugugugaa |
| | | acaaaaaguuagaauaaaaaaaauccacuuaauuuugaauuaugcagaauauagaaaucacauccuagaa |
| | | auaaaacaaaaacgucuuaucaugaguauuaagauaaaauuuaaggcauaaacucacuucuua |
| | | gaauaaguaacucccaacuaacuuucuaggauuuuaaaacauaacacagugaaaacauacauaa |
| | | acauaacucuacauuuuauuuaauucuuaaaguuuaaguguauuauacaagaagaagaguuua |
| | | uauucgagagacagaaaagucagaauuuugguggaucaccaauauacauagcuuacaaa |
| | | aaaacugucuuaauuaaaacccacaacauaauuuuuugagauuuuuaagaaagauucuauuau |
| | | ucuucuuuauacuuaaaaaugugaugauuccuacuuugcccacuuuuauuuuuuauucacauag |
| | | auuuucuuuauuuucuauuagagaagcacuagaauucaugaauagugguugauuugaaguucaa |
| | | aguaauuaauucagauaaaaagacauuugcaguuuucaaaugugaauuuugu |
| | | uauuuaauuaucaauccuucauuuaguguuagacuauauuuuaaaaaugcagguaaugaacca |
| | | gaaauagaauuugguugugcuagaguagagaaacuuuauuuugaugauuguuuugaaaaaaag |
| | | cuucugagaagaaacaaccucuaguacaguauuaaauucauuaagauagcuccuuuucucagaca |
| | | uuuccuuucauguagccugaaaguucaauuugaaauuuuguucuuuccaauuuauucagacua |
| | | auucugccuacuuucuucccccauaagaaccaauuacugcagcuuuauugagacugaaaaaa |

TABLE 2-continued

Sequences of target exon or intron to SCN1A pre-mRNA transcripts.

| SEQ ID NO. | Sequence Type | Sequence |
|---|---|---|
| | | guuaauacaccuccuucuuugcugaaccaaggaauggcuuggaacucuugggaaaagacaauc uuuucuaugaucuuucauugucuaauuuaauacaucauaaauaugacuauagcuuuguauaa uaaacuccccaauacugugccagauguuuucuaagauaaaaguuaauuuuuauguucacaaaaaaa auaaaacuuuucucugggccaaauguaugccaacuuugcaaaucauauccugaagugcacugc ugcagaguacaugcuugcgucauaaaauuccauagaguucgcuuuaacucuaaaucaaucccca guuucaaaguaaaccucucaaacauauuaccuaagcacaaacuucucccugugcucaguuccu uaauuauucucaucccauuucagaaauaacauuuaaaaaauuaugcuuugaucaauaaauacu aaucuaaacuuugcuucauuaacccauucauuuuugucaaccauuauuuuauuccuauauuc aaagcucucucuggguauguuucuuauauucaagacacucaaggcccuggaagauucacgaacauau guuugcaucuuaaaauuuuuagaaaaucuuacaaucugucaggauuacacugaacucuaguac agaguaauaugggguaccagauaaguguggagcaacucuuccacguagacuggaaacagcacuaa augcuauuuauaggcuacuuucugaacuuaaccuuguuuuaaccucauuuuuucucauaugcca aaugagaacgcaauacugaauuaucuguacaguucuguucaguacuagaauucugauucuug aauucaaaggggaaaacauuccucuuuauuuuggaggcuaaacugggggacaaaguuaggcu ccaugaaagaagugcuauuugaacuaaagccuuuaagaggggagaguauuucagaagaggag cuauuagacaaggaauuucaauguaaauggcaucucaaucaccuggcaauuauauuuagcacac gguuauuauauuaauugaaguggcaugaaguauagaugaccaggaaguuaaaacuggaaau auagauugugagugaugugaauaccaagguaagaaaaauauuuguuaguuaccagagagcc aauaauaacuuucaagugggacuuggggaagauuaaauucaucuuuacauagauuaaaaugaag gagaagguuaggagacagaugacagugcaaguaugaaauaacagagggcaguucuaggugguu gacugugagaauggaaaagaggugggcaaagcugagaaacguuucaaagaaaaaaugugagaca gguaaugugaaaagaaaaucgagaaauaggguauagauaaucagguguucgcucauacucuaaa uugggguuugaaggcaaaauacguauuuuaauuaguacucugguauacacacuagaaacag cauuguaaucuggauaguggacaaaauauucagaaaagaagggaaaaaguaaccuugauuucaa uuuccaaaucucuaaucugaaagaaaaucuaaauucuauucaucccauuuaaaauaaauuuuauauaa cgagaauuuaugaaguccauuguauuaaugcagacagucagaugagauaaggcaaagguca cgugucagcuuugguaguugcaucggccacaucauuugguucugccuggauaacucaacccaaa uuaauuuuucauacucaucccccuccaccuuugucauuacuggguauuccuuauuuucuuugggcc cacuuaucacacuguuuuuaugguuccccagaaggccuagaguucuuuacaggcuuuaaacagg gaucagaaguauaagaaauuggcucaugauauuuuuuuuuucagacaggcaguuaaaaaaaauu guucuaaaaauacacuggcaucaaauggcaaauagaagauguuuugacgacuacuuccauugg aucagacugacaagaauaauacaagcacauaggguggaauuaaacuuagcuauuaauguccaag uuugaggcagcugcccuuauaagcauuuuuaggcucuguuuuagcuucccucuuuagccacu ccugugcagcuccagugggagguauggaggaaaaagcaaggaagccaucccuauguuguuuc caaacaugaacacucaagauuuuuaacuaguggccagaaguaaagaggggggaaaacauccuu cuauagaaaaaaaaaaaguagauaauaauuugaacacagaacuucaugugaucacaucagauu ugagaacuauguauggcaucccucuuuuucuuaaaaugcuuggaaaaugauuucuaauuauguu ucauuugaaauaaguuuuuugaauuaaacucaguaaaugaaacaacugacaugacuggagcu ugaaauaaacgaugugaugaucuaaugaaauacauaaugcaaauugucuugcuucuuaugca aaaauuauuagucuaugcaaugcaugaauaauuaaagacaauuauauuaggguauuuaauaaua uuuuuauauuuaucaucugaauuuuuuuagaguuauuuuuaaaaauauauuuggucaaaucaacuc agguccaaauguuuuuaguuuuuguucuuuaauauauuugccuuuuuaaaaugaguuaaaacuucu guauaggcuuuuuaacuuuucuuuauucugauaacacaauucugacuucaucuggcagcaag uuccucugauuuuccuuuuccuuuaaccuuuuaaugcuucucccuccuuuuuuuuaaaaac auuuuuguuucauuucuugguuauauugccuauagauguguuuuccuaagaguguauugcuuaag aaaaaaaaaugaauuuuaagauuuuuuugaaccuugcuuuuuacauauccuagaauaaauagca uugauagaaaaaaagaauggaaagaccagagauuacuaggggaauuuuuuuucuuuauuaac agauaagaauucugacuuuucuuuuuuuccauuuguguauuag |
| 7 | Exon 23 (Exon 20x) pre-mRNA | GAUAAUCUUGCUCCAACUUGGAUGGGGUGGAGCGCUGGUUC CUCCCCUGAGCCCUUUAUUAUGG |
| 10 | Intron 21 pre-mRNA | guaagaaaaaggaaaacucugcagcguugauauauugucaaagcuaggcugaguucaacuuaac uaacgaaaaacacgugcaugcaaaaggaauggcaacccuuugcaaacuugcuacuuuacccuu uucucuguugcauauuuacuucuuggugauaugcaagagaaaaucggcucuuugaaaauga uuuaauaucauuuaucugcuuugcuaauuaaaaugaccuuaguucauaaucgaucuuggggag uuuccuuauaauuccuauacaaaggggggaggggcagauacucucuuuaaagaacuaaguuga gucauguaauaauuaccuagagauaaauuuguuucauaucguucuccucuaugacagcccau caguacuuaaggggauccuauggaaaguaaugugaaucacaaaguguaugaauacaaaggaaa aaaugaagaauuguaaaguguuugucuuuacaaugccaaaauucucauuauuugaauauau ccaagggcagauauuaaccauugacuggaguauaauaauacugccucaacuguaacuaaauua augacauugaauaaguaagacacuaaauuaauuacuauaaaaucauauuaauuaugacacaau acagcugauaaggaaaaagaacaguguauuuuuauucauugccauacaugcgucgucaaccuua acuuaaaccucgguucucaguuacacagaguuuuaugugcucuuuugagcaaagcauuauu cccucuccauaauucaacacguaucagauuuuugcauuuauuggcucauuguuaugaugau uauuucaaagcauuauacaaucauuauaugaagaugugccgugugaaauauauauuuuuuuauu aagauccaaaauuuacgcucuuuaaaccaaucagaugaaaugauauaaggcaaagagugcucau uguccugacacuuacaaaccaaggcuccaacaaacaggcuccucucugcaccacauagagggcu uucagccuguguccccccauaaaaaccuauuauaaauuuuuauuauacuauacuguaagaaacc uguccaauuuuuuaauuucucuagcacauaugaaauccuuccaguagauccaaguaagcac aaaggagcuuugauucucacacaagaaaucacauuuguauuaaaaauguaucauaaauuuucu cccaauuaugcaaaacuuaaaugcuuuuccaauuaaaagagcacuuucguuucagaauagcaa uuucaguugucaaggaaaacauuguuuuuauacauuuuauauaaaaauacaugagcuaaauu uaaauucacauuuuuucaacuuuuuuauggguuuuuuuuauguuucuuuuuucuuucgcauuuuuu aacaauccagccauuaccucuccucucccuguccccucccuauaguuucucaucucauuccuccu |

TABLE 2-continued

Sequences of target exon or intron to SCN1A pre-mRNA transcripts.

| SEQ ID NO. | Sequence Type | Sequence |
|---|---|---| cccccuugccucugagaggaugcucccuccccucacuaggccucccucuuccccagggcuucaa
guuccucaaggauuauacacaucuucucccacugagaccaggccaggcagucccucugcuucug
cccagccuguguauguuccugcuugguagcucagucucuggaagcucccuggggucugggu
uaguugggacugcuggucuuccuauggaguuaccucccccuucaacuucuucaauccuuccc
cuaauucaaccacaggguauccagacuucaguccaaugguugagguguaaauauuggcaucugu
cucugucagcuguuguuaggggcucagaggacagccaugcuaggcuccugccuacaagcagc
acaccauaacaucaguaauagugucaggccuuuaaugaauaaugcuacguauauaagguugu
uagauuauacuucaacuuugaucuuuuagaauauuauuaaaauccagucguuuauuuuuuaua
uguaauauugacuuuccauaacaaaugagucuauuuuccuuuuuguguagaaauaacuuuauc
aauuauuguuaauaaugcuuuugucaauuauuguugauaugcuucucuuuuuuaaaacugg
agucaucaaaacaaaaauucuggguagauauuacgaagcugacuccuuggucagcuuggcaca
uagugagaccacaaauaucucaaggucacggcaauuccucaccaccaguuuggcauugugaag
ucaaaaccaaccuucuguugauucuggguuuuuguauuucuaguaugagacauuuucuacuuu
guaagaguauauaacguguggauggcggcgagguuugggcaugaugaugauuguaagcgggaa
gugagcuagaguaucuucagaaacucucacuuuuauccuccuuggcagcauagaaccgcaaucg
cuguguccgagugucaaccaggcagucauuuuguuuugggguuuuuugucacucuuucaaag
caugugcuucuacgcaacacuaccaaacacagcaugcugcauagugcuugagaaggaguuaga
aaguaacaaacgaguuaucaucacguugcccuuugugguuuugcaugucuuaugcacacuuuu
ggcugacagcuuuugaacauuuauuguauuucaaauuuccaguccaaauuuuuuuuucaacu
ugugaaauugaacggaaugaaccgaugucgugaauaccuuagggucaaauaaaacuuguauuu
aaauucguaguuuuaauuucccaagcugggaaaaucguaaaaaccuuuuccaaagaacucaag
ucuuaguugcuagggaaacaggcagugagcaucauauacaaaaaguaacaccaaaugu ucugu
cauaucagcuuucuaacuaauaauaaacuauauauuucuauuuuauauaggauaaucuugcu
ccaacuuggauggggguggagcggugguuccuccccucagcccuuuauuauggguacuguauu
accccuuuugcuaccuuuaaaccuugcacugugacuuuaugugguagugggauugagggaggga
guggaagggguacaauugcaccacaguagggacaauacaggauuuauuuccaaauccacuacu
uuuaaugagcuuaaacuucuuuugggaaaaaaaaguuaucucgacuuaccaucucguggau
uauaaccccagaaguacauaucuuuauuacguuucacugaauaugauuuagcuauuuauacu
ucauugucccauuuaugggggaaauuacucaauuggugaggggguggggggaccccuggguguaggau
gcugaugaaaacguuuucauuugucaagcucaugguagugacagagcauauaguccuuauuu
uuucaacacacugcucuggucccucaauggggccagucacauuccaucaguugaucguugaug
ugugcgagcaguggcuaaagguacaacaggccagguaucucagggguugccaauggguuaugau
cauucucaucuuuauugcauaaaaaugugaaauuuugcgaaagguagcaaggcaagauccug
ugaaacaagggaauacaaaaaaaaaaaaagaugugcuuuuaaguuauaaaaccaaaacaugugaa
aagucaacuucauugaaguauaaagaauaggauaugcaugaaaaacaaaaaaaucaugagcac
uaagaaauugguguauaagccaacuccuuguaagcuacccccaauuaacuuccagaaucuuag
aaggcaucacagugcaccccaaaauaaaaagccaaacugacacuucugcuuccucuuaaaaugu
aggagucuuggauaagaaagauaauuuuuuauugu uuguggaagaaaaaaaauuguuuggauaa
uugaggcauuuaucuaucaaaaauauuuaucuuaauaaaauuucacaacacugauuuaguug
uuggcuuuucuaaaaauuuuuuuauauuucauauuaagaacucaugauuuuuacuuuccauuu
uuuaaauucuuauucacauauggguuuucucuauuucuuuagaaaagcuauagaacccauggu
uuccggugacuuaaaaaacuaauucuaaaugucuucacuuagaugauacuuucaaaugcacuga
aauuucuaauaucaacaagaauauuugccugguccuaauuuuucacugauuuaauaaaaagua
ugaacccuaaagaagaaauagacuugaagaacugguuguguagacaauacagaaauucugcugg
gagauguccuuuuaaaacauuguuagaagagacaaccucuacaauccaccauuaagcauacu
ucucucuuagacaucuccuuuuuauguaccuuuauaaccucaaugu guuucuuuccaauugacuu
agaccaacacuucccagcgcaucccacaugggagccaauuacugacucucccuagagacugcaa
agaauuaauauuguagaaccaagggauggu uugggcucuugggagaggcaauccguuugugau
cuuuugcucuggaugu uaaaugaaaucgcaacuuuaaguggauuuucaguggcaaauccucug
auccuaugccaaaauguuucucuaagacaaacauccuuguaaaauaaaugucucacugggccaaa
ucuauggcaaauuugcacguuuuccugaacugcauucuauauaguauuugccauccugaau
ucacuaaugggcauuacuuuuuaauucaaaaccaguccccuucuucaaaggaaaucucucccauu
uauuacauuaugcaaacugcuuucuuaugcaguggguuaaauccuuagccaggcaaguauag
gacuggaauuugggauauccagaacccucagaaaaugucggaugggcauaguagcuuuacaugua
auuccagagcuagaaagaugaaacuagcccuguccucaagcucugaauucaguuggugcaaua
aauaagaaagaaucccccccccccgaccccuacaucucuuuccucuacaucuauacauguauuuc
ccauacagcucuaugcuuccacauauaugcucacauaugugcaugcacacuugcacacauaug
uacacuugacacauugaagcaucauaauaucuaacaauuggaauauaaagaaaaauauuuaacuuuc
acacagagcagucagagaaaaccauuagaggguugaaacucuugaaaaaacuugcaggauaaaca
gaaaagaguaugagaugccaauucugguucuacuuucugaaccuaacuuguuuuaccuucauu
agcuaauuuuccaaaugaaccccaagcaccaaaauuguccuuuauugcucuuuuccaguacuaaa
uuauaauuccucaauucgaaggcaaacacucucaucuucuucaaugaugguguagaguuagac
ucaauaaacgacaugu uauauuugagcuaaagccuggaggagggagauuauuucaagggcaag
uacuuggcagggaguuucaagaaagaaggcucucaauucucagacuaacaccuuagcgugga
gugacugucacagaggaggggugaaguguaugucaccaguuagggaagcugaaagggaaaug
uaucaggcuugugagaaccuucagcagccaagucuagcaccugagcacaaucccagaacug
accccacaugguggaaaggagaggaauaaauuccugcaaauuuuccugugaccuccacccaagu
gcuauagaaaaugcaugcaugcccacaugcacacacaaauaaacauaguugcaaacuguuuug
aggaaaauaaccucacaaacugucgagugaugu aaaugcaaagaaagagaaaugu uuucuaa
uggcuagagaaccauuaaggaauuuuucaaaaugggacauggga uagauaaaauuuaguauuc
auacugaaagaaggcaagcaaauaaaaucugauaagaauguaauuucuuaguaaccgaggacag
agcgaagauagagaacaggccaauggcaaggugg aaagguuugaaggaagcagcaugaaac
cuacagacuguaccaaaauguucagugu caugagugu uuaaaagugaaaagcuugcauguua
guauggauuucauauccucggcagacagagcaccucacugu gaguggggagaugaaguauuca
gaaaugagaaacaacuacucucaauuucagu guucauaucucaaauccaauaaacaacuuuaggg TABLE 2-continued Sequences of target exon or intron to SCN1A pre-mRNA transcripts.

| SEQ ID NO. | Sequence Type | Sequence |
|---|---|---|
| | | guacaauuuuuuaaaaaauuacauuaaaaauguuuuuaaaucucuucuuaauaauuuaaaaau |
| | | uaaauugaaaauaacuuuaaaaaguaauauauacaggaaagccugugugcuaauuuuuuagg |
| | | gaggccauaaagggagauaguugcucauuaauuucuacacaucagccuaucuuuggcuucug |
| | | ccuugauagcgcacucugaauuaucuucuucauguucaucccucaucuuuauuguuacuggu |
| | | uucauuuccuuggccacauagcccacuauuuuguauucccaauggauauuguuccuuaca |
| | | aaguucagccagggcucagaaguacaaggaauuggcucuuauacuucugucagacaggcaaaa |
| | | acuucuaaaauuauacuauaauaaaaaucaaagagaugauauucauaauuaaacuaacaaaagu |
| | | ggcaggccccccuccccccaacaugaguagaauuaaucugacguccauguucaagucugaaac |
| | | acacuugccaauuaagagcacauuagggccagccuuuaucucccucuuaguuacuaaugugca |
| | | guucaauggugagcuauagagaaggaagccaagacuaccauaugucaaauauaaaaaaaaaaa |
| | | aucccauuuuaaaucuguaguccccgaauuaaggacaagagagagggaaauaucuuugacauua |
| | | gaaaauggagaaaauauuuuagcacaggacuuuacucagucacaucagaguuguaaaguacgu |
| | | augacauccucucuuuuuccuguuuuccugagaaaaugaucucucuaguguuucauuuaagau |
| | | aaguuuauugaauuaaacucaguaaaugaaacaacugacaugacuggagcuugaaauaaacga |
| | | ugugaugaucuacugaaauacaugaugcuaaauugucuugcuucuuaugcaaaaacuacuau |
| | | uaguuauagcaaugcauggauaauuaaggccaaaaauauauuagaugaguuaaaaauaguuuua |
| | | uauuuauacaucugaauuuuaauuuauauuuaaaguauauuggucccaaucaauucaugccca |
| | | aauguuuuaguucuauucuuugagauacuguuuuguuuugggauuuuuuuuuuaugagcuaa |
| | | ucucuugccuaggaguuccuacuucucucuccuccuuuuauuuuuucuaauaaacuacacau |
| | | gugucuucauccaggagcuaacuucucccauuuugcuuuuccuuuagcaccuuuuuuauauauu |
| | | agauucuuucuuuucuccaucucuuugcauauugccuauauuucuuuuccuaagcauaaua |
| | | uuuaaaaaagacugaguuuuauguuaagauuauuucugcuuugcucuuacacagauaggaua |
| | | aguagucuugauagaaaauaaaucaaugauuccuagggggaugucuuuuugcuuuuaaucaa |
| | | uaaggauucugacuucucuuucucuccauuuuguguauuag |
| 11 | Exon 21x pre-mRNA | GAUAAUCUUGCUCCAACUUGGAUGGGGUGGAGCGGUGG UUCCUCCCCUCAGCCCUUUAUUAUGG |

Example 2: Confirmation of NIE Via Cycloheximide Treatment

RT-PCR analysis using cytoplasmic RNA from DMSO-treated (CHX−) or cycloheximide-treated (CHX+) mouse Neuro 2A cells (FIG. 3A) and RenCell VM (human neuro-progenitor cells) (FIG. 3B) and primers in exon 20 and exon 23 confirmed the presence of a band corresponding to the NMD-inducing exon (20x). The identity of the product was confirmed by sequencing. Densitometry analysis of the bands was performed to calculate percent exon 20x inclusion of total SCN1A transcript. Treatment of RenCell VM with cycloheximide (CHX+) to inhibit NMD led to a 2-fold increase of the product corresponding to the NMD-inducing exon 20x in the cytoplasmic fraction (cf. light grey bar, CHX−, to dark grey bar, CHX+).

Example 3: SCN1A Exon 23 (Exon 20x) Region ASO Walk

ASOs were designed to cover a region from about 1000 to about 100 nucleotides upstream of the 5' end of the SCN1A exon 23 (exon 20x) gene by shifting 5 nucleotides at a time. ASOs were also designed to cover a second region from about 1000 to about 100 nucleotides downstream from the 3' end of the SCN1A exon 23 (exon 20x) gene by shifting 5 nucleotides at a time. A list of ASOs targeting SCN1A is summarized in Table 3. Sequences of ASOs are summarized in Table 4.

TABLE 3

List of ASOs targeting SCN1A

| Gene SEQ ID NO. | Pre-mRNA SEQ ID NO. | ASOs SEQ ID NO. | NIE |
|---|---|---|---|
| SEQ ID NO. 1 | SEQ ID NO. 2 | SEQ ID NOs: 12-731 | Exon 23 (Exon 20x) |

TABLE 4

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS22-986 | 166864788 | 166864806 | 12 | ATGAATTTAATA AACTTT | 372 | AUGAAUUUAAUA AACUUU |
| SCN1A-IVS22-981 | 166864783 | 166864801 | 13 | GACCAATGAATT TAATAA | 373 | GACCAAUGAAUU UAAUAA |
| SCN1A-IVS22-976 | 166864778 | 166864796 | 14 | CACTTGACCAAT GAATTT | 374 | CACUUGACCAAU GAAUUU |
| SCN1A-IVS22-971 | 166864773 | 166864791 | 15 | CTGAGCACTTGA CCAATG | 375 | CUGAGCACUUGA CCAAUG |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS22-966 | 166864768 | 166864786 | 16 | AATATCTGAGCA CTTGAC | 376 | AAUAUCUGAGCA CUUGAC |
| SCN1A-IVS22-961 | 166864763 | 166864781 | 17 | ATGGAAATATCT GAGCAC | 377 | AUGGAAAUAUCU GAGCAC |
| SCN1A-IVS22-956 | 166864758 | 166864776 | 18 | AATGTATGGAAA TATCTG | 378 | AAUGUAUGGAAA UAUCUG |
| SCN1A-IVS22-951 | 166864753 | 166864771 | 19 | AGTGTAATGTAT GGAAAT | 379 | AGUGUAAUGUAU GGAAAU |
| SCN1A-IVS22-946 | 166864748 | 166864766 | 20 | AATGAAGTGTAA TGTATG | 380 | AAUGAAGUGUAA UGUAUG |
| SCN1A-IVS22-941 | 166864743 | 166864761 | 21 | ATAGAAATGAAG TGTAAT | 381 | AUAGAAAUGAAG UGUAAU |
| SCN1A-IVS22-936 | 166864738 | 166864756 | 22 | TTTTTATAGAAAT GAAGT | 382 | UUUUUAUAGAAA UGAAGU |
| SCN1A-IVS22-931 | 166864733 | 166864751 | 23 | CAGCTTTTTTATA GAAAT | 383 | CAGCUUUUUUAU AGAAAU |
| SCN1A-IVS22-926 | 166864728 | 166864746 | 24 | AAGATCAGCTTT TTTATA | 384 | AAGAUCAGCUUU UUUAUA |
| SCN1A-IVS22-921 | 166864723 | 166864741 | 25 | CCGATAAGATCA GCTTTT | 385 | CCGAUAAGAUCA GCUUUU |
| SCN1A-IVS22-916 | 166864718 | 166864736 | 26 | GTATACCGATAA GATCAG | 386 | GUAUACCGAUAA GAUCAG |
| SCN1A-IVS22-911 | 166864713 | 166864731 | 27 | TAAAGTATACC GATAAG | 387 | UAAAAGUAUACC GAUAAG |
| SCN1A-IVS22-906 | 166864708 | 166864726 | 28 | AAAATTAAAAGT ATACCG | 388 | AAAAUUAAAAGU AUACCG |
| SCN1A-IVS22-901 | 166864703 | 166864721 | 29 | CTGAGAAAATTA AAAGTA | 389 | CUGAGAAAAUUA AAAGUA |
| SCN1A-IVS22-896 | 166864698 | 166864716 | 30 | TATTTCTGAGAA AATTAA | 390 | UAUUUCUGAGAA AAUUAA |
| SCN1A-IVS22-891 | 166864693 | 166864711 | 31 | ATGGTTATTTCTG AGAAA | 391 | AUGGUUAUUUCU GAGAAA |
| SCN1A-IVS22-886 | 166864688 | 166864706 | 32 | TAGATATGGTTA TTTCTG | 392 | UAGAUAUGGUUA UUUCUG |
| SCN1A-IVS22-881 | 166864683 | 166864701 | 33 | AATTATAGATAT GGTTAT | 393 | AAUUAUAGAUAU GGUUAU |
| SCN1A-IVS22-876 | 166864678 | 166864696 | 34 | TTAATAATTATA GATATG | 394 | UUAAUAAUUAUA GAUAUG |
| SCN1A-IVS22-871 | 166864673 | 166864691 | 35 | ATTGATTAATAA TTATAG | 395 | AUUGAUUAAUAA UUAUAG |
| SCN1A-IVS22-866 | 166864668 | 166864686 | 36 | GCATTATTGATTA ATAAT | 396 | GCAUUAUUGAUU AAUAAU |
| SCN1A-IVS22-861 | 166864663 | 166864681 | 37 | AAAAGGCATTAT TGATTA | 397 | AAAAGGCAUUAU UGAUUA |
| SCN1A-IVS22-856 | 166864658 | 166864676 | 38 | AATATAAAAGGC ATTATT | 398 | AAUAUAAAAGGC AUUAUU |
| SCN1A-IVS22-851 | 166864653 | 166864671 | 39 | CTTTTAATATAAA AGGCA | 399 | CUUUUAAUAUAA AAGGCA |
| SCN1A-IVS22-846 | 166864648 | 166864666 | 40 | AACCTCTTTTAAT ATAAA | 400 | AACCUCUUUUAA UAUAAA |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS22-841 | 166864643 | 166864661 | 41 | AAACTAACCTCT TTTAAT | 401 | AAACUAACCUCU UUUAAU |
| SCN1A-IVS22-836 | 166864638 | 166864656 | 42 | TTCAAAAACTAA CCTCTT | 402 | UUCAAAAACUAA CCUCUU |
| SCN1A-IVS22-831 | 166864633 | 166864651 | 43 | CAAGTTTCAAAA ACTAAC | 403 | CAAGUUUCAAAA ACUAAC |
| SCN1A-IVS22-826 | 166864628 | 166864646 | 44 | AACTCCAAGTTT CAAAAA | 404 | AACUCCAAGUUU CAAAAA |
| SCN1A-IVS22-821 | 166864623 | 166864641 | 45 | TCTAAAACTCCA AGTTTC | 405 | UCUAAAACUCCA AGUUUC |
| SCN1A-IVS22-816 | 166864618 | 166864636 | 46 | TTATGTCTAAAA CTCCAA | 406 | UUAUGUCUAAAA CUCCAA |
| SCN1A-IVS22-811 | 166864613 | 166864631 | 47 | GGATTTTATGTCT AAAAC | 407 | GGAUUUUAUGUC UAAAAC |
| SCN1A-IVS22-806 | 166864608 | 166864626 | 48 | TATAAGGATTTT ATGTCT | 408 | UAUAAGGAUUUU AUGUCU |
| SCN1A-IVS22-801 | 166864603 | 166864621 | 49 | GCATTTATAAGG ATTTTA | 409 | GCAUUUAUAAGG AUUUUA |
| SCN1A-IVS22-796 | 166864598 | 166864616 | 50 | TATCAGCATTTAT AAGGA | 410 | UAUCAGCAUUUA UAAGGA |
| SCN1A-IVS22-791 | 166864593 | 166864611 | 51 | ATCACTATCAGC ATTTAT | 411 | AUCACUAUCAGC AUUUAU |
| SCN1A-IVS22-786 | 166864588 | 166864606 | 52 | GTTATATCACTAT CAGCA | 412 | GUUAUAUCACUA UCAGCA |
| SCN1A-IVS22-781 | 166864583 | 166864601 | 53 | TATTAGTTATATC ACTAT | 413 | UAUUAGUUAUAU CACUAU |
| SCN1A-IVS22-776 | 166864578 | 166864596 | 54 | TAAACTATTAGTT ATATC | 414 | UAAACUAUUAGU UAUAUC |
| SCN1A-IVS22-771 | 166864573 | 166864591 | 55 | CCATTTAAACTAT TAGTT | 415 | CCAUUUAAACUA UUAGUU |
| SCN1A-IVS22-766 | 166864568 | 166864586 | 56 | TCTGACCATTTAA ACTAT | 416 | UCUGACCAUUUA AACUAU |
| SCN1A-IVS22-761 | 166864563 | 166864581 | 57 | ATAAATCTGACC ATTTAA | 417 | AUAAAUCUGACC AUUUAA |
| SCN1A-IVS22-756 | 166864558 | 166864576 | 58 | TATTCATAAATCT GACCA | 418 | UAUUCAUAAAUC UGACCA |
| SCN1A-IVS22-751 | 166864553 | 166864571 | 59 | AGCCATATTCAT AAATCT | 419 | AGCCAUAUUCAU AAAUCU |
| SCN1A-IVS22-746 | 166864548 | 166864566 | 60 | AATAGAGCCATA TTCATA | 420 | AAUAGAGCCAUA UUCAUA |
| SCN1A-IVS22-741 | 166864543 | 166864561 | 61 | TGAGGAATAGAG CCATAT | 421 | UGAGGAAUAGAG CCAUAU |
| SCN1A-IVS22-736 | 166864538 | 166864556 | 62 | CATTATGAGGAA TAGAGC | 422 | CAUUAUGAGGAA UAGAGC |
| SCN1A-IVS22-731 | 166864533 | 166864551 | 63 | GTTGTCATTATGA GGAAT | 423 | GUUGUCAUUAUG AGGAAU |
| SCN1A-IVS22-726 | 166864528 | 166864546 | 64 | TGTATGTTGTCAT TATGA | 424 | UGUAUGUUGUCA UUAUGA |
| SCN1A-IVS22-721 | 166864523 | 166864541 | 65 | CTGTGTGTATGTT GTCAT | 425 | CUGUGUGUAUGU UGUCAU |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS22-716 | 166864518 | 166864536 | 66 | TAGTGCTGTGTGT ATGTT | 426 | UAGUGCUGUGUG UAUGUU |
| SCN1A-IVS22-711 | 166864513 | 166864531 | 67 | CATTTTAGTGCTG TGTGT | 427 | CAUUUUAGUGCU GUGUGU |
| SCN1A-IVS22-706 | 166864508 | 166864526 | 68 | TTAGTCATTTTAG TGCTG | 428 | UUAGUCAUUUUA GUGCUG |
| SCN1A-IVS22-701 | 166864503 | 166864521 | 69 | AGAGATTAGTCA TTTTAG | 429 | AGAGAUUAGUCA UUUUAG |
| SCN1A-IVS22-696 | 166864498 | 166864516 | 70 | ATTGAAGAGATT AGTCAT | 430 | AUUGAAGAGAUU AGUCAU |
| SCN1A-IVS22-691 | 166864493 | 166864511 | 71 | CACGTATTGAAG AGATTA | 431 | CACGUAUUGAAG AGAUUA |
| SCN1A-IVS22-686 | 166864488 | 166864506 | 72 | CCAAACACGTAT TGAAGA | 432 | CCAAACACGUAU UGAAGA |
| SCN1A-IVS22-681 | 166864483 | 166864501 | 73 | CAATGCCAAACA CGTATT | 433 | CAAUGCCAAACA CGUAUU |
| SCN1A-IVS22-676 | 166864478 | 166864496 | 74 | CTCTACAATGCC AAACAC | 434 | CUCUACAAUGCC AAACAC |
| SCN1A-IVS22-671 | 166864473 | 166864491 | 75 | TTTGACTCTACAA TGCCA | 435 | UUUGACUCUACA AUGCCA |
| SCN1A-IVS22-666 | 166864468 | 166864486 | 76 | GTTATTTTGACTC TACAA | 436 | GUUAUUUUGACU CUACAA |
| SCN1A-IVS22-661 | 166864463 | 166864481 | 77 | ATAACGTTATTTT GACTC | 437 | AUAACGUUAUUU UGACUC |
| SCN1A-IVS22-656 | 166864458 | 166864476 | 78 | CAATTATAACGT TATTTT | 438 | CAAUUAUAACGU UAUUUU |
| SCN1A-IVS22-651 | 166864453 | 166864471 | 79 | AGAATCAATTAT AACGTT | 439 | AGAAUCAAUUAU AACGUU |
| SCN1A-IVS22-646 | 166864448 | 166864466 | 80 | AAAATAGAATCA ATTATA | 440 | AAAAUAGAAUCA AUUAUA |
| SCN1A-IVS22-641 | 166864443 | 166864461 | 81 | TATAAAAATAG AATCAA | 441 | UAUAAAAAUAG AAUCAA |
| SCN1A-IVS22-636 | 166864438 | 166864456 | 82 | AGAAGTATAAAA AATAGA | 442 | AGAAGUAUAAAA AAUAGA |
| SCN1A-IVS22-631 | 166864433 | 166864451 | 83 | ACACTAGAAGTA TAAAAA | 443 | ACACUAGAAGUA UAAAAA |
| SCN1A-IVS22-626 | 166864428 | 166864446 | 84 | TCCAAACACTAG AAGTAT | 444 | UCCAAACACUAG AAGUAU |
| SCN1A-IVS22-621 | 166864423 | 166864441 | 85 | AAATATCCAAAC ACTAGA | 445 | AAAUAUCCAAAC ACUAGA |
| SCN1A-IVS22-616 | 166864418 | 166864436 | 86 | AAATAAAATATC CAAACA | 446 | AAAUAAAAUAUC CAAACA |
| SCN1A-IVS22-611 | 166864413 | 166864431 | 87 | TTACAAAATAAA ATATCC | 447 | UUACAAAAUAAA AUAUCC |
| SCN1A-IVS22-606 | 166864408 | 166864426 | 88 | TATTTTTACAAAA TAAAA | 448 | UAUUUUUACAAA AUAAAA |
| SCN1A-IVS22-601 | 166864403 | 166864421 | 89 | GATTATATTTTTA CAAAA | 449 | GAUUAUAUUUUU ACAAAA |
| SCN1A-IVS22-596 | 166864398 | 166864416 | 90 | TTCATGATTATAT TTTTA | 450 | UUCAUGAUUAUA UUUUUA |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS22-591 | 166864393 | 166864411 | 91 | CATCATTCATGAT TATAT | 451 | CAUCAUUCAUGA UUAUAU |
| SCN1A-IVS22-586 | 166864388 | 166864406 | 92 | CTCACCATCATTC ATGAT | 452 | CUCACCAUCAUU CAUGAU |
| SCN1A-IVS22-581 | 166864383 | 166864401 | 93 | CCAACCTCACCA TCATTC | 453 | CCAACCUCACCA UCAUUC |
| SCN1A-IVS22-576 | 166864378 | 166864396 | 94 | TATATCCAACCTC ACCAT | 454 | UAUAUCCAACCU CACCAU |
| SCN1A-IVS22-571 | 166864373 | 166864391 | 95 | ATTCTTATATCCA ACCTC | 455 | AUUCUUAUAUCC AACCUC |
| SCN1A-IVS22-566 | 166864368 | 166864386 | 96 | TCATCATTCTTAT ATCCA | 456 | UCAUCAUUCUUA UAUCCA |
| SCN1A-IVS22-561 | 166864363 | 166864381 | 97 | CATAATCATCATT CTTAT | 457 | CAUAAUCAUCAU UCUUAU |
| SCN1A-IVS22-556 | 166864358 | 166864376 | 98 | CCAATCATAATC ATCATT | 458 | CCAAUCAUAAUC AUCAUU |
| SCN1A-IVS22-551 | 166864353 | 166864371 | 99 | ACTTCCCAATCAT AATCA | 459 | ACUUCCCAAUCA UAAUCA |
| SCN1A-IVS22-546 | 166864348 | 166864366 | 100 | ATCTCACTTCCCA ATCAT | 460 | AUCUCACUUCCC AAUCAU |
| SCN1A-IVS22-541 | 166864343 | 166864361 | 101 | TTCAAATCTCACT TCCCA | 461 | UUCAAAUCUCAC UUCCCA |
| SCN1A-IVS22-536 | 166864338 | 166864356 | 102 | GCATGTTCAAAT CTCACT | 462 | GCAUGUUCAAAU CUCACU |
| SCN1A-IVS22-531 | 166864333 | 166864351 | 103 | TCTGAGCATGTTC AAATC | 463 | UCUGAGCAUGUU CAAAUC |
| SCN1A-IVS22-526 | 166864328 | 166864346 | 104 | GAGTTTCTGAGC ATGTTC | 464 | GAGUUUCUGAGC AUGUUC |
| SCN1A-IVS22-521 | 166864323 | 166864341 | 105 | AATGAGAGTTTC TGAGCA | 465 | AAUGAGAGUUUC UGAGCA |
| SCN1A-IVS22-516 | 166864318 | 166864336 | 106 | AATTAAATGAGA GTTTCT | 466 | AAUUAAAUGAGA GUUUCU |
| SCN1A-IVS22-511 | 166864313 | 166864331 | 107 | CAAAGAATTAAA TGAGAG | 467 | CAAAGAAUUAAA UGAGAG |
| SCN1A-IVS22-506 | 166864308 | 166864326 | 108 | TAGGGCAAAGAA TTAAAT | 468 | UAGGGCAAAGAA UUAAAU |
| SCN1A-IVS22-501 | 166864303 | 166864321 | 109 | GCTGCTAGGGCA AAGAAT | 469 | GCUGCUAGGGCA AAGAAU |
| SCN1A-IVS22-496 | 166864298 | 166864316 | 110 | TTTATGCTGCTAG GGCAA | 470 | UUUAUGCUGCUA GGGCAA |
| SCN1A-IVS22-491 | 166864293 | 166864311 | 111 | GTGATTTTATGCT GCTAG | 471 | GUGAUUUUAUGC UGCUAG |
| SCN1A-IVS22-486 | 166864288 | 166864306 | 112 | CTATTGTGATTTT ATGCT | 472 | CUAUUGUGAUUU UAUGCU |
| SCN1A-IVS22-481 | 166864283 | 166864301 | 113 | CGCAGCTATTGT GATTTT | 473 | CGCAGCUAUUGU GAUUUU |
| SCN1A-IVS22-476 | 166864278 | 166864296 | 114 | TTTGACGCAGCT ATTGTG | 474 | UUUGACGCAGCU AUUGUG |
| SCN1A-IVS22-471 | 166864273 | 166864291 | 115 | TACGCTTTGACG CAGCTA | 475 | UACGCUUUGACG CAGCUA |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS22-466 | 166864268 | 166864286 | 116 | TGAGTTACGCTTT GACGC | 476 | UGAGUUACGCUU UGACGC |
| SCN1A-IVS22-461 | 166864263 | 166864281 | 117 | GTGCCTGAGTTA CGCTTT | 477 | GUGCCUGAGUUA CGCUUU |
| SCN1A-IVS22-456 | 166864258 | 166864276 | 118 | AATGAGTGCCTG AGTTAC | 478 | AAUGAGUGCCUG AGUUAC |
| SCN1A-IVS22-451 | 166864253 | 166864271 | 119 | AATAAAATGAGT GCCTGA | 479 | AAUAAAAUGAGU GCCUGA |
| SCN1A-IVS22-446 | 166864248 | 166864266 | 120 | ACAAAAATAAAA TGAGTG | 480 | ACAAAAAUAAAA UGAGUG |
| SCN1A-IVS22-441 | 166864243 | 166864261 | 121 | GAACAACAAAAA TAAAAT | 481 | GAACAACAAAAA UAAAAU |
| SCN1A-IVS22-436 | 166864238 | 166864256 | 122 | TAACAGAACAAC AAAAAT | 482 | UAACAGAACAAC AAAAAU |
| SCN1A-IVS22-431 | 166864233 | 166864251 | 123 | AAAAATAACAGA ACAACA | 483 | AAAAAUAACAGA ACAACA |
| SCN1A-IVS22-426 | 166864228 | 166864246 | 124 | TTTGAAAAAATA ACAGAA | 484 | UUUGAAAAAAUA ACAGAA |
| SCN1A-IVS22-421 | 166864223 | 166864241 | 125 | CATGCTTTGAAA AAATAA | 485 | CAUGCUUUGAAA AAAUAA |
| SCN1A-IVS22-416 | 166864218 | 166864236 | 126 | AAGCACATGCTT TGAAAA | 486 | AAGCACAUGCUU UGAAAA |
| SCN1A-IVS22-411 | 166864213 | 166864231 | 127 | CATAAAAGCACA TGCTTT | 487 | CAUAAAAGCACA UGCUUU |
| SCN1A-IVS22-406 | 166864208 | 166864226 | 128 | TGTTGCATAAAA GCACAT | 488 | UGUUGCAUAAAA GCACAU |
| SCN1A-IVS22-401 | 166864203 | 166864221 | 129 | AGTAATGTTGCA TAAAAG | 489 | AGUAAUGUUGCA UAAAAG |
| SCN1A-IVS22-396 | 166864198 | 166864216 | 130 | TATTCAGTAATGT TGCAT | 490 | UAUUCAGUAAUG UUGCAU |
| SCN1A-IVS22-391 | 166864193 | 166864211 | 131 | TGCTTTATTCAGT AATGT | 491 | UGCUUUAUUCAG UAAUGU |
| SCN1A-IVS22-386 | 166864188 | 166864206 | 132 | CAACATGCTTTAT TCAGT | 492 | CAACAUGCUUUA UUCAGU |
| SCN1A-IVS22-381 | 166864183 | 166864201 | 133 | CTGTACAACATG CTTTAT | 493 | CUGUACAACAUG CUUUAU |
| SCN1A-IVS22-376 | 166864178 | 166864196 | 134 | AAGCACTGTACA ACATGC | 494 | AAGCACUGUACA ACAUGC |
| SCN1A-IVS22-371 | 166864173 | 166864191 | 135 | TTATCAAGCACT GTACAA | 495 | UUAUCAAGCACU GUACAA |
| SCN1A-IVS22-366 | 166864168 | 166864186 | 136 | ACTTCTTATCAAG CACTG | 496 | ACUUCUUAUCAA GCACUG |
| SCN1A-IVS22-361 | 166864163 | 166864181 | 137 | TTCTAACTTCTTA TCAAG | 497 | UUCUAACUUCUU AUCAAG |
| SCN1A-IVS22-356 | 166864158 | 166864176 | 138 | TTACTTTCTAACT TCTTA | 498 | UUACUUUCUAAC UUCUUA |
| SCN1A-IVS22-351 | 166864153 | 166864171 | 139 | ATTTGTTACTTTC TAACT | 499 | AUUUGUUACUUU CUAACU |
| SCN1A-IVS22-346 | 166864148 | 166864166 | 140 | AATTTATTTGTTA CTTTC | 500 | AAUUUAUUUGUU ACUUUC |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS22-341 | 166864143 | 166864161 | 141 | ATGATAATTTATT TGTTA | 501 | AUGAUAAUUUAU UUGUUA |
| SCN1A-IVS22-336 | 166864138 | 166864156 | 142 | ACGTGATGATAA TTTATT | 502 | ACGUGAUGAUAA UUUAUU |
| SCN1A-IVS22-331 | 166864133 | 166864151 | 143 | GTGCAACGTGAT GATAAT | 503 | GUGCAACGUGAU GAUAAU |
| SCN1A-IVS22-326 | 166864128 | 166864146 | 144 | ACAAAGTGCAAC GTGATG | 504 | ACAAAGUGCAAC GUGAUG |
| SCN1A-IVS22-321 | 166864123 | 166864141 | 145 | AAAACACAAAGT GCAACG | 505 | AAAACACAAAGU GCAACG |
| SCN1A-IVS22-316 | 166864118 | 166864136 | 146 | CATGCAAAACAC AAAGTG | 506 | CAUGCAAAACAC AAAGUG |
| SCN1A-IVS22-311 | 166864113 | 166864131 | 147 | TAAACATGCAA AACACA | 507 | UAAACAUGCAA AACACA |
| SCN1A-IVS22-306 | 166864108 | 166864126 | 148 | GTGCATAAAACA TGCAAA | 508 | GUGCAUAAAACA UGCAAA |
| SCN1A-IVS22-301 | 166864103 | 166864121 | 149 | GAAATGTGCATA AAACAT | 509 | GAAAUGUGCAUA AAACAU |
| SCN1A-IVS22-296 | 166864098 | 166864116 | 150 | AGCCAGAAATGT GCATAA | 510 | AGCCAGAAAUGU GCAUAA |
| SCN1A-IVS22-291 | 166864093 | 166864111 | 151 | CTGTCAGCCAGA AATGTG | 511 | CUGUCAGCCAGA AAUGUG |
| SCN1A-IVS22-286 | 166864088 | 166864106 | 152 | AAAAGCTGTCAG CCAGAA | 512 | AAAAGCUGUCAG CCAGAA |
| SCN1A-IVS22-281 | 166864083 | 166864101 | 153 | TGTTTAAAAGCT GTCAGC | 513 | UGUUUAAAAGCU GUCAGC |
| SCN1A-IVS22-276 | 166864078 | 166864096 | 154 | ATAAATGTTTAA AAGCTG | 514 | AUAAAUGUUUAA AAGCUG |
| SCN1A-IVS22-271 | 166864073 | 166864091 | 155 | ATACAATAAATG TTTAAA | 515 | AUACAAUAAAUG UUUAAA |
| SCN1A-IVS22-266 | 166864068 | 166864086 | 156 | TTGAAATACAAT AAATGT | 516 | UUGAAAUACAAU AAAUGU |
| SCN1A-IVS22-261 | 166864063 | 166864081 | 157 | GAAATTTGAAAT ACAATA | 517 | GAAAUUUGAAAU ACAAUA |
| SCN1A-IVS22-256 | 166864058 | 166864076 | 158 | GACTGGAAATTT GAAATA | 518 | GACUGGAAAUUU GAAAUA |
| SCN1A-IVS22-251 | 166864053 | 166864071 | 159 | ATTTGGACTGGA AATTTG | 519 | AUUUGGACUGGA AAUUUG |
| SCN1A-IVS22-246 | 166864048 | 166864066 | 160 | GAAAAATTTGGA CTGGAA | 520 | GAAAAAUUUGGA CUGGAA |
| SCN1A-IVS22-241 | 166864043 | 166864061 | 161 | AAGTTGAAAAAT TTGGAC | 521 | AAGUUGAAAAAU UUGGAC |
| SCN1A-IVS22-236 | 166864038 | 166864056 | 162 | TTTACAAGTTGA AAAATT | 522 | UUUACAAGUUGA AAAAUU |
| SCN1A-IVS22-231 | 166864033 | 166864051 | 163 | TTAATTTTACAAG TTGAA | 523 | UUAAUUUUACAA GUUGAA |
| SCN1A-IVS22-226 | 166864028 | 166864046 | 164 | TCAGTTTAATTTT ACAAG | 524 | UCAGUUUAAUUU UACAAG |
| SCN1A-IVS22-221 | 166864023 | 166864041 | 165 | TTCACTCAGTTTA ATTTT | 525 | UUCACUCAGUUU AAUUUU |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS22-216 | 166864018 | 166864036 | 166 | ATCAATTCACTC AGTTTA | 526 | AUCAAUUCACUC AGUUUA |
| SCN1A-IVS22-211 | 166864013 | 166864031 | 167 | ACGACATCAATT CACTCA | 527 | ACGACAUCAAUU CACUCA |
| SCN1A-IVS22-206 | 166864008 | 166864026 | 168 | TATTCACGACAT CAATTC | 528 | UAUUCACGACAU CAAUUC |
| SCN1A-IVS22-201 | 166864003 | 166864021 | 169 | CTAGATATTCAC GACATC | 529 | CUAGAUAUUCAC GACAUC |
| SCN1A-IVS22-196 | 166863998 | 166864016 | 170 | TTACCCTAGATAT TCACG | 530 | UUACCCUAGAUA UUCACG |
| SCN1A-IVS22-191 | 166863993 | 166864011 | 171 | TTATTTTACCCTA GATAT | 531 | UUAUUUUACCCU AGAUAU |
| SCN1A-IVS22-186 | 166863988 | 166864006 | 172 | AAATTTTATTTTA CCCTA | 532 | AAAUUUUAUUUU ACCCUA |
| SCN1A-IVS22-181 | 166863983 | 166864001 | 173 | AACACAAATTTT ATTTTA | 533 | AACACAAAUUUU AUUUUA |
| SCN1A-IVS22-176 | 166863978 | 166863996 | 174 | ATTTAAACACAA ATTTTA | 534 | AUUUAAACACAA AUUUUA |
| SCN1A-IVS22-171 | 166863973 | 166863991 | 175 | TACAAATTTAAA CACAAA | 535 | UACAAAUUUAAA CACAAA |
| SCN1A-IVS22-166 | 166863968 | 166863986 | 176 | AAAAATACAAAT TTAAAC | 536 | AAAAAUACAAAU UUAAAC |
| SCN1A-IVS22-161 | 166863963 | 166863981 | 177 | AAATTAAAAATA CAAATT | 537 | AAAUUAAAAAUA CAAAUU |
| SCN1A-IVS22-156 | 166863958 | 166863976 | 178 | TTAGGAAATTAA AAATAC | 538 | UUAGGAAAUUAA AAAUAC |
| SCN1A-IVS22-151 | 166863953 | 166863971 | 179 | CTAGGTTAGGAA ATTAAA | 539 | CUAGGUUAGGAA AUUAAA |
| SCN1A-IVS22-146 | 166863948 | 166863966 | 180 | ATTTCCTAGGTTA GGAAA | 540 | AUUUCCUAGGUU AGGAAA |
| SCN1A-IVS22-141 | 166863943 | 166863961 | 181 | TTAAGATTTCCTA GGTTA | 541 | UUAAGAUUUCCU AGGUUA |
| SCN1A-IVS22-136 | 166863938 | 166863956 | 182 | GGTATTTAAGAT TTCCTA | 542 | GGUAUUUAAGAU UUCCUA |
| SCN1A-IVS22-131 | 166863933 | 166863951 | 183 | AAGAAGGTATTT AAGATT | 543 | AAGAAGGUAUUU AAGAUU |
| SCN1A-IVS22-126 | 166863928 | 166863946 | 184 | TGAAAAGAAGG TATTTA | 544 | UGAAAAGAAGG UAUUUA |
| SCN1A-IVS22-121 | 166863923 | 166863941 | 185 | TCTTTTGAAAAA GAAGGT | 545 | UCUUUUGAAAAA GAAGGU |
| SCN1A-IVS22-116 | 166863918 | 166863936 | 186 | TGAGTTCTTTTGA AAAG | 546 | UGAGUUCUUUUG AAAAG |
| SCN1A-IVS22-111 | 166863913 | 166863931 | 187 | AGACTTGAGTTC TTTTGA | 547 | AGACUUGAGUUC UUUUGA |
| SCN1A-IVS22-106 | 166863908 | 166863926 | 188 | CATTAAGACTTG AGTTCT | 548 | CAUUAAGACUUG AGUUCU |
| SCN1A-IVS22-101 | 166863903 | 166863921 | 189 | CTATCCATTAAG ACTTGA | 549 | CUAUCCAUUAAG ACUUGA |
| SCN1A-IVS22-096 | 166863898 | 166863916 | 190 | TTTCCCTATCCAT TAAGA | 550 | UUUCCCUAUCCA UUAAGA |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS22-091 | 166863893 | 166863911 | 191 | GTCTGTTTCCCTATCCAT | 551 | GUCUGUUUCCCUAUCCAU |
| SCN1A-IVS23 + 091 | 166863631 | 166863649 | 192 | TTTCCCTACTGTGGTGCA | 552 | UUUCCCUACUGUGGUGCA |
| SCN1A-IVS23 + 096 | 166863626 | 166863644 | 193 | TGTATTTTCCCTACTGTG | 553 | UGUAUUUUCCCUACUGUG |
| SCN1A-IVS23 + 101 | 166863621 | 166863639 | 194 | AATAATGTATTTTCCCTA | 554 | AAUAAUGUAUUUUCCCUA |
| SCN1A-IVS23 + 106 | 166863616 | 166863634 | 195 | ATGTAAATAATGTATTTT | 555 | AUGUAAAUAAUGUAUUUU |
| SCN1A-IVS23 + 111 | 166863611 | 166863629 | 196 | AGGGATTAGGATTAATGT | 556 | AGGGAUUAGGAUUAAUGU |
| SCN1A-IVS23 + 116 | 166863606 | 166863624 | 197 | AGGGATTAGGATGTAAAT | 557 | AGGGAUUAGGAUGUAAAU |
| SCN1A-IVS23 + 121 | 166863601 | 166863619 | 198 | AAAGAGGGAATTAGGATG | 558 | AAAGAGGGAAUUAGGAUG |
| SCN1A-IVS23 + 126 | 166863596 | 166863614 | 199 | ATTGAAAAGAAGGGATTA | 559 | AUUGAAAAGAAGGGAUUA |
| SCN1A-IVS23 + 131 | 166863591 | 166863609 | 200 | AGACAATTGAAAAGAGGG | 560 | AGACAAUUGAAAAGAGGG |
| SCN1A-IVS23 + 136 | 166863586 | 166863604 | 201 | ATTTAAGACAATTGAAAA | 561 | AUUUAAGACAAUUGAAAA |
| SCN1A-IVS23 + 141 | 166863581 | 166863599 | 202 | ATGAAATTTAAGACAATT | 562 | AUGAAAUUUAAGACAAUU |
| SCN1A-IVS23 + 146 | 166863576 | 166863594 | 203 | TTCAAATGAAATTTAAGA | 563 | UUCAAAUGAAAUUUAAGA |
| SCN1A-IVS23 + 151 | 166863571 | 166863589 | 204 | TTTTTTTCAAATGAAATT | 564 | UUUUUUUCAAAUGAAAUU |
| SCN1A-IVS23 + 156 | 166863566 | 166863584 | 205 | TTTTTTTTTTTTCAAATG | 565 | UUUUUUUUUUUUCAAAUG |
| SCN1A-IVS23 + 161 | 166863561 | 166863579 | 206 | AAGGTTTTTTTTTTTTTC | 566 | AAGGUUUUUUUUUUUUUC |
| SCN1A-IVS23 + 166 | 166863556 | 166863574 | 207 | TCATAAAGGTTTTTTTTT | 567 | UCAUAAAGGUUUUUUUUU |
| SCN1A-IVS23 + 171 | 166863551 | 166863569 | 208 | TAAATTCATAAAGGTTTT | 568 | UAAAUUCAUAAAGGUUUU |
| SCN1A-IVS23 + 176 | 166863546 | 166863564 | 209 | GAGGGTAAATTCATAAAG | 569 | GAGGGUAAAUUCAUAAAG |
| SCN1A-IVS23 + 181 | 166863541 | 166863559 | 210 | CCACAGAGGGTAAATTCA | 570 | CCACAGAGGGUAAAUUCA |
| SCN1A-IVS23 + 186 | 166863536 | 166863554 | 211 | AAAATCCACAGAGGGTAA | 571 | AAAAUCCACAGAGGGUAA |
| SCN1A-IVS23 + 191 | 166863531 | 166863549 | 212 | GGGTTAAAATCCACAGAG | 572 | GGGUUAAAAUCCACAGAG |
| SCN1A-IVS23 + 196 | 166863526 | 166863544 | 213 | CATTGGGATTAAAATCCA | 573 | CAUUGGGAUUAAAAUCCA |
| SCN1A-IVS23 + 201 | 166863521 | 166863539 | 214 | TCAACCATTAGGGTTAAA | 574 | UCAACCAUUAGGGUUAAA |
| SCN1A-IVS23 + 206 | 166863516 | 166863534 | 215 | AGATATCAACCATTGGGA | 575 | AGAUAUCAACCAUUGGGA |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS23 + 211 | 166863511 | 166863529 | 216 | AATAAAGATATC AACCAT | 576 | AAUAAAGAUAUC AACCAU |
| SCN1A-IVS23 + 216 | 166863506 | 166863524 | 217 | AACTTAATAAAG ATATCA | 577 | AACUUAAUAAAG AUAUCA |
| SCN1A-IVS23 + 221 | 166863501 | 166863519 | 218 | AATGAAACTTAA TAAAGA | 578 | AAUGAAACUUAA UAAAGA |
| SCN1A-IVS23 + 226 | 166863496 | 166863514 | 219 | TATTCAATGAAA CTTAAT | 579 | UAUUCAAUGAAA CUUAAU |
| SCN1A-IVS23 + 231 | 166863491 | 166863509 | 220 | AATCATATTCAA TGAAAC | 580 | AAUCAUAUUCAA UGAAAC |
| SCN1A-IVS23 + 236 | 166863486 | 166863504 | 221 | AACTAAATCATA TTCAAT | 581 | AACUAAAUCAUA UUCAAU |
| SCN1A-IVS23 + 241 | 166863481 | 166863499 | 222 | CACATAACTAAA TCATAT | 582 | CACAUAACUAAA UCAUAU |
| SCN1A-IVS23 + 246 | 166863476 | 166863494 | 223 | ATATACACATAA CTAAAT | 583 | AUAUACACAUAA CUAAAU |
| SCN1A-IVS23 + 251 | 166863471 | 166863489 | 224 | ACTCCATATACA CATAAC | 584 | ACUCCAUAUACA CAUAAC |
| SCN1A-IVS23 + 256 | 166863466 | 166863484 | 225 | GGATAACTCCAT ATACAC | 585 | GGAUAACUCCAU AUACAC |
| SCN1A-IVS23 + 261 | 166863461 | 166863479 | 226 | AAGATGGATAAC TCCATA | 586 | AAGAUGGAUAAC UCCAUA |
| SCN1A-IVS23 + 266 | 166863456 | 166863474 | 227 | CCCCAAAGATGG ATAACT | 587 | CCCCAAAGAUGG AUAACU |
| SCN1A-IVS23 + 271 | 166863451 | 166863469 | 228 | AATCTCCCCAAA GATGGA | 588 | AAUCUCCCCAAA GAUGGA |
| SCN1A-IVS23 + 276 | 166863446 | 166863464 | 229 | CCAGTAATCTCC CCAAAG | 589 | CCAGUAAUCUCC CCAAAG |
| SCN1A-IVS23 + 281 | 166863441 | 166863459 | 230 | CCAATCCAGTAA TCTCCC | 590 | CCAAUCCAGUAA UCUCCC |
| SCN1A-IVS23 + 286 | 166863436 | 166863454 | 231 | CCTCACCAATCC AGTAAT | 591 | CCUCACCAAUCC AGUAAU |
| SCN1A-IVS23 + 291 | 166863431 | 166863449 | 232 | CCCGCCCTCACC AATCCA | 592 | CCCGCCCUCACCA AUCCA |
| SCN1A-IVS23 + 296 | 166863426 | 166863444 | 233 | GGTCCCCCGCCC TCACCA | 593 | GGUCCCCCGCCC UCACCA |
| SCN1A-IVS23 + 301 | 166863421 | 166863439 | 234 | ACCAGGGTCCCC CGCCCT | 594 | ACCAGGGUCCCC CGCCCU |
| SCN1A-IVS23 + 306 | 166863416 | 166863434 | 235 | TCTACACCAGGG TCCCCC | 595 | UCUACACCAGGG UCCCCC |
| SCN1A-IVS23 + 311 | 166863411 | 166863429 | 236 | ATCATTCTACACC AGGGT | 596 | AUCAUUCUACAC CAGGGU |
| SCN1A-IVS23 + 316 | 166863406 | 166863424 | 237 | ACATAATCATTCT ACACC | 597 | ACAUAAUCAUUC UACACC |
| SCN1A-IVS23 + 321 | 166863401 | 166863419 | 238 | TTTTCACATAATC ATTCT | 598 | UUUUCACAUAAU CAUUCU |
| SCN1A-IVS23 + 326 | 166863396 | 166863414 | 239 | TTGTTTTTTCACA TAATC | 599 | UUGUUUUUUCAC AUAAUC |
| SCN1A-IVS23 + 331 | 166863391 | 166863409 | 240 | TTAAATTGTTTTT TCACA | 600 | UUAAAUUGUUUU UUCACA |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS23 + 336 | 166863386 | 166863404 | 241 | ACAAGTTAAATT GTTTTT | 601 | ACAAGUUAAAUU GUUUUU |
| SCN1A-IVS23 + 341 | 166863381 | 166863399 | 242 | GCTTAACAAGTT AAATTG | 602 | GCUUAACAAGUU AAAUUG |
| SCN1A-IVS23 + 346 | 166863376 | 166863394 | 243 | CATGAGCTTAAC AAGTTA | 603 | CAUGAGCUUAAC AAGUUA |
| SCN1A-IVS23 + 351 | 166863371 | 166863389 | 244 | AGTATCATGAGC TTAACA | 604 | AGUAUCAUGAGC UUAACA |
| SCN1A-IVS23 + 356 | 166863366 | 166863384 | 245 | CAAACAGTATCA TGAGCT | 605 | CAAACAGUAUCA UGAGCU |
| SCN1A-IVS23 + 361 | 166863361 | 166863379 | 246 | TGCCTCAAACAG TATCAT | 606 | UGCCUCAAACAG UAUCAU |
| SCN1A-IVS23 + 366 | 166863356 | 166863374 | 247 | CTGTATGCCTCA AACAGT | 607 | CUGUAUGCCUCA AACAGU |
| SCN1A-IVS23 + 371 | 166863351 | 166863369 | 248 | AGGGACTGTATG CCTCAA | 608 | AGGGACUGUAUG CCUCAA |
| SCN1A-IVS23 + 376 | 166863346 | 166863364 | 249 | ACAGCAGGGACT GTATGC | 609 | ACAGCAGGGACU GUAUGC |
| SCN1A-IVS23 + 381 | 166863341 | 166863359 | 250 | ACTAAACAGCAA GGGCTG | 610 | ACUAAACAGCAA GGGCUG |
| SCN1A-IVS23 + 386 | 166863336 | 166863354 | 251 | AATGTACTAAAC AGCAGG | 611 | AAUGUACUAAAC AGCAGG |
| SCN1A-IVS23 + 391 | 166863331 | 166863349 | 252 | AGACCAATGTAC TAAACA | 612 | AGACCAAUGUAC UAAACA |
| SCN1A-IVS23 + 396 | 166863326 | 166863344 | 253 | GACCCAGACCAA TGTACT | 613 | GACCCAGACCAA UGUACU |
| SCN1A-IVS23 + 401 | 166863321 | 166863339 | 254 | TTCAGGACCCAG ACCAAT | 614 | UUCAGGACCCAG ACCAAU |
| SCN1A-IVS23 + 406 | 166863316 | 166863334 | 255 | TAATTTTCAGGA CCCAGA | 615 | UAAUUUUCAGGA CCCAGA |
| SCN1A-IVS23 + 411 | 166863311 | 166863329 | 256 | ACTGGTAATTTC AGGAC | 616 | ACUGGUAAUUUU CAGGAC |
| SCN1A-IVS23 + 416 | 166863306 | 166863324 | 257 | ATCTAACTGGTA ATTTTC | 617 | AUCUAACUGGUA AUUUUC |
| SCN1A-IVS23 + 421 | 166863301 | 166863319 | 258 | ATGGTATCTAAC TGGTAA | 618 | AUGGUAUCUAAC UGGUAA |
| SCN1A-IVS23 + 426 | 166863296 | 166863314 | 259 | AACTGATGGTAT CTAACT | 619 | AACUGAUGGUAU CUAACU |
| SCN1A-IVS23 + 431 | 166863291 | 166863309 | 260 | TAATCAACTGAT GGTATC | 620 | UAAUCAACUGAU GGUAUC |
| SCN1A-IVS23 + 436 | 166863286 | 166863304 | 261 | ATCAATAATCAA CTGATG | 621 | AUCAAUAAUCAA CUGAUG |
| SCN1A-IVS23 + 441 | 166863281 | 166863299 | 262 | TACATATCAATA ATCAAC | 622 | UACAUAUCAAUA AUCAAC |
| SCN1A-IVS23 + 446 | 166863276 | 166863294 | 263 | GCTCATACATAT CAATAA | 623 | GCUCAUACAUAU CAAUAA |
| SCN1A-IVS23 + 451 | 166863271 | 166863289 | 264 | TATCTGCTCATAC ATATC | 624 | UAUCUGCUCAUA CAUAUC |
| SCN1A-IVS23 + 456 | 166863266 | 166863284 | 265 | CCTAGTATCTGCT CATAC | 625 | CCUAGUAUCUGC UCAUAC |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS23 + 461 | 166863261 | 166863279 | 266 | TGCACCCTAGTATCTGCT | 626 | UGCACCCUAGUAUCUGCU |
| SCN1A-IVS23 + 466 | 166863256 | 166863274 | 267 | AATATTGCACCCTAGTAT | 627 | AAUAUUGCACCCUAGUAU |
| SCN1A-IVS23 + 471 | 166863251 | 166863269 | 268 | CCTGAAATATTGCACCCT | 628 | CCUGAAAUAUUGCACCCU |
| SCN1A-IVS23 + 476 | 166863246 | 166863264 | 269 | TGAAACCTGAAATATTGC | 629 | UGAAACCUGAAAUAUUGC |
| SCN1A-IVS23 + 481 | 166863241 | 166863259 | 270 | TCTTATGAAACCTGAAAT | 630 | UCUUAUGAAACCUGAAAU |
| SCN1A-IVS23 + 486 | 166863236 | 166863254 | 271 | ACCAGTCTTATGAAACCT | 631 | ACCAGUCUUAUGAAACCU |
| SCN1A-IVS23 + 491 | 166863231 | 166863249 | 272 | TCAATACCAGTCTTATGA | 632 | UCAAUACCAGUCUUAUGA |
| SCN1A-IVS23 + 496 | 166863226 | 166863244 | 273 | CACAATCAATACCAGTCT | 633 | CACAAUCAAUACCAGUCU |
| SCN1A-IVS23 + 501 | 166863221 | 166863239 | 274 | GTGGTCACAATCAATACC | 634 | GUGGUCACAAUCAAUACC |
| SCN1A-IVS23 + 506 | 166863216 | 166863234 | 275 | TGAGAGTGGTCACAATCA | 635 | UGAGAGUGGUCACAAUCA |
| SCN1A-IVS23 + 511 | 166863211 | 166863229 | 276 | AAAAATGAGAGTGGTCAC | 636 | AAAAAUGAGAGUGGUCAC |
| SCN1A-IVS23 + 516 | 166863206 | 166863224 | 277 | CAATAAAAATGAGAGTG | 637 | CAAUAAAAAUGAGAGUG |
| SCN1A-IVS23 + 521 | 166863201 | 166863219 | 278 | TTACACAATAAAAAATGA | 638 | UUACACAAUAAAAAAUGA |
| SCN1A-IVS23 + 526 | 166863196 | 166863214 | 279 | TGAACTTACACAATAAAA | 639 | UGAACUUACACAAUAAAA |
| SCN1A-IVS23 + 531 | 166863191 | 166863209 | 280 | CCATATGAACTTACACAA | 640 | CCAUAUGAACUUACACAA |
| SCN1A-IVS23 + 536 | 166863186 | 166863204 | 281 | TAACCCCATATGAACTTA | 641 | UAACCCCAUAUGAACUUA |
| SCN1A-IVS23 + 541 | 166863181 | 166863199 | 282 | GAAAATAACCCCATATGA | 642 | GAAAAUAACCCCAUAUGA |
| SCN1A-IVS23 + 546 | 166863176 | 166863194 | 283 | ATTTTGAAATAACCCCA | 643 | AUUUUGAAAUAACCCCA |
| SCN1A-IVS23 + 551 | 166863171 | 166863189 | 284 | TTAACATTTGAAAATAA | 644 | UUAACAUUUUGAAAAUAA |
| SCN1A-IVS23 + 556 | 166863166 | 166863184 | 285 | CCTTGTTAACATTTTGAA | 645 | CCUUGUUAACAUUUUGAA |
| SCN1A-IVS23 + 561 | 166863161 | 166863179 | 286 | TTTTGCCTTGTTAACATT | 646 | UUUUGCCUUGUUAACAUU |
| SCN1A-IVS23 + 566 | 166863156 | 166863174 | 287 | TATATTTTTGCCTGTTA | 647 | UAUAUUUUUGCCUUGUUA |
| SCN1A-IVS23 + 571 | 166863151 | 166863169 | 288 | CTTAATATATTTTGCCT | 648 | CUUAAUAUAUUUUUGCCU |
| SCN1A-IVS23 + 576 | 166863146 | 166863164 | 289 | TATTTCTTAATATATTTT | 649 | UAUUUCUUAAUAUAUUUU |
| SCN1A-IVS23 + 581 | 166863141 | 166863159 | 290 | TCAACTATTTCTTAATAT | 650 | UCAACUAUUUCUUAAUAU |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS23 + 586 | 166863136 | 166863154 | 291 | CTTATTCAACTAT TTCTT | 651 | CUUAUUCAACUA UUUCUU |
| SCN1A-IVS23 + 591 | 166863131 | 166863149 | 292 | ATGTGCTTATTCA ACTAT | 652 | AUGUGCUUAUUC AACUAU |
| SCN1A-IVS23 + 596 | 166863126 | 166863144 | 293 | TTCACATGTGCTT ATTCA | 653 | UUCACAUGUGCU UAUUCA |
| SCN1A-IVS23 + 601 | 166863121 | 166863139 | 294 | CACAATTCACAT GTGCTT | 654 | CACAAUUCACAU GUGCUU |
| SCN1A-IVS23 + 606 | 166863116 | 166863134 | 295 | TACAACACAATT CACATG | 655 | UACAACACAAUU CACAUG |
| SCN1A-IVS23 + 611 | 166863111 | 166863129 | 296 | TTGTTTACAACAC AATTC | 656 | UUGUUUACAACA CAAUUC |
| SCN1A-IVS23 + 616 | 166863106 | 166863124 | 297 | ACTTTTTGTTTAC AACAC | 657 | ACUUUUUGUUUA CAACAC |
| SCN1A-IVS23 + 621 | 166863101 | 166863119 | 298 | TTCTAACTTTTTG TTTAC | 658 | UUCUAACUUUUU GUUUAC |
| SCN1A-IVS23 + 626 | 166863096 | 166863114 | 299 | TTTTATTCTAACT TTTTG | 659 | UUUUAUUCUAAC UUUUUG |
| SCN1A-IVS23 + 631 | 166863091 | 166863109 | 300 | GATTTTTTATTC TAACT | 660 | GAUUUUUUAUU CUAACU |
| SCN1A-IVS23 + 636 | 166863086 | 166863104 | 301 | AAGTGGATTTTT TATTC | 661 | AAGUGGAUUUUU UUAUUC |
| SCN1A-IVS23 + 641 | 166863081 | 166863099 | 302 | CAAATAAGTGGA TTTTT | 662 | CAAAUAAGUGGA UUUUUU |
| SCN1A-IVS23 + 646 | 166863076 | 166863094 | 303 | TAATTCAAATAA GTGGAT | 663 | UAAUUCAAAUAA GUGGAU |
| SCN1A-IVS23 + 651 | 166863071 | 166863089 | 304 | CTGCATAATTCA AATAAG | 664 | CUGCAUAAUUCA AAUAAG |
| SCN1A-IVS23 + 656 | 166863066 | 166863084 | 305 | CTATTCTGCATAA TTCAA | 665 | CUAUUCUGCAUA AUUCAA |
| SCN1A-IVS23 + 661 | 166863061 | 166863079 | 306 | GTATTCTATTCTG CATAA | 666 | GUAUUCUAUUCU GCAUAA |
| SCN1A-IVS23 + 666 | 166863056 | 166863074 | 307 | GGTATGTATTCTA TTCTG | 667 | GGUAUGUAUUCU AUUCUG |
| SCN1A-IVS23 + 671 | 166863051 | 166863069 | 308 | TTCTAGGTATGTA TTCTA | 668 | UUCUAGGUAUGU AUUCUA |
| SCN1A-IVS23 + 676 | 166863046 | 166863064 | 309 | TTTATTTCTAGGT ATGTA | 669 | UUUAUUUCUAGG UAUGUA |
| SCN1A-IVS23 + 681 | 166863041 | 166863059 | 310 | TTTGTTTTATTTC TAGGT | 670 | UUUGUUUUAUUU CUAGGU |
| SCN1A-IVS23 + 686 | 166863036 | 166863054 | 311 | ACGTTTTTGTTTT ATTTC | 671 | ACGUUUUUGUUU UAUUUC |
| SCN1A-IVS23 + 691 | 166863031 | 166863049 | 312 | ATAAGACGTTTTT GTTTT | 672 | AUAAGACGUUUUU UGUUUU |
| SCN1A-IVS23 + 696 | 166863026 | 166863044 | 313 | TCATGATAAGAC GTTTTT | 673 | UCAUGAUAAGAC GUUUUU |
| SCN1A-IVS23 + 701 | 166863021 | 166863039 | 314 | AATACTCATGAT AAGACG | 674 | AAUACUCAUGAU AAGACG |
| SCN1A-IVS23 + 706 | 166863016 | 166863034 | 315 | ATCTTAATACTCA TGATA | 675 | AUCUUAAUACUC AUGAUA |

TABLE 4-continued

| | | | | | | |
|---|---|---|---|---|---|---|
| | | Sequences of ASOs targeting human SCN1A | | | | |
| SEQUENCE NAME | Chr2 Start | Chr2 End | SEQ ID NO: | ASO sequence | SEQ ID NO: | ASO sequence |
| SCN1A-IVS23 + 711 | 166863011 | 166863029 | 316 | ATTTTATCTTAAT ACTCA | 676 | AUUUUAUCUUAA UACUCA |
| SCN1A-IVS23 + 716 | 166863006 | 166863024 | 317 | CTTAAATTTTATC TTAAT | 677 | CUUAAAUUUUAU CUUAAU |
| SCN1A-IVS23 + 721 | 166863001 | 166863019 | 318 | TATGCCTTAAATT TTATC | 678 | UAUGCCUUAAAU UUUAUC |
| SCN1A-IVS23 + 726 | 166862996 | 166863014 | 319 | GAGTTTATGCCTT AAATT | 679 | GAGUUUAUGCCU UAAAUU |
| SCN1A-IVS23 + 731 | 166862991 | 166863009 | 320 | GAAGTGAGTTTA TGCCTT | 680 | GAAGUGAGUUUA UGCCUU |
| SCN1A-IVS23 + 736 | 166862986 | 166863004 | 321 | TCTAAGAAGTGA GTTTAT | 681 | UCUAAGAAGUGA GUUUAU |
| SCN1A-IVS23 + 741 | 166862981 | 166862999 | 322 | CTTATTCTAAGA AGTGAG | 682 | CUUAUUCUAAGA AGUGAG |
| SCN1A-IVS23 + 746 | 166862976 | 166862994 | 323 | AGTTACTTATTCT AAGAA | 683 | AGUUACUUAUUC UAAGAA |
| SCN1A-IVS23 + 751 | 166862971 | 166862989 | 324 | TTGGGAGTTACTT ATTCT | 684 | UUGGGAGUUACU UAUUCU |
| SCN1A-IVS23 + 756 | 166862966 | 166862984 | 325 | GTTAGTTGGGAG TTACTT | 685 | GUUAGUUGGGAG UUACUU |
| SCN1A-IVS23 + 761 | 166862961 | 166862979 | 326 | AGAAAGTTAGTT GGGAGT | 686 | AGAAAGUUAGUU GGGAGU |
| SCN1A-IVS23 + 766 | 166862956 | 166862974 | 327 | ATCCTAGAAAGT TAGTTG | 687 | AUCCUAGAAAGU UAGUUG |
| SCN1A-IVS23 + 771 | 166862951 | 166862969 | 328 | TTAAAATCCTAG AAAGTT | 688 | UUAAAAUCCUAG AAAGUU |
| SCN1A-IVS23 + 776 | 166862946 | 166862964 | 329 | ATGTTTTAAAATC CTAGA | 689 | AUGUUUUAAAAU CCUAGA |
| SCN1A-IVS23 + 781 | 166862941 | 166862959 | 330 | GTGTTATGTTTTA AAATC | 690 | GUGUUAUGUUUU AAAAUC |
| SCN1A-IVS23 + 786 | 166862936 | 166862954 | 331 | TCACTGTGTTATG TTTTA | 691 | UCACUGUGUUAU GUUUUA |
| SCN1A-IVS23 + 791 | 166862931 | 166862949 | 332 | TGTTTTCACTGTG TTATG | 692 | UGUUUUCACUGU GUUAUG |
| SCN1A-IVS23 + 796 | 166862926 | 166862944 | 333 | ATGTATGTTTTCA CTGTG | 693 | AUGUAUGUUUUC ACUGUG |
| SCN1A-IVS23 + 801 | 166862921 | 166862939 | 334 | TGTTTATGTATGT TTTCA | 694 | UGUUUAUGUAUG UUUUCA |
| SCN1A-IVS23 + 806 | 166862916 | 166862934 | 335 | AGTTATGTTTATG TATGT | 695 | AGUUAUGUUUAU GUAUGU |
| SCN1A-IVS23 + 811 | 166862911 | 166862929 | 336 | TGTAGAGTTATG TTTATG | 696 | UGUAGAGUUAUG UUUAUG |
| SCN1A-IVS23 + 816 | 166862906 | 166862924 | 337 | TAAAATGTAGAG TTATGT | 697 | UAAAAUGUAGAG UUAUGU |
| SCN1A-IVS23 + 821 | 166862901 | 166862919 | 338 | ATAAATAAAATG TAGAGT | 698 | AUAAAUAAAAUG UAGAGU |
| SCN1A-IVS23 + 826 | 166862896 | 166862914 | 339 | TAAGAATAAATA AAATGT | 699 | UAAGAAUAAAUA AAAUGU |
| SCN1A-IVS23 + 831 | 166862891 | 166862909 | 340 | AACTTTAAGAAT AAATAA | 700 | AACUUUAAGAAU AAAUAA |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS23 + 836 | 166862886 | 166862904 | 341 | ACTTAAACTTTA AGAATA | 701 | ACUUAAACUUUA AGAAUA |
| SCN1A-IVS23 + 841 | 166862881 | 166862899 | 342 | AATACACTTAAA CTTTAA | 702 | AAUACACUUAAA CUUUAA |
| SCN1A-IVS23 + 846 | 166862876 | 166862894 | 343 | TGTATAATACAC TTAAAC | 703 | UGUAUAAUACAC UUAAAC |
| SCN1A-IVS23 + 851 | 166862871 | 166862889 | 344 | CTTCTTGTATAAT ACACT | 704 | CUUCUUGUAUAA UACACU |
| SCN1A-IVS23 + 856 | 166862866 | 166862884 | 345 | CTCTTCTTCTTGT ATAAT | 705 | CUCUUCUUCUUG UAUAAU |
| SCN1A-IVS23 + 861 | 166862861 | 166862879 | 346 | ATAAACTCTTCTT CTTGT | 706 | AUAAACUCUUCU UCUUGU |
| SCN1A-IVS23 + 866 | 166862856 | 166862874 | 347 | CGAATATAAACT CTTCTT | 707 | CGAAUAUAAACU CUUCUU |
| SCN1A-IVS23 + 871 | 166862851 | 166862869 | 348 | TCTCTCGAATATA AACTC | 708 | UCUCUCGAAUAU AAACUC |
| SCN1A-IVS23 + 876 | 166862846 | 166862864 | 349 | TTCTGTCTCTCGA ATATA | 709 | UUCUGUCUCUCG AAUAUA |
| SCN1A-IVS23 + 881 | 166862841 | 166862859 | 350 | ACTTTTTCTGTCT CTCGA | 710 | ACUUUUUCUGUC UCUCGA |
| SCN1A-IVS23 + 886 | 166862836 | 166862854 | 351 | TTCTGACTTTTTC TGTCT | 711 | UUCUGACUUUUU CUGUCU |
| SCN1A-IVS23 + 891 | 166862831 | 166862849 | 352 | AAAAATTCTGAC TTTTTC | 712 | AAAAAUUCUGAC UUUUUC |
| SCN1A-IVS23 + 896 | 166862826 | 166862844 | 353 | CAAACAAAAATT CTGACT | 713 | CAAACAAAAAUU CUGACU |
| SCN1A-IVS23 + 901 | 166862821 | 166862839 | 354 | TGATCCAAACAA AAATTC | 714 | UGAUCCAAACAA AAAUUC |
| SCN1A-IVS23 + 906 | 166862816 | 166862834 | 355 | ATTGGTGATCCA AACAAA | 715 | AUUGGUGAUCCA AACAAA |
| SCN1A-IVS23 + 911 | 166862811 | 166862829 | 356 | GATATATTGGTG ATCCAA | 716 | GAUAUAUUGGUG AUCCAA |
| SCN1A-IVS23 + 916 | 166862806 | 166862824 | 357 | GCTATGATATATT GGTGA | 717 | GCUAUGAUAUAU UGGUGA |
| SCN1A-IVS23 + 921 | 166862801 | 166862819 | 358 | TGTAAGCTATGA TATATT | 718 | UGUAAGCUAUGA UAUAUU |
| SCN1A-IVS23 + 926 | 166862796 | 166862814 | 359 | TTTTTTGTAAGCT ATGAT | 719 | UUUUUUGUAAGC UAUGAU |
| SCN1A-IVS23 + 931 | 166862791 | 166862809 | 360 | ACAGTTTTTTGT AAGCT | 720 | ACAGUUUUUUUG UAAGCU |
| SCN1A-IVS23 + 936 | 166862786 | 166862804 | 361 | TTAAGACAGTTT TTTGT | 721 | UUAAGACAGUUU UUUGU |
| SCN1A-IVS23 + 941 | 166862781 | 166862799 | 362 | TTTAATTAAGAC AGTTTT | 722 | UUUAAUUAAGAC AGUUUU |
| SCN1A-IVS23 + 946 | 166862776 | 166862794 | 363 | TGGGTTTTAATTA AGACA | 723 | UGGGUUUUAAUU AAGACA |
| SCN1A-IVS23 + 951 | 166862771 | 166862789 | 364 | TGTTGTGGGTTTT AATTA | 724 | UGUUGUGGGUUU UAAUUA |
| SCN1A-IVS23 + 956 | 166862766 | 166862784 | 365 | AATTATGTTGTG GGTTTT | 725 | AAUUAUGUUGUG GGUUUU |

TABLE 4-continued

Sequences of ASOs targeting human SCN1A

| SEQUENCE NAME | Chr2 Start | Chr2 End | SEQ ID NO: | ASO sequence | SEQ ID NO: | ASO sequence |
|---|---|---|---|---|---|---|
| SCN1A-IVS23 + 961 | 166862761 | 166862779 | 366 | AAAAAAATTATG TTGTGG | 726 | AAAAAAAUUAUG UUGUGG |
| SCN1A-IVS23 + 966 | 166862756 | 166862774 | 367 | AATCTAAAAAAA TTATGT | 727 | AAUCUAAAAAAA UUAUGU |
| SCN1A-IVS23 + 971 | 166862751 | 166862769 | 368 | TTAAAATCTAA AAAAT | 728 | UUAAAAAUCUAA AAAAU |
| SCN1A-IVS23 + 976 | 166862746 | 166862764 | 369 | CTTTCTTAAAAAT CTAAA | 729 | CUUUCUUAAAAA UCUAAA |
| SCN1A-IVS23 + 981 | 166862741 | 166862759 | 370 | AGAATCTTTCTTA AAAAT | 730 | AGAAUCUUUCUU AAAAU |
| SCN1A-IVS23 + 986 | 166862736 | 166862754 | 371 | ATAATAGAATCT TTCTTA | 731 | AUAAUAGAAUCU UUCUUA |

Figure 5A:
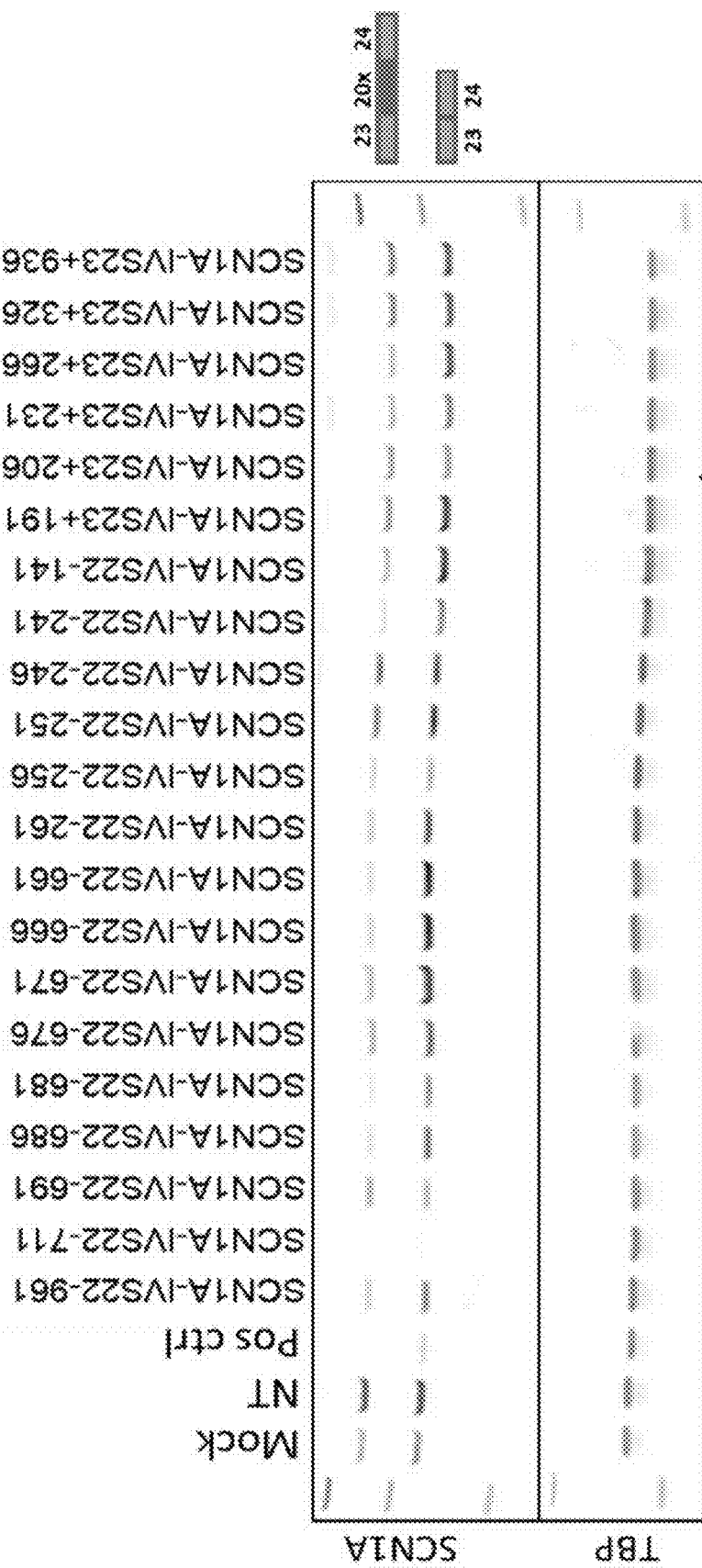
FIG. 5A depicts SCN1A exon 20x region ASOs selected from an extended ASO walk evaluated by RT-PCR. A representative PAGE shows SYBR-safe-stained RT-PCR products of SCN1A mock-treated, control ASO treated (NT), SCN1A exon 20x region ASOs from an extended walk in RenCells via nucleofection at 1 uM for 24 hrs. Mock=No ASO; control NT=non-targeting control; Posctrl=positive control.
Figure 5B:
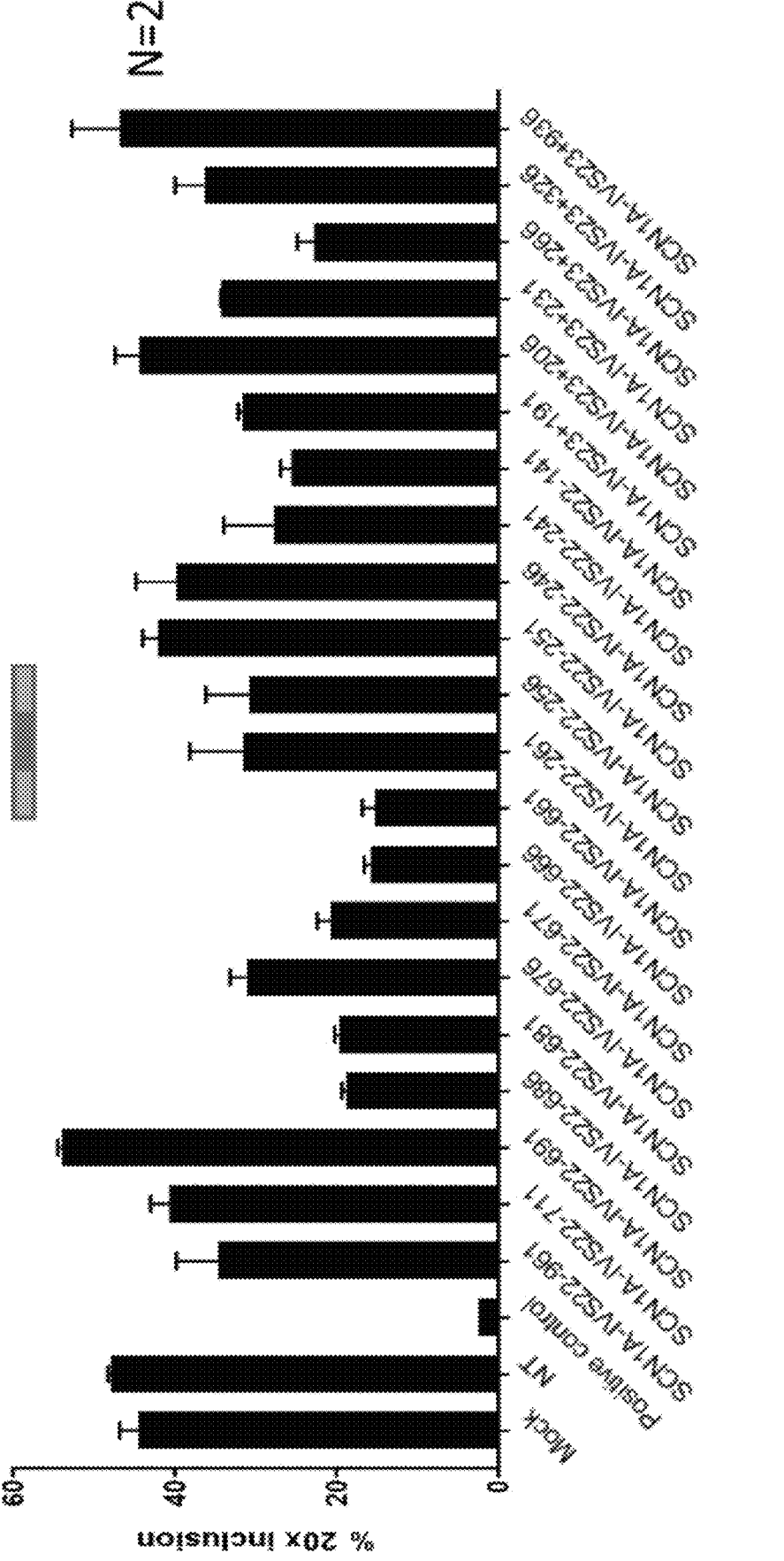
FIG. 5B depicts a graph plotting the percent exon 20x inclusion from the data in FIG. 5A.
Figure 5C:
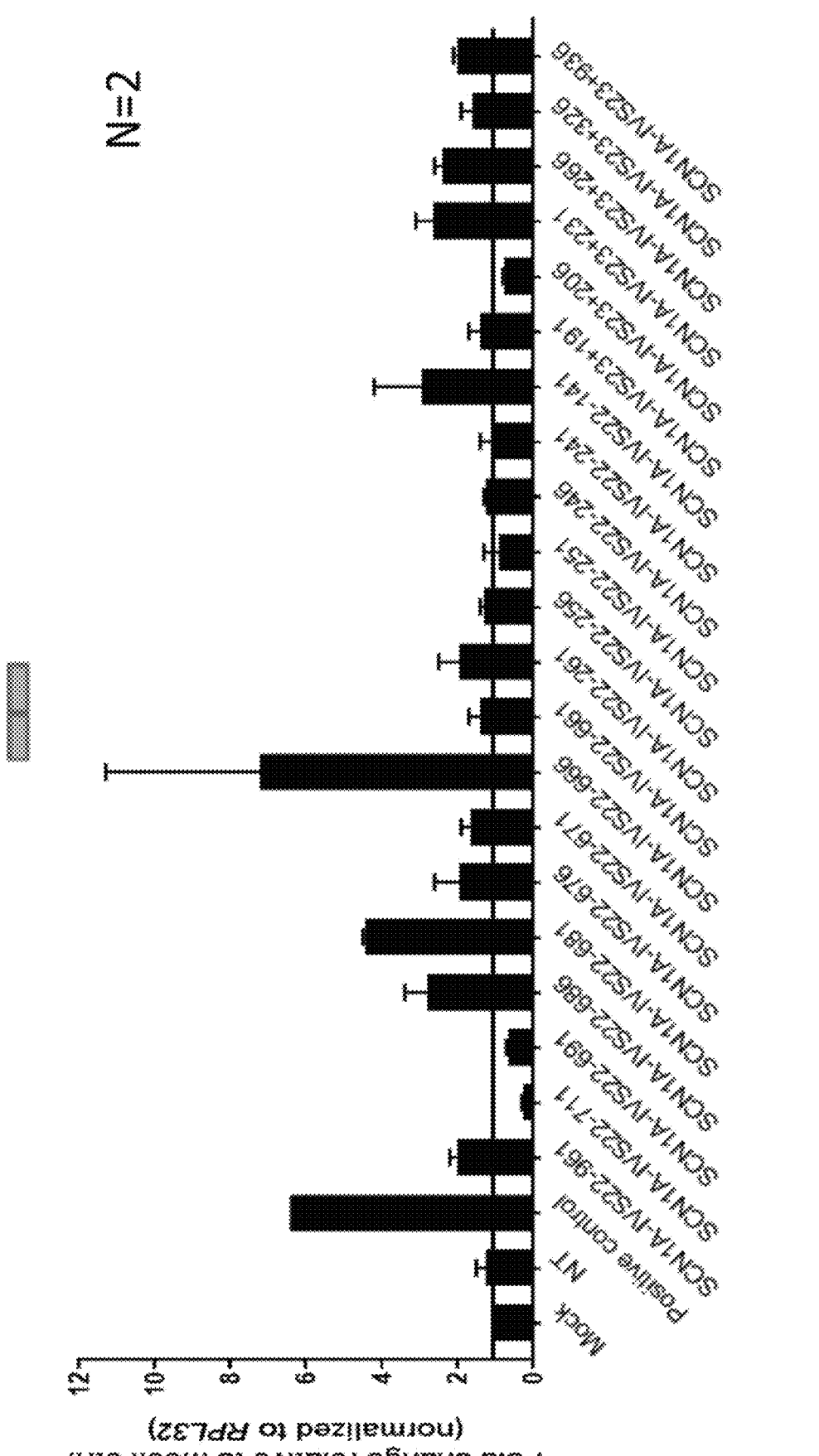
FIG. 5C depicts a graph of qPCR results of an extended ASO walk using the samples of FIG. 5A normalized to RPL32 internal control and the fold-change of SCN1A mRNA relative to mock is plotted.

Example 4: SCN1A Exon 23 (Exon 20x) Region Extended ASO Walk Evaluated by RT-PCR ASO walk sequences can be evaluated by for example RT-PCR. In FIG. 5A, a representative PAGE shows SYBR-safe-stained RT-PCR products of SCN1A mock-treated, control ASO treated, targeting the exon 20x region as described herein in the Example 3 and in the description of FIG. 3, at 1 µM concentration in RenCells by nucleofection. Two products, one comprising the exon 20x and one excluding exon 20x were quantified and the percent exon 20x inclusion is plotted in the bar graph (FIG. 5B). Taqman q PCR products were also normalized to RPL32 internal control and fold-change relative to mock is plotted in the bar graph (FIG. 5C).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of modulating expression of Nav1.1 protein in a cell having a pre-mRNA that contains a non-sense mediated mRNA decay-inducing exon (NMD exon) and that encodes Nav1.1 protein, the method comprising contacting a therapeutic agent or a vector encoding the therapeutic agent to the cell, whereby the therapeutic agent modulates exclusion of the NMD exon from the pre-mRNA encoding Nav1.1 protein, thereby modulating a level of processed mRNA encoding Nav1.1 protein, and modulating expression of Nav1.1 protein in the cell, wherein the therapeutic agent binds to a targeted region of the pre-mRNA encoding Nav1.1, and wherein the targeted region is:

from about 1000 nucleotides upstream from the 5' end of the NMD exon to about 100 nucleotides upstream from the 5' end of the NMD exon; or from about 100 nucleotides downstream of the 3' end of the NMD exon to about 1000 nucleotides downstream of the 3' end of the NMD exon.

2. The method of claim 1, wherein the therapeutic agent interferes with binding of a factor involved in splicing of the NMD exon from a region of the targeted region.

3. The method of claim 1, wherein the targeted region is at most 500 nucleotides upstream of 5' end of the NMD exon.

4. The method of claim 1, wherein the targeted region is at least 500 nucleotides upstream of 5' end of the NMD exon.

5. The method of claim 1, wherein the targeted region is at most 500 nucleotides downstream of 3' end of the NMD exon.

6. The method of claim 1, wherein the targeted region is at least 500 nucleotides downstream of 3' end of the NMD exon.

7. The method of claim 1, wherein the NMD exon comprises a sequence with at least 95% sequence identity to SEQ ID NO: 7.

8. The method of claim 1, wherein the targeted region is within an intronic sequence flanking the NMD exon.

9. The method of claim 1, wherein the targeted region is comprised within sequence with at least 95% sequence identity to SEQ ID NO: 6.

10. The method of claim 1, wherein the therapeutic agent is an antisense oligomer (ASO).

11. The method of claim 10, wherein the ASO comprises a sequence that is at least about 95% identical to any one of SEQ ID NOs: 12-731.

12. The method of claim 1, wherein the therapeutic agent promotes exclusion of the NMD exon from the pre-mRNA.

13. The method of claim 12, wherein the therapeutic agent increases a level of the processed mRNA encoding Nav1.1 protein in the cell.

14. The method of claim 13, wherein the therapeutic agent increases a level of Nav1.1 protein in the cell.

15. The method of claim 14, wherein an amount of the Nav1.1 protein in the cell contacted with the therapeutic agent is increased at least 1.1-fold compared to a total amount of Nav1.1 protein in a control cell.

16. The method of claim 1, wherein the ASO consists of a sequence selected from the group consisting of SEQ ID NOs: 72, 73, 76, 181, 220, 432, 433, 436, 541 and 580.

17. The method of claim 1, wherein the method comprises contacting a vector encoding the therapeutic agent to the cell, wherein the vector is a viral vector.

* * * * *

SEQUENCE LISTING

```
<160> NUMBER OF SEQ ID NOS: 732

<210> SEQ ID NO 1

<400> SEQUENCE: 1

000

<210> SEQ ID NO 2
<211> LENGTH: 8579
<212> TYPE: RNA
<213> ORGANISM: Homo sapiens

<400> SEQUENCE: 2
uugcugauuu guauuaggua ccauagagug aggcgaggau gaagccgaga ggauacugca      60
gaggucucug gugcaugugu guaugugugc guuugugugu guuugugugu cugugguguuc    120 ugccccagug agacugcagc ccuuguaaau acuuugacac cuuuugcaag aaggaaucug    180
aacaauugca acugaaggca cauuguuauc aucucgucuu ugggugaugc uguuccucac    240
ugcagaugga uaauuuuccu uuuaaucaga acagcauaag aauuauuucu gaguggaggu    300
gaggcuuguc caaaugucuu ugcuaucaug gauuuccuga cuccuaccug uuugagguuu    360
gggcaauuau gaauaaggcu gcuguauaca uccgugugca ggauuuugug uggacauaag    420
uuuucaacuc cuuugguuaa auccuaagga auuucauaug cagaauaaau gguaauuaaa    480
```

```
augugcagga ugacaagaug gagcaaacag ugcuuguacc accaggaccu gacagcuuca     540
acuucuucac cagagaaucu cuugcggcua uugaaagacg cauugcagaa gaaaaggcaa     600
agaaucccaa accagacaaa aaagaugacg acgaaaaugg cccaaagcca aauagugacu     660
uggaagcugg aaagaacccu ccauuuauuu auggagacau uccuccagag auggugucag     720
agccccugga ggaccuggac cccuacuaua ucaauaagaa aacuuuuaua guauugaaua     780
aagggaaggc caucuuccgg uucagugcca ccucugcccu guacauuuua acucccuuca     840
auccucuuag gaaaauagcu auuaagauuu gguacauuc auuauucagc augcuaauua     900
ugugcacuau uuugacaaac ugugugu uuu ugacaaugag uaaccccuccu gauuggacaa     960 agaauguaga auacaccuuc acaggaauau auacuuuuga aucacuuaua aaaauuauug    1020 caagggauu cuguuuagaa gauuuuacuu uccuucggga uccauggaac uggcucgauu    1080
ucacugucau uacauuugcg uacgucacag aguuugugga ccugggcaau gucucggcau    1140
ugagaacauu cagaguucuc cgagcauuga agacgauuuc agucauucca ggccugaaaa    1200
ccauuguggg agcccugauc cagucugug agaagcucuc agauguaaug auccugacug    1260
uguucugucu gagcguauuu gcucuaauug ggcugcagcu uuucaugggc aaccugagga    1320
auaaauguau acaauggccu cccaccaaug cuuccuugga ggaacauagu auagaaaaga    1380
auauaacugu gaauuauaau gguacacuua uaaaugaaac ugucuuugag uuugacugga    1440
agucauauau ucaagauuca agauaucauu auuuccugga ggguuuuuua gaugcacuac    1500
uauguggaaa uagcucugau gcaggccaau guccagaggg auauaugugu gugaaagcug    1560
guagaaaucc caauuauggc uacacaagcu uugauaccuu caguugggcu uuuuuguccu    1620
uguuucgacu aaugacucag gacuucuggg aaaaucuuua ucaacugaca uuacgugcug    1680
cugggaaaac guacaugaua uuuuuuguau uggucauuuu cuugggcuca uucuaccuaa    1740
uaaauuugau ccuggcugug guggccaugg ccuacgagga acagaaucag gccaccuugg    1800
aagaagcaga acagaaagag gccgaauuuc agcagaugau ugaacagcuu aaaaagcaac    1860
aggaggcagc ucagcaggca gcaacggcaa cugccucaga acauccaga gagcccagug    1920 cagcaggcag gcucucagac agcucaucug aagcccucuaa guugaguucc aagagugcua    1980
aggaaagaag aaaucggagg aagaaaagaa aacagaaaga gcagucuggu ggggaagaga    2040
aagaugagga ugaauuccaa aaaucugaau cugaggacag caucaggagg aaagguuuuc    2100
gcuucuccau ugaagggaac cgauugacau augaaaagag guacuccuc ccacaccagu    2160 cuuuguugag cauccguggc ucccuauuuu caccaaggcg aaauagcaga acaagccuuu    2220
ucagcuuuag agggcgagca aaggaugugg gaucugagaa cgacuucgca gaugaugagc    2280
acagcaccuu ugaggauaac gagagccgua gagauuccuu guuugugccc cgacgacacg    2340
gagagagacg caacagcaac cugagucaga ccaguagguc aucccggaug cuggcagugu    2400
uuccagcgaa ugggaagaug cacagcacug uggauugcaa ugguguggu uccuugguug    2460 guggaccuuc aguccuaca ucgccuguug dacagcuucu gccagaggga acaaccacug    2520
aaacugaaau gagaaagaga aggucaaguu cuuuccacgu uuccauggac uuucuagaag    2580
auccuuccca aaggcaacga gcaaugagua uagccagcau ucuaacaaau acaguagaag    2640
aacuugaaga auccaggcag aaaaugcccac ccuguuggua uaaauuuucc aacauauucu    2700
uaaucuggga cuguucucca uauugguuaa aagugaaaca uguugucaac cugguuguga    2760
uggacccauu uguugaccug gccaucacca ucuguauugu cuuaaauacu cuuuucaugg    2820
```

-continued

```
ccauggagca cuauccaaug acggaccauu ucaauaaugu gcuuacagua ggaaacuugg   2880
uuuucacugg gaucuuuaca gcagaaaugu uucugaaaau uauugccaug gauccuuacu   2940
auuauuucca agaaggcugg aauaucuuug acgguuuuau ugugacgcuu agccugguag   3000
aacuuggacu cgccaaugug gaaggauuau cguuccuccg uucauuucga uugcugcgag   3060
uuuucaaguu ggcaaaaucu uggccaacgu uaaauaugcu aauaaagauc aucggcaauu   3120
ccgugggggc ucugggaaau uuaacccucg ucuuggccau caucgucuuc auuuuugccg   3180
uggucggcau gcagcucuuu gguaaaagcu acaaagauug ugucugcaag aucgccagug   3240
auugucaacu cccacgcugg cacaugaaug acuucuucca cuccuuccug auuuguguucc   3300 gcgugcugug ugggagugg auagagacca ugugggacug uauggagguu gcuggucaag   3360
ccaugugccu uacugucuuc augaugguca uggugauugg aaaccuagug guccugaauc   3420
ucuuucuggc cuugcuucug agcucauuua gugcagacaa ccuugcagcc acugaugaug   3480
auaaugaaau gaauaaucuc caaauugcug uggauaggau gcacaaagga guagcuuaug   3540
ugaaaagaaa aauauaugaa uuuauucaac aguccuucau uaggaaacaa aagauuuuag   3600
augaaauuaa accacuugau gaucuaaaca acaagaaaga caguuguaug uccaaucaua   3660
cagcagaaau ugggaaagau cuugacuauc uuaaagaugu aaauggaacu acaaguggua   3720
uaggaacugg cagcagaguu gaaaaauaca uuauugauga aagugauuac augucauuca   3780
uaaacaaccc cagucuuacu gugacuguac caauugcugu aggagaaucu gacuuugaaa   3840
auuuaaacac ggaagacuuu aguagugaau cggaucugga agaaagcaaa gagaaacuga   3900
augaaagcag uagcucauca gaagguagca cuguggacau cggcgcaccu guagaagaac   3960
agcccguagu ggaaccugaa gaaacucuug aaccagaagc uuguuucacu gaaggcugug   4020
uacaaagauu caagguuguu caaaucaaug uggaagaagg cagaggaaaa caauggugga   4080
accugagaag gacguguuuc cgaauaguug aacauaacug guuugagacc uucauuguuu   4140
ucaugauucu ccuuaguagu ggugcucugg cauuugaaga uauauauauu gaucagcgaa   4200
agacgauuaa gacgauguug gaauaugcug acaagguuuu cacuuacauu uucauucugg   4260
aaaugcuucu aaaaugggug gcauauggcu aucaaacaua uuucaccaau gccuggugu u   4320 ggcuggacuu cuuaauuguu gauguuucau ggucaguuu aacagcaaau gccuugggu u   4380 acucagaacu uggagccauc aaaaucucuc a ggacacuaag agcucugaga ccucuaagag   4440
ccuuaucucg auuugaaggg augagggugg uugugaaugc ccuuuuagga gcaauuccau   4500
ccaucaugaa ugugcuucug guuugucuua uauucuggcu aauuuucagc aucaugggcg   4560
uaaauuuguu ugcuggcaaa uucuaccacu guauuaacac cacaacuggu gacagguuug   4620
acaucgaaga cgugaauaau cauacugauu gccuaaaacu aauagaaaga aaugagacug   4680
cucgauggaa aaaugugaaa guaaacuuug auaauguagg auuuggguau cucucuuugc   4740
uucaaguugc cacauucaaa ggauggaugg auauaaugua ugcagcaguu gauuccagaa   4800
auguggaacu ccagccuaag uaugaagaaa gucuguacau guaucuuuac uuuguuauuu   4860
ucaucaucuu ugggucuuc uucaccuuga accuguuuau uggugucauc auagauaauu   4920
ucaaccagca gaaaaagaag uuuggaggc aagacaucuu uaugcagaa gaacagaaga   4980 aauacuauaa ugcaaugaaa aaauuaggau cgaaaaaacc gcaaaagccu auaccucgac   5040
caggaaacaa auuucaagga auggucuuug acuucguaac cagacaaguu uuugacauaa   5100
gcaucaugau ucucaucugu cuuaacaugg ucacaaugau gguggaaaca gaugaccaga   5160
gugaauaugu gacuaccauu uugucacgca ucaaucuggu guucauugug cuauuuacug   5220
```

-continued

```
gagagugugu acugaaacuc aucucucuac gccauuauua uuuuaccauu ggauggaaua    5280
uuuuugauuu ugugguuguc auucucucca uuguagguau guuucuugcc gagcugauag    5340
aaaaguauuu cguguccccu acccuguucc gagugauccg ucuugcuagg auuggccgaa    5400
uccuacgucu gaucaaagga gcaaaggggga uccgcacgcu gcucuuugcu uugaugaugu    5460
cccuuccugc guuguuuaac aucggccucc uacucuuccu agucauguuc aucuacgcca    5520
ucuuugggau guccaacuuu gccuauguua agagggaagu ugggaucgau gacauguuca    5580
acuuugagac cuuuggcaac agcaugaucu gccuauucca aauuacaacc ucugcuggcu    5640
gggauggauu gcuagcaccc auucucaaca guaagccacc cgacugugac ccaauaaaag    5700
uuaacccugg aagcucaguu aagggagacu gugggaaccc aucuguugga auuuucuuuu    5760
uugucaguua caucaucaua uccuuccugg uguggugaa cauguacauc gcggucaucc    5820
uggagaacuu caguguugcu acgaagaaa gugcagagcc ucgagugag gaugacuuug    5880 agauguucua ugagguuugg gagaaguuug aucccgaugc aacucaguuc auggaauuug    5940
aaaaauuauc ucaguuugca gcugcgcuug aaccgccucu caaucugcca caaccaaaca    6000
aacuccagcu cauugccaug gauuugccca uggugagugg ugaccggauc cacugucuug    6060
auaucuuauu ugcuuuuaca aagcggguuc uaggagagag uggagagaug gaugcucuac    6120
gaauacagau ggaagagcga uucauggcuu ccaauccuuc caaggucucc uaucagccaa    6180
ucacuacuac uuuaaaacga aaacaagagg aaguaucugc ugucauuauu cagcgugcuu    6240
acagacgcca ccuuuuaaag cgaacuguaa aacaagcuuc cuuuacguac aauaaaaaca    6300
aaaucaaagg uggggcuaau cuucuuauaa aagaagacau gauaauugac agaauaaaug    6360
aaaacucuau uacagaaaaa acugaucuga ccaugccac ugcagcuugu ccaccuuccu    6420
augaccgggu gacaaagcca auuguggaaa aacaugagca agaaggcaaa gaugaaaaag    6480
ccaaagggaa auaaaugaaa auaaauaaaa auaauugggu gacaaauugu uuacagccug    6540
ugaaggugau guauuuuuau caacaggacu ccuuuaggag gucaaugcca aacugacugu    6600
uuuuacacaa aucccuuaa ggucagugcc uacaauaaga cagugacccc uugucagcaa    6660
acugugacuc uguguaaagg ggagaugacc uugacaggag guuacuguuc ucacuaccag    6720
cugacacugc ugaagauaag augcacaaug gcuagucaga cguagggac caguuucaag    6780 gggugcaaac cugugauuuu ggggguuguuu aacaugaaac acuuuagugu aguaauugua    6840
uccacuguuu gcauuucaac ugccacauuu gucacauuuu uauggaaucu guuaguggau    6900 ucaucuuuu guuaauccau guguuuauua uaugugacua uuuuuuguaaa cgaaguuucu    6960 guugagaaau aggcuaagga ccucuauaac agguaugcca ccuggggggu auggcaacca    7020 caugcccuc ccagcuacac aaagucgugg uuugcaugag ggcaugcugc acuuagagau    7080
caugcaugag aaaaagucac aagaaaaaca aauucuuaaa uuucaccaua uuucugggag    7140
ggguaauugg gugauaagug gaggugcuuu guugaucuug uuuugcgaaa uccagccccu    7200
agaccaagua gauuauuugu ggguaggcca guaaaucuua gcaggugcaa acuucauuca    7260
aauguuugga gucauaaaug uuauguuucu uuuuguguga uuaaaaaaaa aaccugaaua    7320
gugaauauug ccccucaccc uccaccgcca gaagacugaa uugaccaaaa uuacucuuua    7380
uaaauuucug cuuuuuccug cacuuugu uu agccaucuuc ggcucucagc aagguugaca    7440
cuguauaugu uaaugaaaug cuauuuauua uguaaauagu cauuuuaccc uguggugcac    7500
guuugagcaa acaaauaaug accuaagcac aguauuuauu gcaucaaaua uguaccacaa    7560
```

```
gaaauguaga gugcaagcuu uacacaggua auaaaaugua uucuguacca uuuauagaua      7620
guuuggaugc uaucaaugca uguuuauauu accaugcugc uguaucuggu uucucucacu      7680
gcucagaauc ucauuuauga gaaaccauau gucagaggua aagucaagga aauuguucaa      7740
cagaucucau uuauuuaagu cauuaagcaa uaguuugcag cacuuuaaca gcuuuuuggu      7800
uauuuuuaca uuuuaagugg auaacauaug guauauagcc agacuguaca gacauguuua      7860
aaaaaacaca cugcuuaacc uauuaaauau guguuuagaa uuuuauaagc aaauauaaau      7920
acuguaaaaa gucacuuuau uuuauuuuuc agcauuaugu acauaaauau gaagaggaaa      7980
uuaucuucag guugauauca caaucacuuu ucuuacuuuc uguccauagu acuuuuucau      8040
gaaagaaauu ugcuaaauaa gacaugaaaa caagacuggg uaguuguaga uuucugcuuu      8100
uuaaauuaca uuugcuaauu uuagauuauu ucacaauuuu aaggagcaaa auagguucac      8160
gauucauauc caaauuaugc uuugcaauug gaaaaggguu uaaaauuuua uuuauauuuc      8220
ugguaguacc ugcacuaacu gaauugaagg uagugcuuau guuauuuuug uucuuuuuuu      8280
cugacuucgg uuuauguuuu cauuucuuug gaguaaugcu gcucuagauu guucuaaaua      8340 gaauguggc uucauaauuu uuuuuuccac aaaaacagag uagucaacuu auauagucaa      8400
uuacaucagg acauuuugug uuucuuacag aagcaaacca uaggcuccuc uuuuccuuaa      8460
aacuacuuag auaaacugua uucgugaacu gcaugcugga aaaugcuacu auuaugcuaa      8520
auaaugcuaa ccaacauuua aaaugugcaa aacuaauaaa gauuacauuu uuuauuuua      8579
```

```
<210> SEQ ID NO 3
<211> LENGTH: 2425
<212> TYPE: DNA
<213> ORGANISM: Homo sapiens

<400> SEQUENCE: 3
gtaagaaaaa tgaaagaacc tgaagtattg tatatagcca aaattaaact aaattaaatt        60
tagaaaaagg aaaatctatg catgcaaaag gaatggcaaa ttcttgcaaa attgctactt       120 tattgttta tctgttgcat atttacttct aggtgatatg caagagaaat aggcctctct       180
tgaaatgata taatatcatt tatctgctgt gcttatttaa atgactttat ttcctaatcc       240
atcttgggag tttccttaca aatctatata caaaaaaaag ctgatgcatt attaaagtac       300
tatgtgtaat gatataatgg taatctaaag taaattctat atcaggtact tattctttgt       360
gatgatatac tgtacttaac gagttttcct gaaaataatg tgaatcacac atgtgcctaa       420
gtatgagtgt taagaaaaaa atgaaaggag ttgttaaaac ttttgtctgt ataatgccaa       480
agtttgcatt atttgaatat attcaagatt agatggttag atattaagtg ttgactgaat       540
ttataaaact agtaatacta acttaaagat tacatacaaa tccacatcat ttttataaca       600
ataaagtaaa acacttataa tgaacagaaa atataatttt gactcattac tataggtaat       660
ttatacatta accttaactt gcatcttatt ggtcagagtc acacaaatg ttattttatc       720 cttttcaaag atgcaataat cattttccat catgcataac agattagaaa ttttgccatt       780
attgacttat tttccatgcc ttttttacg gcatgaagca ttagtttata gatatataat       840
ataaaaaatt agttctgctt tttttaaaa aaaatatta tcaaaacaaa acactgaatt       900
gtgtgattcc aatagaaaaa cactgctctt tcacctccta aggtgtagtt acttttatgg       960
aaactaagct gtattgtaga cttccatttg cactttgtag attgtttata gccttatgtt      1020
ctcttctcaa gtcttattat aaatgtcact ttgtaagaac gtaggacttg tcttcgattt      1080
ccctaacata tatgaaaact ttgtcctcat tatcgacaac tcagaacaat ataatacaag      1140
```

-continued

```
tagtcctctt ttatttctca cagagagcct caaattttca ccaaaatgtt aacagaaatt      1200
atctctgggg tgtataagaa ttaagtctgt tttccaatta aatgtcactt tgttttgttt      1260
cagactggca gtttcagttc tggagaaaaa aaatgtcatt tgtgtacatt ctacttgaaa      1320
acatgttgcc tgaatcaaaa taatatattt tatatggctt gtgaaatctg aacaatgcta      1380
aacatttgaa aatattataa acctttaca tttgaccatt tgaaagttta ttaaattcat       1440
tggtcaagtg ctcagatatt tccatacatt acacttcatt tctataaaaa agctgatctt      1500
atcggtatac ttttaatttt ctcagaaata accatatcta taattattaa tcaataatgc      1560
cttttatatt aaaagaggtt agtttttgaa acttggagtt ttagacataa aatccttata      1620
aatgctgata gtgatataac taatagttta aatggtcaga tttatgaata tggctctatt      1680
cctcataatg acaacataca cacagcacta aaatgactaa tctcttcaat acgtgtttgg      1740
cattgtagag tcaaaataac gttataattg attctatttt ttatacttct agtgtttgga      1800
tattttattt tgtaaaaata taatcatgaa tgatggtgag gttggatata agaatgatga      1860
ttatgattgg gaagtgagat ttgaacatgc tcagaaactc tcatttaatt ctttgcccta      1920
gcagcataaa atcacaatag ctgcgtcaaa gcgtaactca ggcactcatt ttattttgt      1980 tgttctgtta tttttttcaaa gcatgtgctt ttatgcaaca ttactgaata aagcatgttg      2040
tacagtgctt gataagaagt tagaaagtaa caaataaatt atcatcacgt tgcactttgt      2100
gttttgcatg ttttatgcac atttctggct gacagctttt aaacatttat tgtatttcaa      2160
atttccagtc caaattttttc aacttgtaaa attaaactga gtgaattgat gtcgtgaata      2220
tctagggtaa aataaaattt gtgtttaaat ttgtatttt aatttcctaa cctaggaaat       2280
cttaaatacc ttcttttttca aaagaactca agtcttaatg gataggggaa cagacgggaga      2340 gcatcatgaa caaaaagtaa caccaaatgt tctgtcatat cagatttcta actaataaca      2400
aactatatat ttctattttg tatag                                            2425
```

<210> SEQ ID NO 4
<211> LENGTH: 64
<212> TYPE: DNA
<213> ORGANISM: Homo sapiens

<400> SEQUENCE: 4

```
gataatcttg ctccaacttg gatggggtgg agcgctggtt cctcccctga gccctttatt         60
atgg                                                                     64
```

<210> SEQ ID NO 5
<211> LENGTH: 4476
<212> TYPE: DNA
<213> ORGANISM: Homo sapiens

<400> SEQUENCE: 5

```
gtactgtatt acccctttg ctacctttaa tccttgcact gtgacttatg tgtagtgggg          60
tgagggaggg attgggaagg gtactattat tgcaccacag tagggaaaat acattattta         120
catcctaatc ccctctttc aattgtctta aatttcattt gaaaaaaaaa aaaacctta           180 tgaatttacc ctctgtggat tttaacccca atggttgata tctttattaa gtttcattga         240
atatgattta gttatgtgta tatggagtta tccatctttg gggagattac tggattggtg         300
agggcggggg accctggtgt agaatgatta tgtgaaaaaa caatttaact tgttaagctc         360
atgatactgt ttgaggcata cagcccctgc tgtttagtac attggtctgg gtcctgaaaa         420
```

-continued

```
ttaccagtta gataccatca gttgattatt gatatgtatg agcagatact agggtgcaat      480
atttcaggtt tcataagact ggtattgatt gtgaccactc tcattttta ttgtgtaagt      540 tcatatgggg ttattttcaa aatgttaaca aggcaaaaat atattaagaa atagttgaat      600
aagcacatgt gaattgtgtt gtaaacaaaa agttagaata aaaaaatcca cttatttgaa      660
ttatgcagaa tagaatacat acctagaaat aaaacaaaaa cgtcttatca tgagtattaa      720
gataaaattt aaggcataaa ctcacttctt agaataagta actcccaact aactttctag      780
gattttaaaa cataacacag tgaaaacata cataaacata actctacatt ttatttattc      840
ttaaagttta agtgtattat acaagaagaa gagtttatat tcgagagaca gaaaaagtca      900
gaatttttgt ttggatcacc aatatatcat agcttacaaa aaaactgtct taattaaaac      960
ccacaacata attttttag attttttaaga aagattctat tattcttctt tatacttaaa     1020
aatggatgat tcctactttg cccacttttta ttttttattca catagatttt ctttatttct     1080
attagagaag cactagaatt catgaatagt gttgatttga agttcaaagt aattaattca     1140 gataaaaga catttctgca tgtatgaaaa tttctaatgt gaatttgcat atttaattat     1200
caatccttca tttagtgtag acttatttt aaaaatgcag gtaatgaacc agaaatagaa     1260
ttggttgtgc tagagtagag aaactttatt tgatgattgt tttgaaaaaa aagcttctga     1320
gaagaaacaa cctctagtac agtattaatt cattaagata gctcctttct cagacatttc     1380
ctttcatgta gcctgaaagt tcaatttgaa atttgttctt tccaatttat tcagactaat     1440
tctgcctact ttcttccccc cataagaacc aattactgca gctttattga gactgaaaaa     1500
agttaataca cctccttctt tgctgaacca aggaatggct tggaactctt gggaaaagac     1560
aatcttttct atgatctttc attgtctaat ttaatacatc ataaatatga ctatagcttt     1620
gtataataaa ctccccaata ctgtgccaga tgttttctaa gataaagtta ttttatgttc     1680
acaaaaaaaa taaaactttt ctctgggcca aatgtatgcc aactttgcaa atcatatcct     1740
gaagtgcact gctgcagagt acatgcttgc gtcataaatt ccatagagtt cgctttaact     1800
ctaaatcaat ccccagtttc aaagtaaacc tctcaaacat attacctaag cacaaacttc     1860
tccctgtgct cagttcctta attattctca tcccatattc agaaataaca tttaaaaatt     1920
atgctttgat caataaatac taatctaaac tttgcttcat taacccattc attttttgtca     1980 accattattt tattcctata ttcaaagctc tctggtatgt tcttatattc aagacactca     2040
aggccctgga agattcacga acatatgttt gcatcttaaa tttttagaaa atcttacaat     2100
ctgtcaggat tacactgaac tctagtacag agtaatatgg gtaccagata agtgggagca     2160
actcttccac gtagactgga aacagcacta aatgctattt ataggctact ttctgaactt     2220
aacttgtttt aacctcattt ttctcatatg ccaaatgaga acgcaatact gaattatctg     2280
tacagttctg ttcagtacta gaattctgat tcttgaattc aaaggggaaa acattcctct     2340
ttattttgga ggctaaactg ggggacaaag ttaggctcca tgaaagaagt gctatttgaa     2400
ctaaagcctt taagagggga gagtatttca gaagaggagc tattagacaa ggaatttcaa     2460
tgtaaatggc atctcaatca cctggcaatt atattagcac acggttatta tattaattga     2520
agtggcatga agtatagatg accagggaag ttaaaactgg aaatatagat tgtgagtga     2580 tgtgaatacc aaggtaagaa aaatatttgt tagttaccag agagccaata aataactttc     2640
aagtgggact tggggaagat taattcatct tacatagatt aaatgaagga gaaggttagg     2700
agacagatga cagtgcaagt atgaaataac agagggcagt tctaggtggt gactgtgaga     2760
atggaaaaga ggtggcaaag ctgagaaacg tttcaaagaa aaaatgtgag acaggtaatg     2820
```

-continued

```
tgaaaagaaa atcgagaaat aggtatagat aatcagtgtt ctgctcatac tctaaattgg        2880
gtgttgaagg caaaatacgt attttaatta gtactctgtg tatacacact agaaacagca        2940
ttgtaatctg gatagtggac aaaatattca gaaaagaagg gaaatagtaa cttgatttca        3000
atttccaaat ctctaatctg aaagaaatct aattctattc atccatttaa aataaattat        3060
ataacgagaa tttatgaagt ccattgtatt aatgcagaca gtcagatgag ataaggcaaa        3120
gtgtcacgtg tcagcttggt agttgcatcg gccacatcat ttggttctgc ctggataact        3180
caaccaaatt aatttttcat actcatcccc tccacctttg tcattactgg tattcttatt        3240
ttctttggcc cacttatcac actgttttat gttccccaga aggcctagag ttctttacag        3300
gctttaaaca gggatcagaa gtataagaaa ttggctcatg tatttttttt tcagacaggc        3360
agttaaaaaa aattgttcta aaaatacact ggcatcaaat ggcaaataga agatgttttg        3420
acgactactt ccattggatc agactgacaa gaataataca agcacatagg tggaattaaa        3480
cttagctatt aatgtccaag tttgaggcag ctgcccctta taagcatttt agggtctgtt        3540
tttagcttcc ctcttagcca ctcctgtgca gctccagtgg gaggtatgga ggaaaaagca        3600
aggaagccat ccctatgttg tttccaaaca tgaacactca agatttttaa ctagtggtcc        3660
agaagtaaag aggggaaaa catccttcta tagaaaaaaa aaaagtaga taataattga        3720 acacagaact tcatgtgatc acatcagatt tgagaactat gtatggcatc cctctttttc        3780
ttattttcct aagaaatgat ttctattatg tttcatttga aataagtttt ttgaattaaa        3840
ctcagtaaat gaaacaactg acatgactgg agcttgaaat aaacgatgtg atgatctaat        3900
gaaatacata atgcaaattg tcttgcttct tatgcaaaaa ttattagtca tagcaatgca        3960
tgaataatta aagacaatta tattaggtat ttaataatat tttttatatt tatcatctga        4020 attttttaagt tattttaaaa atatattggt caaatcaact caggtccaaa tgtttttagtt        4080 ttgttctttta atatattgcc tttttaaaat gagtttaaact tctgtatagg ctttttttaact        4140 tttctttatt ctgataacac aattctgact tcatctggca gcaagttcct ctgatttttcc        4200 ttttccttta accttttaat gcttctccct ccctttttttt taaaaacatt tttgtttcat        4260
ttcttggtta tattgcctat agttgtttttc ctaagtgtat tgcttaagaa aaaaaaatga        4320
attttaagat tttttttgaac cttgctttta catatcctag aataaatagc attgatagaa        4380
aaaaagaatg gaaagaccag agattactag gggaatttttt ttttctttatt aacagataag        4440 aattctgact tttcttttttt tccatttgtg tattag                                 4476
```

```
<210> SEQ ID NO 6
<211> LENGTH: 6901
<212> TYPE: RNA
<213> ORGANISM: Homo sapiens

<400> SEQUENCE: 6
guaagaaaaa ugaagaacc ugaaguauug uauauagcca aaauuaaacu aaauuaaauu          60
uagaaaaagg aaaaucuaug caugcaaaag gaauggcaaa uucuugcaaa auugcuacuu        120
uauuguuuua ucuguugcau auuuacuucu aggugauaug caagagaaau aggccucucu        180
ugaaaugaua uaauaucauu uaucugcugu gcuuauuuaa augacuuuau uuccuaaucc        240
aucuugggag uuuccuuaca aaucuauaua caaaaaaaag cugaugcauu auuaaaguac        300
uauguguaau gauauaaugg uaaucuaaag uaaauucuau aucagguacu uauucuuugu        360
gaugauauac uguacuuaac gaguuuuccu gaaaauaaug ugaaucacac augugccuaa        420
```

```
guaugagugu uaagaaaaaa augaaaggag uuguuaaaac uuuugucugu auaaugccaa        480
aguuugcauu auuugaauau auucaagauu agauggguag auauuaagug uugacugaau        540
uuauaaaacu aguaauacua acuuaaagau uacauacaaa uccacaucau uuuuauaaca        600
auaaaguaaa acacuuauaa ugaacagaaa auauaauuuu gacucauuac uauagguaau        660
uuauacauua accuuaacuu gcaucuuauu ggucagaguc acacaaaaug uuauuuuauc        720
cuuuucaaag augcaauaau cauuuuccau caugcauaac agauuagaaa uuuugccauu        780
auugacuuau uuuccaugcc uuuuuuuacg gcaugaagca uuaguuuaua gauauauaau        840
auaaaaaauu aguucugcuu uuuuuuaaaa aaaaauauua ucaaaacaaa acacugaauu        900
gugugauucc aauagaaaaa cacugcucuu ucaccuccua agguguaguu acuuuuaugg        960
aaacuaagcu guauuguaga cuuccauuug cacuuuguag auuguuuaua gccuuauguu       1020
cucuucucaa gucuuauuau aaaugucacu uuguaagaac guaggacuug ucuucgauuu       1080
cccuaacaua uaugaaaacu uugcccucau uaucgacaac ucagaacauu auaauacaag       1140
uaguccucuu uuauuucuca cagagagccu caaauuuuca ccaaaauguu aacagaaauu       1200
aucucugggg uguauaagaa uuaagucugu uuuccaauua aaugucacuu uguuuuguuu       1260
cagacuggca guuucaguuc uggagaaaaa aaaugucauu uguguacauu cuacuugaaa       1320
acauguugcc ugaaucaaaa uaauauauuu uauauggcuu gugaaaucug aacaaugcua       1380
aacauuugaa aauauuauaa accuuuuaca uuugaccauu ugaaaguuua uuaaauucau       1440
uggucaagug cucagauauu uccauacauu acacuucauu ucuauaaaaa agcugaucuu       1500
aucgguauac uuuuaauuuu cucagaaaua accauaucua uaauuauuaa ucaauaaugc       1560
cuuuuauauu aaaagaggu aguuuuugaa acuggaguu uuagacauaa aauccuuaua       1620
aaugcugaua gugauauaac uaauaguuua aauggucaga uuuaugaaua uggcucuauu       1680
ccucauaaug acaacauaca cacagcacua aaaugacuaa ucucuucaau acguguuugg       1740
cauuguagag ucaaaauaac guuauaauug auucuauuuu uuauacuucu aguguuugga       1800
uauuuuauuu uguaaaaaua uaaucaugaa ugauggugag guuggauaua agaaugauga       1860
uuaugauugg gaagugagau uugaacaugc ucagaaacuc ucauuuaauu cuuugcccua       1920
gcagcauaaa aucacaauag cugcgucaaa gcguaacuca ggcacucauu uuauuuuugu       1980
uguucuguua uuuuuucaaa gcaugugcuu uuaugcaaca uuacugaaua aagcauguug       2040
uacagugcuu gauaagaagu uagaaaguaa caaauaaauu aucaucacgu ugcacuuugu       2100
guuuugcaug uuuuaugcac auuucuggcu gacagcuuuu aaacauuuau uguauuucaa       2160
auuuccaguc caaauuuuuc aacuuguaaa auuaaacuga gugaauugau gucgugaaua       2220 ucuagggaa aauaaaauuu guguuuaaau uuguauuuuu aauuuccaa ccuaggaaau        2280 cuuaaauacc uucuuuuuca aaagaacuca agucuuaaug gauaggaaa cagacggaga       2340 gcaucaugaa caaaaaguaa caccaaaugu ucugucauau cagauuucua acuaauaaca       2400
aacuauauau uucuauuuug uauagguacu guauuacccc uuuugcuacc uuuaauccuu       2460
gcacugugac uuaugugag uggggugagg gagggauugg gaaggguacu auuauugcac       2520
cacaguaggg aaaauacauu auuuacaucc uaauccccuc uuuucaauug ucuuaaauuu       2580
cauuugaaaa aaaaaaaac cuuuaugaau uuacccucug uggauuuuaa ccccaauggu       2640
ugauaucuuu auuaaguuuc auugaauaug auuuaguuau uguauauggg aguuauccau       2700 cuuugggag auuacuggau uggugagggc gggggacccu ggguagaau gauuaugug        2760 aaaaacaauu uaacuuguua agcucaugau acuguuugag gcaucuagcc ccugcuguuu       2820
```

```
aguacauugg ucuggguccu gaaaauuacc aguuagauac caucaguuga uuauugauau   2880
guaugagcag auacuagggu gcaauauuuc agguuucaua agacuggrau ugauugugac   2940
cacucucauu uuuuauugug uaaguucaua uggggguauu uucaaaaugu uaacaaggca   3000
aaaauauauu aagaaauagu ugaauaagca caugugaauu guguuguaaa caaaaaguua   3060
gaauaaaaaa auccacuuau uugaauuaug cagaauagaa uacauaccua gaaauaaaac   3120
aaaaacgucu uaucaugagu auuaagauaa aauuuaaggc auaaacucac uucuuagaau   3180
aaguaacucc caacuaacuu ucuaggauuu uaaaacauaa cacagugaaa acauacauaa   3240
acauaacucu acauuuuauu uauucuuaaa guuuaagugu auuauacaag aagaagaguu   3300
uauauucgag agacagaaaa agucagaauu uuuguuugga ucaccaauau aucauagcuu   3360
acaaaaaaac ugucuuaauu aaaacccaca acauaauuuu uuuagauuuu uaagaaagau   3420
ucuauuauuc uucuuuauac uuaaaaaugg augauccua cuuugcccac uuuuauuuuu   3480
auucacauag auuuucuuua uuucuauuag agaagcacua gaauucauga auaguguuga   3540
uuugaaguuc aaaguaauua auucagauaa aaagacauuu cugcauguau gaaaauuucu   3600
aaugugaauu ugcauauuua auuaucaauc cuucauuuag uguagacuua uuuuuaaaaa   3660 ugcaggguaau gaaccagaaa uagaauuggu ugugcuagag uagagaaacu uuauuugaug   3720
auuguuuuga aaaaaaagcu ucugagaaga aacaaccucu aguacaguau uaauucauua   3780
agauagcucc uuucucagac auuuccuuuc auguagccug aaaguucaau uugaaauuug   3840
uucuuuccaa uuuauucaga cuaauucugc cuacuuucuu ccccccauaa gaaccaauua   3900
cugcagcuuu auugagacug aaaaaaguua auacaccucc uucuuugcug aaccaaggaa   3960
uggcuuggaa cucuugggaa aagacaaucu uuucuaugau cuuucauugu cuaauuuaau   4020
acaucauaaa uaugacuaua gcuuuguaua auaaacuccc caauacugug ccagauguuu   4080
ucuaagauaa aguuauuuua uguucacaaa aaaaauaaaa cuuuucucug ggccaaaugu   4140
augccaacuu ugcaaaucau auccugaagu gcacugcugc agaguacaug cuugcgucau   4200
aaauuccaua gaguucgcuu uaacucuaaa ucauccccca guuucaaagu aaaccucuca   4260
aacauauuac cuaagcacaa acuucucccu gugcucaguu ccuuaauuau ucucauccca   4320
uauucagaaa uaacauuuaa aaauuaugcu uugaucaaua aauacuaaauc uaaacuuugc   4380 uucauuaacc cauucauuuu ugucaaccau uauuuuauuc cuauauucaa agcucucugg   4440
uauguucuua uauucaagac acucaaggcc cuggaagauu cacgaacaua uguuugcauc   4500
uuaaauuuuu agaaaaucuu acaaucugu aggauuacac ugaacucuag uacagaguaa   4560 uaugggguacc agauaagugg gagcaacucu uccacguaga cuggaaacag cacuaaaugc   4620
uauuuauagg cuacuuucug aacuuaacuu guuuaaccu cauuuuucuc auaugccaaa   4680
ugagaacgca auacugaauu aucuguacag uucguucag uacuagaauu cugauucuug   4740
aauucaaagg ggaaaacauu ccucuuuauu uuggaggcua aacuggggga caaaguuagg   4800
cuccaugaaa gaagugcuau uugaacuaaa gccuuuaaga ggggagagua uuucagaaga   4860
ggagcuauua gacaaggaau uucaauguaa auggcaucuc aaucaccugg caauuauauu   4920
agcacacggu uauuauauua auugaagugg caugaaguau agaugaccag ggaaguuaaa   4980
acuggaaaua uagauugugg agugaugugua auaccaaggu aagaaaaaua uuuguuaguu   5040
accagagagc caauaaauaa cuuucaagug ggacuugggg aagauuaauu caucuuacau   5100
agauuaaaug aaggagaagg uuaggagaca gaugacagug caaguaugaa auaacagagg   5160
```

```
gcaguucuag guggugacug ugagaaugga aaagaggugg caaagcugag aaacguuuca       5220
aagaaaaaau gugagacagg uaaugugaaa agaaaaucga gaaauaggua uagauaauca       5280
guguucugcu cauacucuaa auugggcuguu gaaggcaaaa uacguauuuu aauuaguacu      5340
cuguguauac acacuagaaa cagcauugua aucuggaugau uggacaaaau auucagaaaa      5400
gaagggaaau aguaacuuga uuucaauuuc caaaucucua aucugaaaga aaucuaauuc       5460
uauucaucca uuuaaaauaa auuauauaac gagaauuuau gaaguccauu guauuaaugc       5520
agacagucag augagauaag gcaaaguguc acgugucagc uugguaguug caucggccac       5580
aucauuuggu ucugccugga uaacucaacc aaauuaauuu uucauacuca uccccuccac      5640
cuuugucauu acugguauuc uuauuuucuu uggcccacuu aucacacugu uuuauguucc      5700
ccagaaggcc uagaguucuu uacaggcuuu aaacagggau cagaaguaua agaaauuggc      5760
ucauguauuu uuuuuucaga caggcaguua aaaaaaauug uucuaaaaau acacuggcau      5820
caaauggcaa auagaagaug uuuugacgac uacuuccauu ggaucagacu gacaagaaua      5880
auacaagcac auagguggaa uuaaacuuag cuauuaaugu ccaaguuuga ggcagcugcc      5940
ccuuauaagc auuuuagggu cuguuuuuag cuucccucuu agccacuccu gugcagcucc      6000
aguggagggu auggaggaaa aagcaaggaa gccaucccua uguugguuuucc aaacaugaac     6060 acucaagauu uuuaacuagu gguccagaag uaaagagggg gaaaacaucc uucuauagaa       6120
aaaaaaaaaa guagauaaua auugaacaca gaacuucaug ugaucacauc agauuugaga       6180
acuauguaug gcaucccucu uuuucuuauu uuccaagaa augauuucua uuauguuuca        6240
uuugaaauaa guuuuuugaa uuaaacucag uaaaugaaac aacugacaug acuggagcuu       6300
gaaauaaacg augugaugau cuaaugaaau acauaaugca aauugucuug cuucuuaugc       6360
aaaaauuauu agucauagca augcaugaau aauuaaagac aauuauauua gguauuuaau       6420
aauauuuuuu auauuuauca ucugaauuuu uaaguuauuu uaaaaauaua uuggucaaau       6480
caacucaggu ccaaauguuu uaguuuugu cuuuaauaua uugccuuuuu aaaaugaguu        6540
aaacuucugu auaggcuuuu uaacuuuucu uuauucugau aacacaauuc ugacuucauc       6600
uggcagcaag uuccucugau uuuccuuuuc cuuuaaccuu uuaaugcuuc ucccuccccuu      6660 uuuuuuaaaa acauuuuugu uucauuucuu gguuauauug ccuauaguug uuuuuccuaag      6720 uguauugcuu aagaaaaaaa aaugaauuuu aagauuuuuu ugaaccuugc uuuuacauau       6780
ccuagaauaa auagcauuga uagaaaaaaa gaauggaaag accagagauu acuaggggaa       6840
uuuuuuuucu uuauuaacag auaagaauuc ugacuuuucu uuuuuuccau uuguguauua       6900
g                                                                      6901
```

```
<210> SEQ ID NO 7
<211> LENGTH: 64
<212> TYPE: RNA
<213> ORGANISM: Homo sapiens

<400> SEQUENCE: 7
gauaaucuug cuccaacuug gaugggugg agcgcugguu ccuccccuga gcccuuuauu        60
augg                                                                   64

<210> SEQ ID NO 8

<400> SEQUENCE: 8

000
```

-continued

```
<210> SEQ ID NO 9
<211> LENGTH: 8320
<212> TYPE: RNA
<213> ORGANISM: Mus musculus

<400> SEQUENCE: 9
auguaagucu gucuagguca aguguaggag acucacuacc ggccugugga aacucaugga      60
acuguuucuu cagauuaaca cuucaggggc uaucgaggcu gcaggaagcu gagcuuuaac     120
uacauacauc uuucggggga aucucacaug aagaguaaag aguaauuaaa augugcagga     180
ugacaagaug gagcaaacag ugcuuguacc accaggaccu gacagcuuca acuucuucac     240
cagagaaucc cuugcagcua uugaaaggcg cauugcagaa gagaaggcua agaaucccaa     300
gccagacaaa aaagaugaug augaaaaugg cccaaagcca aacagugacu uggaagcugg     360
gaagaaccuu ccauuuaucu auggagacau uccuccagag auggugucgg agccucugga     420
ggaccuggac cccuacuaua ucaauaagaa gacuuuuaua guauugaaua aagggaaggc     480
caucuuccgg uucagugcca ccuccgcccu guacauuuua acacccuuca auccucuuag     540
gaaaauagcu auuaagauuu ugguacacuc auuauucagc auguuaauca ugugcacuau     600
uuugacaaac uguguauuua ugacaaugag uaacccuccc gacuggacaa agaaugugga     660
guacaccuuc acaggaauau auacuuuuga aucacuaaua aaaauuauug caaggggcuu     720
cuguuuagaa gauuuuacuu uccuucgcga cccauggaac uggcuggacu ucacugucau     780
uacauucgca uaugugacgg aguuugugga ccugggcaau gucucagcau ugagaacauu     840
cagaguucuu cgagcauuga aaacuauuuc agucauucca ggccugaaga ccaucguggg     900
ggcccugauc cagucgguga agaagcuguc ugacgucaug auacucacug uguucugucu     960
caguuguuuc gcacucaucg gguugcagcu cuucaugggc aaccgagga  auaaaugugu    1020 acaguggccu cccaccaacg cuucccuuga ggaacauagc auagagaaga auauaacuau    1080
ggauuacaau ggcacacuug uaaaugaaac cguuucgag uuugacugga aaucauacau    1140
ucaagacuca agauaucauu auuuccugga ggguguuuua gaugcacugc ugugguggaaa    1200 uagcucugau gcaggccaau guccagaagg auauaugugu guaaaagcug guagaaaccc    1260
uaauuauggu uacacaagcu uugauaccuu caguugggca uuuuugucccc uguuucgacu    1320 gaugacucag gacuucuggg aaaaucuaua ccaacugaca uugcgugcug cuggcaaaac    1380
cuacaugaua uuuuuugugc uggucauuuu cuugggcuca uucuaccuga uaaacuugau    1440
ccuggcugug guggccaugg ccuaugagga gcagaaucag gccacacugg aggaggcuga    1500
acagaaagag gcagaauuuc agcagauguu ggagcaacuu aagaagcagc aagaggcugc    1560
acagcaggca gcggcuacaa cagccucaga acauuccagg gagcccagug cagcaggcag    1620
gcucucagau agcucuucag aagccucuaa guugaguucg aagagugcua aagaaagacg    1680
aaaucggagg aaaaaaagga aacagaaaga gcagucugga ggagaagaga agaugauga    1740 ugaauuccac aagucugagu cugaagacag caucaggagg aaggguuuc gcuucuccau    1800 agaagggaau agacugacau augaaaagag guacucuccc ccgcaucagu cucuguuaag    1860
cauucguggu ucccuguucu ccccaagacg caauagcaga acaagucuuu ucagcuuuag    1920
agggcgagcc aaggaugugg ggcugagaa ugacuuugcu gaugaugaac acagcaccuu    1980
ugaggauaau gagagccgua gagacucacu guucguuccc cgaagacacg gagagcgacg    2040
caacaguaac cugagccaga ccagcagguc cucccgaaug cuggcggugu uuccagccaa    2100
ugggaagaug cacagcacgg uggauugcaa uggugugguu ccuugguug guggacccuc    2160
```

```
aguucccaca ucgccaguug gacagcuucu gccagaggug auaauagaua agccagcuac   2220
ugaugacaau ggaacaacca cugaaacuga gaugagaaag aggaggucga gcucuuucca   2280
uguuuccaug gacuuucuag aagauccuuc ccagaggcaa agggcaauga gcauagccag   2340
caucuuaaca aauacaguag aagaacuaga agaauccagg cagaaauguc cacccuguug   2400
guauaaauuu uccaacauau ucuuaauuug ggacuguucu ccauauuggc ugaaaguuaa   2460
acauauuguc aaccggugg  ugauggaccc auuuguugau cuggccauua ccaucugcau   2520
uguguuaaau acgcucuuca uggcuaugga gcacuacccc augacugaac auuucaacca   2580
uguucuuaca gugggaaacu uggucuucac ugggauuuuc acagcagaaa uguuccugaa   2640
aaucaucgca auggauccuu acauuacuu  ccaagaaggc uggaauaucu uugaugguuu   2700
cauugugaca cucagccugg uagaacuugg ccuugccaau guggaaggau ugucaguucu   2760
ccguucauuu cgacugcucc gaguguucaa guuggcaaag ucuuggccca cacugaauau   2820
gcucauuaag aucauuggua acucgggggg agcacugggc aaccgacuc  uggguguuggc   2880 caucauuguc uuuauuuuug ccgugguugg caugcagcug uuuggaaaaa guuacaaaga   2940
uugugucugc aaaauugcca cugacugcaa acucccacgu uggcacauga acgacuucuu   3000
ccacucguuc cugaucgugu uccgcgugcu guguggggag uggauagaga ccauguggga   3060
cugcauggag guggcaggac aagcuaugug ccuuacuguc uucaugaugg ucauggugau   3120
ugggaaccuu guggucuuga accucuuucu ggccuugcuu cugagcucau uuagugcaga   3180
caaccuugca gccacugaug augacaauga gaugaacaac cugcagauug cuguggacag   3240
gaugcacaaa ggaauagcuu auguaaaaag aaaaauauau gaauucauuc aacaauccuu   3300
uguuaagaaa cagaagauuc uagaugaaau uaagccacuu gaugaucuaa acaacagaaa   3360
agacaauugu aucucuaacc acacaacaga aauugggaaa gaucuggacu gucugaaaga   3420
ugugaaugga accacaagug gcauagggac gggcagcagu guggagaagu acaucauuga   3480
ugagagugau uauaugucau ucauaaacaa ccccagccuc acugugacug ugcccauugc   3540 uguggagag  ucugacuuug agaacuuaaa cacagaagac uuuagcagug aaucagaucu   3600
agaagaaagc aaagagaaac ucaacgaaag caguagcucc ucagagggaa gcacaguaga   3660
cauuggggcg ccugcagagg aacagccugu cauugaacca gaagaaaccc uugagcccga   3720
agcuugcuuc acugaaggcu guguccagag auucaagugc ugucaaauca gcguggaaga   3780
aggaagaggg aaacaguggu ggaaccuacg gaggacgugc uuccgaauag uugaacacaa   3840
cugguuugag accuucauug uguucaugau ucuccugagu aguggugccc uggccuuuga   3900
ggauauauau auugaucagc gaaagacgau caaaaccaug cuggaguaug cugacaaagu   3960
cuucacuuac auuuucaucc uggagaugcu ccucaaaugg guggccuaug cuaucaaac   4020 auacuucacc aaugccuggu guuggcuaga cuucuuaauu guugauguuu cauuggucag   4080
uuuaacagca aaugccuugg guuacucuga acucgggggcc aucaaaucccc uaaggacacu   4140 aagagcucug agaccccuaa gagccuuauc acgauuugaa gggaugaggg ugguugugaa   4200
ugcccuguua ggagcaauuc cauccaucau gaaugugcuu cugguuuugcc uuauauucug   4260 gcuaauuuuc agcaucaugg gcguaaauuu guuugcuggc aaauucuacc acuguguuaa   4320
caccacaacu ggugacauau uugaaucag  cgaagucaau aaucauucug auugccuaaa   4380
acuaauagaa agaaaugaga ccgcccgguug gaaaaaugug aaaguaaacu uugauaaugu   4440
aggauuuggg uaucuuucuu ugcuucaagu ugccacauuu aagggcugga uggauaucau   4500
```

-continued

```
guaugcugca guugauucca gaaauguuga acuacagccu aaguaugagg aaagccugua   4560
cauguauuug uacuucguca ucuucaucau cuucgggucc uucuuuaccc ugaaccuguu   4620 uauuggguguc auuaucgaca auuucaacca gcaaaagaag aaguuuggag gucaagacau   4680
cuuuaugaca gaagaacaga agaaauacua uaaugcaaug aagaaauuag gaucaaaaaa   4740
gccacaaaag ccuaucccuc gaccuggaaa caaauuucaa ggaaugguuu uugacuuugu   4800
aaccagacaa guguuugaua ucagcaucau gauccucauc ugucugaaca ugguugaccau   4860 gaugguggaa acggaugacc agagcgauua ugugacaagc auuuugucac gcaucaaccu   4920
ggguuucauc guccuguuca ccggcgagug ugugcucaag cucaucucgc uccgccauua   4980
uuauuucacc auuggaugga acauuuucga uuuuguggug gucauccucu ccauuguagg   5040
gauguuucuu gcggagcuaa uagaaaagua uuuugugucu ccacccugu uccgagucau    5100 ccgccuggcc aggauuggac gaauccuacg ccugaucaaa ggugccaagg ggauccgcac   5160
gcugcucuuu gcucugauga uguccccucc ugcgcuguuu aacaucggcc uccugcuuuu   5220
ucucgucaug uucaucuacg ccaucuuugg gauguccaac uuugccuaug uuaagagggga  5280 aguugggauu gaugacaugu ucaacuuuga gaccuucggc aacagcauga ucugccuguu   5340
ccaaaucacc accucugcgg gcugggaugg acugcuggcc cccauccuca acagcaaacc   5400
cccugacugu gacccuaaua aaguuaaccc uggaagcucg gugaagggag acuguggggaa  5460 cccaucugug gggauuuucu uuuuugucag cuacaucauc auauccuucc ugguuguggug  5520 gaacauguac auugcuguca uccuggagaa cuucagcguu gccacagaag aaagugcaga   5580
gccucugagu gaggacgacu uugagauguu cuacgagguc ugggagaagu ucgacccuga   5640
cgccacccag uucauggaau uugaaaaauu aucucaguuu gcagcugcuc uagaaccccc   5700
ucucaauuug ccacaaccaa acaaacuuca gcucauugcc auggaccugc ccauggugag   5760
uggagaccgc auccacugcc uggacaucuu auuugcuuuu acaaagcggg uguuggguga   5820
gaguggagag augggaugcuc uucgaauccca gauggaagag cgguucaugg cuuccaaccc   5880
cuccaagguc ucuuaucagc ccaucacuac uacauuaaaa cgcaaacaag aggaggugguc   5940 agcuguuauc auucagcgag cuuauaggcg ccaccuuuug aagcgaacag uaaaacaagc   6000
uucauucaca uacaauaaga acaaacucaa aggugggggcu aaucuucuug uaaaagaaga   6060
caugcucauu gacagaauaa acgaaaacuc uauuacggag aaaacugacc ugacaauguc   6120
cacagcagcu uguccgcccu ccuacgaucg ggugacaaag ccaaucgugg agaaacacga   6180
gcaggaaggg aaggaugaaa aagccaaagg gaaaugaaca aaaacaacaa aaaaaauaa    6240 uaaauugggu gacaaauugu uuacagccug ugaagucaaa aggacuccuu uaagaaguca   6300
augccaaacu gacuguuuuu acacaaauuc acuuuaaggu cagugccuca auaagacagu   6360
gacccccuug ucggcaaacu cuguugacugu guaaagggga gauaaccuug acaggagggu   6420
acguuucuaa cuaccagcug acacugcuga agacaagaga caaauggcua ugcagacugu   6480
agggaucagu cuaaaggggu gcagagcuau aauuuggggg uuaaugugaa acacuuuagu   6540
guaguaacuc uauccaccgu uugcauuuca acugccacau uugucagguu uuuuacaaac   6600
ucuguuagug gauucaucuu uuuuuuaauc caugguguugu uuguuacaug ugacuauuuu   6660
uguaagcagg guuucuguug ggaaauagac uaaaggaacu cuuuucccgg ugugucaccu   6720 gggagugguug acauccuuau ggcccucccg ucugcacaac ggugugguuu cgcaugaggg   6780
cauguugcac cuuaggauca ugcaugagaa aaagucgaaa ggaaagcaaa gacaguucuu   6840
caacaguucu augucaucug uguuucugcg gggggagggg gcgguacgga ggugaucgcu   6900
```

-continued

```
agaucguggg cuuugcugag cugggguuugu caaaaucuag uccuuagucc aaggagauug      6960
uucagacagg ucaucaaguc uuaggaggug caaacuucau ucaaaugucu ggagucacgc      7020
uacauuucug uucacugucu cugaaagguc ucuaaauuau gacucugacu cccuacccc       7080 aacccuagca gagcgaauug accaaaagaa cccuuuauaa auccccgcuu ccuccugcac      7140
uuuguuuagc caucuucagc ucucagcaag guugacacug uaugüguuaa ugaaaugcua      7200 uuuauuaugu aaauagucau uuuacucugu ggugcacguu ugagcaaaca aauaaugacg      7260
uaagcacagu auuuauugca ucaaauaugu accacgagaa auguagagug caagcugucc      7320
accggaaaua uacuguacuc uguaccauug uagauagugu ggaugcugcc aaugcauguc      7380
gauauuacca cguugcggua ucuaguuucu cucagcacuc agaaucucac ucacgagaaa      7440
ccauagguca guggcuaagu caaggaaacu guucagcaga cuucauuucu uuaagucauu      7500
aagcaauagu uugcagcacu uuaacaaugu uuggguuguu uuuaaaauuu aaguggauaa      7560
cguucaaugu auagccagac uguacauacg uguucaaaag acaacacuac ugcuuaaccu      7620
guuaaaaaca uguuuagagu uuuauaagca aauauaaaua cguacaaag ucacuuucuu       7680 uuacuuuuca gcauuaugua cauaugaaga ggaaauuauc uucagguuga uaucacaauc      7740
acuuuucuua cuuucugucc acagcaguuu uucauggaag auauuugcua acuaagaaau      7800
gaaacuauga cuggguagug guagaucucu gcuuuuuuau uacaauuguu aauuuuggau      7860
uauuucauaa uuuuaagggg caaaauacac ucacaacuuc acaccaaau uaugauuugc       7920 aauuggaaaa gguauaacau uugauuuaua uuuauuguag uguuugugcu aacagaugac      7980
cagagugcuu uuuuuucuca uuuuuuucuu uauuucccca auuucuguuu auuuuucuuu      8040
gcuuugaaau caugcuucuu uagaauuguuc uaaauauaaa uguggcuuc agaauuucuu       8100 uuccucaaaa ucagagagga uuacacuuau auagucaauu acaucaagau auuuguguuu      8160
cuuacagaag cagaccguag gcaccucuuu uucuuaaaaa aaaaauauuu aggcaaaccg      8220
uauucaugaa cugcauguug gaaaaugcua cuauuagccc aaaaugaugc uaaucacaau      8280
uaaaaaaugu gcaaaucaa uaaaauuaau uuuuuauuuu                            8320
```

<210> SEQ ID NO 10
<211> LENGTH: 7597
<212> TYPE: RNA
<213> ORGANISM: Mus musculus

<400> SEQUENCE: 10

```
guaagaaaaa ggaaaacucu gcagcguugu auauugucaa agcuaggcug aguucaacuu       60
aacuaacgaa aaacacgugc augcaaaagg aauggcaacc cuuugcaaac uugcuacuuu       120
acccuuuucu cuguugcaua uuuacuucuu ggugauaugc aagagaaaau cggccucuuu       180
gaaaaugauu uaauaucauu uaucugcuuu gcuaauuaaa augaccuuag uucauaaucg       240
aucuggggag uuuccuuaua auuccuaaua caaaggggga ggggcagaua cucucuuaaa       300
gaacuaaguu gagucaugua auaauuaccu agagauaauu uuguuucaua ucguucuccu       360
cuaugacagc ccaucaguac uuaagggauc cuauggaaag uaaugugaau cacaaaugug       420
uaugaauaca aaggaaaaaa ugaagaauug uuaaaugüuu ugucuuuaca augccaaaau       480
ucucauuauu ugaauauauc caagggcaga uauuaaccau ugacuggagu auaauaauac       540
ugccucaacu guaacuaaau uaaugacauu gaauaaguaa gacacuaauu uaauuacuau       600
aaauacauac acaucuuaug acaauacagc ugauaaggaa aaagaacaug uauuuuuauu       660
```

-continued

```
cauugccaua cauggcucgu caaccuuaac uuaaaccucg guucucaguu acacagaguu      720
uuauguugcu cuuuugagca aagcauuauu ccccucucca uaauucaaca cguaucagau      780
uuuugcauuu auuggcucau uguuaugaug auuauuucaa agcauuauac aaucauuuau      840
agaagaugug ccgugugaaa auuauuuuuu uauuaagauc caaaauuuac gcucuuuaaa      900
ccaaucagau gaaauguaua aggcaaagag ugcucauugu ccugacacuu acaaaccaag      960
gcuccaacaa acaggcuccu cucugcacca cauagagggc uuucagccug uguccccca     1020 uaaaaaccua uuauaaauuu uauuauacua uacuguaaga aaccuguccaa auuuuuaauu    1080 ucucuagcac auaugaaaac uucucuucag uagauccaag uaagcacaaa ggagcuuuga    1140
uucucacaca agaaaucaca uuuguauuaa aaauguauca uaaauuuucu cccaauuaug    1200
caaaacuuaa augcuuuucc aauuaaaaga gcacuuucgu uucagaauag caauuucagu    1260
ugucaaggaa aacauuguuu uuauacauuu uauauaaaaa uacaugagcu aaauuuaaau    1320
ucacauuuuu caacuuuuua ugguuuuuuu auguuucuuu uucuuucgca uuuuuuaaca    1380
auccagccau uaccucuccu cccugucccc cuccauagu uucucaucuc auuccuccuc     1440
ccccuugccu cugagaggau gcucccuccc ucacuaggcc ucccucuucc ccagggcuuc    1500
aaguuccuca aggauuauac acaucuucuc ccacugagac caggccaggc aguccucugc    1560
uucugcccag ccugugauag uuccugcuug guagcucagu cucuggaagc ucccuggggu    1620 cugggguuagu ugggacugcu ggucuuccua uggaguuacc cucccuuca acuucuucaa    1680 uccuuccccu aauucaacca cagguaucca gacuucaguc caaugguuga gguguaaauau   1740 uggcaucugu cucugucagc uguuguuagg ggcucagagg acagccaugc uaggcuccug    1800
ccuacaagca gcacaccaua acaucaguaa uagugucagg ccuuuaauga auaaugcuac    1860
guauauaagg uuguuagauu auacuucaac uuugaucuuu uagaauauua uuaaauccag    1920
ucguuuauuu uuuauaugua auauugacuu uccauaacaa augagucuau uuuccuuuug    1980
uguagaaaua acuuuaucaa uuauuguuaa uaaugcuuuu gucaauuauu guugauaugc    2040
uucucuuuuu uaaaacugga gucaucaaaa caaaaauucu gggguagauau uacgaagcug   2100 acuccuuggu cagcuuggca cauagugaga ccacaaauau cucaagguca cggcaauucc    2160
ucaccaccag uuuggcauug ugaagucaaa accaaccuuc uguugauucu gguuuuugua    2220 uuuucuaguau gagacauuuu cuacuuugua agaguauaua acuguggaug gcggcgaggu   2280 uggggcaugau gaugauugua agcgggaagu gagcuagagu aucuucagaa acucucacuu   2340
uauccuccuu ggcagcauag aaccgcaauc gcugugguccg agucucaacc aggcagucau   2400
uuuguuuugg guuuuuuguc acucuuucaa agcaugugcu ucuacgcaac acuaccaaac    2460
acagcaugcu gcauagugcu ugagaaggag uuagaaagua acaaacgagu uaucaucacg    2520
uugcccuuug uguuuugcau gucuuaugca cacuuuuggc ugacagcuuu ugaacauuua    2580
uuguauuuca aauuuccagu ccaaauuuuu uuuucaacuu gugaaauuga acggaaugaa    2640
ccgaugucgu gaauaccuag ggucaaauaa aacuuguauu uaaauucgua guuuuaauuu    2700
cccaagcugg gaaaaucgua aaaaccuuuu ccaaagaacu caagucuuag uugcuaggga    2760
aacaggcagu gagcaucaua uacaaaaagu aacaccaaau guucugucau aucagcuuuc    2820
uaacuaauaa uaaacuauau auuucuauuu uauauaggau aaucuugcuc caacuuggau    2880 ggggguggagc gguggguuccu ccccucagcc cuuuauuaug gguacuguau uaccccuuuu   2940
gcuaccuuua auccuugcac ugugacuauu ugugaguggg auugagggag ggagugggaa    3000
ggguacaauu gcaccacagu agggacaaua caggauuuau uuccaaaucc acuacuuuua    3060
```

```
augagcuuaa acuucuuuug ggaaaaaaaa aguuaucucu gacuuaccau cuguggauua    3120
uaaccccaga aguacauauc uuuauuacgu uucacugaau augauuuagc uauuuauacu    3180
ucauugucca uuuaugggga aauuacucaa uuggugaggg uggggaccc uggugaugga     3240 ugcugaugaa aacguuuuca uuugucaagc ucauggaguu gacagagcau auaguccuua    3300
uuuuuucaac acacugcucu gguccuccaa ugggccaguc acauccauc aguugaucgu     3360 ugaugugugc gagcaguggc uaaagguaca acaggccagg uaucucaggg uugccaaugg     3420
uuaugaucau ucucaucuuu auugcauaaa aaugugguau uugcagaaag uagcaaggca     3480
agaucccugu gaaacaaggg aauacaaaaa aaaaaaaaga ugugcuuuaa guuauaaaac     3540
caaaacaugu gaaaagucaa cuucauugaa guauaaagaa uaggauaugc augaaaaaca     3600
aaaaaaucau gagcacuaag aaauuggugu auaagccaac uccuuguaag cuaccccaau     3660
uaacuuccca gaaucuuaga aggcaucaca gugcacccca aaauaaaaag ccaaacugac     3720
acuucugcuu ccucuuaaaa uguaggaguc uuggauaaga aagauaauuu uuauuguuug     3780
gaagaaaaaa aaauuguuug gauaauugag gcauuuaucu aucaaaaaua uuuaucuuaa     3840
uaaaauuuca caacacugau uuaguuguug gcuuuucuaa aaauuuuuua uauuucauau     3900
uaagaacuca ugauuuuuac uuuccauuuu uuaaauucuu auucacauau gguuuuucuc     3960
uauuucuuag aaaagcuaua gaacccaugg uuuccgguga cuuaaaaaac uaacucaaau     4020
gucuucacuu agaugauacu uucaaaugca cugaaauuuc uaauaucaac aagaauauuu     4080
gccugguccu aauuuuucac ugauuuaaua aaaaguauga acccuaaaga agaaauagac     4140
uugaagaacu gguuguguga caauacagaa auucugcugg gagaugupcu uuuaaaacau     4200 uguuagaaga gacaaccucu acaauccacc cauuaagcau acuucucucu uagacaucuc     4260
cuuuuaugua ccuuauaacc ucaauguguu cuuuccaauu gacuuagacc aacacuuccc     4320
agcgcauccc acaugggagc caauuacuga cucucccuag agacugcaaa gaauuaauau     4380
uguagaacca agggaugguu gggcucuugg gagaggcaau ccguuuguga ucuuuugcuc     4440
uggauguuaa ugaaaucgca acuuuaagug gauuuucagu ggcaaauccu cugauccuau     4500
gccaaauguu cucuaagaca aacauccuug uaaaauaaau gucucacugg gccaaaucua     4560
uggcaaauuu gcacguuuuc cugaacugca uuccuauaua guauuugcca uccugaauuc     4620
acuaaugggc auuacuuuua auucaaaacc agucccuucu ucaaaggaaa ucucucccau     4680
uuauuacauu augcaaacug cuuucuuaug cagugguuaa auccuuagcc aggcaaguau     4740
gaggacugga auuuggauau ccagaacccu cagaaauguc ggaugggcau aguagcuuac     4800
auguaauucc agagcuagaa agaugaaacu agcccugucc ucaagcucug aauucaguug     4860
gugcaauaaa uaagaaagaa ucccccccc cgaccccuac aucucuuucc ucuacaucua     4920
uacauguauu ucccauacag cucuaugcuu ccacauauau gcucacauau gugcaugcac     4980
acuugcacac auauguacac uugacacauu gaagcaucau aaucuaacaa uuggaauaua     5040
agaaaauauu uaacuuucac acagagcagu cagagaaaac cauaagaggu ugaaacucuu     5100
gaaaaaacuu gcaggauaaa cagaaaagag uaugagaugc caauucuggu cuacuuucug     5160
aaccuaacuu guuuuaccuu cauuagucua auuuuccaaa ugaaccccaa gcaccaaauu     5220
guccuuauug cucuuuccag uacuaaauua uaauuccuca auucgaaggc aaacacucuc     5280
aucuuuguua aggauguuua gaguuagacu caauaaacga cauguauauu ugagcuaaag     5340
ccuggaggag ggagauuauu ucaagggcaa guacuuggcg gggaguuuca aagaaagaag     5400
```

-continued

```
gcucucaauu cucagacuaa caccuuagcg uggagugacu gucacagagg agggugaagu      5460
guaugucacc aguuagggaa gcugaaaggg gaaauguauc aggcuuguga gaauccuuca      5520
gcagccaagu cuagcaccug agcacaaucc ccagaacuga ccccacaugg uggaaaggag      5580
aggaauaauu ccugcaaauu uuccugugac cuccacccaa gugcuauaga aaaugcaugc      5640
augcccacau gcacacacaa auaaacauag uugcaaacug uuuugaggaa aauaaccuca      5700
caaacugucg agugauguaa augccaaaga aagagaaaug uuuucuaaug gcuagagaac      5760
cauuaaggaa uuuuucaaaa ugggacaugg gauagauaaa uuuaguaucc auacugaaag      5820
aaggcaagca aauaaaaucu gauaagaaug uaauucuuag uaaccgagga cagagcgaag      5880
auagagaaca gggccaaugg ccaaggugga aagguuugaa ggaagcagca ugaaaccuac      5940
agacuuguac caaaauguuc agugucauga guguuaaaag ugaaaagcuu gcauguuagu      6000
auggauuuca uauccucggc agacagagca ccucacugug aguggggagau gaaguauuca      6060 gaaaugagaa acaacuacuc aauuucagug uucauaucuc aaauccaaua aacaacuuua      6120
gggguacaau uuuuuaaaaa auuacauuaa aauguuuuua aaucucuucu uaauaauuua      6180
aaaauuaaau ugaaaauaac uuuaaaaagu aauauauaca ggaaagccug ugugcuaauu      6240
uuuuagggag gccauaaagg gagauaguug cucauuaauu ucuacacauc agccuaucuu      6300
uggcuucugc cuugauagcg cacucugaau uaucuucuuc auguucaucc cucaucuuua      6360
uuguuacugg uuucauuuuc cuuggccaca uagcccacua uuuuguauuc cccaauggau      6420
auuguuccuu acaaaguuca gccagggcuc agaaguacaa ggaauuggcu cuuauacuuc      6480
ugucagacag gcaaaaacuu cuaaaauuau acuauaauaa aaaucaaaga gaugauauuc      6540
auaauuaaac uaacaaaagu ggcaggcccc cccuccccca acaugaguag aauuaaucug      6600
acguccaugu ucaagucuga aacacacuug ccaauuaaga gcacauuagg gccagccuuu      6660
aucucccucu uaguuacuaa ugugcaguuc aauggugagc uauagagaag gaagccaaga      6720
cuaccauaug ucaaauauaa aaaaaaaaaa ucccauuuua aaucuguagu cccgaauuaa      6780
ggacaagaga gagggaaaua ucuuugacau uagaaaaugg agaaaauauu uuagcacagg      6840
acuuuacuca gucacaucag aguugauaag uacguaugac aucccucuuu uuccuguuuu      6900
ccugagaaaa ugaucucucu aguguuucau uuaagauaag uuuauugaau uaaacucagu      6960
aaaugaaaca acugacauga cuggagcuug aaauaaacga ugugaugauc uacugaaaua      7020
caugaugcua aauugucuug cuucuuaugc aaaaacuacu auuaguuaua gcaaugcaug      7080
gauaauuaag gccaaaaaua uauuagaugu uaaaaauagu uuuauauuua uacaucugaa      7140
uuuuaauuua uauuuaaagu auauuggucc aaucaauuca ugcccaaaug uuuuaguucu      7200
auucuuugag auacuguuuu guuuugggau uuuuuuuuau gagcuaaucu cuugccuagg      7260
aguuccuacu ucucucuccu ccuuuuauuu uuucuaauaa acuacacaug ugucuucauc      7320
caggagcuaa cuucucccau uuugcuuuuc cuuuagcacc uuuuuuauau uagauuucuu      7380
ucuuuucucc aucucuuugc auauugccua uauuucuuuu ccuaagcaua auauuuaaaa      7440
aagacugagu uuuauguuaa gauuauuucu gcuuugcucu uacacagaua ggauaaguag      7500
ucuugauaga aaauaaauca augauuccua ggggaugauc uuuuugcuuu uaaucaauaa      7560
ggauucugac uucucuuucu cuccauuugu guauuag                               7597
```

<210> SEQ ID NO 11
<211> LENGTH: 64
<212> TYPE: RNA
<213> ORGANISM: Mus musculus -continued

---

<400> SEQUENCE: 11
gauaaucuug cuccaacuug gauggggugg agcggugguu ccucccuca gcccuuuauu      60 augg                                                                 64

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 12
atgaatttaa taaacttt                                                  18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 13
gaccaatgaa tttaataa                                                  18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 14
cacttgacca atgaattt                                                  18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 15
ctgagcactt gaccaatg                                                  18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 16
aatatctgag cacttgac                                                  18

<210> SEQ ID NO 17
<211> LENGTH: 18
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 17
atggaaatat ctgagcac                                                    18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aatgtatgga aatatctg                                                    18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
agtgtaatgt atggaaat                                                    18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aatgaagtgt aatgtatg                                                    18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atagaaatga agtgtaat                                                    18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tttttataga aatgaagt                                                    18

<210> SEQ ID NO 23
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 23
cagctttttt atagaaat                                                  18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aagatcagct tttttata                                                  18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccgataagat cagctttt                                                  18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gtataccgat aagatcag                                                  18

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
taaaagtata ccgataag                                                  18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
aaaattaaaa gtataccg                                                  18

<210> SEQ ID NO 29
<211> LENGTH: 18
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 29
ctgagaaaat taaaagta                                                      18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tatttctgag aaaattaa                                                      18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
atggttattt ctgagaaa                                                      18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tagatatggt tatttctg                                                      18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aattatagat atggttat                                                      18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ttaataatta tagatatg                                                      18

<210> SEQ ID NO 35
<211> LENGTH: 18
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 35
attgattaat aattatag                                              18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcattattga ttaataat                                              18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
aaaaggcatt attgatta                                              18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
aatataaaag gcattatt                                              18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cttttaatat aaaaggca                                              18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aacctctttt aatataaa                                              18

<210> SEQ ID NO 41
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 41
aaactaacct cttttaat                                                    18

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ttcaaaaact aacctctt                                                    18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
caagtttcaa aaactaac                                                    18

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aactccaagt ttcaaaaa                                                    18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tctaaaactc caagtttc                                                    18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttatgtctaa aactccaa                                                    18

<210> SEQ ID NO 47
<211> LENGTH: 18
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 47
ggattttatg tctaaaac                                                  18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tataaggatt ttatgtct                                                  18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gcatttataa ggatttta                                                  18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tatcagcatt tataagga                                                  18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
atcactatca gcatttat                                                  18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gttatatcac tatcagca                                                  18

<210> SEQ ID NO 53
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 53
tattagttat atcactat                                               18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
taaactatta gttatatc                                               18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ccatttaaac tattagtt                                               18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tctgaccatt taaactat                                               18

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
ataaatctga ccatttaa                                               18

<210> SEQ ID NO 58
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
tattcataaa tctgacca                                               18

<210> SEQ ID NO 59
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 59
agccatattc ataaatct                                                      18

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
aatagagcca tattcata                                                      18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgaggaatag agccatat                                                      18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cattatgagg aatagagc                                                      18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gttgtcatta tgaggaat                                                      18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tgtatgttgt cattatga                                                      18

<210> SEQ ID NO 65
<211> LENGTH: 18
<212> TYPE: DNA
<213> ORGANISM: Artificial Sequence
<220> FEATURE:
```

<223> OTHER INFORMATION: Description of Artificial Sequence: Synthetic
     oligonucleotide

<400> SEQUENCE: 65
ctgtgtgtat gttgtcat                                                          18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 66
tagtgctgtg tgtatgtt                                                          18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 67
cattttagtg ctgtgtgt                                                          18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 68
ttagtcattt tagtgctg                                                          18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 69
agagattagt cattttag                                                          18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 70
attgaagaga ttagtcat                                                          18

-continued

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cacgtattga agagatta                                                   18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ccaaacacgt attgaaga                                                   18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
caatgccaaa cacgtatt                                                   18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ctctacaatg ccaaacac                                                   18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
tttgactcta caatgcca                                                   18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gttattttga ctctacaa                                                   18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ataacgttat tttgactc                                                  18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
caattataac gttatttt                                                  18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
agaatcaatt ataacgtt                                                  18

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
aaaatagaat caattata                                                  18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81 tataaaaat agaatcaa                                                   18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
agaagtataa aaaataga                                                  18

-continued

```
<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
acactagaag tataaaaa                                                             18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tccaaacact agaagtat                                                             18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aaatatccaa acactaga                                                             18

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aaataaaata tccaaaca                                                             18

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ttacaaaata aaatatcc                                                             18

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
tatttttaca aaataaaa                                                             18

<210> SEQ ID NO 89
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gattatattt ttacaaaa                                            18

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ttcatgatta tatttta                                             18

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
catcattcat gattatat                                            18

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ctcaccatca ttcatgat                                            18

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ccaacctcac catcattc                                            18

<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tatatccaac ctcaccat                                            18

<210> SEQ ID NO 95
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
attcttatat ccaacctc                                              18

<210> SEQ ID NO 96
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tcatcattct tatatcca                                              18

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
cataatcatc attcttat                                              18

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
ccaatcataa tcatcatt                                              18

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
acttcccaat cataatca                                              18

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
atctcacttc ccaatcat                                              18

<210> SEQ ID NO 101
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 101
ttcaaatctc acttccca                                               18

<210> SEQ ID NO 102
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gcatgttcaa atctcact                                               18

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tctgagcatg ttcaaatc                                               18

<210> SEQ ID NO 104
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gagtttctga gcatgttc                                               18

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
aatgagagtt tctgagca                                               18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aattaaatga gagtttct                                               18

<210> SEQ ID NO 107
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 107
caaagaatta aatgagag                                                        18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tagggcaaag aattaaat                                                        18

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gctgctaggg caaagaat                                                        18

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tttatgctgc tagggcaa                                                        18

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gtgattttat gctgctag                                                        18

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ctattgtgat tttatgct                                                        18

<210> SEQ ID NO 113
<211> LENGTH: 18
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 113
cgcagctatt gtgatttt                                                    18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tttgacgcag ctattgtg                                                    18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tacgctttga cgcagcta                                                    18

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tgagttacgc tttgacgc                                                    18

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gtgcctgagt tacgcttt                                                    18

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
aatgagtgcc tgagttac                                                    18

<210> SEQ ID NO 119
<211> LENGTH: 18
<212> TYPE: DNA

-continued

<213> ORGANISM: Artificial Sequence
<220> FEATURE:
<223> OTHER INFORMATION: Description of Artificial Sequence: Synthetic
     oligonucleotide

<400> SEQUENCE: 119
aataaaatga gtgcctga                                            18

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 120
acaaaaataa aatgagtg                                            18

<210> SEQ ID NO 121
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 121
gaacaacaaa aataaaat                                            18

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 122
taacagaaca acaaaaat                                            18

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 123
aaaaataaca gaacaaca                                            18

<210> SEQ ID NO 124
<211> LENGTH: 18
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 124
tttgaaaaaa taacagaa                                            18

<210> SEQ ID NO 125
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 125
catgctttga aaaaataa                                                       18

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
aagcacatgc tttgaaaa                                                       18

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
cataaaagca catgcttt                                                       18

<210> SEQ ID NO 128
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tgttgcataa aagcacat                                                       18

<210> SEQ ID NO 129
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
agtaatgttg cataaaag                                                       18

<210> SEQ ID NO 130
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tattcagtaa tgttgcat                                                       18

<210> SEQ ID NO 131
<211> LENGTH: 18
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 131
tgctttattc agtaatgt                                                      18

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
caacatgctt tattcagt                                                      18

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ctgtacaaca tgctttat                                                      18

<210> SEQ ID NO 134
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
aagcactgta caacatgc                                                      18

<210> SEQ ID NO 135
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ttatcaagca ctgtacaa                                                      18

<210> SEQ ID NO 136
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
acttcttatc aagcactg                                                      18

<210> SEQ ID NO 137
<211> LENGTH: 18
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 137
ttctaacttc ttatcaag                                              18

<210> SEQ ID NO 138
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
ttactttcta acttctta                                              18

<210> SEQ ID NO 139
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
atttgttact ttctaact                                              18

<210> SEQ ID NO 140
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
aatttatttg ttactttc                                              18

<210> SEQ ID NO 141
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
atgataattt atttgtta                                              18

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
acgtgatgat aatttatt                                              18

<210> SEQ ID NO 143
<211> LENGTH: 18
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 143
gtgcaacgtg atgataat                                                      18

<210> SEQ ID NO 144
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
acaaagtgca acgtgatg                                                      18

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
aaaacacaaa gtgcaacg                                                      18

<210> SEQ ID NO 146
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
catgcaaaac acaaagtg                                                      18

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
taaaacatgc aaaacaca                                                      18

<210> SEQ ID NO 148
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
gtgcataaaa catgcaaa                                                      18

<210> SEQ ID NO 149
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 149
gaaatgtgca taaaacat                                                  18

<210> SEQ ID NO 150
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
agccagaaat gtgcataa                                                  18

<210> SEQ ID NO 151
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ctgtcagcca gaaatgtg                                                  18

<210> SEQ ID NO 152
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
aaaagctgtc agccagaa                                                  18

<210> SEQ ID NO 153
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tgtttaaaag ctgtcagc                                                  18

<210> SEQ ID NO 154
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ataaatgttt aaaagctg                                                  18

<210> SEQ ID NO 155
<211> LENGTH: 18
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 155
atacaataaa tgtttaaa                                                      18

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ttgaaataca ataaatgt                                                      18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
gaaatttgaa atacaata                                                      18

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gactggaaat tgaaata                                                       18

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
atttggactg gaaatttg                                                      18

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
gaaaaatttg gactggaa                                                      18

<210> SEQ ID NO 161
<211> LENGTH: 18
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 161
aagttgaaaa atttggac                                                  18

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tttacaagtt gaaaaatt                                                  18

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
ttaattttac aagttgaa                                                  18

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tcagtttaat tttacaag                                                  18

<210> SEQ ID NO 165
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
ttcactcagt ttaatttt                                                  18

<210> SEQ ID NO 166
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
atcaattcac tcagttta                                                  18

<210> SEQ ID NO 167
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 167
acgacatcaa ttcactca                                                    18

<210> SEQ ID NO 168
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tattcacgac atcaattc                                                    18

<210> SEQ ID NO 169
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ctagatattc acgacatc                                                    18

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
ttaccctaga tattcacg                                                    18

<210> SEQ ID NO 171
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ttattttacc ctagatat                                                    18

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
aaattttatt ttaccota                                                    18

<210> SEQ ID NO 173
<211> LENGTH: 18
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 173
aacacaaatt ttatttta                                                18

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
atttaaacac aaatttta                                                18

<210> SEQ ID NO 175
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
tacaaattta aacacaaa                                                18

<210> SEQ ID NO 176
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
aaaaatacaa atttaaac                                                18

<210> SEQ ID NO 177
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
aaattaaaaa tacaaatt                                                18

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ttaggaaatt aaaaatac                                                18

<210> SEQ ID NO 179
<211> LENGTH: 18
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 179
ctaggttagg aaattaaa                                                       18

<210> SEQ ID NO 180
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
atttcctagg ttaggaaa                                                       18

<210> SEQ ID NO 181
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ttaagatttc ctaggtta                                                       18

<210> SEQ ID NO 182
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ggtatttaag atttccta                                                       18

<210> SEQ ID NO 183
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
aagaaggtat ttaagatt                                                       18

<210> SEQ ID NO 184
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tgaaaaagaa ggtattta                                                       18

<210> SEQ ID NO 185
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 185
tcttttgaaa aagaaggt                                                    18

<210> SEQ ID NO 186
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
tgagttcttt tgaaaaag                                                    18

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
agacttgagt tcttttga                                                    18

<210> SEQ ID NO 188
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cattaagact tgagttct                                                    18

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ctatccatta agacttga                                                    18

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tttccctatc cattaaga                                                    18

<210> SEQ ID NO 191
<211> LENGTH: 18
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 191
gtctgtttcc ctatccat                                                                18

<210> SEQ ID NO 192
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
tttccctact gtggtgca                                                                18

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tgtattttcc ctactgtg                                                                18

<210> SEQ ID NO 194
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
aataatgtat tttcccta                                                                18

<210> SEQ ID NO 195
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
atgtaaataa tgtatttt                                                                18

<210> SEQ ID NO 196
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ttaggatgta aataatgt                                                                18

```
<210> SEQ ID NO 197
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
agggattagg atgtaaat                                                      18

<210> SEQ ID NO 198
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
aaagagggaa ttaggatg                                                      18

<210> SEQ ID NO 199
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
attgaaaaga agggatta                                                      18

<210> SEQ ID NO 200
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
agacaattga aaagaggg                                                      18

<210> SEQ ID NO 201
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
atttaagaca attgaaaa                                                      18

<210> SEQ ID NO 202
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
atgaaattta agacaatt                                                      18
```

-continued

```
<210> SEQ ID NO 203
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ttcaaatgaa atttaaga                                                          18

<210> SEQ ID NO 204
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
tttttttcaa atgaaatt                                                          18

<210> SEQ ID NO 205
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
tttttttttt ttcaaatg                                                          18

<210> SEQ ID NO 206
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
aaggtttttt ttttttc                                                           18

<210> SEQ ID NO 207
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tcataaaggt tttttttt                                                          18

<210> SEQ ID NO 208
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
taaattcata aaggtttt                                                          18
```

-continued

```
<210> SEQ ID NO 209
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
gagggtaaat tcataaag                                                      18

<210> SEQ ID NO 210
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ccacagaggg taaattca                                                      18

<210> SEQ ID NO 211
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
aaaatccaca gagggtaa                                                      18

<210> SEQ ID NO 212
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gggttaaaat ccacagag                                                      18

<210> SEQ ID NO 213
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
cattgggatt aaaatcca                                                      18

<210> SEQ ID NO 214
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
tcaaccatta gggttaaa                                                      18

<210> SEQ ID NO 215
```

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
agatatcaac cattggga                                                      18

<210> SEQ ID NO 216
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
aataaagata tcaaccat                                                      18

<210> SEQ ID NO 217
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
aacttaataa agatatca                                                      18

<210> SEQ ID NO 218
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
aatgaaactt aataaaga                                                      18

<210> SEQ ID NO 219
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tattcaatga aacttaat                                                      18

<210> SEQ ID NO 220
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
aatcatattc aatgaaac                                                      18

<210> SEQ ID NO 221
<211> LENGTH: 18
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
aactaaatca tattcaat                                                 18

<210> SEQ ID NO 222
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
cacataacta aatcatat                                                 18

<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
atatacacat aactaaat                                                 18

<210> SEQ ID NO 224
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
actccatata cacataac                                                 18

<210> SEQ ID NO 225
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
ggataactcc atatacac                                                 18

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
aagatggata actccata                                                 18

<210> SEQ ID NO 227
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 227
ccccaaagat ggataact                                                    18

<210> SEQ ID NO 228
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
aatctcccca aagatgga                                                    18

<210> SEQ ID NO 229
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ccagtaatct ccccaaag                                                    18

<210> SEQ ID NO 230
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
ccaatccagt aatctccc                                                    18

<210> SEQ ID NO 231
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
cctcaccaat ccagtaat                                                    18

<210> SEQ ID NO 232
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
cccgccctca ccaatcca                                                    18

<210> SEQ ID NO 233
<211> LENGTH: 18
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 233 ggtccccgc cctcacca                                                           18

<210> SEQ ID NO 234
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
accagggtcc cccgccct                                                          18

<210> SEQ ID NO 235
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tctacaccag ggtccccc                                                          18

<210> SEQ ID NO 236
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
atcattctac accagggt                                                          18

<210> SEQ ID NO 237
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
acataatcat tctacacc                                                          18

<210> SEQ ID NO 238
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
ttttcacata atcattct                                                          18

<210> SEQ ID NO 239
<211> LENGTH: 18
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 239
ttgttttttc acataatc                                                    18

<210> SEQ ID NO 240
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
ttaaattgtt ttttcaca                                                    18

<210> SEQ ID NO 241
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
acaagttaaa ttgttttt                                                    18

<210> SEQ ID NO 242
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
gcttaacaag ttaaattg                                                    18

<210> SEQ ID NO 243
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
catgagctta acaagtta                                                    18

<210> SEQ ID NO 244
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
agtatcatga gcttaaca                                                    18

```
<210> SEQ ID NO 245
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
caaacagtat catgagct                                                   18

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tgcctcaaac agtatcat                                                   18

<210> SEQ ID NO 247
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
ctgtatgcct caaacagt                                                   18

<210> SEQ ID NO 248
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
agggactgta tgcctcaa                                                   18

<210> SEQ ID NO 249
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
acagcaggga ctgtatgc                                                   18

<210> SEQ ID NO 250
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
actaaacagc aagggctg                                                   18
```

-continued

<210> SEQ ID NO 251
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
aatgtactaa acagcagg                                                   18

<210> SEQ ID NO 252
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
agaccaatgt actaaaca                                                   18

<210> SEQ ID NO 253
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gacccagacc aatgtact                                                   18

<210> SEQ ID NO 254
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
ttcaggaccc agaccaat                                                   18

<210> SEQ ID NO 255
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
taattttcag gacccaga                                                   18

<210> SEQ ID NO 256
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
actggtaatt ttcaggac                                                   18

-continued

```
<210> SEQ ID NO 257
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
atctaactgg taattttc                                                  18

<210> SEQ ID NO 258
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
atggtatcta actggtaa                                                  18

<210> SEQ ID NO 259
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
aactgatggt atctaact                                                  18

<210> SEQ ID NO 260
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
taatcaactg atggtatc                                                  18

<210> SEQ ID NO 261
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
atcaataatc aactgatg                                                  18

<210> SEQ ID NO 262
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tacatatcaa taatcaac                                                  18

<210> SEQ ID NO 263
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gctcatacat atcaataa                                                     18

<210> SEQ ID NO 264
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
tatctgctca tacatatc                                                     18

<210> SEQ ID NO 265
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
cctagtatct gctcatac                                                     18

<210> SEQ ID NO 266
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
tgcaccctag tatctgct                                                     18

<210> SEQ ID NO 267
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
aatattgcac cctagtat                                                     18

<210> SEQ ID NO 268
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
cctgaaatat tgcaccct                                                     18

<210> SEQ ID NO 269
<211> LENGTH: 18
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
tgaaacctga aatattgc                                                     18

<210> SEQ ID NO 270
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
tcttatgaaa cctgaaat                                                     18

<210> SEQ ID NO 271
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
accagtctta tgaaacct                                                     18

<210> SEQ ID NO 272
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tcaataccag tcttatga                                                     18

<210> SEQ ID NO 273
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
cacaatcaat accagtct                                                     18

<210> SEQ ID NO 274
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gtggtcacaa tcaatacc                                                     18

<210> SEQ ID NO 275
<211> LENGTH: 18
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 275
tgagagtggt cacaatca                                                      18

<210> SEQ ID NO 276
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
aaaaatgaga gtggtcac                                                      18

<210> SEQ ID NO 277
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
caataaaaaa tgagagtg                                                      18

<210> SEQ ID NO 278
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
ttacacaata aaaaatga                                                      18

<210> SEQ ID NO 279
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
tgaacttaca caataaaa                                                      18

<210> SEQ ID NO 280
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ccatatgaac ttacacaa                                                      18

<210> SEQ ID NO 281
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 281
taaccccata tgaactta                                                      18

<210> SEQ ID NO 282
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
gaaaataacc ccatatga                                                      18

<210> SEQ ID NO 283
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
attttgaaaa taacccca                                                      18

<210> SEQ ID NO 284
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ttaacatttt gaaaataa                                                      18

<210> SEQ ID NO 285
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
ccttgttaac attttgaa                                                      18

<210> SEQ ID NO 286
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
ttttgccttg ttaacatt                                                      18

<210> SEQ ID NO 287
<211> LENGTH: 18
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 287
tatatttttg ccttgtta                                                  18

<210> SEQ ID NO 288
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
cttaatatat ttttgcct                                                  18

<210> SEQ ID NO 289
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
tatttcttaa tatatttt                                                  18

<210> SEQ ID NO 290
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
tcaactattt cttaatat                                                  18

<210> SEQ ID NO 291
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
cttattcaac tatttctt                                                  18

<210> SEQ ID NO 292
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
atgtgcttat tcaactat                                                  18
```

```
<210> SEQ ID NO 293
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ttcacatgtg cttattca                                                  18

<210> SEQ ID NO 294
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
cacaattcac atgtgctt                                                  18

<210> SEQ ID NO 295
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
tacaacacaa ttcacatg                                                  18

<210> SEQ ID NO 296
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
ttgtttacaa cacaattc                                                  18

<210> SEQ ID NO 297
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
actttttgtt tacaacac                                                  18

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
ttctaacttt ttgtttac                                                  18
```

-continued

```
<210> SEQ ID NO 299
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
ttttattcta actttttg                                                         18

<210> SEQ ID NO 300
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
gattttttta ttctaact                                                         18

<210> SEQ ID NO 301
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
aagtggattt ttttattc                                                         18

<210> SEQ ID NO 302
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
caaataagtg gatttttt                                                         18

<210> SEQ ID NO 303
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
taattcaaat aagtggat                                                         18

<210> SEQ ID NO 304
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
ctgcataatt caaataag                                                         18
```

```
<210> SEQ ID NO 305
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
ctattctgca taattcaa                                                         18

<210> SEQ ID NO 306
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
gtattctatt ctgcataa                                                         18

<210> SEQ ID NO 307
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
ggtatgtatt ctattctg                                                         18

<210> SEQ ID NO 308
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ttctaggtat gtattcta                                                         18

<210> SEQ ID NO 309
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
tttatttcta ggtatgta                                                         18

<210> SEQ ID NO 310
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
tttgttttat ttctaggt                                                         18

<210> SEQ ID NO 311
```

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
acgtttttgt tttatttc                                                    18

<210> SEQ ID NO 312
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
ataagacgtt tttgtttt                                                    18

<210> SEQ ID NO 313
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
tcatgataag acgttttt                                                    18

<210> SEQ ID NO 314
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
aatactcatg ataagacg                                                    18

<210> SEQ ID NO 315
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
atcttaatac tcatgata                                                    18

<210> SEQ ID NO 316
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
attttatctt aatactca                                                    18

<210> SEQ ID NO 317
<211> LENGTH: 18
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
cttaaatttt atcttaat                                                    18

<210> SEQ ID NO 318
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 318
tatgccttaa attttatc                                                    18

<210> SEQ ID NO 319
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gagtttatgc cttaaatt                                                    18

<210> SEQ ID NO 320
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gaagtgagtt tatgcctt                                                    18

<210> SEQ ID NO 321
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
tctaagaagt gagtttat                                                    18

<210> SEQ ID NO 322
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
cttattctaa gaagtgag                                                    18

<210> SEQ ID NO 323
<211> LENGTH: 18
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 323
agttacttat tctaagaa                                                          18

<210> SEQ ID NO 324
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
ttgggagtta cttattct                                                          18

<210> SEQ ID NO 325
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gttagttggg agttactt                                                          18

<210> SEQ ID NO 326
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
agaaagttag ttgggagt                                                          18

<210> SEQ ID NO 327
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
atcctagaaa gttagttg                                                          18

<210> SEQ ID NO 328
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
ttaaaatcct agaaagtt                                                          18

<210> SEQ ID NO 329
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 329
atgttttaaa atcctaga                                                         18

<210> SEQ ID NO 330
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
gtgttatgtt ttaaaatc                                                         18

<210> SEQ ID NO 331
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
tcactgtgtt atgtttta                                                         18

<210> SEQ ID NO 332
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
tgttttcact gtgttatg                                                         18

<210> SEQ ID NO 333
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
atgtatgttt tcactgtg                                                         18

<210> SEQ ID NO 334
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
tgtttatgta tgttttca                                                         18

<210> SEQ ID NO 335
<211> LENGTH: 18
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 335
agttatgttt atgtatgt                                                18

<210> SEQ ID NO 336
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
tgtagagtta tgtttatg                                                18

<210> SEQ ID NO 337
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
taaaatgtag agttatgt                                                18

<210> SEQ ID NO 338
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
ataaataaaa tgtagagt                                                18

<210> SEQ ID NO 339
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
taagaataaa taaaatgt                                                18

<210> SEQ ID NO 340
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
aactttaaga ataaataa                                                18
```

-continued

```
<210> SEQ ID NO 341
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
acttaaactt taagaata                                                    18

<210> SEQ ID NO 342
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
aatacactta aactttaa                                                    18

<210> SEQ ID NO 343
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
tgtataatac acttaaac                                                    18

<210> SEQ ID NO 344
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
cttcttgtat aatacact                                                    18

<210> SEQ ID NO 345
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
ctcttcttct tgtataat                                                    18

<210> SEQ ID NO 346
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
ataaactctt cttcttgt                                                    18
```

-continued

```
<210> SEQ ID NO 347
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
cgaatataaa ctcttctt                                                  18

<210> SEQ ID NO 348
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
tctctcgaat ataaactc                                                  18

<210> SEQ ID NO 349
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
ttctgtctct cgaatata                                                  18

<210> SEQ ID NO 350
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
actttttctg tctctcga                                                  18

<210> SEQ ID NO 351
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
ttctgacttt ttctgtct                                                  18

<210> SEQ ID NO 352
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
aaaaattctg actttttc                                                  18
```

<210> SEQ ID NO 353
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
caaacaaaaa ttctgact                                                          18

<210> SEQ ID NO 354
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
tgatccaaac aaaaattc                                                          18

<210> SEQ ID NO 355
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
attggtgatc caaacaaa                                                          18

<210> SEQ ID NO 356
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
gatatattgg tgatccaa                                                          18

<210> SEQ ID NO 357
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
gctatgatat attggtga                                                          18

<210> SEQ ID NO 358
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
tgtaagctat gatatatt                                                          18

<210> SEQ ID NO 359

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359 tttttttgtaa gctatgat                                                      18

<210> SEQ ID NO 360
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
acagtttttt tgtaagct                                                       18

<210> SEQ ID NO 361
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
ttaagacagt tttttttgt                                                      18

<210> SEQ ID NO 362
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
tttaattaag acagtttt                                                       18

<210> SEQ ID NO 363
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
tgggttttaa ttaagaca                                                       18

<210> SEQ ID NO 364
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
tgttgtgggt tttaatta                                                       18

<210> SEQ ID NO 365
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
aattatgttg tgggtttt                                                  18

<210> SEQ ID NO 366
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
aaaaaaatta tgttgtgg                                                  18

<210> SEQ ID NO 367
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
aatctaaaaa aattatgt                                                  18

<210> SEQ ID NO 368
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
ttaaaaatct aaaaaaat                                                  18

<210> SEQ ID NO 369
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
ctttcttaaa aatctaaa                                                  18

<210> SEQ ID NO 370
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
agaatctttc ttaaaaat                                                  18

<210> SEQ ID NO 371
<211> LENGTH: 18
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 371
ataatagaat ctttctta                                                   18

<210> SEQ ID NO 372
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
augaauuuaa uaaacuuu                                                   18

<210> SEQ ID NO 373
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
gaccaaugaa uuuaauaa                                                   18

<210> SEQ ID NO 374
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
cacuugacca augaauuu                                                   18

<210> SEQ ID NO 375
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
cugagcacuu gaccaaug                                                   18

<210> SEQ ID NO 376
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
aauaucugag cacuugac                                                   18

<210> SEQ ID NO 377
<211> LENGTH: 18
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 377
auggaaauau cugagcac                                                         18

<210> SEQ ID NO 378
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
aauguaugga aauaucug                                                         18

<210> SEQ ID NO 379
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
aguguaaugu auggaaau                                                         18

<210> SEQ ID NO 380
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
aaugaagugu aauguaug                                                         18

<210> SEQ ID NO 381
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
auagaaauga aguguaau                                                         18

<210> SEQ ID NO 382
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
uuuuuauaga aaugaagu                                                         18

<210> SEQ ID NO 383
<211> LENGTH: 18
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 383
cagcuuuuuu auagaaau                                                       18

<210> SEQ ID NO 384
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
aagaucagcu uuuuaua                                                        18

<210> SEQ ID NO 385
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
ccgauaagau cagcuuuu                                                       18

<210> SEQ ID NO 386
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
guauaccgau aagaucag                                                       18

<210> SEQ ID NO 387
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
uaaaaguaua ccgauaag                                                       18

<210> SEQ ID NO 388
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
aaaauuaaaa guauaccg                                                       18

-continued

```
<210> SEQ ID NO 389
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
cugagaaaau uaaaagua                                                        18

<210> SEQ ID NO 390
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
uauuucugag aaaauuaa                                                        18

<210> SEQ ID NO 391
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
augguuauuu cugagaaa                                                        18

<210> SEQ ID NO 392
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
uagauauggu uauuucug                                                        18

<210> SEQ ID NO 393
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
aauuauagau augguuau                                                        18

<210> SEQ ID NO 394
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
uuaauaauua uagauaug                                                        18
```

```
<210> SEQ ID NO 395
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
auugauuaau aauuauag                                                18

<210> SEQ ID NO 396
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
gcauuauuga uuaauaau                                                18

<210> SEQ ID NO 397
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
aaaaggcauu auugauua                                                18

<210> SEQ ID NO 398
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
aauauaaaag gcauuauu                                                18

<210> SEQ ID NO 399
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
cuuuuaauau aaaaggca                                                18

<210> SEQ ID NO 400
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
aaccucuuuu aauauaaa                                                18
```

-continued

<210> SEQ ID NO 401
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
aaacuaaccu cuuuuaau                                                    18

<210> SEQ ID NO 402
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
uucaaaaacu aaccucuu                                                    18

<210> SEQ ID NO 403
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
caaguuucaa aaacuaac                                                    18

<210> SEQ ID NO 404
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
aacuccaagu uucaaaaa                                                    18

<210> SEQ ID NO 405
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
ucuaaaacuc caaguuuc                                                    18

<210> SEQ ID NO 406
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
uuaugucuaa aacuccaa                                                    18

<210> SEQ ID NO 407

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
ggauuuuaug ucuaaaac                                                    18

<210> SEQ ID NO 408
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
uauaaggauu uuaugucu                                                    18

<210> SEQ ID NO 409
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
gcauuuauaa ggauuuua                                                    18

<210> SEQ ID NO 410
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
uaucagcauu uauaagga                                                    18

<210> SEQ ID NO 411
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 411
aucacuauca gcauuuau                                                    18

<210> SEQ ID NO 412
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
guuauaucac uaucagca                                                    18

<210> SEQ ID NO 413
<211> LENGTH: 18
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
uauuaguuau aucacuau                                                      18

<210> SEQ ID NO 414
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
uaaacuauua guuauauc                                                      18

<210> SEQ ID NO 415
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
ccauuuaaac uauuaguu                                                      18

<210> SEQ ID NO 416
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
ucugaccauu uaaacuau                                                      18

<210> SEQ ID NO 417
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 417
auaaaucuga ccauuuaa                                                      18

<210> SEQ ID NO 418
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
uauucauaaa ucugacca                                                      18

<210> SEQ ID NO 419
<211> LENGTH: 18
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 419
agccauauuc auaaaucu                                               18

<210> SEQ ID NO 420
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
aauagagcca uauucaua                                               18

<210> SEQ ID NO 421
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
ugaggaauag agccauau                                               18

<210> SEQ ID NO 422
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
cauuaugagg aauagagc                                               18

<210> SEQ ID NO 423
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
guugucauua ugaggaau                                               18

<210> SEQ ID NO 424
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
uguauguugu cauuauga                                               18

<210> SEQ ID NO 425
<211> LENGTH: 18
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 425
cuguguguau guugucau                                                   18

<210> SEQ ID NO 426
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
uagugcugug uguauguu                                                   18

<210> SEQ ID NO 427
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
cauuuuagug cugugugu                                                   18

<210> SEQ ID NO 428
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
uuagucauuu uagugcug                                                   18

<210> SEQ ID NO 429
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
agagauuagu cauuuuag                                                   18

<210> SEQ ID NO 430
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
auugaagaga uuagucau                                                   18

<210> SEQ ID NO 431
<211> LENGTH: 18
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 431
cacguauuga agagauua                                                    18

<210> SEQ ID NO 432
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
ccaaacacgu auugaaga                                                    18

<210> SEQ ID NO 433
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
caaugccaaa cacguauu                                                    18

<210> SEQ ID NO 434
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
cucuacaaug ccaaacac                                                    18

<210> SEQ ID NO 435
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
uuugacucua caaugcca                                                    18

<210> SEQ ID NO 436
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
guuauuuuga cucuacaa                                                    18
```

```
<210> SEQ ID NO 437
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
auaacguuau uuugacuc                                                   18

<210> SEQ ID NO 438
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
caauuauaac guuauuuu                                                   18

<210> SEQ ID NO 439
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
agaaucaauu auaacguu                                                   18

<210> SEQ ID NO 440
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
aaaauagaau caauuaua                                                   18

<210> SEQ ID NO 441
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
uauaaaaaau agaaucaa                                                   18

<210> SEQ ID NO 442
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
agaaguauaa aaaauaga                                                   18
```

-continued

```
<210> SEQ ID NO 443
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
acacuagaag uauaaaaa                                                        18

<210> SEQ ID NO 444
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
uccaaacacu agaaguau                                                        18

<210> SEQ ID NO 445
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
aaauauccaa acacuaga                                                        18

<210> SEQ ID NO 446
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
aaauaaaaua uccaaaca                                                        18

<210> SEQ ID NO 447
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
uuacaaaaua aaauaucc                                                        18

<210> SEQ ID NO 448
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
uauuuuuaca aaauaaaa                                                        18
```

-continued

```
<210> SEQ ID NO 449
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
gauuauauuu uuacaaaa                                                        18

<210> SEQ ID NO 450
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
uucaugauua uauuuuua                                                        18

<210> SEQ ID NO 451
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
caucauucau gauuauau                                                        18

<210> SEQ ID NO 452
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
cucaccauca uucaugau                                                        18

<210> SEQ ID NO 453
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
ccaaccucac caucauuc                                                        18

<210> SEQ ID NO 454
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
uauauccaac cucaccau                                                        18

<210> SEQ ID NO 455
```

<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
auucuuauau ccaaccuc                                                        18

<210> SEQ ID NO 456
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
ucaucauucu uauaucca                                                        18

<210> SEQ ID NO 457
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
cauaaucauc auucuuau                                                        18

<210> SEQ ID NO 458
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
ccaaucauaa ucaucauu                                                        18

<210> SEQ ID NO 459
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
acuucccaau cauaauca                                                        18

<210> SEQ ID NO 460
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
aucucacuuc ccaaucau                                                        18

<210> SEQ ID NO 461
<211> LENGTH: 18

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
uucaaaucuc acuuccca                                                      18

<210> SEQ ID NO 462
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
gcauguucaa aucucacu                                                      18

<210> SEQ ID NO 463
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
ucugagcaug uucaaauc                                                      18

<210> SEQ ID NO 464
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
gaguuucuga gcauguuc                                                      18

<210> SEQ ID NO 465
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
aaugagaguu ucugagca                                                      18

<210> SEQ ID NO 466
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
aauuaaauga gaguuucu                                                      18

<210> SEQ ID NO 467
<211> LENGTH: 18
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 467
caaagaauua aaugagag                                                 18

<210> SEQ ID NO 468
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
uagggcaaag aauuaaau                                                 18

<210> SEQ ID NO 469
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
gcugcuaggg caaagaau                                                 18

<210> SEQ ID NO 470
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
uuuaugcugc uagggcaa                                                 18

<210> SEQ ID NO 471
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
gugauuuuau gcugcuag                                                 18

<210> SEQ ID NO 472
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
cuauugugau uuuaugcu                                                 18

<210> SEQ ID NO 473
<211> LENGTH: 18
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 473
cgcagcuauu gugauuuu                                                        18

<210> SEQ ID NO 474
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
uuugacgcag cuauugug                                                        18

<210> SEQ ID NO 475
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
uacgcuuuga cgcagcua                                                        18

<210> SEQ ID NO 476
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
ugaguuacgc uuugacgc                                                        18

<210> SEQ ID NO 477
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
gugccugagu uacgcuuu                                                        18

<210> SEQ ID NO 478
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
aaugagugcc ugaguuac                                                        18

<210> SEQ ID NO 479
<211> LENGTH: 18
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 479
aauaaaauga gugccuga                                                    18

<210> SEQ ID NO 480
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
acaaaaauaa aaugagug                                                    18

<210> SEQ ID NO 481
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
gaacaacaaa aauaaaau                                                    18

<210> SEQ ID NO 482
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
uaacagaaca acaaaaau                                                    18

<210> SEQ ID NO 483
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
aaaaauaaca gaacaaca                                                    18

<210> SEQ ID NO 484
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
uuugaaaaaa uaacagaa                                                    18

```
<210> SEQ ID NO 485
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
caugcuuuga aaaaauaa                                                       18

<210> SEQ ID NO 486
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486
aagcacaugc uuugaaaa                                                       18

<210> SEQ ID NO 487
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
cauaaaagca caugcuuu                                                       18

<210> SEQ ID NO 488
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
uguugcauaa aagcacau                                                       18

<210> SEQ ID NO 489
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
aguaauguug cauaaaag                                                       18

<210> SEQ ID NO 490
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 490
uauucaguaa uguugcau                                                       18
```

-continued

```
<210> SEQ ID NO 491
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
ugcuuuauuc aguaaugu                                                       18

<210> SEQ ID NO 492
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
caacaugcuu uauucagu                                                       18

<210> SEQ ID NO 493
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
cuguacaaca ugcuuuau                                                       18

<210> SEQ ID NO 494
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
aagcacugua caacaugc                                                       18

<210> SEQ ID NO 495
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
uuaucaagca cuguacaa                                                       18

<210> SEQ ID NO 496
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
acuucuuauc aagcacug                                                       18
```

```
<210> SEQ ID NO 497
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
uucuaacuuc uuaucaag                                                       18

<210> SEQ ID NO 498
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
uuacuuucua acuucuua                                                       18

<210> SEQ ID NO 499
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
auuuguuacu uucuaacu                                                       18

<210> SEQ ID NO 500
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
aauuuauuug uuacuuuc                                                       18

<210> SEQ ID NO 501
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
augauaauuu auuuguua                                                       18

<210> SEQ ID NO 502
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
acgugaugau aauuuauu                                                       18

<210> SEQ ID NO 503
```

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
gugcaacgug augauaau                                                          18

<210> SEQ ID NO 504
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
acaaagugca acgugaug                                                          18

<210> SEQ ID NO 505
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
aaaacacaaa gugcaacg                                                          18

<210> SEQ ID NO 506
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
caugcaaaac acaaagug                                                          18

<210> SEQ ID NO 507
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
uaaaacaugc aaaacaca                                                          18

<210> SEQ ID NO 508
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 508
gugcauaaaa caugcaaa                                                          18

<210> SEQ ID NO 509
<211> LENGTH: 18
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
gaaaugugca uaaaacau                                                   18

<210> SEQ ID NO 510
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
agccagaaau gugcauaa                                                   18

<210> SEQ ID NO 511
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
cugucagcca gaaaugug                                                   18

<210> SEQ ID NO 512
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
aaaagcuguc agccagaa                                                   18

<210> SEQ ID NO 513
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
uguuuaaaag cugucagc                                                   18

<210> SEQ ID NO 514
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
auaaauguuu aaaagcug                                                   18

<210> SEQ ID NO 515
<211> LENGTH: 18
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 515
auacaauaaa uguuuaaa                                                    18

<210> SEQ ID NO 516
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
uugaaauaca auaaaugu                                                    18

<210> SEQ ID NO 517
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
gaaauuugaa auacaaua                                                    18

<210> SEQ ID NO 518
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
gacuggaaau uugaaaua                                                    18

<210> SEQ ID NO 519
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
auuuggacug gaaauuug                                                    18

<210> SEQ ID NO 520
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
gaaaaauuug gacuggaa                                                    18

<210> SEQ ID NO 521
<211> LENGTH: 18
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 521
aaguugaaaa auuuggac                                                          18

<210> SEQ ID NO 522
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
uuuacaaguu gaaaaauu                                                          18

<210> SEQ ID NO 523
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
uuaauuuuac aaguugaa                                                          18

<210> SEQ ID NO 524
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
ucaguuuaau uuuacaag                                                          18

<210> SEQ ID NO 525
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
uucacucagu uuaauuuu                                                          18

<210> SEQ ID NO 526
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
aucaauucac ucaguuua                                                          18

<210> SEQ ID NO 527
<211> LENGTH: 18
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 527
acgacaucaa uucacuca                                                      18

<210> SEQ ID NO 528
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
uauucacgac aucaauuc                                                      18

<210> SEQ ID NO 529
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
cuagauauuc acgacauc                                                      18

<210> SEQ ID NO 530
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
uuacccuaga uauucacg                                                      18

<210> SEQ ID NO 531
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
uuauuuuacc cuagauau                                                      18

<210> SEQ ID NO 532
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
aaauuuuauu uuacccua                                                      18

-continued

```
<210> SEQ ID NO 533
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
aacacaaauu uuauuuua                                                    18

<210> SEQ ID NO 534
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
auuuaaacac aaauuuua                                                    18

<210> SEQ ID NO 535
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
uacaaauuua aacacaaa                                                    18

<210> SEQ ID NO 536
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
aaaaauacaa auuuaaac                                                    18

<210> SEQ ID NO 537
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
aaauuaaaaa uacaaauu                                                    18

<210> SEQ ID NO 538
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
uuaggaaauu aaaaauac                                                    18
```

<210> SEQ ID NO 539
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
cuagguuagg aaauuaaa                                                          18

<210> SEQ ID NO 540
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
auuuccuagg uuaggaaa                                                          18

<210> SEQ ID NO 541
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
uuaagauuuc cuagguua                                                          18

<210> SEQ ID NO 542
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
gguauuuaag auuuccua                                                          18

<210> SEQ ID NO 543
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
aagaagguau uuaagauu                                                          18

<210> SEQ ID NO 544
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
ugaaaaagaa gguauuua                                                          18

<210> SEQ ID NO 545
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
ucuuuugaaa aagaaggu                                                          18

<210> SEQ ID NO 546
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
ugaguucuuu ugaaaaag                                                          18

<210> SEQ ID NO 547
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
agacuugagu ucuuuuga                                                          18

<210> SEQ ID NO 548
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
cauuaagacu ugaguucu                                                          18

<210> SEQ ID NO 549
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
cuauccauua agacuuga                                                          18

<210> SEQ ID NO 550
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
uuucccuauc cauuaaga                                                          18

<210> SEQ ID NO 551

-continued

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
gucuguuucc cuauccau                                                          18

<210> SEQ ID NO 552
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
uuucccuacu guggugca                                                          18

<210> SEQ ID NO 553
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
uguauuuucc cuacugug                                                          18

<210> SEQ ID NO 554
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
aauaauguau uucccua                                                           18

<210> SEQ ID NO 555
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
auguaaauaa uguauuuu                                                          18

<210> SEQ ID NO 556
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
uuaggaugua aauaaugu                                                          18

<210> SEQ ID NO 557
<211> LENGTH: 18
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
agggauuagg auguaaau                                                     18

<210> SEQ ID NO 558
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
aaagagggaa uuaggaug                                                     18

<210> SEQ ID NO 559
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
auugaaaaga agggauua                                                     18

<210> SEQ ID NO 560
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
agacaauuga aaagaggg                                                     18

<210> SEQ ID NO 561
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
auuuaagaca auugaaaa                                                     18

<210> SEQ ID NO 562
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
augaaauuua agacaauu                                                     18

<210> SEQ ID NO 563
<211> LENGTH: 18
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 563
uucaaaugaa auuuaaga                                                          18

<210> SEQ ID NO 564
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
uuuuuuucaa augaaauu                                                         18

<210> SEQ ID NO 565
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
uuuuuuuuuu uucaaaug                                                         18

<210> SEQ ID NO 566
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
aagguuuuuu uuuuuuuc                                                         18

<210> SEQ ID NO 567
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
ucauaaaggu uuuuuuuu                                                         18

<210> SEQ ID NO 568
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
uaaauucaua aagguuuu                                                         18

<210> SEQ ID NO 569
<211> LENGTH: 18
<212> TYPE: RNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 569
gaggguaaau ucauaaag                                                    18

<210> SEQ ID NO 570
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570
ccacagaggg uaaauuca                                                    18

<210> SEQ ID NO 571
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
aaaauccaca gaggguaa                                                    18

<210> SEQ ID NO 572
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
ggguuaaaau ccacagag                                                    18

<210> SEQ ID NO 573
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
cauugggauu aaaaucca                                                    18

<210> SEQ ID NO 574
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
ucaaccauua ggguuaaa                                                    18

<210> SEQ ID NO 575
<211> LENGTH: 18
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 575
agauaucaac cauuggga                                                   18

<210> SEQ ID NO 576
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
aauaaagaua ucaaccau                                                   18

<210> SEQ ID NO 577
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
aacuuaauaa agauauca                                                   18

<210> SEQ ID NO 578
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
aaugaaacuu aauaaaga                                                   18

<210> SEQ ID NO 579
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
uauucaauga aacuuaau                                                   18

<210> SEQ ID NO 580
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
aaucauauuc aaugaaac                                                   18
```

-continued

```
<210> SEQ ID NO 581
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
aacuaaauca uauucaau                                                      18

<210> SEQ ID NO 582
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
cacauaacua aaucauau                                                      18

<210> SEQ ID NO 583
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
auauacacau aacuaaau                                                      18

<210> SEQ ID NO 584
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
acuccauaua cacauaac                                                      18

<210> SEQ ID NO 585
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
ggauaacucc auauacac                                                      18

<210> SEQ ID NO 586
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
aagauggaua acuccaua                                                      18
```

```
<210> SEQ ID NO 587
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
ccccaaagau ggauaacu                                                   18

<210> SEQ ID NO 588
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
aaucucccca aagaugga                                                   18

<210> SEQ ID NO 589
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
ccaguaaucu ccccaaag                                                   18

<210> SEQ ID NO 590
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
ccaauccagu aaucuccc                                                   18

<210> SEQ ID NO 591
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
ccucaccaau ccaguaau                                                   18

<210> SEQ ID NO 592
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
cccgcccuca ccaaucca                                                   18
```

-continued

<210> SEQ ID NO 593
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593 gguccccgc ccucacca                                                          18

<210> SEQ ID NO 594
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
accagggucc cccgcccu                                                         18

<210> SEQ ID NO 595
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
ucuacaccag gguccccc                                                         18

<210> SEQ ID NO 596
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
aucauucuac accagggu                                                         18

<210> SEQ ID NO 597
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
acauaaucau ucuacacc                                                         18

<210> SEQ ID NO 598
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
uuuucacaua aucauucu                                                         18

<210> SEQ ID NO 599

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599 uuguuuuuc acauaauc                                                      18

<210> SEQ ID NO 600
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
uuaaauuguu uuuucaca                                                     18

<210> SEQ ID NO 601
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
acaaguuaaa uuguuuuu                                                     18

<210> SEQ ID NO 602
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
gcuuaacaag uuaaauug                                                     18

<210> SEQ ID NO 603
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
caugagcuua acaaguua                                                     18

<210> SEQ ID NO 604
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
aguaucauga gcuuaaca                                                     18

<210> SEQ ID NO 605
<211> LENGTH: 18
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
caaacaguau caugagcu                                                        18

<210> SEQ ID NO 606
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
ugccucaaac aguaucau                                                        18

<210> SEQ ID NO 607
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
cuguaugccu caaacagu                                                        18

<210> SEQ ID NO 608
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
agggacugua ugccucaa                                                        18

<210> SEQ ID NO 609
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
acagcaggga cuguaugc                                                        18

<210> SEQ ID NO 610
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
acuaaacagc aagggcug                                                        18

<210> SEQ ID NO 611
<211> LENGTH: 18
<212> TYPE: RNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 611
aauguacuaa acagcagg                                                 18

<210> SEQ ID NO 612
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
agaccaaugu acuaaaca                                                 18

<210> SEQ ID NO 613
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
gacccagacc aauguacu                                                 18

<210> SEQ ID NO 614
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
uucaggaccc agaccaau                                                 18

<210> SEQ ID NO 615
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
uaauuuucag gacccaga                                                 18

<210> SEQ ID NO 616
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
acugguaauu uucaggac                                                 18

<210> SEQ ID NO 617
<211> LENGTH: 18
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 617
aucuaacugg uaauuuuc                                              18

<210> SEQ ID NO 618
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
augguaucua acugguaa                                             18

<210> SEQ ID NO 619
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
aacugauggu aucuaacu                                             18

<210> SEQ ID NO 620
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
uaaucaacug augguauc                                            18

<210> SEQ ID NO 621
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
aucaauaauc aacgaug                                             18

<210> SEQ ID NO 622
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
uacauaucaa uaaucaac                                            18

<210> SEQ ID NO 623
<211> LENGTH: 18
<212> TYPE: RNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 623
gcucauacau aucaauaa                                                18

<210> SEQ ID NO 624
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
uaucugcuca uacauauc                                                18

<210> SEQ ID NO 625
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
ccuaguaucu gcucauac                                                18

<210> SEQ ID NO 626
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
ugcacccuag uaucugcu                                                18

<210> SEQ ID NO 627
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 627
aauauugcac ccuaguau                                                18

<210> SEQ ID NO 628
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
ccugaaauau ugcacccu                                                18
```

-continued

```
<210> SEQ ID NO 629
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 629
ugaaaccuga aauauugc                                                    18

<210> SEQ ID NO 630
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
ucuuaugaaa ccugaaau                                                    18

<210> SEQ ID NO 631
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
accagucuua ugaaaccu                                                    18

<210> SEQ ID NO 632
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
ucaauaccag ucuuauga                                                    18

<210> SEQ ID NO 633
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
cacaaucaau accagucu                                                    18

<210> SEQ ID NO 634
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
guggucacaa ucaauacc                                                    18
```

-continued

```
<210> SEQ ID NO 635
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
ugagaguggu cacaauca                                                   18

<210> SEQ ID NO 636
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
aaaaaugaga guggucac                                                   18

<210> SEQ ID NO 637
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
caauaaaaaa ugagagug                                                   18

<210> SEQ ID NO 638
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
uuacacaaua aaaauga                                                    18

<210> SEQ ID NO 639
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
ugaacuuaca caauaaaa                                                   18

<210> SEQ ID NO 640
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
ccauaugaac uuacacaa                                                   18
```

```
<210> SEQ ID NO 641
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
uaaccccaua ugaacuua                                                   18

<210> SEQ ID NO 642
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
gaaaauaacc ccauauga                                                   18

<210> SEQ ID NO 643
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
auuuugaaaa uaacccca                                                   18

<210> SEQ ID NO 644
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
uuaacauuuu gaaaauaa                                                   18

<210> SEQ ID NO 645
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
ccuuguuaac auuuugaa                                                   18

<210> SEQ ID NO 646
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
uuuugccuug uuaacauu                                                   18

<210> SEQ ID NO 647
```

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
uauauuuuug ccuuguua                                                             18

<210> SEQ ID NO 648
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
cuuaauauau uuuugccu                                                             18

<210> SEQ ID NO 649
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649
uauuucuuaa uauauuuu                                                             18

<210> SEQ ID NO 650
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
ucaacuauuu cuuaauau                                                             18

<210> SEQ ID NO 651
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
cuuauucaac uauuucuu                                                             18

<210> SEQ ID NO 652
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
augugcuuau ucaacuau                                                             18

<210> SEQ ID NO 653
<211> LENGTH: 18
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
uucacaugug cuuauuca                                                    18

<210> SEQ ID NO 654
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
cacaauucac augugcuu                                                    18

<210> SEQ ID NO 655
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 655
uacaacacaa uucacaug                                                    18

<210> SEQ ID NO 656
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
uuguuuacaa cacaauuc                                                    18

<210> SEQ ID NO 657
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657 acuuuuguu uacaacac                                                     18

<210> SEQ ID NO 658
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
uucuaacuuu uuguuuac                                                    18

<210> SEQ ID NO 659
<211> LENGTH: 18
<212> TYPE: RNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 659
uuuuauucua acuuuuug                                           18

<210> SEQ ID NO 660
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660 gauuuuuua uucuaacu                                            18

<210> SEQ ID NO 661
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
aaguggauuu uuuuauuc                                           18

<210> SEQ ID NO 662
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
caaauaagug gauuuuuu                                           18

<210> SEQ ID NO 663
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
uaauucaaau aaguggau                                           18

<210> SEQ ID NO 664
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
cugcauaauu caaauaag                                           18

<210> SEQ ID NO 665
<211> LENGTH: 18
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 665
cuauucugca uaauucaa                                                        18

<210> SEQ ID NO 666
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 666
guauucuauu cugcauaa                                                        18

<210> SEQ ID NO 667
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
gguauguauu cuauucug                                                        18

<210> SEQ ID NO 668
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
uucuagguau guauucua                                                        18

<210> SEQ ID NO 669
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
uuuauuucua gguaugua                                                        18

<210> SEQ ID NO 670
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
uuuguuuuau uucuaggu                                                        18

<210> SEQ ID NO 671
<211> LENGTH: 18
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 671 acguuuugu uuuauuuc                                                    18

<210> SEQ ID NO 672
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 672
auaagacguu uuuguuuu                                                   18

<210> SEQ ID NO 673
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
ucaugauaag acguuuu                                                    18

<210> SEQ ID NO 674
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
aauacucaug auaagacg                                                   18

<210> SEQ ID NO 675
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
aucuuaauac ucaugaua                                                   18

<210> SEQ ID NO 676
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 676
auuuuaucuu aauacuca                                                   18

```
<210> SEQ ID NO 677
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 677
cuuaaauuuu aucuuaau                                                      18

<210> SEQ ID NO 678
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 678
uaugccuuaa auuuuauc                                                      18

<210> SEQ ID NO 679
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 679
gaguuuaugc cuuaaauu                                                      18

<210> SEQ ID NO 680
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
gaagugaguu uaugccuu                                                      18

<210> SEQ ID NO 681
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
ucuaagaagu gaguuuau                                                      18

<210> SEQ ID NO 682
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 682
cuuauucuaa gaagugag                                                      18
```

-continued

<210> SEQ ID NO 683
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 683
aguuacuuau ucuaagaa                                                      18

<210> SEQ ID NO 684
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 684
uugggaguua cuuauucu                                                      18

<210> SEQ ID NO 685
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
guuaguuggg aguuacuu                                                      18

<210> SEQ ID NO 686
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
agaaaguuag uugggagu                                                      18

<210> SEQ ID NO 687
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
auccuagaaa guuaguug                                                      18

<210> SEQ ID NO 688
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 688
uuaaaauccu agaaaguu                                                      18

-continued

```
<210> SEQ ID NO 689
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 689 auguuuaaa auccuaga                                                      18

<210> SEQ ID NO 690
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
guguuauguu uuaaaauc                                                     18

<210> SEQ ID NO 691
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
ucacuguguu auguuua                                                      18

<210> SEQ ID NO 692
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 692
uguuuucacu guguuaug                                                     18

<210> SEQ ID NO 693
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 693
auguauguuu ucacugug                                                     18

<210> SEQ ID NO 694
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 694
uguuuaugua uguuuuca                                                     18

<210> SEQ ID NO 695
```

-continued

```
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 695
aguuauguuu auguaugu                                                     18

<210> SEQ ID NO 696
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
uguagaguua uguuuaug                                                     18

<210> SEQ ID NO 697
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 697
uaaaauguag aguuaugu                                                     18

<210> SEQ ID NO 698
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
auaaauaaaa uguagagu                                                     18

<210> SEQ ID NO 699
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
uaagaauaaa uaaaaugu                                                     18

<210> SEQ ID NO 700
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
aacuuuaaga auaaauaa                                                     18

<210> SEQ ID NO 701
<211> LENGTH: 18
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
acuuaaacuu uaagaaua                                                    18

<210> SEQ ID NO 702
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
aauacacuua aacuuuaa                                                    18

<210> SEQ ID NO 703
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
uguauaauac acuuaaac                                                    18

<210> SEQ ID NO 704
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
cuucuuguau aauacacu                                                    18

<210> SEQ ID NO 705
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
cucuucuucu uguauaau                                                    18

<210> SEQ ID NO 706
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
auaaacucuu cuucuugu                                                    18

<210> SEQ ID NO 707
<211> LENGTH: 18
<212> TYPE: RNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 707
cgaauauaaa cucuucuu                                                  18

<210> SEQ ID NO 708
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
ucucucgaau auaaacuc                                                  18

<210> SEQ ID NO 709
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
uucugucucu cgaauaua                                                  18

<210> SEQ ID NO 710
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
acuuuuucug ucucucga                                                  18

<210> SEQ ID NO 711
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
uucugacuuu uucugucu                                                  18

<210> SEQ ID NO 712
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
aaaaauucug acuuuuuc                                                  18

<210> SEQ ID NO 713
<211> LENGTH: 18
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 713
caaacaaaaa uucugacu                                                    18

<210> SEQ ID NO 714
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
ugauccaaac aaaaauuc                                                    18

<210> SEQ ID NO 715
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
auuggugauc caaacaaa                                                    18

<210> SEQ ID NO 716
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
gauauauugg ugauccaa                                                    18

<210> SEQ ID NO 717
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
gcuaugauau auugguga                                                    18

<210> SEQ ID NO 718
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
uguaagcuau gauauauu                                                    18

<210> SEQ ID NO 719
<211> LENGTH: 18
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 719
uuuuuuguaa gcuaugau                                                    18

<210> SEQ ID NO 720
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 720
acaguuuuuu uguaagcu                                                    18

<210> SEQ ID NO 721
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 721
uuaagacagu uuuuuugu                                                    18

<210> SEQ ID NO 722
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
uuuaauuaag acaguuuu                                                    18

<210> SEQ ID NO 723
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
uggguuuuaa uuaagaca                                                    18

<210> SEQ ID NO 724
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
uguugugggu uuuaauua                                                    18

```
<210> SEQ ID NO 725
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
aauuauguug uggguuuu                                                    18

<210> SEQ ID NO 726
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
aaaaaaauua uguugugg                                                    18

<210> SEQ ID NO 727
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 727
aaucuaaaaa aauuaugu                                                    18

<210> SEQ ID NO 728
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 728
uuaaaaaucu aaaaaaau                                                    18

<210> SEQ ID NO 729
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 729
cuuucuuaaa aaucuaaa                                                    18

<210> SEQ ID NO 730
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 730
agaaucuuuc uuaaaaau                                                    18
```

-continued

```
<210> SEQ ID NO 731
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 731
auaauagaau cuuucuua                                                      18

<210> SEQ ID NO 732
<211> LENGTH: 264
<212> TYPE: DNA
<213> ORGANISM: Homo sapiens

<400> SEQUENCE: 732
ggaaacagac ggagagcatc atgaacaaaa agtaacacca aatgttctgt catatcagat      60
ttctaactaa taacaaacta tatatttcta ttttgtatag gataatcttg ctccaacttg     120
gatggggtgg agcgctggtt cctcccctga gccctttatt atgggtactg tattacccct     180
tttgctacct ttaatccttg cactgtgact tatgtgtagt ggggtgaggg agggattggg     240
aagggtacta ttattgcacc acag                                            264
```